US008927699B2

(12) United States Patent
Jestin et al.

(10) Patent No.: US 8,927,699 B2
(45) Date of Patent: *Jan. 6, 2015

(54) **METHODS FOR OBTAINING THERMOSTABLE ENZYMES, DNA POLYMERASE I VARIANTS FROM *THERMUS AQUATICUS* HAVING NEW CATALYTIC ACTIVITIES, METHODS FOR OBTAINING THE SAME, AND APPLICATIONS TO THE SAME**

(75) Inventors: Jean-Luc Jestin, Paris (FR); Sophie Vichier-Guerre, Gif sur Yvette (FR); Stephane Ferris, Mennecy (FR)

(73) Assignees: Institut Pasteur, Paris (FR); Centre National de la Recherche Scientifique (CNRS), Paris (FR)

( * ) Notice: Subject to any disclaimer, the term of this patent is extended or adjusted under 35 U.S.C. 154(b) by 2026 days.

This patent is subject to a terminal disclaimer.

(21) Appl. No.: 10/590,810

(22) PCT Filed: Feb. 25, 2005

(86) PCT No.: PCT/IB2005/000734
§ 371 (c)(1),
(2), (4) Date: Jan. 17, 2007

(87) PCT Pub. No.: WO2005/083068
PCT Pub. Date: Sep. 9, 2005

(65) Prior Publication Data
US 2008/0014609 A1      Jan. 17, 2008

Related U.S. Application Data

(63) Continuation-in-part of application No. 10/787,219, filed on Feb. 27, 2004, now Pat. No. 7,417,133.

(51) Int. Cl.
*C12N 9/12*     (2006.01)
*C07H 21/02*    (2006.01)
*C07K 14/435*   (2006.01)
*A61K 38/00*    (2006.01)

(52) U.S. Cl.
CPC ........ *C07K 14/43563* (2013.01); *C12N 9/1252* (2013.01); *A61K 38/00* (2013.01)
USPC ....... 536/23.1; 435/194; 435/183; 435/320.1; 435/252.3

(58) Field of Classification Search
None
See application file for complete search history.

(56) References Cited

U.S. PATENT DOCUMENTS 5,436,149 A    7/1995   Barnes
5,691,142 A   11/1997   Dahlberg et al.
6,130,045 A *  10/2000  Wurst et al. .............. 435/6.12
6,214,557 B1   4/2001   Barnes et al.
2005/0191635 A1  9/2005  Jestin et al.
2005/0250131 A1  11/2005 Jestin et al.

FOREIGN PATENT DOCUMENTS

EP    0 745 676    12/1996
WO    98 23733    6/1998

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Temple F. Smith, et al., "Comparison of Biosequences", Advances in Applied Mathematics, vol. 2, 1981, pp. 482-489.
Saul B. Needleman, et al., "A General Method Applicable to the Search for Similarities in the Amino Acid Sequence of Two Proteins", J. Mol. Biol., vol. 48, 1970, pp. 443-453.
Relevant extract of "Current Protocols in Molecular Biology", Chapter 2, F. M. Ausubel, et al., John Willey & Sons, Inc., 2000, pp. (2.9.1)-(2.10.16).
Jean-Luc Jestin, et al., "Improving the display of proteins on filamentous phage", Res. Microbiol., vol. 152, 2001, pp. 187-191.
Peter Kristensen, et al., "Proteolytic selection for protein folding using filamentous bacteriophages", Folding & Design, vol. 3, No. 5, pp. 321-328.
Henrik Pedersen, et al., "A Method for directed evolution and functional cloning of enzymes", Proc. Natl. Acad. Sci. USA, vol. 95, Sep. 1998, pp. 10523-10528.
Jean-Luc Jestin, et al., "A Method for the selection of Catalytic Activity Using Phage Display and Proximity Coupling", Angew. Chem. Int. Ed., vol. 38, No. 8, 1999, pp. 1124-1127.
Frances C. Lawyer, et al., "Isolation, Characterization, and Expression in *Escherichia coli* of the DNA Polymerase Gene from *Thermus aquaticus*", The Journal of Biological Chemistry, vol. 264, No. 11, Apr. 15, 1989, pp. 6427-6437.
Sophie Vichier-Guerre, et al., "Iterative Cycles of In Vitro Protein Selection for DNA Polymerase Activity", Biocatalysis and Biotransformation, vol. 21, No. 2, 2003, pp. 75-78.
Gang Xia, et al., "Direct evolution of novel polymerase activities: Mutation of a DNA polymerase into an efficient RNA polymerase", Proc. Natl. Acad. Sci. USA, vol. 99, No. 10, May 14, 2002, pp. 6597-6602.

* cited by examiner

*Primary Examiner* — Richard Hutson
(74) *Attorney, Agent, or Firm* — Oblon, Spivak, McClelland, Maier & Neustadt, L.L.P.

(57) ABSTRACT

A thermostable mutant DNA polymerase; a method for obtaining the thermostable mutant DNA polymerase by identifying a thermostable mutant polypeptide exhibiting enzymatic activity, wherein the thermostable mutant polypeptide is a variant of DNA polymerase I obtained from *Thermus aquaticus*; a polynucleotide, an expression vector, and a host cell encoding the thermostable mutant DNA polymerase; and a method of performing a reverse transcription polymerase chain reaction (RT-PCR) utilizing the thermostable mutant DNA polymerase, as well as a kit for facilitating the same.

18 Claims, 6 Drawing Sheets

SEQUENCE LISTING

```
<160> NUMBER OF SEQ ID NOS: 108

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
taacaatagg ccggccaccc cttc                                            24

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 2
gagtttttgt tctgcggc                                               18

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tttaatcatc tgcagtaccg ggagctc                                     27

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttcattcttg ctagctcctg ggagaggc                                    28

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(17)
<223> OTHER INFORMATION: This region may encompass the bases "car" or
      "avy"
<220> FEATURE:
<221> NAME/KEY: modified_base
<222> LOCATION: (24)..(26)
<223> OTHER INFORMATION: This region may encompass the bases "car" or
      "avy"

<400> SEQUENCE: 5
ccggccaccc cttcnnnctc aacnnncggg accagctgga aag                   43

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(19)
<223> OTHER INFORMATION: This region may encompass the bases "ytg" or
      "rbt"
<220> FEATURE:
<221> NAME/KEY: modified_base
<222> LOCATION: (20)..(22)
<223> OTHER INFORMATION: This region may encompass the bases "ytg" or
      "rbt"
<220> FEATURE:
<221> NAME/KEY: modified_base
<222> LOCATION: (26)..(28)
<223> OTHER INFORMATION: This region may encompass the bases "ytg" or
      "rbt"
<220> FEATURE:
<221> NAME/KEY: modified_base
<222> LOCATION: (44)..(46)
<223> OTHER INFORMATION: This region may encompass the bases "ytg" or
      "rbt"

<400> SEQUENCE: 6
ggatgaggtc cggcaannnn nnaatnnngg tgctcttcag cttnnngagc tcccggtact    60
gcagg                                                                65

<210> SEQ ID NO 7
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(19)
<223> OTHER INFORMATION: This region may encompass the bases "car" or
      "avy"
<220> FEATURE:
<221> NAME/KEY: modified_base
<222> LOCATION: (32)..(34)
<223> OTHER INFORMATION: This region may encompass the bases "car" or
      "avy"
<220> FEATURE:
<221> NAME/KEY: modified_base
<222> LOCATION: (41)..(43)
<223> OTHER INFORMATION: This region may encompass the bases "car" or
      "avy"

<400> SEQUENCE: 7
caaccagacg gccacgnnna cgggcaggct annnagctcc nnnccccaacc tccagaacat    60 cc                                                                   62

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(16)
<223> OTHER INFORMATION: This region may encompass the bases "ytg" or
      "rbt"
<220> FEATURE:
<221> NAME/KEY: modified_base
<222> LOCATION: (23)..(25)
<223> OTHER INFORMATION: This region may encompass the bases "ytg" or
      "rbt"

<400> SEQUENCE: 8
ccgcctcccg cacnnncttc acnnnggcct ctaggtctgg cac                      43

<210> SEQ ID NO 9
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(22)
<223> OTHER INFORMATION: This region may encompass the bases "car" or
      "avy"
<220> FEATURE:
<221> NAME/KEY: modified_base
<222> LOCATION: (38)..(40)

```
<223> OTHER INFORMATION: This region may encompass the bases "car" or
      "avy"
<220> FEATURE:
<221> NAME/KEY: modified_base
<222> LOCATION: (44)..(46)
<223> OTHER INFORMATION: This region may encompass the bases "car" or
      "avy"
<220> FEATURE:
<221> NAME/KEY: modified_base
<222> LOCATION: (47)..(49)
<223> OTHER INFORMATION: This region may encompass the bases "car" or
      "avy"

<400> SEQUENCE: 9
cctgcagtac cgggagctcn nnaagctgaa gagcaccnnn attnnnnnnt tgccggacct    60
catcc                                                               65

<210> SEQ ID NO 10
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(22)
<223> OTHER INFORMATION: This region may encompass the bases "ytg" or
      "rbt"
<220> FEATURE:
<221> NAME/KEY: modified_base
<222> LOCATION: (29)..(31)
<223> OTHER INFORMATION: This region may encompass the bases "ytg" or
      "rbt"
<220> FEATURE:
<221> NAME/KEY: modified_base
<222> LOCATION: (44)..(46)
<223> OTHER INFORMATION: This region may encompass the bases "ytg" or
      "rbt"

<400> SEQUENCE: 10
ggatgttctg gaggttgggn nnggagctnn ntagcctgcc cgtnnncgtg gccgtctggt    60
tg                                                                  62

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: This region may encompass the bases "car" or
      "avy"
<220> FEATURE:
<221> NAME/KEY: modified_base
<222> LOCATION: (28)..(30)
<223> OTHER INFORMATION: n is a, c, g, or t
<220> FEATURE:
<221> NAME/KEY: modified_base
<222> LOCATION: (28)..(30)
<223> OTHER INFORMATION: This region may encompass the bases "car" or
      "avy"

<400> SEQUENCE: 11
gtgccagacc tagaggccnn ngtgaagnnn gtgcgggagg cgg                     43

<210> SEQ ID NO 12
<211> LENGTH: 30
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
aaauacaaca auaaaacgcc acaucuugcg                                      30

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taacacgaca aagcgcaaga tgtggcgt                                        28

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaatacaaca ataaaacgcc acatcttgcg                                      30

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttcattcttg ctagctcctg ggagaggc                                        28

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gagaagatcc tgcagtaccg ggagc                                           25

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gaccaacatc aagactgcc                                                  19

<210> SEQ ID NO 18
<211> LENGTH: 18
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 18
ttggccagga acttgtcc                18

<210> SEQ ID NO 19
<211> LENGTH: 1688
<212> TYPE: DNA
<213> ORGANISM: Thermus aquaticus
<220> FEATURE:
<221> NAME/KEY: CDS
<222> LOCATION: (3)..(1688)

<400> SEQUENCE: 19

```
cc atg gcc tct ggt ggc ggt ggc tgt ggt ggc ggt ggc agc ccc aag       47
   Met Ala Ser Gly Gly Gly Gly Cys Gly Gly Gly Gly Ser Pro Lys
   1               5                   10                  15 gcc ctg gag gag gcc ccc tgg ccc ccg ccg gaa ggg gcc ttc gtg ggc       95
Ala Leu Glu Glu Ala Pro Trp Pro Pro Pro Glu Gly Ala Phe Val Gly
                20                  25                  30 ttt gtg ctt tcc cgc aag gag ccc atg tgg gcc gat ctt ctg gcc ctg     143
Phe Val Leu Ser Arg Lys Glu Pro Met Trp Ala Asp Leu Leu Ala Leu
            35                  40                  45 gcc gcc gcc agg ggg ggc cgg gtc cac cgg gcc ccc gag cct tat aaa     191
Ala Ala Ala Arg Gly Gly Arg Val His Arg Ala Pro Glu Pro Tyr Lys
        50                  55                  60 gcc ctc agg gac ctg aag gag gcg cgg ggg ctt ctc gcc aaa gac ctg     239
Ala Leu Arg Asp Leu Lys Glu Ala Arg Gly Leu Leu Ala Lys Asp Leu
    65                  70                  75 agc gtt ctg gcc ctg agg gaa ggc ctt ggc ctc ccg ccc ggc gac gac     287
Ser Val Leu Ala Leu Arg Glu Gly Leu Gly Leu Pro Pro Gly Asp Asp
80                  85                  90                  95 ccc atg ctc ctc gcc tac ctc ctg gac cct tcc aac acc acc ccc gag     335
Pro Met Leu Leu Ala Tyr Leu Leu Asp Pro Ser Asn Thr Thr Pro Glu
                100                 105                 110 ggg gtg gcc cgg cgc tac ggc ggg gag tgg acg gag gag gcg ggg gag     383
Gly Val Ala Arg Arg Tyr Gly Gly Glu Trp Thr Glu Glu Ala Gly Glu
            115                 120                 125 cgg gcc gcc ctt tcc gag agg ctc ttc gcc aac ctg tgg ggg agg ctt     431
Arg Ala Ala Leu Ser Glu Arg Leu Phe Ala Asn Leu Trp Gly Arg Leu
        130                 135                 140 gag ggg gag gag agg ctc ctt tgg ctt tac cgg gag gtg gag agg ccc     479
Glu Gly Glu Glu Arg Leu Leu Trp Leu Tyr Arg Glu Val Glu Arg Pro
    145                 150                 155 ctt tcc gct gtc ctg gcc cac atg gag gcc acg ggg gtg cgc ctg gac     527
Leu Ser Ala Val Leu Ala His Met Glu Ala Thr Gly Val Arg Leu Asp
160                 165                 170                 175 gtg gcc tat ctc agg gcc ttg tcc ctg gag gtg gcc gag gag atc gcc     575
Val Ala Tyr Leu Arg Ala Leu Ser Leu Glu Val Ala Glu Glu Ile Ala
                180                 185                 190 cgc ctc gag gcc gag gtc ttc cgc ctg gcc ggc cac ccc ttc aac ctc     623
Arg Leu Glu Ala Glu Val Phe Arg Leu Ala Gly His Pro Phe Asn Leu
            195                 200                 205 aac tcc cgg gac cag ctg gaa agg gtc ctc ttt gac gag cta ggg ctt     671
Asn Ser Arg Asp Gln Leu Glu Arg Val Leu Phe Asp Glu Leu Gly Leu
        210                 215                 220 ccc gcc atc ggc aag acg gag aag acc ggc aag cgc tcc acc agc gcc     719
Pro Ala Ile Gly Lys Thr Glu Lys Thr Gly Lys Arg Ser Thr Ser Ala
    225                 230                 235
```

```
gcc gtc ctg gag gcc ctt cgc gag gcc cac ccc atc gtg gag aag atc    767
Ala Val Leu Glu Ala Leu Arg Glu Ala His Pro Ile Val Glu Lys Ile
240             245                 250                 255 ctg cag tac cgg gag ctc acc aag ctg aag agc acc tac att ggc ccc    815
Leu Gln Tyr Arg Glu Leu Thr Lys Leu Lys Ser Thr Tyr Ile Gly Pro
                260                 265                 270 ttg ccg gac ctc atc cac ccc agg acg ggc cgc ctc cac acc cgc ttc    863
Leu Pro Asp Leu Ile His Pro Arg Thr Gly Arg Leu His Thr Arg Phe
            275                 280                 285 aac cag acg gcc acg gcc acg ggc agg cta agt agc tcc gat ccc aac    911
Asn Gln Thr Ala Thr Ala Thr Gly Arg Leu Ser Ser Ser Asp Pro Asn
        290                 295                 300 ctc cag aac gtc ccc gtc cgc acc ccg ctt ggg cag agg atc cgc cgg    959
Leu Gln Asn Val Pro Val Arg Thr Pro Leu Gly Gln Arg Ile Arg Arg
    305                 310                 315 gcc ttc atc gcc gag gag ggg tgg cta ttg gtg gcc ctg gac tat agc    1007
Ala Phe Ile Ala Glu Glu Gly Trp Leu Leu Val Ala Leu Asp Tyr Ser
320             325                 330                 335 cag ata gag ctc agg gtg ctg gcc cac ctc tcc ggc gac gag aac ctg    1055
Gln Ile Glu Leu Arg Val Leu Ala His Leu Ser Gly Asp Glu Asn Leu
                340                 345                 350 atc cgg gtc ttc cag gag ggg cgg gat atc cac acg gag acc gcc agc    1103
Ile Arg Val Phe Gln Glu Gly Arg Asp Ile His Thr Glu Thr Ala Ser
            355                 360                 365 tgg atg ttc ggc gtc ccc cgg gag gcc gtg gac ccc ctg atg cgc cgg    1151
Trp Met Phe Gly Val Pro Arg Glu Ala Val Asp Pro Leu Met Arg Arg
        370                 375                 380 gcg gcc aag acc atc aac ttc ggg gtc ctc tac ggc atg tcg gcc cac    1199
Ala Ala Lys Thr Ile Asn Phe Gly Val Leu Tyr Gly Met Ser Ala His
    385                 390                 395 cgc ctc tcc cag gag cta gcc atc cct tac gag gag gcc cag gcc ttc    1247
Arg Leu Ser Gln Glu Leu Ala Ile Pro Tyr Glu Glu Ala Gln Ala Phe
400             405                 410                 415 att gag cgc tac ttt cag agc ttc ccc aag gtg cgg gcc tgg att gag    1295
Ile Glu Arg Tyr Phe Gln Ser Phe Pro Lys Val Arg Ala Trp Ile Glu
                420                 425                 430 aag acc ctg gag gag ggt agg agg cgg ggg tac gtg gag acc ctc ttc    1343
Lys Thr Leu Glu Glu Gly Arg Arg Arg Gly Tyr Val Glu Thr Leu Phe
            435                 440                 445 ggc cgc cgc cgc tac gtg cca gac cta gag gcc cgg gtg aag agc gtg    1391
Gly Arg Arg Arg Tyr Val Pro Asp Leu Glu Ala Arg Val Lys Ser Val
        450                 455                 460 cgg gag gcg gcc gag cgc atg gcc ttc aac atg ccc gtc cag ggc acc    1439
Arg Glu Ala Ala Glu Arg Met Ala Phe Asn Met Pro Val Gln Gly Thr
    465                 470                 475 gcc gcc gac ctc acg aag ctg gct atg gtg aag ctc ttc ccc agg ctg    1487
Ala Ala Asp Leu Thr Lys Leu Ala Met Val Lys Leu Phe Pro Arg Leu
480             485                 490                 495 gag gaa atg ggg gcc agg atg ctc ctt cag gtc cac gac gag ctg gtc    1535
Glu Glu Met Gly Ala Arg Met Leu Leu Gln Val His Asp Glu Leu Val
                500                 505                 510 ctc gag gcc cca aaa gag ggg gcg gag gcc gtg gcc cgg ctg gcc aag    1583
Leu Glu Ala Pro Lys Glu Gly Ala Glu Ala Val Ala Arg Leu Ala Lys
            515                 520                 525 gag gtc atg gag ggg gtg tat ccc ctg gcc gtg ccc ctg gag gtg gag    1631
Glu Val Met Glu Gly Val Tyr Pro Leu Ala Val Pro Leu Glu Val Glu
        530                 535                 540 gtg ggg ata ggg gag gac tgg ctc tcc gcc aag gag gcg gcc gca ctg    1679
Val Gly Ile Gly Glu Asp Trp Leu Ser Ala Lys Glu Ala Ala Ala Leu
```

```
            545                 550                 555
gtg ccg cgc                                                          1688
Val Pro Arg
560
```

<210> SEQ ID NO 20
<211> LENGTH: 562
<212> TYPE: PRT
<213> ORGANISM: Thermus aquaticus

<400> SEQUENCE: 20

```
Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20              25                  30

Val Leu Ser Arg Lys Glu Pro Met Trp Ala Asp Leu Leu Ala Leu
            35                  40                  45

Ala Ala Arg Gly Gly Arg Val His Arg Ala Pro Glu Pro Tyr Lys Ala
50                      55                      60

Leu Arg Asp Leu Lys Glu Ala Arg Gly Leu Leu Ala Lys Asp Leu Ser
65                  70                      75                  80

Val Leu Ala Leu Arg Glu Gly Leu Gly Leu Pro Pro Gly Asp Asp Pro
                85                  90                      95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
            195                 200                 205

Ser Arg Asp Gln Leu Glu Arg Val Leu Phe Asp Glu Leu Gly Leu Pro
210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Gly Pro Leu
            260                 265                 270

Pro Asp Leu Ile His Pro Arg Thr Gly Arg Leu His Thr Arg Phe Asn
        275                 280                 285

Gln Thr Ala Thr Ala Thr Gly Arg Leu Ser Ser Ser Asp Pro Asn Leu
    290                 295                 300

Gln Asn Val Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350
```

-continued

```
Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Arg Ala
    370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Thr Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Gly Ala Glu Ala Val Ala Arg Leu Ala Lys Glu
        515                 520                 525

Val Met Glu Gly Val Tyr Pro Leu Ala Val Pro Leu Glu Val Glu Val
530                 535                 540

Gly Ile Gly Glu Asp Trp Leu Ser Ala Lys Glu Ala Ala Ala Leu Val
545                 550                 555                 560

Pro Arg

<210> SEQ ID NO 21
<211> LENGTH: 1688
<212> TYPE: DNA
<213> ORGANISM: Thermus aquaticus
<220> FEATURE:
<221> NAME/KEY: CDS
<222> LOCATION: (3)..(1688)

<400> SEQUENCE: 21 cc atg gcc tct ggt ggc ggt ggc tgt ggt ggc ggt ggc agc ccc aag        47
   Met Ala Ser Gly Gly Gly Gly Cys Gly Gly Gly Gly Ser Pro Lys
   1               5                   10                  15 gcc ctg gag gag gcc ccc tgg ccc ccg ccg gaa ggg gcc ttc gtg ggc        95
Ala Leu Glu Glu Ala Pro Trp Pro Pro Pro Glu Gly Ala Phe Val Gly
                20                  25                  30 ttt gtg ctt tcc cgc aag gag ccc atg tgg gcc gat ctt ctg gcc ctg       143
Phe Val Leu Ser Arg Lys Glu Pro Met Trp Ala Asp Leu Leu Ala Leu
            35                  40                  45 gcc gcc gcc agg ggg ggc cgg gtc cac cgg gcc ccc gag cct tat aaa       191
Ala Ala Ala Arg Gly Gly Arg Val His Arg Ala Pro Glu Pro Tyr Lys
        50                  55                  60 gcc ctc agg gac ctg aag gag gcg cgg ggg ctt ctc gcc aaa gac ctg       239
Ala Leu Arg Asp Leu Lys Glu Ala Arg Gly Leu Leu Ala Lys Asp Leu
65                  70                  75 agc gtt ctg gcc ctg agg gaa ggc ctt ggc ctc ccg ccc ggc gac gac       287
Ser Val Leu Ala Leu Arg Glu Gly Leu Gly Leu Pro Pro Gly Asp Asp
80                  85                  90                  95 ccc atg ctc ctc gcc tac ctc ctg gac cct tcc aac acc acc ccc gag       335
Pro Met Leu Leu Ala Tyr Leu Leu Asp Pro Ser Asn Thr Thr Pro Glu
```

```
                100              105                110
ggg gtg gcc cgg cgc tac ggc ggg gag tgg acg gag gag gcg ggg gag     383
Gly Val Ala Arg Arg Tyr Gly Gly Glu Trp Thr Glu Glu Ala Gly Glu
            115                  120                 125 cgg gcc gcc ctt tcc gag agg ctc ttc gcc aac ctg tgg ggg agg ctt     431
Arg Ala Ala Leu Ser Glu Arg Leu Phe Ala Asn Leu Trp Gly Arg Leu
        130                  135                 140 gag ggg gag gag agg ctc ctt tgg ctt tac cgg gag gtg gag agg ccc     479
Glu Gly Glu Glu Arg Leu Leu Trp Leu Tyr Arg Glu Val Glu Arg Pro
    145                 150                  155 ctt tcc gct gtc ctg gcc cac atg gag gcc acg ggg gtg cgc ctg gac     527
Leu Ser Ala Val Leu Ala His Met Glu Ala Thr Gly Val Arg Leu Asp
160                 165                  170                 175 gtg gcc tat ctc agg gcc ttg tcc ctg gag gtg gcc gag gag atc gcc     575
Val Ala Tyr Leu Arg Ala Leu Ser Leu Glu Val Ala Glu Glu Ile Ala
                180                  185                 190 cgc ctc gag gcc gag gtc ttc cgc ctg gcc ggc cac ccc ttc aac ctc     623
Arg Leu Glu Ala Glu Val Phe Arg Leu Ala Gly His Pro Phe Asn Leu
            195                  200                 205 aac tcc cgg gac cag ctg gaa agg gtc ctc ttt gac gag cta ggg ctt     671
Asn Ser Arg Asp Gln Leu Glu Arg Val Leu Phe Asp Glu Leu Gly Leu
        210                  215                 220 ccc gcc atc ggc aag acg gag aag acc ggc aag cgc tcc acc agc gcc     719
Pro Ala Ile Gly Lys Thr Glu Lys Thr Gly Lys Arg Ser Thr Ser Ala
    225                 230                  235 gcc gtc ctg ggg gcc ctc cgc gag gcc cac ccc atc gtg gag aag atc     767
Ala Val Leu Gly Ala Leu Arg Glu Ala His Pro Ile Val Glu Lys Ile
240                 245                  250                 255 ctg cag tac cgg gag ctc acc aag ctg aag agc acc tac att gac ccc     815
Leu Gln Tyr Arg Glu Leu Thr Lys Leu Lys Ser Thr Tyr Ile Asp Pro
                260                  265                 270 ttg ccg gac ctc atc cac ccc agg acg ggc cgc ctc cac acc cgc ttc     863
Leu Pro Asp Leu Ile His Pro Arg Thr Gly Arg Leu His Thr Arg Phe
            275                  280                 285 aac cag acg gcc acg gcc acg ggc agg cta agt agc tcc gat ccc aac     911
Asn Gln Thr Ala Thr Ala Thr Gly Arg Leu Ser Ser Ser Asp Pro Asn
        290                  295                 300 ctc cag aac atc ccc gtc cgc acc ccg ctt ggg cag agg atc cgc cgg     959
Leu Gln Asn Ile Pro Val Arg Thr Pro Leu Gly Gln Arg Ile Arg Arg
    305                 310                  315 gcc ttc atc gcc gag gag ggg tgg cta ttg gtg acc ctg gac tat agc    1007
Ala Phe Ile Ala Glu Glu Gly Trp Leu Leu Val Thr Leu Asp Tyr Ser
320                 325                  330                 335 cag ata gag ctc agg gtg ctg gcc cac ctc tcc ggc gac gag aac ctg    1055
Gln Ile Glu Leu Arg Val Leu Ala His Leu Ser Gly Asp Glu Asn Leu
                340                  345                 350 atc cgg gtc ttc cag gag ggg cgg gac atc cac acg gag acc gcc agc    1103
Ile Arg Val Phe Gln Glu Gly Arg Asp Ile His Thr Glu Thr Ala Ser
            355                  360                 365 tgg atg ttc ggc gtc ccc cgg gag gcc gtg gac ccc ctg atg cgc cgg    1151
Trp Met Phe Gly Val Pro Arg Glu Ala Val Asp Pro Leu Met Arg Arg
        370                  375                 380 gcg gcc aag acc atc aac ttc ggg gtc ctc tac ggc atg tcg gcc cac    1199
Ala Ala Lys Thr Ile Asn Phe Gly Val Leu Tyr Gly Met Ser Ala His
    385                 390                  395 cgc ctc tcc cag gag cta gcc atc cct tac gag gag gcc cag gcc ttc    1247
Arg Leu Ser Gln Glu Leu Ala Ile Pro Tyr Glu Glu Ala Gln Ala Phe
400                 405                  410                 415 att gag cgc tac ttt cag agc ttc ccc aag gtg cgg gcc tgg att gag    1295
```

```
Ile Glu Arg Tyr Phe Gln Ser Phe Pro Lys Val Arg Ala Trp Ile Glu
                420                 425                 430 aag acc ctg gag gag ggc agg agg cgg ggg tac gtg gag acc ctc ttc     1343
Lys Thr Leu Glu Glu Gly Arg Arg Arg Gly Tyr Val Glu Thr Leu Phe
            435                 440                 445 ggc cgc cgc cgc tac gtg cca gac cta gag gcc cgg gtg aag agc gtg     1391
Gly Arg Arg Arg Tyr Val Pro Asp Leu Glu Ala Arg Val Lys Ser Val
        450                 455                 460 cgg gag gcg gcc gag cgc atg gcc ttc aac atg ccc gtc cag ggc acc     1439
Arg Glu Ala Ala Glu Arg Met Ala Phe Asn Met Pro Val Gln Gly Thr
465                 470                 475 gcc gcc gac ctc atg aag ctg gct atg gtg aag ctc ttc ccc agg ctg     1487
Ala Ala Asp Leu Met Lys Leu Ala Met Val Lys Leu Phe Pro Arg Leu
480                 485                 490                 495 gag gaa atg ggg gcc agg atg ctc ctt cag gtc cac gac gag ctg gtc     1535
Glu Glu Met Gly Ala Arg Met Leu Leu Gln Val His Asp Glu Leu Val
                500                 505                 510 ctc gag gcc cca aaa gag ggg gcg gag gcc gtg gcc cgg ctg gcc aag     1583
Leu Glu Ala Pro Lys Glu Gly Ala Glu Ala Val Ala Arg Leu Ala Lys
            515                 520                 525 gag gtc atg gag ggg gtg tat ccc ctg gcc gtg ccc ctg gag gtg gag     1631
Glu Val Met Glu Gly Val Tyr Pro Leu Ala Val Pro Leu Glu Val Glu
        530                 535                 540 gtg ggg ata ggg gag gac agg ctc tcc gcc aag gag gcg gcc gca ctg     1679
Val Gly Ile Gly Glu Asp Arg Leu Ser Ala Lys Glu Ala Ala Ala Leu
545                 550                 555 gtg ccg cgc                                                         1688
Val Pro Arg
560

<210> SEQ ID NO 22
<211> LENGTH: 562
<212> TYPE: PRT
<213> ORGANISM: Thermus aquaticus

<400> SEQUENCE: 22

Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu
            35                  40                  45

Ala Ala Arg Gly Gly Arg Val His Arg Ala Pro Glu Pro Tyr Lys Ala
        50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
        130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175
```

Ala Tyr Leu Arg Ala Leu Ser Leu Glu Val Ala Glu Ile Ala Arg
            180                 185                 190

Leu Glu Ala Glu Val Phe Arg Leu Ala Gly His Pro Phe Asn Leu Asn
        195                 200                 205

Ser Arg Asp Gln Leu Glu Arg Val Leu Phe Asp Glu Leu Gly Leu Pro
210                 215                 220

Ala Ile Gly Lys Thr Glu Lys Thr Gly Lys Arg Ser Thr Ser Ala Ala
225                 230                 235                 240

Val Leu Gly Ala Leu Arg Glu Ala His Pro Ile Val Glu Lys Ile Leu
            245                 250                 255

Gln Tyr Arg Glu Leu Thr Lys Leu Lys Ser Thr Tyr Ile Asp Pro Leu
        260                 265                 270

Pro Asp Leu Ile His Pro Arg Thr Gly Arg Leu His Thr Arg Phe Asn
        275                 280                 285

Gln Thr Ala Thr Ala Thr Gly Arg Leu Ser Ser Ser Asp Pro Asn Leu
    290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Thr Leu Asp Tyr Ser Gln
            325                 330                 335

Ile Glu Leu Arg Val Leu Ala His Leu Ser Gly Asp Glu Asn Leu Ile
        340                 345                 350

Arg Val Phe Gln Glu Gly Arg Asp Ile His Thr Glu Thr Ala Ser Trp
    355                 360                 365

Met Phe Gly Val Pro Arg Glu Ala Val Asp Pro Leu Met Arg Arg Ala
370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
            405                 410                 415

Glu Arg Tyr Phe Gln Ser Phe Pro Lys Val Arg Ala Trp Ile Glu Lys
        420                 425                 430

Thr Leu Glu Glu Gly Arg Arg Gly Tyr Val Glu Thr Leu Phe Gly
        435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
            485                 490                 495

Glu Met Gly Ala Arg Met Leu Leu Gln Val His Asp Glu Leu Val Leu
        500                 505                 510

Glu Ala Pro Lys Glu Gly Ala Glu Ala Val Ala Arg Leu Ala Lys Glu
    515                 520                 525

Val Met Glu Gly Val Tyr Pro Leu Ala Val Pro Leu Glu Val Glu Val
530                 535                 540

Gly Ile Gly Glu Asp Arg Leu Ser Ala Lys Glu Ala Ala Leu Val
545                 550                 555                 560

Pro Arg

<210> SEQ ID NO 23
<211> LENGTH: 1688
<212> TYPE: DNA

<213> ORGANISM: Thermus aquaticus
<220> FEATURE:
<221> NAME/KEY: CDS
<222> LOCATION: (3)..(1688)

<400> SEQUENCE: 23

```
cc atg gcc tct ggt ggc ggt ggc tgt ggt ggc ggt ggc agc ccc aag      47
   Met Ala Ser Gly Gly Gly Gly Cys Gly Gly Gly Gly Ser Pro Lys
   1               5                  10                  15 gcc ctg gag gag gcc ccc tgg ccc ccg ccg gaa ggg gcc ttc gtg ggc      95
Ala Leu Glu Glu Ala Pro Trp Pro Pro Pro Glu Gly Ala Phe Val Gly
                20                  25                  30 ttt gtg ctt tcc cgc aag gag ccc atg tgg gcc gat ctt ctg gcc ctg     143
Phe Val Leu Ser Arg Lys Glu Pro Met Trp Ala Asp Leu Leu Ala Leu
             35                  40                  45 gcc gcc gcc agg ggg ggc cgg gtc cac cgg gcc ccc gag cct tat aaa     191
Ala Ala Ala Arg Gly Gly Arg Val His Arg Ala Pro Glu Pro Tyr Lys
         50                  55                  60 gcc ctc agg gac ctg aag gag gcg cgg ggg ctt ctc gcc aaa gac ctg     239
Ala Leu Arg Asp Leu Lys Glu Ala Arg Gly Leu Leu Ala Lys Asp Leu
     65                  70                  75 agc gtt ctg gcc ctg agg gaa ggc ctt ggc ctc ccg ccc ggc gac gac     287
Ser Val Leu Ala Leu Arg Glu Gly Leu Gly Leu Pro Pro Gly Asp Asp
 80                  85                  90                  95 ccc atg ctc ctc gcc tac ctc ctg gac cct tcc aac acc acc ccc gag     335
Pro Met Leu Leu Ala Tyr Leu Leu Asp Pro Ser Asn Thr Thr Pro Glu
                100                 105                 110 ggg gtg gcc cgg cgc tac ggc ggg gag tgg acg gag gag gcg ggg gag     383
Gly Val Ala Arg Arg Tyr Gly Gly Glu Trp Thr Glu Glu Ala Gly Glu
            115                 120                 125 cgg gcc gcc ctt tcc gag agg ctc ttc gcc aac ctg tgg ggg agg ctt     431
Arg Ala Ala Leu Ser Glu Arg Leu Phe Ala Asn Leu Trp Gly Arg Leu
        130                 135                 140 gag ggg gag gag agg ctc ctt tgg ctt tac cgg gag gtg gag agg ccc     479
Glu Gly Glu Glu Arg Leu Leu Trp Leu Tyr Arg Glu Val Glu Arg Pro
145                 150                 155 ctt tcc gct gtc ctg gcc cac atg gag gcc acg ggg gtg cgc ctg gac     527
Leu Ser Ala Val Leu Ala His Met Glu Ala Thr Gly Val Arg Leu Asp
160                 165                 170                 175 gtg gcc tat ctc agg gcc ttg tcc ctg gag gtg gcc gag gag atc gcc     575
Val Ala Tyr Leu Arg Ala Leu Ser Leu Glu Val Ala Glu Glu Ile Ala
                180                 185                 190 cgc ctc gag gcc gag gtc ttc cgc ctg gcc ggc cac ccc ttc caa ctc     623
Arg Leu Glu Ala Glu Val Phe Arg Leu Ala Gly His Pro Phe Gln Leu
            195                 200                 205 aac caa cgg gac cag ctg gaa agg gtc ctc ttt gac gag cta ggg ctt     671
Asn Gln Arg Asp Gln Leu Glu Arg Val Leu Phe Asp Glu Leu Gly Leu
        210                 215                 220 ccc gcc atc ggc aag acg gag aag acc ggc aag cgc tcc acc agc gcc     719
Pro Ala Ile Gly Lys Thr Glu Lys Thr Gly Lys Arg Ser Thr Ser Ala
225                 230                 235 gcc gtc ctg gag gcc ctc cgc gag gcc cac ccc atc gtg gag aag atc     767
Ala Val Leu Glu Ala Leu Arg Glu Ala His Pro Ile Val Glu Lys Ile
240                 245                 250                 255 ctg cag tac cgg gag ctc aac aag ctg aag agc acc caa att act cag     815
Leu Gln Tyr Arg Glu Leu Asn Lys Leu Lys Ser Thr Gln Ile Thr Gln
                260                 265                 270 ttg ccg gac ctc atc cac ccc agg acg ggc cgc ctc cac acc cgc ttc     863
Leu Pro Asp Leu Ile His Pro Arg Thr Gly Arg Leu His Thr Arg Phe
            275                 280                 285
```

| | | | | | | | | | | | | | | | |
|---|---|---|---|---|---|---|---|---|---|---|---|---|---|---|---|
| aac | cag | acg | gcc | acg | caa | acg | ggc | agg | cta | agt | agc | tcc | cag | ccc | aac |
| Asn | Gln | Thr | Ala | Thr | Gln | Thr | Gly | Arg | Leu | Ser | Ser | Ser | Gln | Pro | Asn |
| | | 290 | | | | 295 | | | | 300 | | | | | |

911

| ctc | cag | aac | atc | ccc | gtc | cgc | acc | ccg | ctt | ggg | cag | agg | atc | cgc | cgg |
|---|---|---|---|---|---|---|---|---|---|---|---|---|---|---|---|
| Leu | Gln | Asn | Ile | Pro | Val | Arg | Thr | Pro | Leu | Gly | Gln | Arg | Ile | Arg | Arg |
| 305 | | | | | 310 | | | | | 315 | | | | | |

959

| acc | ttc | atc | gcc | gag | gag | ggg | agg | cta | ttg | gtg | gcc | ctg | gac | tat | aac |
|---|---|---|---|---|---|---|---|---|---|---|---|---|---|---|---|
| Thr | Phe | Ile | Ala | Glu | Glu | Gly | Arg | Leu | Leu | Val | Ala | Leu | Asp | Tyr | Asn |
| 320 | | | | | 325 | | | | | 330 | | | | | 335 |

1007

| cag | ata | gag | ctc | agg | gtg | ctg | gcc | cac | ctc | tcc | ggc | gac | gag | aac | ctg |
|---|---|---|---|---|---|---|---|---|---|---|---|---|---|---|---|
| Gln | Ile | Glu | Leu | Arg | Val | Leu | Ala | His | Leu | Ser | Gly | Asp | Glu | Asn | Leu |
| | | | | 340 | | | | | 345 | | | | | 350 | |

1055

| atc | cgg | gtc | ttc | cag | gag | ggg | cgg | gac | atc | cac | acg | gag | acc | gcc | agc |
|---|---|---|---|---|---|---|---|---|---|---|---|---|---|---|---|
| Ile | Arg | Val | Phe | Gln | Glu | Gly | Arg | Asp | Ile | His | Thr | Glu | Thr | Ala | Ser |
| | | | 355 | | | | | 360 | | | | | 365 | | |

1103

| tgg | atg | ttc | ggc | gtc | ccc | cgg | gag | gcc | gtg | gac | ccc | ctg | atg | cgc | cgg |
|---|---|---|---|---|---|---|---|---|---|---|---|---|---|---|---|
| Trp | Met | Phe | Gly | Val | Pro | Arg | Glu | Ala | Val | Asp | Pro | Leu | Met | Arg | Arg |
| | | | 370 | | | | | 375 | | | | | 380 | | |

1151

| gcg | gcc | aag | acc | atc | aac | ttc | ggg | gtc | ctc | tac | ggc | atg | tcg | gcc | cac |
|---|---|---|---|---|---|---|---|---|---|---|---|---|---|---|---|
| Ala | Ala | Lys | Thr | Ile | Asn | Phe | Gly | Val | Leu | Tyr | Gly | Met | Ser | Ala | His |
| 385 | | | | | 390 | | | | | 395 | | | | | |

1199

| cgc | ctc | tcc | cag | gag | cta | gcc | atc | cct | tac | gag | gag | gcc | cag | gcc | ttc |
|---|---|---|---|---|---|---|---|---|---|---|---|---|---|---|---|
| Arg | Leu | Ser | Gln | Glu | Leu | Ala | Ile | Pro | Tyr | Glu | Glu | Ala | Gln | Ala | Phe |
| 400 | | | | | 405 | | | | | 410 | | | | | 415 |

1247

| att | gag | cgc | tac | ttt | cag | agc | ttc | ccc | aag | gtg | cgg | gcc | tgg | att | gag |
|---|---|---|---|---|---|---|---|---|---|---|---|---|---|---|---|
| Ile | Glu | Arg | Tyr | Phe | Gln | Ser | Phe | Pro | Lys | Val | Arg | Ala | Trp | Ile | Glu |
| | | | | 420 | | | | | 425 | | | | | 430 | |

1295

| aag | acc | ctg | gag | gag | ggc | agg | agg | cgg | ggg | tac | gtg | gag | acc | ctc | ttc |
|---|---|---|---|---|---|---|---|---|---|---|---|---|---|---|---|
| Lys | Thr | Leu | Glu | Glu | Gly | Arg | Arg | Arg | Gly | Tyr | Val | Glu | Thr | Leu | Phe |
| | | | | 435 | | | | | 440 | | | | | 445 | |

1343

| ggc | cgc | cgc | cgc | tac | ctg | cca | gac | cta | gag | gcc | cag | gtg | aag | aat | gtg |
|---|---|---|---|---|---|---|---|---|---|---|---|---|---|---|---|
| Gly | Arg | Arg | Arg | Tyr | Leu | Pro | Asp | Leu | Glu | Ala | Gln | Val | Lys | Asn | Val |
| | | | 450 | | | | | 455 | | | | | 460 | | |

1391

| cgg | gag | gcg | gcc | gag | cgc | agg | gcc | ttc | aac | atg | ccc | gtc | cag | ggc | acc |
|---|---|---|---|---|---|---|---|---|---|---|---|---|---|---|---|
| Arg | Glu | Ala | Ala | Glu | Arg | Arg | Ala | Phe | Asn | Met | Pro | Val | Gln | Gly | Thr |
| 465 | | | | | 470 | | | | | 475 | | | | | |

1439

| gcc | gcc | gac | ctc | atg | aag | ctg | gct | atg | gtg | aag | ctc | ttc | ccc | agg | ctg |
|---|---|---|---|---|---|---|---|---|---|---|---|---|---|---|---|
| Ala | Ala | Asp | Leu | Met | Lys | Leu | Ala | Met | Val | Lys | Leu | Phe | Pro | Arg | Leu |
| 480 | | | | | 485 | | | | | 490 | | | | | 495 |

1487

| gag | gaa | atg | ggg | gcc | agg | atg | ctc | ctt | cag | gtc | cac | gac | gag | ctg | gtc |
|---|---|---|---|---|---|---|---|---|---|---|---|---|---|---|---|
| Glu | Glu | Met | Gly | Ala | Arg | Met | Leu | Leu | Gln | Val | His | Asp | Glu | Leu | Val |
| | | | | 500 | | | | | 505 | | | | | 510 | |

1535

| ctc | gag | gcc | cca | aaa | gag | ggg | gcg | gag | gcc | gtg | gcc | cgg | ctg | gcc | aag |
|---|---|---|---|---|---|---|---|---|---|---|---|---|---|---|---|
| Leu | Glu | Ala | Pro | Lys | Glu | Gly | Ala | Glu | Ala | Val | Ala | Arg | Leu | Ala | Lys |
| | | | | 515 | | | | | 520 | | | | | 525 | |

1583

| gag | gtc | atg | gag | ggg | gtg | tat | ccc | ctg | gcc | gtg | cct | ctg | gag | gtg | gag |
|---|---|---|---|---|---|---|---|---|---|---|---|---|---|---|---|
| Glu | Val | Met | Glu | Gly | Val | Tyr | Pro | Leu | Ala | Val | Pro | Leu | Glu | Val | Glu |
| | | | 530 | | | | | 535 | | | | | 540 | | |

1631

| gtg | ggg | ata | ggg | gag | gac | tgg | ctc | tcc | gcc | aag | gag | gcg | gcc | gca | ctg |
|---|---|---|---|---|---|---|---|---|---|---|---|---|---|---|---|
| Val | Gly | Ile | Gly | Glu | Asp | Trp | Leu | Ser | Ala | Lys | Glu | Ala | Ala | Ala | Leu |
| | | | 545 | | | | | 550 | | | | | 555 | | |

1679

| gtg | ccg | cgc |
|---|---|---|
| Val | Pro | Arg |
| 560 | | |

1688

<210> SEQ ID NO 24
<211> LENGTH: 562
<212> TYPE: PRT
<213> ORGANISM: Thermus aquaticus

<400> SEQUENCE: 24

```
Met Ala Ser Gly Gly Gly Cys Gly Gly Gly Ser Pro Lys Ala
1               5                   10              15

Leu Glu Glu Ala Pro Trp Pro Pro Glu Gly Ala Phe Val Gly Phe
            20              25              30

Val Leu Ser Arg Lys Glu Pro Met Trp Ala Asp Leu Leu Ala Leu Ala
        35              40              45

Ala Ala Arg Gly Gly Arg Val His Arg Ala Pro Glu Pro Tyr Lys Ala
    50              55              60

Leu Arg Asp Leu Lys Glu Ala Arg Gly Leu Leu Ala Lys Asp Leu Ser
65              70              75              80

Val Leu Ala Leu Arg Glu Gly Leu Gly Leu Pro Pro Gly Asp Asp Pro
                85              90              95

Met Leu Leu Ala Tyr Leu Leu Asp Pro Ser Asn Thr Thr Pro Glu Gly
            100             105             110

Val Ala Arg Arg Tyr Gly Gly Glu Trp Thr Glu Glu Ala Gly Glu Arg
            115             120             125

Ala Ala Leu Ser Glu Arg Leu Phe Ala Asn Leu Trp Gly Arg Leu Glu
    130             135             140

Gly Glu Glu Arg Leu Leu Trp Leu Tyr Arg Glu Val Glu Arg Pro Leu
145             150             155             160

Ser Ala Val Leu Ala His Met Glu Ala Thr Gly Val Arg Leu Asp Val
                165             170             175

Ala Tyr Leu Arg Ala Leu Ser Leu Glu Val Ala Glu Glu Ile Ala Arg
            180             185             190

Leu Glu Ala Glu Val Phe Arg Leu Ala Gly His Pro Phe Gln Leu Asn
        195             200             205

Gln Arg Asp Gln Leu Glu Arg Val Leu Phe Asp Glu Leu Gly Leu Pro
    210             215             220

Ala Ile Gly Lys Thr Glu Lys Thr Gly Lys Arg Ser Thr Ser Ala Ala
225             230             235             240

Val Leu Glu Ala Leu Arg Glu Ala His Pro Ile Val Glu Lys Ile Leu
            245             250             255

Gln Tyr Arg Glu Leu Asn Lys Leu Lys Ser Thr Gln Ile Thr Gln Leu
        260             265             270

Pro Asp Leu Ile His Pro Arg Thr Gly Arg Leu His Thr Arg Phe Asn
    275             280             285

Gln Thr Ala Thr Gln Thr Gly Arg Leu Ser Ser Ser Gln Pro Asn Leu
    290             295             300

Gln Asn Ile Pro Val Arg Thr Pro Leu Gly Gln Arg Ile Arg Arg Thr
305             310             315             320

Phe Ile Ala Glu Glu Gly Arg Leu Leu Val Ala Leu Asp Tyr Asn Gln
            325             330             335

Ile Glu Leu Arg Val Leu Ala His Leu Ser Gly Asp Glu Asn Leu Ile
            340             345             350

Arg Val Phe Gln Glu Gly Arg Asp Ile His Thr Glu Thr Ala Ser Trp
    355             360             365

Met Phe Gly Val Pro Arg Glu Ala Val Asp Pro Leu Met Arg Arg Ala
    370             375             380

Ala Lys Thr Ile Asn Phe Gly Val Leu Tyr Gly Met Ser Ala His Arg
385             390             395             400

Leu Ser Gln Glu Leu Ala Ile Pro Tyr Glu Glu Ala Gln Ala Phe Ile
            405             410             415
```

```
Glu Arg Tyr Phe Gln Ser Phe Pro Lys Val Arg Ala Trp Ile Glu Lys
            420                 425                 430

Thr Leu Glu Glu Gly Arg Arg Gly Tyr Val Glu Thr Leu Phe Gly
                435                 440                 445

Arg Arg Arg Tyr Leu Pro Asp Leu Glu Ala Gln Val Lys Asn Val Arg
450                 455                 460

Glu Ala Ala Glu Arg Ala Phe Asn Met Pro Val Gln Gly Thr Ala
465                 470                 475                 480

Ala Asp Leu Met Lys Leu Ala Met Val Lys Leu Phe Pro Arg Leu Glu
            485                 490                 495

Glu Met Gly Ala Arg Met Leu Leu Gln Val His Asp Glu Leu Val Leu
            500                 505                 510

Glu Ala Pro Lys Glu Gly Ala Glu Ala Val Ala Arg Leu Ala Lys Glu
            515                 520                 525

Val Met Glu Gly Val Tyr Pro Leu Ala Val Pro Leu Glu Val Glu Val
            530                 535                 540

Gly Ile Gly Glu Asp Trp Leu Ser Ala Lys Glu Ala Ala Ala Leu Val
545                 550                 555                 560

Pro Arg

<210> SEQ ID NO 25
<211> LENGTH: 1688
<212> TYPE: DNA
<213> ORGANISM: Thermus aquaticus
<220> FEATURE:
<221> NAME/KEY: CDS
<222> LOCATION: (3)..(1688)

<400> SEQUENCE: 25 cc atg gcc tct ggt ggc ggt ggc tgt ggt ggc ggt ggc agc ccc aag        47
   Met Ala Ser Gly Gly Gly Gly Cys Gly Gly Gly Gly Ser Pro Lys
   1               5                   10                  15 gcc ctg gag gag gcc ccc tgg ccc ccg ccg gaa ggg gcc ttc gtg ggc       95
Ala Leu Glu Glu Ala Pro Trp Pro Pro Pro Glu Gly Ala Phe Val Gly
                20                  25                  30 ttt gtg ctt tcc cgc aag gag ccc atg tgg gcc gat ctt ctg gcc ctg      143
Phe Val Leu Ser Arg Lys Glu Pro Met Trp Ala Asp Leu Leu Ala Leu
                35                  40                  45 gcc gcc gcc agg ggg ggc cgg gtc cac cgg gcc ccc gag cct tat aaa      191
Ala Ala Ala Arg Gly Gly Arg Val His Arg Ala Pro Glu Pro Tyr Lys
            50                  55                  60 gcc ctc agg gac ctg aag gag gcg cgg ggg ctt ctc gcc aaa gac ctg      239
Ala Leu Arg Asp Leu Lys Glu Ala Arg Gly Leu Leu Ala Lys Asp Leu
65                  70                  75 agc gtt ctg gcc ctg agg gaa ggc ctt ggc ctc ccg ccc ggc gac gac      287
Ser Val Leu Ala Leu Arg Glu Gly Leu Gly Leu Pro Pro Gly Asp Asp
80                  85                  90                  95 ccc atg ctc ctc gcc tac ctc ctg gac cct tcc aac acc acc ccc gag      335
Pro Met Leu Leu Ala Tyr Leu Leu Asp Pro Ser Asn Thr Thr Pro Glu
                100                 105                 110 ggg gtg gcc cgg cgc tac ggc ggg gag tgg acg gag gag gcg ggg gag      383
Gly Val Ala Arg Arg Tyr Gly Gly Glu Trp Thr Glu Glu Ala Gly Glu
            115                 120                 125 cgg gcc gcc ctt tcc gag agg ctc ttc gcc aac ctg tgg ggg agg ctt      431
Arg Ala Ala Leu Ser Glu Arg Leu Phe Ala Asn Leu Trp Gly Arg Leu
        130                 135                 140 gag ggg gag gag agg ctc ctt tgg ctt tac cgg gag gtg gag agg ccc      479
Glu Gly Glu Glu Arg Leu Leu Trp Leu Tyr Arg Glu Val Glu Arg Pro
145                 150                 155
```

| | | |
|---|---|---|
| ctt tcc gct gtc ctg gcc cac atg gag gcc acg ggg gtg cgc ctg gac<br>Leu Ser Ala Val Leu Ala His Met Glu Ala Thr Gly Val Arg Leu Asp<br>160                       165                     170                  175 | 527 |
| gtg gcc tat ctc agg gcc ttg tcc ctg gag gtg gcc gag gag atc gcc<br>Val Ala Tyr Leu Arg Ala Leu Ser Leu Glu Val Ala Glu Glu Ile Ala<br>                   180                     185                     190 | 575 |
| cgc ctc gag gcc gag gtc ttc cgc ctg gcc ggc cac ccc ttc aac ctc<br>Arg Leu Glu Ala Glu Val Phe Arg Leu Ala Gly His Pro Phe Asn Leu<br>               195                     200                     205 | 623 |
| aac tcc cgg gac cag ctg gaa agg gtc ctc ttt gac gag cta ggg ctt<br>Asn Ser Arg Asp Gln Leu Glu Arg Val Leu Phe Asp Glu Leu Gly Leu<br>        210                     215                     220 | 671 |
| ccc gcc atc ggc aag acg gag aag acc ggc aag cgc tcc acc agc gcc<br>Pro Ala Ile Gly Lys Thr Glu Lys Thr Gly Lys Arg Ser Thr Ser Ala<br>225                       230                     235 | 719 |
| gcc gtc ctg gag gcc ctc cgc gag gcc cac ccc atc gtg gag aag atc<br>Ala Val Leu Glu Ala Leu Arg Glu Ala His Pro Ile Val Glu Lys Ile<br>240                       245                     250                  255 | 767 |
| ctg cag tac cgg gag ctc acc aag ctg aag agc acc tac att gac ccc<br>Leu Gln Tyr Arg Glu Leu Thr Lys Leu Lys Ser Thr Tyr Ile Asp Pro<br>                   260                     265                     270 | 815 |
| ttg ccg gac ctc atc cac ccc agg acg ggc cgc ctc cac acc cgc ttc<br>Leu Pro Asp Leu Ile His Pro Arg Thr Gly Arg Leu His Thr Arg Phe<br>               275                     280                     285 | 863 |
| aac cag acg gcc acg gcc acg ggc agg cta agt agc tcc gat ccc aac<br>Asn Gln Thr Ala Thr Ala Thr Gly Arg Leu Ser Ser Ser Asp Pro Asn<br>        290                     295                     300 | 911 |
| ctc cag aac atc ccc gtc cgc acc ccg ctt ggg cag agg atc cgc cgg<br>Leu Gln Asn Ile Pro Val Arg Thr Pro Leu Gly Gln Arg Ile Arg Arg<br>305                       310                     315 | 959 |
| gcc ttc atc gcc gag gag ggg tgg cta ttg gtg gcc ctg gac tat agc<br>Ala Phe Ile Ala Glu Glu Gly Trp Leu Leu Val Ala Leu Asp Tyr Ser<br>320                       325                     330                  335 | 1007 |
| cag ata gag ctc agg gtg ctg gcc cac ctc tcc ggc gac gag aac ctg<br>Gln Ile Glu Leu Arg Val Leu Ala His Leu Ser Gly Asp Glu Asn Leu<br>                   340                     345                     350 | 1055 |
| atc cgg gtc ttc cag gag ggg cgg gac atc cac acg gag acc gcc agc<br>Ile Arg Val Phe Gln Glu Gly Arg Asp Ile His Thr Glu Thr Ala Ser<br>               355                     360                     365 | 1103 |
| tgg atg ttc ggc gtc ccc cgg gag gcc gtg gac ccc ctg atg cgc cgg<br>Trp Met Phe Gly Val Pro Arg Glu Ala Val Asp Pro Leu Met Arg Arg<br>        370                     375                     380 | 1151 |
| gcg gcc aag acc atc aac ttc ggg gtc ctc tac ggc atg tcg gcc cac<br>Ala Ala Lys Thr Ile Asn Phe Gly Val Leu Tyr Gly Met Ser Ala His<br>385                       390                     395 | 1199 |
| cgc ctc tcc cag gag cta gcc atc cct tac gag gag gcc cag gcc ttc<br>Arg Leu Ser Gln Glu Leu Ala Ile Pro Tyr Glu Glu Ala Gln Ala Phe<br>400                       405                     410                  415 | 1247 |
| att gag cgc tac ttt cag agc ttc ccc aag gtg cgg gcc tgg att gag<br>Ile Glu Arg Tyr Phe Gln Ser Phe Pro Lys Val Arg Ala Trp Ile Glu<br>                   420                     425                     430 | 1295 |
| aag acc ctg gag gag ggc agg agg cgg ggg tac gtg gag acc ctc ttc<br>Lys Thr Leu Glu Glu Gly Arg Arg Arg Gly Tyr Val Glu Thr Leu Phe<br>               435                     440                     445 | 1343 |
| ggc cgc cgc cgc tac gtg cca gac cta gag gcc cgg gtg aag agc gtg<br>Gly Arg Arg Arg Tyr Val Pro Asp Leu Glu Ala Arg Val Lys Ser Val<br>        450                     455                     460 | 1391 |
| cgg gag gcg gcc gag cgc atg gcc ttc aac atg ccc gtc cag ggc acc<br>Arg Glu Ala Ala Glu Arg Met Ala Phe Asn Met Pro Val Gln Gly Thr | 1439 |

```
          465                 470                 475
gcc gcc gac ctc atg aag ctg gct atg gtg aag ctg ttc ccc agg ctg   1487
Ala Ala Asp Leu Met Lys Leu Ala Met Val Lys Leu Phe Pro Arg Leu
480                 485                 490                 495 gag gaa atg ggg gcc agg atg ctc ctt cag gtc cac gac gag ctg gtc   1535
Glu Glu Met Gly Ala Arg Met Leu Leu Gln Val His Asp Glu Leu Val
                500                 505                 510 ctc gag gcc cca aaa gag agg gcg gag gcc gtg gcc cgg ctg gcc aag   1583
Leu Glu Ala Pro Lys Glu Arg Ala Glu Ala Val Ala Arg Leu Ala Lys
            515                 520                 525 gag gtc atg gag ggg gtg tat ccc ctg gcc gtg ccc ctg gag gtg gag   1631
Glu Val Met Glu Gly Val Tyr Pro Leu Ala Val Pro Leu Glu Val Glu
        530                 535                 540 gtg ggg ata ggg gag gac tgg ctc tcc gcc aag gag gcg gcc gca ctg   1679
Val Gly Ile Gly Glu Asp Trp Leu Ser Ala Lys Glu Ala Ala Ala Leu
    545                 550                 555 gtg ccg cgc                                                        1688
Val Pro Arg
560

<210> SEQ ID NO 26
<211> LENGTH: 562
<212> TYPE: PRT
<213> ORGANISM: Thermus aquaticus

<400> SEQUENCE: 26

Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu
                35                  40                  45

Ala Ala Arg Gly Gly Arg Val His Arg Ala Pro Glu Pro Tyr Lys Ala
            50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
        130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
                180                 185                 190

Leu Glu Ala Glu Val Phe Arg Leu Ala Gly His Pro Phe Asn Leu Asn
            195                 200                 205

Ser Arg Asp Gln Leu Glu Arg Val Leu Phe Asp Glu Leu Gly Leu Pro
        210                 215                 220

Ala Ile Gly Lys Thr Glu Lys Thr Gly Lys Arg Ser Thr Ser Ala Ala
225                 230                 235                 240
```

-continued

```
Val Leu Glu Ala Leu Arg Glu Ala His Pro Ile Val Glu Lys Ile Leu
            245                 250                 255

Gln Tyr Arg Glu Leu Thr Lys Leu Lys Ser Thr Tyr Ile Asp Pro Leu
        260                 265                 270

Pro Asp Leu Ile His Pro Arg Thr Gly Arg Leu His Thr Arg Phe Asn
    275                 280                 285

Gln Thr Ala Thr Ala Thr Gly Arg Leu Ser Ser Asp Pro Asn Leu
290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
        355                 360                 365

Met Phe Gly Val Pro Arg Glu Ala Val Asp Pro Leu Met Arg Arg Ala
    370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Gly Tyr Val Glu Thr Leu Phe Gly
        435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Arg Ala Glu Ala Val Ala Arg Leu Ala Lys Glu
        515                 520                 525

Val Met Glu Gly Val Tyr Pro Leu Ala Val Pro Leu Glu Val Glu Val
    530                 535                 540

Gly Ile Gly Glu Asp Trp Leu Ser Ala Lys Glu Ala Ala Ala Leu Val
545                 550                 555                 560

Pro Arg
```

```
<210> SEQ ID NO 27
<211> LENGTH: 1688
<212> TYPE: DNA
<213> ORGANISM: Thermus aquaticus
<220> FEATURE:
<221> NAME/KEY: CDS
<222> LOCATION: (3)..(1688)

<400> SEQUENCE: 27 cc atg gcc tct ggt ggc ggt ggc tgt ggt ggc ggt ggc agc ccc aag       47
   Met Ala Ser Gly Gly Gly Gly Cys Gly Gly Gly Gly Ser Pro Lys
   1               5                  10                  15 gcc ctg gag gag gcc ccc tgg ccc ccg ccg gaa ggg gcc ttc gtg ggc       95
Ala Leu Glu Glu Ala Pro Trp Pro Pro Pro Glu Gly Ala Phe Val Gly
```

-continued

```
                   20                  25                  30
ttt gtg ctt tcc cgc aag gag ccc atg tgg gcc gat ctt ctg gcc ctg      143
Phe Val Leu Ser Arg Lys Glu Pro Met Trp Ala Asp Leu Leu Ala Leu
             35                  40                  45 gcc gcc gcc agg ggg ggc cgg gtc cac cgg gcc ccc gag cct tat aaa      191
Ala Ala Ala Arg Gly Gly Arg Val His Arg Ala Pro Glu Pro Tyr Lys
         50                  55                  60 gcc ctc agg gac ctg aag gag gcg cgg ggg ctt ctc gcc aaa gac ctg      239
Ala Leu Arg Asp Leu Lys Glu Ala Arg Gly Leu Leu Ala Lys Asp Leu
     65                  70                  75 agc gtt ctg gcc ctg agg gaa ggc ctt ggc ctc ccg ccc ggc gac gac      287
Ser Val Leu Ala Leu Arg Glu Gly Leu Gly Leu Pro Pro Gly Asp Asp
 80                  85                  90                  95 ccc atg ctc ctc gcc tac ctc ctg gac cct tcc aac acc acc ccc gag      335
Pro Met Leu Leu Ala Tyr Leu Leu Asp Pro Ser Asn Thr Thr Pro Glu
                100                 105                 110 ggg gtg gcc cgg cgc tac ggc ggg gag tgg acg gag gag gcg ggg gag      383
Gly Val Ala Arg Arg Tyr Gly Gly Glu Trp Thr Glu Glu Ala Gly Glu
            115                 120                 125 cgg gcc gcc ctt tcc gag agg ctc ttc gcc aac ctg tgg ggg agg ctt      431
Arg Ala Ala Leu Ser Glu Arg Leu Phe Ala Asn Leu Trp Gly Arg Leu
        130                 135                 140 gag ggg gag gag agg ctc ctt tgg ctt tac cgg gag gtg gag agg ccc      479
Glu Gly Glu Glu Arg Leu Leu Trp Leu Tyr Arg Glu Val Glu Arg Pro
    145                 150                 155 ctt tcc gct gtc ctg gcc cac atg gag gcc acg ggg gtg cgc ctg gac      527
Leu Ser Ala Val Leu Ala His Met Glu Ala Thr Gly Val Arg Leu Asp
160                 165                 170                 175 gtg gcc tat ctc agg gcc ttg tcc ctg gag gtg gcc gag gag atc gcc      575
Val Ala Tyr Leu Arg Ala Leu Ser Leu Glu Val Ala Glu Glu Ile Ala
                180                 185                 190 cgc ctc gag gcc gag gtc ttc cgc ctg gcc ggc cac ccc ttc aac ctc      623
Arg Leu Glu Ala Glu Val Phe Arg Leu Ala Gly His Pro Phe Asn Leu
            195                 200                 205 aac tcc cgg gac cag ctg gaa agg gtc ctc ttt gac gag cta ggg ctt      671
Asn Ser Arg Asp Gln Leu Glu Arg Val Leu Phe Asp Glu Leu Gly Leu
        210                 215                 220 ccc gcc atc ggc aag acg gag aag acc ggc aag cgc tcc acc agc gcc      719
Pro Ala Ile Gly Lys Thr Glu Lys Thr Gly Lys Arg Ser Thr Ser Ala
    225                 230                 235 gtc gtc ctg gag gcc ctc cgc gag gcc cac ccc atc gtg gag aag atc      767
Val Val Leu Glu Ala Leu Arg Glu Ala His Pro Ile Val Glu Lys Ile
240                 245                 250                 255 ctg cag tac cgg gag ctc acc aag ctg aag agc acc tac att gac ccc      815
Leu Gln Tyr Arg Glu Leu Thr Lys Leu Lys Ser Thr Tyr Ile Asp Pro
                260                 265                 270 ttg ccg gac ctc atc cac ccc agg acg ggc cgc ctc cac acc cgc ttc      863
Leu Pro Asp Leu Ile His Pro Arg Thr Gly Arg Leu His Thr Arg Phe
            275                 280                 285 aac cag acg gcc acg gcc acg ggc agg cta agt agc tcc gat ccc aac      911
Asn Gln Thr Ala Thr Ala Thr Gly Arg Leu Ser Ser Ser Asp Pro Asn
        290                 295                 300 ctc cag aac atc ccc gtc cgc acc ccg ctt ggg cag agg atc cgc cgg      959
Leu Gln Asn Ile Pro Val Arg Thr Pro Leu Gly Gln Arg Ile Arg Arg
    305                 310                 315 gcc ttc atc gcc gag gag ggg tgg cta ttg gtg gcc ctg gac tat agc     1007
Ala Phe Ile Ala Glu Glu Gly Trp Leu Leu Val Ala Leu Asp Tyr Ser
320                 325                 330                 335 cag ata gag ctc agg gtg ctg gcc cac ctc tcc ggc gac gag aac ctg     1055
Gln Ile Glu Leu Arg Val Leu Ala His Leu Ser Gly Asp Glu Asn Leu
```

```
Gln Ile Glu Leu Arg Val Leu Ala His Leu Ser Gly Asp Glu Asn Leu
                340                 345                 350 atc cgg gtc ttc cag gag ggg cgg gac atc cac acg gag acc gcc agc      1103
Ile Arg Val Phe Gln Glu Gly Arg Asp Ile His Thr Glu Thr Ala Ser
            355                 360                 365 tgg atg ttc ggc gtc ccc cgg gag gcc gtg gac ccc ctg atg cgc cgg      1151
Trp Met Phe Gly Val Pro Arg Glu Ala Val Asp Pro Leu Met Arg Arg
        370                 375                 380 gcg gcc aag agc atc aac ttc ggg gtc ctc tac ggc atg tcg gcc cac      1199
Ala Ala Lys Ser Ile Asn Phe Gly Val Leu Tyr Gly Met Ser Ala His
    385                 390                 395 cgc ctc tcc cag gag cta gcc atc cct tac gag gag gcc cag gcc ttc      1247
Arg Leu Ser Gln Glu Leu Ala Ile Pro Tyr Glu Glu Ala Gln Ala Phe
400                 405                 410                 415 att gag cgc tac ttt cag agc ttc ccc aag gtg cgg gcc tgg att gag      1295
Ile Glu Arg Tyr Phe Gln Ser Phe Pro Lys Val Arg Ala Trp Ile Glu
                420                 425                 430 aag acc ctg gag gag ggc agg agg cgg ggg tac gtg gag acc ctc ttc      1343
Lys Thr Leu Glu Glu Gly Arg Arg Arg Gly Tyr Val Glu Thr Leu Phe
            435                 440                 445 ggc cgc cgc cgc tac gtg cca gac cta gag gcc cgg gtg aag agc gtg      1391
Gly Arg Arg Arg Tyr Val Pro Asp Leu Glu Ala Arg Val Lys Ser Val
        450                 455                 460 cgg gag gcg gcc gag cgc atg gcc ttc aac atg ccc gtc cag ggc acc      1439
Arg Glu Ala Ala Glu Arg Met Ala Phe Asn Met Pro Val Gln Gly Thr
    465                 470                 475 gcc gcc gac ctc atg aag ctg gct atg gtg aag ctc tcc ccc agg ctg      1487
Ala Ala Asp Leu Met Lys Leu Ala Met Val Lys Leu Ser Pro Arg Leu
480                 485                 490                 495 gag gaa atg ggg gcc agg atg ctc ctt cag gtc cac gac gag ctg gtc      1535
Glu Glu Met Gly Ala Arg Met Leu Leu Gln Val His Asp Glu Leu Val
                500                 505                 510 ctc gag gcc cca aaa gag ggg gcg gag gcc gtg gcc cgg ctg gcc aag      1583
Leu Glu Ala Pro Lys Glu Gly Ala Glu Ala Val Ala Arg Leu Ala Lys
            515                 520                 525 gag gtc atg gag ggg gtg tat ccc ctg gcc gtg ccc ctg gag gtg gag      1631
Glu Val Met Glu Gly Val Tyr Pro Leu Ala Val Pro Leu Glu Val Glu
        530                 535                 540 gtg ggg ata ggg gag gac cgg ctc tcc gcc aag gag gcg gcc gca ctg      1679
Val Gly Ile Gly Glu Asp Arg Leu Ser Ala Lys Glu Ala Ala Ala Leu
    545                 550                 555 gtg ccg cgc                                                          1688
Val Pro Arg
560

<210> SEQ ID NO 28
<211> LENGTH: 562
<212> TYPE: PRT
<213> ORGANISM: Thermus aquaticus

<400> SEQUENCE: 28

Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu Ala
            35                  40                  45

Ala Ala Arg Gly Gly Arg Val His Arg Ala Pro Glu Pro Tyr Lys Ala
        50                  55                  60
```

-continued

Leu Arg Asp Leu Lys Glu Ala Arg Gly Leu Leu Ala Lys Asp Leu Ser
 65                  70                  75                  80

Val Leu Ala Leu Arg Glu Gly Leu Gly Leu Pro Pro Gly Asp Asp Pro
                 85                  90                  95

Met Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
        130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205

Ser Arg Asp Gln Leu Glu Arg Val Leu Phe Asp Glu Leu Gly Leu Pro
210                 215                 220

Ala Ile Gly Lys Thr Glu Lys Thr Gly Lys Arg Ser Thr Ser Ala Val
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Pro Asp Leu Ile His Pro Arg Thr Gly Arg Leu His Thr Arg Phe Asn
        275                 280                 285

Gln Thr Ala Thr Ala Thr Gly Arg Leu Ser Ser Ser Asp Pro Asn Leu
        290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
        355                 360                 365

Met Phe Gly Val Pro Arg Glu Ala Val Asp Pro Leu Met Arg Arg Ala
        370                 375                 380

Ala Lys Ser Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Val Arg
        450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Ser Pro Arg Leu Glu

```
                     485                 490                 495
Glu Met Gly Ala Arg Met Leu Leu Gln Val His Asp Glu Leu Val Leu
            500                 505                 510

Glu Ala Pro Lys Glu Gly Ala Glu Ala Val Ala Arg Leu Ala Lys Glu
            515                 520                 525

Val Met Glu Gly Val Tyr Pro Leu Ala Val Pro Leu Glu Val Glu Val
            530                 535                 540

Gly Ile Gly Glu Asp Arg Leu Ser Ala Lys Glu Ala Ala Leu Val
545                 550                 555                 560

Pro Arg

<210> SEQ ID NO 29
<211> LENGTH: 1688
<212> TYPE: DNA
<213> ORGANISM: Thermus aquaticus
<220> FEATURE:
<221> NAME/KEY: CDS
<222> LOCATION: (3)..(1688)

<400> SEQUENCE: 29
```

| | | | | | | | | | | | | | | | | |
|---|---|---|---|---|---|---|---|---|---|---|---|---|---|---|---|---|
| cc | atg | gcc | tct | ggt | ggc | ggt | ggc | tgt | ggt | ggc | ggt | ggc | agc | ccc | aag | 47 |
| | Met | Ala | Ser | Gly | Gly | Gly | Gly | Cys | Gly | Gly | Gly | Gly | Ser | Pro | Lys | |
| | 1 | | | 5 | | | | | 10 | | | | | 15 | | |
| gcc | ctg | gag | gag | gcc | ccc | tgg | ccc | ccg | ccg | gaa | ggg | gcc | ttc | gtg | ggc | 95 |
| Ala | Leu | Glu | Glu | Ala | Pro | Trp | Pro | Pro | Pro | Glu | Gly | Ala | Phe | Val | Gly | |
| | | | 20 | | | | | 25 | | | | | 30 | | | |
| ttt | gtg | ctt | tcc | cgc | aag | gag | ccc | atg | tgg | gcc | gat | ctt | ctg | gcc | ctg | 143 |
| Phe | Val | Leu | Ser | Arg | Lys | Glu | Pro | Met | Trp | Ala | Asp | Leu | Leu | Ala | Leu | |
| | | | 35 | | | | | 40 | | | | | 45 | | | |
| gcc | gcc | gcc | agg | ggg | ggc | cgg | gtc | cac | cgg | gcc | ccc | gag | cct | tat | aaa | 191 |
| Ala | Ala | Ala | Arg | Gly | Gly | Arg | Val | His | Arg | Ala | Pro | Glu | Pro | Tyr | Lys | |
| | | 50 | | | | | 55 | | | | | 60 | | | | |
| gcc | ctc | agg | gac | ctg | aag | gag | gcg | cgg | ggg | ctt | ctc | gcc | aaa | gac | ctg | 239 |
| Ala | Leu | Arg | Asp | Leu | Lys | Glu | Ala | Arg | Gly | Leu | Leu | Ala | Lys | Asp | Leu | |
| | 65 | | | | | 70 | | | | | 75 | | | | | |
| agc | gtt | ctg | gcc | ctg | agg | gaa | ggc | ctt | ggc | ctc | ccg | ccc | ggc | gac | gac | 287 |
| Ser | Val | Leu | Ala | Leu | Arg | Glu | Gly | Leu | Gly | Leu | Pro | Pro | Gly | Asp | Asp | |
| 80 | | | | | 85 | | | | | 90 | | | | | 95 | |
| ccc | atg | ctc | ctc | gcc | tac | ctc | ctg | gac | cct | tcc | aac | acc | acc | ccc | gag | 335 |
| Pro | Met | Leu | Leu | Ala | Tyr | Leu | Leu | Asp | Pro | Ser | Asn | Thr | Thr | Pro | Glu | |
| | | | 100 | | | | | 105 | | | | | 110 | | | |
| ggg | gtg | gcc | cgg | cgc | tac | ggc | ggg | gag | tgg | acg | gag | gag | gcg | ggg | gag | 383 |
| Gly | Val | Ala | Arg | Arg | Tyr | Gly | Gly | Glu | Trp | Thr | Glu | Glu | Ala | Gly | Glu | |
| | | | 115 | | | | | 120 | | | | | 125 | | | |
| cgg | gcc | gcc | ctt | tcc | gag | agg | ctc | ttc | gcc | aac | ctg | tgg | ggg | agg | ctt | 431 |
| Arg | Ala | Ala | Leu | Ser | Glu | Arg | Leu | Phe | Ala | Asn | Leu | Trp | Gly | Arg | Leu | |
| | | 130 | | | | | 135 | | | | | 140 | | | | |
| gag | ggg | gag | gag | agg | ctc | ctt | tgg | ctt | tac | cgg | gag | gtg | gag | agg | ccc | 479 |
| Glu | Gly | Glu | Glu | Arg | Leu | Leu | Trp | Leu | Tyr | Arg | Glu | Val | Glu | Arg | Pro | |
| | 145 | | | | | 150 | | | | | 155 | | | | | |
| ctt | tcc | gct | gtc | ctg | gcc | cac | atg | gag | gcc | acg | ggg | gtg | cgc | ctg | gac | 527 |
| Leu | Ser | Ala | Val | Leu | Ala | His | Met | Glu | Ala | Thr | Gly | Val | Arg | Leu | Asp | |
| 160 | | | | | 165 | | | | | 170 | | | | | 175 | |
| gtg | gcc | tat | ctc | agg | gcc | ttg | tcc | ctg | gag | gtg | gcc | gag | gag | atc | gcc | 575 |
| Val | Ala | Tyr | Leu | Arg | Ala | Leu | Ser | Leu | Glu | Val | Ala | Glu | Glu | Ile | Ala | |
| | | | 180 | | | | | 185 | | | | | 190 | | | |
| cgc | ctc | gag | gcc | gag | gtc | ttc | cgc | ctg | gcc | ggc | cac | ccc | ttc | aac | ctc | 623 |
| Arg | Leu | Glu | Ala | Glu | Val | Phe | Arg | Leu | Ala | Gly | His | Pro | Phe | Asn | Leu | |
| | | | 195 | | | | | 200 | | | | | 205 | | | |

```
aac tcc cgg gac cag ctg gaa agg gtc ctc ttt gac gag cta ggg ctt       671
Asn Ser Arg Asp Gln Leu Glu Arg Val Leu Phe Asp Glu Leu Gly Leu
            210                 215                 220 ccc gcc atc ggc aag acg gag aag acc ggc aag cgc tcc acc agc gcc       719
Pro Ala Ile Gly Lys Thr Glu Lys Thr Gly Lys Arg Ser Thr Ser Ala
225                 230                 235 gcc gtc ctg gag gcc ctc cgc gag gcc cac ccc atc gtg gag aag atc       767
Ala Val Leu Glu Ala Leu Arg Glu Ala His Pro Ile Val Glu Lys Ile
240                 245                 250                 255 ctg cag tac cgg gag ctc acc aag ctg aag agc acc tac att gac ccc       815
Leu Gln Tyr Arg Glu Leu Thr Lys Leu Lys Ser Thr Tyr Ile Asp Pro
            260                 265                 270 ttg ccg gac ctc atc cac ccc agg acg ggc cgc ctc cac acc cgc ttc       863
Leu Pro Asp Leu Ile His Pro Arg Thr Gly Arg Leu His Thr Arg Phe
                275                 280                 285 aac cag acg gtc acg gcc acg ggc agg cta agt agc tcc gat ccc aac       911
Asn Gln Thr Val Thr Ala Thr Gly Arg Leu Ser Ser Ser Asp Pro Asn
            290                 295                 300 ctc cag aac atc ccc gtc cgc acc ccg ctt ggg cag agg atc cgc cgg       959
Leu Gln Asn Ile Pro Val Arg Thr Pro Leu Gly Gln Arg Ile Arg Arg
305                 310                 315 gcc ttc atc gcc gag gag ggg tgg cta ttg gtg gcc ctg gac tat agc      1007
Ala Phe Ile Ala Glu Glu Gly Trp Leu Leu Val Ala Leu Asp Tyr Ser
320                 325                 330                 335 cag ata gag ctc agg gtg ctg gcc cac ctc tcc ggc gac gag aac ctg      1055
Gln Ile Glu Leu Arg Val Leu Ala His Leu Ser Gly Asp Glu Asn Leu
            340                 345                 350 atc cgg gtc ttc cag gag ggg cgg gac atc cac acg gag acc gcc agc      1103
Ile Arg Val Phe Gln Glu Gly Arg Asp Ile His Thr Glu Thr Ala Ser
                355                 360                 365 tgg atg ttc ggc gtc ccc cgg gag gcc gtg gac ccc ctg atg cgc cgg      1151
Trp Met Phe Gly Val Pro Arg Glu Ala Val Asp Pro Leu Met Arg Arg
            370                 375                 380 gcg gcc aag acc atc aac ttc ggg gtc ctc tac ggc atg tcg gcc cac      1199
Ala Ala Lys Thr Ile Asn Phe Gly Val Leu Tyr Gly Met Ser Ala His
385                 390                 395 cgc ctc tcc cag gag cta gcc atc cct tac gag gag gcc cag gcc ttc      1247
Arg Leu Ser Gln Glu Leu Ala Ile Pro Tyr Glu Glu Ala Gln Ala Phe
400                 405                 410                 415 att gag cgc tac ttt cag agc ttc ccc aag gtg cgg gcc tgg att gag      1295
Ile Glu Arg Tyr Phe Gln Ser Phe Pro Lys Val Arg Ala Trp Ile Glu
            420                 425                 430 aag acc ctg gag gag ggc agg agg cgg ggg tac gtg gag acc ctc ttc      1343
Lys Thr Leu Glu Glu Gly Arg Arg Arg Gly Tyr Val Glu Thr Leu Phe
                435                 440                 445 ggc cgc cgc cgc tac gtg cca gac cta gag gcc cgg gtg aag agc gtg      1391
Gly Arg Arg Arg Tyr Val Pro Asp Leu Glu Ala Arg Val Lys Ser Val
            450                 455                 460 cgg gag gcg gcc gag cgc atg gcc tac aac atg ccc gtc cag ggc acc      1439
Arg Glu Ala Ala Glu Arg Met Ala Tyr Asn Met Pro Val Gln Gly Thr
465                 470                 475 gcc gcc gac ctc atg aag ctg gct atg gtg aag ctc ttc ccc agg ctg      1487
Ala Ala Asp Leu Met Lys Leu Ala Met Val Lys Leu Phe Pro Arg Leu
480                 485                 490                 495 gag gaa atg ggg gcc agg atg ctc ctt cag gtc cac gac gag ctg gtc      1535
Glu Glu Met Gly Ala Arg Met Leu Leu Gln Val His Asp Glu Leu Val
            500                 505                 510 ctc gag gcc cca aaa gag ggg gcg gag gcc gtg gcc cgg ctg gcc aag      1583
Leu Glu Ala Pro Lys Glu Gly Ala Glu Ala Val Ala Arg Leu Ala Lys
                515                 520                 525
```

```
gag gtc atg gag ggg gtg tat ccc ctg gcc gtg ccc ctg gag gtg gag    1631
Glu Val Met Glu Gly Val Tyr Pro Leu Ala Val Pro Leu Glu Val Glu
        530                 535                 540 gtg ggg ata ggg gag gac tgg ctc tcc gcc aag gag gcg gcc gca ctg    1679
Val Gly Ile Gly Glu Asp Trp Leu Ser Ala Lys Glu Ala Ala Ala Leu
545                 550                 555 gtg ccg cgc                                                        1688
Val Pro Arg
560
```

<210> SEQ ID NO 30
<211> LENGTH: 562
<212> TYPE: PRT
<213> ORGANISM: Thermus aquaticus

<400> SEQUENCE: 30

```
Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu
            35                  40                  45

Ala Ala Arg Gly Gly Arg Val His Arg Ala Pro Glu Pro Tyr Lys Ala
        50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
        115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205

Ser Arg Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Pro Asp Leu Ile His Pro Arg Thr Gly Arg Leu His Thr Arg Phe Asn
        275                 280                 285

Gln Thr Val Thr Ala Thr Gly Arg Leu Ser Ser Ser Asp Pro Asn Leu
    290                 295                 300

Gln Asn Ile Pro Val Arg Thr Pro Leu Gly Gln Arg Ile Arg Arg Ala
```

-continued

```
                305                 310                 315                 320
        Phe Ile Ala Glu Glu Gly Trp Leu Leu Val Ala Leu Asp Tyr Ser Gln
                        325                 330                 335

Ile Glu Leu Arg Val Leu Ala His Leu Ser Gly Asp Glu Asn Leu Ile
                        340                 345                 350

Arg Val Phe Gln Glu Gly Arg Asp Ile His Thr Glu Thr Ala Ser Trp
                        355                 360                 365

Met Phe Gly Val Pro Arg Glu Ala Val Asp Pro Leu Met Arg Arg Ala
                        370                 375                 380

Ala Lys Thr Ile Asn Phe Gly Val Leu Tyr Gly Met Ser Ala His Arg
        385                 390                 395                 400

Leu Ser Gln Glu Leu Ala Ile Pro Tyr Glu Glu Ala Gln Ala Phe Ile
                        405                 410                 415

Glu Arg Tyr Phe Gln Ser Phe Pro Lys Val Arg Ala Trp Ile Glu Lys
                        420                 425                 430

Thr Leu Glu Glu Gly Arg Arg Gly Tyr Val Glu Thr Leu Phe Gly
                        435                 440                 445

Arg Arg Arg Tyr Val Pro Asp Leu Glu Ala Arg Val Lys Ser Val Arg
        450                 455                 460

Glu Ala Ala Glu Arg Met Ala Tyr Asn Met Pro Val Gln Gly Thr Ala
        465                 470                 475                 480

Ala Asp Leu Met Lys Leu Ala Met Val Lys Leu Phe Pro Arg Leu Glu
                        485                 490                 495

Glu Met Gly Ala Arg Met Leu Leu Gln Val His Asp Glu Leu Val Leu
                        500                 505                 510

Glu Ala Pro Lys Glu Gly Ala Glu Ala Val Ala Arg Leu Ala Lys Glu
                        515                 520                 525

Val Met Glu Gly Val Tyr Pro Leu Ala Val Pro Leu Glu Val Glu Val
                        530                 535                 540

Gly Ile Gly Glu Asp Trp Leu Ser Ala Lys Glu Ala Ala Ala Leu Val
        545                 550                 555                 560

Pro Arg

<210> SEQ ID NO 31
<211> LENGTH: 1688
<212> TYPE: DNA
<213> ORGANISM: Thermus aquaticus
<220> FEATURE:
<221> NAME/KEY: CDS
<222> LOCATION: (3)..(1688)

<400> SEQUENCE: 31 cc atg gcc tct ggt ggc ggt ggc tgt ggt ggc ggt ggc agc ccc aag         47
   Met Ala Ser Gly Gly Gly Gly Cys Gly Gly Gly Gly Ser Pro Lys
   1               5                   10                  15 gcc ctg gag gag gcc ccc tgg ccc ccg ccg gaa ggg gcc ttc gtg ggc        95
Ala Leu Glu Glu Ala Pro Trp Pro Pro Pro Glu Gly Ala Phe Val Gly
                20                  25                  30 ttt gtg ctt tcc cgc aag gag ccc atg tgg gcc gat ctt ctg gcc ctg       143
Phe Val Leu Ser Arg Lys Glu Pro Met Trp Ala Asp Leu Leu Ala Leu
            35                  40                  45 gcc gcc gcc agg ggg ggc cgg gtc cac cgg gcc ccc gag cct tat aaa       191
Ala Ala Ala Arg Gly Gly Arg Val His Arg Ala Pro Glu Pro Tyr Lys
        50                  55                  60 gcc ctc agg gac ctg aag gag gcg cgg ggg ctt ctc gcc aaa gac ctg       239
Ala Leu Arg Asp Leu Lys Glu Ala Arg Gly Leu Leu Ala Lys Asp Leu
    65                  70                  75
```

-continued

| | |
|---|---|
| agc gtt ctg gcc ctg agg gaa ggc ctt ggc ctc ccg ccc ggc gac gac<br>Ser Val Leu Ala Leu Arg Glu Gly Leu Gly Leu Pro Pro Gly Asp Asp<br>80                     85                     90                    95 | 287 |
| ccc atg ctc ctc gcc tac ctc ctg gac cct tcc aac acc acc ccc gag<br>Pro Met Leu Leu Ala Tyr Leu Leu Asp Pro Ser Asn Thr Thr Pro Glu<br>                     100                     105                     110 | 335 |
| ggg gtg gcc cgg cgc tac ggc ggg gag tgg acg gag gag gcg ggg gag<br>Gly Val Ala Arg Arg Tyr Gly Gly Glu Trp Thr Glu Glu Ala Gly Glu<br>               115                     120                     125 | 383 |
| cgg gcc gcc ctt tcc gag agg ctc ttc gcc aac ctg tgg ggg agg ctt<br>Arg Ala Ala Leu Ser Glu Arg Leu Phe Ala Asn Leu Trp Gly Arg Leu<br>130                     135                     140 | 431 |
| gag ggg gag gag agg ctc ctt tgg ctt tac cgg gag gtg gag agg ccc<br>Glu Gly Glu Glu Arg Leu Leu Trp Leu Tyr Arg Glu Val Glu Arg Pro<br>145                     150                     155 | 479 |
| ctt tcc gct gtc ctg gcc cac atg gag gcc acg ggg gtg cgc ctg gac<br>Leu Ser Ala Val Leu Ala His Met Glu Ala Thr Gly Val Arg Leu Asp<br>160                     165                     170                     175 | 527 |
| gtg gcc tat ctc agg gcc ttg tcc ctg gag gtg gcc gag gag atc gcc<br>Val Ala Tyr Leu Arg Ala Leu Ser Leu Glu Val Ala Glu Glu Ile Ala<br>                     180                     185                     190 | 575 |
| cgc ctc gag gcc gag gtc ttc cgc ctg gcc ggc cac ccc ttc aac ctc<br>Arg Leu Glu Ala Glu Val Phe Arg Leu Ala Gly His Pro Phe Asn Leu<br>               195                     200                     205 | 623 |
| aac tcc cgg gac cag ctg gaa agg gtc ctc ttt gac gag cta ggg ctt<br>Asn Ser Arg Asp Gln Leu Glu Arg Val Leu Phe Asp Glu Leu Gly Leu<br>210                     215                     220 | 671 |
| ccc gcc atc ggc aag acg gag aag acc ggc aag cgc tcc acc agc gcc<br>Pro Ala Ile Gly Lys Thr Glu Lys Thr Gly Lys Arg Ser Thr Ser Ala<br>225                     230                     235 | 719 |
| gcc gtc ctg gag gcc ctc cgc gag gcc cac ccc atc gtg gag aag atc<br>Ala Val Leu Glu Ala Leu Arg Glu Ala His Pro Ile Val Glu Lys Ile<br>240                     245                     250                     255 | 767 |
| ctg cag tac cgg gag ctc acc aag ctg aag agc acc tac att gac ccc<br>Leu Gln Tyr Arg Glu Leu Thr Lys Leu Lys Ser Thr Tyr Ile Asp Pro<br>                     260                     265                     270 | 815 |
| ttg ccg gac ctc atc cac ccc agg acg ggc cgc ctc cac acc cgc ttc<br>Leu Pro Asp Leu Ile His Pro Arg Thr Gly Arg Leu His Thr Arg Phe<br>               275                     280                     285 | 863 |
| aac cag acg gcc acg gcc acg ggc agg cta agt agc tcc gat ccc aac<br>Asn Gln Thr Ala Thr Ala Thr Gly Arg Leu Ser Ser Ser Asp Pro Asn<br>290                     295                     300 | 911 |
| ctc cag aac atc ccc gtc cgc acc ccg ctt ggg cag agg atc cgc cgg<br>Leu Gln Asn Ile Pro Val Arg Thr Pro Leu Gly Gln Arg Ile Arg Arg<br>305                     310                     315 | 959 |
| gcc ttc atc gcc gag gag ggg tgg cta ttg gtg gcc ctg gac tat agc<br>Ala Phe Ile Ala Glu Glu Gly Trp Leu Leu Val Ala Leu Asp Tyr Ser<br>320                     325                     330                     335 | 1007 |
| cag ata gag ctc agg gtg ctg gcc cac ctc tcc ggc gac gag aac ctg<br>Gln Ile Glu Leu Arg Val Leu Ala His Leu Ser Gly Asp Glu Asn Leu<br>                     340                     345                     350 | 1055 |
| atc cgg gtc ttc cag gag ggg cgg gac atc cac acg gag acc gcc agc<br>Ile Arg Val Phe Gln Glu Gly Arg Asp Ile His Thr Glu Thr Ala Ser<br>               355                     360                     365 | 1103 |
| tgg atg ttc ggc gtc ccc cgg gag gcc gtg gac ccc ctg atg cgc cgg<br>Trp Met Phe Gly Val Pro Arg Glu Ala Val Asp Pro Leu Met Arg Arg<br>                     370                     375                     380 | 1151 |
| gcg gcc aag acc atc aac ttc ggg gtc ctc tac ggc atg tcg gcc cac<br>Ala Ala Lys Thr Ile Asn Phe Gly Val Leu Tyr Gly Met Ser Ala His | 1199 |

```
                    385                 390                 395
cgc ctc tcc cag gag cta gcc atc cct tac gag gag gcc cag gcc ttc    1247
Arg Leu Ser Gln Glu Leu Ala Ile Pro Tyr Glu Glu Ala Gln Ala Phe
400                 405                 410                 415 att gag cgc tac ttt cag agc ttc ccc aag gtg cgg gcc tgg att gag    1295
Ile Glu Arg Tyr Phe Gln Ser Phe Pro Lys Val Arg Ala Trp Ile Glu
                420                 425                 430 aag acc ctg gag gag ggc agg agg cgg ggg tac gtg gag acc ctc ttc    1343
Lys Thr Leu Glu Glu Gly Arg Arg Arg Gly Tyr Val Glu Thr Leu Phe
            435                 440                 445 ggc cgc cgc cgc tac gtg cca gac cta gag gcc cgg gtg aag agc gtg    1391
Gly Arg Arg Arg Tyr Val Pro Asp Leu Glu Ala Arg Val Lys Ser Val
450                 455                 460 cgg gag gcg gcc gag cgc atg gcc ttc aac atg ccc gtc cag ggc acc    1439
Arg Glu Ala Ala Glu Arg Met Ala Phe Asn Met Pro Val Gln Gly Thr
465                 470                 475 gcc gcc gac ctc atg aag ctg gct atg gtg aag ctc ttc ccc agg ctg    1487
Ala Ala Asp Leu Met Lys Leu Ala Met Val Lys Leu Phe Pro Arg Leu
480                 485                 490                 495 gag gaa atg ggg gcc agg atg ctc ctt cag gtc cac gac gag ctg gtc    1535
Glu Glu Met Gly Ala Arg Met Leu Leu Gln Val His Asp Glu Leu Val
                500                 505                 510 ctc gag gcc cca aaa gag ggg gcg gag gcc gtg gcc cgg ctg gcc aag    1583
Leu Glu Ala Pro Lys Glu Gly Ala Glu Ala Val Ala Arg Leu Ala Lys
            515                 520                 525 gag gtc atg gag ggg gtg tat ccc ctg gcc gtg ccc ctg gag gtg gag    1631
Glu Val Met Glu Gly Val Tyr Pro Leu Ala Val Pro Leu Glu Val Glu
530                 535                 540 gtg ggg ata ggg gag gac cgg ctc tcc gcc aag gag gcg gcc gca ctg    1679
Val Gly Ile Gly Glu Asp Arg Leu Ser Ala Lys Glu Ala Ala Ala Leu
545                 550                 555 gtg ccg cgc                                                         1688
Val Pro Arg
560

<210> SEQ ID NO 32
<211> LENGTH: 562
<212> TYPE: PRT
<213> ORGANISM: Thermus aquaticus

<400> SEQUENCE: 32

Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu
            35                  40                  45

Ala Ala Arg Gly Gly Arg Val His Arg Ala Pro Glu Pro Tyr Lys Ala
50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Pro
            85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
```

```
            130                 135                 140
Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Ile Ala Arg
                180                 185                 190

Leu Glu Ala Glu Val Phe Arg Leu Ala Gly His Pro Phe Asn Leu Asn
                195                 200                 205

Ser Arg Asp Gln Leu Glu Arg Val Leu Phe Asp Glu Leu Gly Leu Pro
210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
                260                 265                 270

Pro Asp Leu Ile His Pro Arg Thr Gly Arg Leu His Thr Arg Phe Asn
                275                 280                 285

Gln Thr Ala Thr Ala Thr Gly Arg Leu Ser Ser Ser Asp Pro Asn Leu
                290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
                355                 360                 365

Met Phe Gly Val Pro Arg Glu Ala Val Asp Pro Leu Met Arg Arg Ala
                370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
                420                 425                 430

Thr Leu Glu Glu Gly Arg Arg Arg Gly Tyr Val Glu Thr Leu Phe Gly
                435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
                500                 505                 510

Glu Ala Pro Lys Glu Gly Ala Glu Ala Val Ala Arg Leu Ala Lys Glu
                515                 520                 525

Val Met Glu Gly Val Tyr Pro Leu Ala Val Pro Leu Glu Val Glu Val
                530                 535                 540

Gly Ile Gly Glu Asp Arg Leu Ser Ala Lys Glu Ala Ala Ala Leu Val
545                 550                 555                 560
```

Pro Arg

<210> SEQ ID NO 33
<211> LENGTH: 1688
<212> TYPE: DNA
<213> ORGANISM: Thermus aquaticus
<220> FEATURE:
<221> NAME/KEY: CDS
<222> LOCATION: (3)..(1688)

<400> SEQUENCE: 33

| | | | | | | | | | | | | | | | | |
|---|---|---|---|---|---|---|---|---|---|---|---|---|---|---|---|---|
| cc | atg | gcc | tct | ggt | ggc | ggt | ggc | tgt | ggt | ggc | ggt | ggc | agc | ccc | aag | 47 |
| | Met | Ala | Ser | Gly | Gly | Gly | Gly | Cys | Gly | Gly | Gly | Gly | Ser | Pro | Lys | |
| | 1 | | | 5 | | | | | 10 | | | | | 15 | | |

| gcc | ctg | gag | gag | gcc | ccc | tgg | ccc | ccg | ccg | gaa | ggg | gcc | ttc | gtg | ggc | 95 |
|---|---|---|---|---|---|---|---|---|---|---|---|---|---|---|---|---|
| Ala | Leu | Glu | Glu | Ala | Pro | Trp | Pro | Pro | Pro | Glu | Gly | Ala | Phe | Val | Gly | |
| | | | 20 | | | | | 25 | | | | | 30 | | | |

| ttt | gtg | ctt | tcc | cgc | aag | gag | ccc | atg | tgg | gcc | gat | ctt | ctg | gcc | ctg | 143 |
|---|---|---|---|---|---|---|---|---|---|---|---|---|---|---|---|---|
| Phe | Val | Leu | Ser | Arg | Lys | Glu | Pro | Met | Trp | Ala | Asp | Leu | Leu | Ala | Leu | |
| | | | 35 | | | | | 40 | | | | | 45 | | | |

| gcc | gcc | gcc | agg | ggg | ggc | cgg | gtc | cac | cgg | gcc | ccc | gag | cct | tat | aaa | 191 |
|---|---|---|---|---|---|---|---|---|---|---|---|---|---|---|---|---|
| Ala | Ala | Ala | Arg | Gly | Gly | Arg | Val | His | Arg | Ala | Pro | Glu | Pro | Tyr | Lys | |
| | | 50 | | | | | 55 | | | | | 60 | | | | |

| gcc | ctc | agg | gac | ctg | aag | gag | gcg | cgg | ggg | ctt | ctc | gcc | aaa | gac | ctg | 239 |
|---|---|---|---|---|---|---|---|---|---|---|---|---|---|---|---|---|
| Ala | Leu | Arg | Asp | Leu | Lys | Glu | Ala | Arg | Gly | Leu | Leu | Ala | Lys | Asp | Leu | |
| | 65 | | | | | 70 | | | | | 75 | | | | | |

| agc | gtt | ctg | gcc | ctg | agg | gaa | ggc | ctt | ggc | ctc | ccg | ccc | ggc | gac | gac | 287 |
|---|---|---|---|---|---|---|---|---|---|---|---|---|---|---|---|---|
| Ser | Val | Leu | Ala | Leu | Arg | Glu | Gly | Leu | Gly | Leu | Pro | Pro | Gly | Asp | Asp | |
| 80 | | | | | 85 | | | | | 90 | | | | | 95 | |

| ccc | atg | ctc | ctc | gcc | tac | ctc | ctg | gac | cct | tcc | aac | acc | acc | ccc | gag | 335 |
|---|---|---|---|---|---|---|---|---|---|---|---|---|---|---|---|---|
| Pro | Met | Leu | Leu | Ala | Tyr | Leu | Leu | Asp | Pro | Ser | Asn | Thr | Thr | Pro | Glu | |
| | | | 100 | | | | | 105 | | | | | 110 | | | |

| ggg | gtg | gcc | cgg | cgc | tac | ggc | ggg | gag | tgg | acg | gag | gag | gcg | ggg | gag | 383 |
|---|---|---|---|---|---|---|---|---|---|---|---|---|---|---|---|---|
| Gly | Val | Ala | Arg | Arg | Tyr | Gly | Gly | Glu | Trp | Thr | Glu | Glu | Ala | Gly | Glu | |
| | | | 115 | | | | | 120 | | | | | 125 | | | |

| cgg | gcc | gcc | ctt | tcc | gag | agg | ctc | ttc | gcc | aac | ctg | tgg | ggg | agg | ctt | 431 |
|---|---|---|---|---|---|---|---|---|---|---|---|---|---|---|---|---|
| Arg | Ala | Ala | Leu | Ser | Glu | Arg | Leu | Phe | Ala | Asn | Leu | Trp | Gly | Arg | Leu | |
| | | 130 | | | | | 135 | | | | | 140 | | | | |

| gag | ggg | gag | gag | agg | ctc | ctt | tgg | ctt | tac | cgg | gag | gtg | gag | agg | ccc | 479 |
|---|---|---|---|---|---|---|---|---|---|---|---|---|---|---|---|---|
| Glu | Gly | Glu | Glu | Arg | Leu | Leu | Trp | Leu | Tyr | Arg | Glu | Val | Glu | Arg | Pro | |
| | 145 | | | | | 150 | | | | | 155 | | | | | |

| ctt | tcc | gct | gtc | ctg | gcc | cac | atg | gag | gcc | acg | ggg | gtg | cgc | ctg | gac | 527 |
|---|---|---|---|---|---|---|---|---|---|---|---|---|---|---|---|---|
| Leu | Ser | Ala | Val | Leu | Ala | His | Met | Glu | Ala | Thr | Gly | Val | Arg | Leu | Asp | |
| 160 | | | | | 165 | | | | | 170 | | | | | 175 | |

| gtg | gcc | tat | ctc | agg | gcc | ttg | tcc | ctg | gag | gtg | gcc | gag | gag | atc | gcc | 575 |
|---|---|---|---|---|---|---|---|---|---|---|---|---|---|---|---|---|
| Val | Ala | Tyr | Leu | Arg | Ala | Leu | Ser | Leu | Glu | Val | Ala | Glu | Glu | Ile | Ala | |
| | | | 180 | | | | | 185 | | | | | 190 | | | |

| cgc | ctc | gag | gcc | gag | gtc | ttc | cgc | ctg | gcc | ggc | cac | ccc | ttc | aac | ctc | 623 |
|---|---|---|---|---|---|---|---|---|---|---|---|---|---|---|---|---|
| Arg | Leu | Glu | Ala | Glu | Val | Phe | Arg | Leu | Ala | Gly | His | Pro | Phe | Asn | Leu | |
| | | | 195 | | | | | 200 | | | | | 205 | | | |

| aac | tcc | cgg | gac | cag | ctg | gaa | agg | gtc | ctc | ttt | gac | gag | cta | ggg | ctt | 671 |
|---|---|---|---|---|---|---|---|---|---|---|---|---|---|---|---|---|
| Asn | Ser | Arg | Asp | Gln | Leu | Glu | Arg | Val | Leu | Phe | Asp | Glu | Leu | Gly | Leu | |
| | | 210 | | | | | 215 | | | | | 220 | | | | |

| ccc | gcc | atc | ggc | aag | acg | gag | aag | acc | ggc | aag | cgc | tcc | acc | agc | gcc | 719 |
|---|---|---|---|---|---|---|---|---|---|---|---|---|---|---|---|---|
| Pro | Ala | Ile | Gly | Lys | Thr | Glu | Lys | Thr | Gly | Lys | Arg | Ser | Thr | Ser | Ala | |
| | 225 | | | | | 230 | | | | | 235 | | | | | |

| gcc | gtc | ctg | gag | gcc | ctc | cgc | gag | gcc | cac | ccc | atc | gtg | gag | aag | atc | 767 |
|---|---|---|---|---|---|---|---|---|---|---|---|---|---|---|---|---|
| Ala | Val | Leu | Glu | Ala | Leu | Arg | Glu | Ala | His | Pro | Ile | Val | Glu | Lys | Ile | |
| 240 | | | | | 245 | | | | | 250 | | | | | 255 | |

| ctg | cag | tac | cgg | gag | ctc | acc | aag | ctg | aag | agc | acc | tac | att | gac | ccc | 815 |
|---|---|---|---|---|---|---|---|---|---|---|---|---|---|---|---|---|

```
Leu Gln Tyr Arg Glu Leu Thr Lys Leu Lys Ser Thr Tyr Ile Asp Pro
                260                 265                 270 ttg ccg gac ctc atc cac ccc agg acg ggc cgc ctc cac acc cgc ttc       863
Leu Pro Asp Leu Ile His Pro Arg Thr Gly Arg Leu His Thr Arg Phe
            275                 280                 285 aac cag acg gcc acg gcc acg ggc agg cta agt agc tcc gat ccc aac       911
Asn Gln Thr Ala Thr Ala Thr Gly Arg Leu Ser Ser Ser Asp Pro Asn
        290                 295                 300 ctc cag aac atc ccc gtc cgc acc ccg ctt ggg cag agg atc cgc cgg       959
Leu Gln Asn Ile Pro Val Arg Thr Pro Leu Gly Gln Arg Ile Arg Arg
    305                 310                 315 gcc ttc atc gcc gag gag ggg tgg cta ttg gtg gcc ctg gac tat agc      1007
Ala Phe Ile Ala Glu Glu Gly Trp Leu Leu Val Ala Leu Asp Tyr Ser
320                 325                 330                 335 cag ata gag ctc agg gtg ctg gcc cac ctc tcc ggc gac gag aac ctg      1055
Gln Ile Glu Leu Arg Val Leu Ala His Leu Ser Gly Asp Glu Asn Leu
                340                 345                 350 atc cgg gtc ttc cag gag ggg cgg gac atc cac acg gag acc gcc agc      1103
Ile Arg Val Phe Gln Glu Gly Arg Asp Ile His Thr Glu Thr Ala Ser
            355                 360                 365 tgg atg ttc ggc gtc ccc cgg gag gcc gtg gac ccc ctg atg cgc cgg      1151
Trp Met Phe Gly Val Pro Arg Glu Ala Val Asp Pro Leu Met Arg Arg
        370                 375                 380 gcg gcc aag acc atc aac ttc ggg gtc ctc tac ggc atg tcg gcc cac      1199
Ala Ala Lys Thr Ile Asn Phe Gly Val Leu Tyr Gly Met Ser Ala His
    385                 390                 395 cgc ctc tcc cag gag cta gcc atc cct tac gag gag gcc cag gcc ttc      1247
Arg Leu Ser Gln Glu Leu Ala Ile Pro Tyr Glu Glu Ala Gln Ala Phe
400                 405                 410                 415 att gag cgc tac ttt ctg agc ttc ccc aag gtg cgg gcc tgg att gag      1295
Ile Glu Arg Tyr Phe Leu Ser Phe Pro Lys Val Arg Ala Trp Ile Glu
                420                 425                 430 aag acc ctg gag gag ggc agg agg cgg ggg tac gtg gag acc ctc ttc      1343
Lys Thr Leu Glu Glu Gly Arg Arg Arg Gly Tyr Val Glu Thr Leu Phe
            435                 440                 445 ggc cgc cgc cgc tac gtg cca gac cta gag gcc cgg gtg aag agc gtg      1391
Gly Arg Arg Arg Tyr Val Pro Asp Leu Glu Ala Arg Val Lys Ser Val
        450                 455                 460 cgg gag gcg gcc gag cgc aag gcc ttc aac atg ccc gtc cag ggc acc      1439
Arg Glu Ala Ala Glu Arg Lys Ala Phe Asn Met Pro Val Gln Gly Thr
    465                 470                 475 gcc gcc gac ctc atg aag ctg gct atg gtg aag ctc ttc ccc agg ctg      1487
Ala Ala Asp Leu Met Lys Leu Ala Met Val Lys Leu Phe Pro Arg Leu
480                 485                 490                 495 gag gaa atg ggg gcc agg atg ctc ctt cag gtc cac gac gag ctg gtc      1535
Glu Glu Met Gly Ala Arg Met Leu Leu Gln Val His Asp Glu Leu Val
                500                 505                 510 ctc gag gcc cca aaa gag ggg gcg gag gcc gtg gcc cgg ctg gcc aag      1583
Leu Glu Ala Pro Lys Glu Gly Ala Glu Ala Val Ala Arg Leu Ala Lys
            515                 520                 525 gag gtc atg gag ggg gtg tat ccc ctg gcc gtg ctc ctg gag gtg gag      1631
Glu Val Met Glu Gly Val Tyr Pro Leu Ala Val Leu Leu Glu Val Glu
        530                 535                 540 gtg ggg ata ggg gag gac tgg ctc tcc gcc aag gag gcg gcc gca ctg      1679
Val Gly Ile Gly Glu Asp Trp Leu Ser Ala Lys Glu Ala Ala Ala Leu
    545                 550                 555 gtg ccg cgc                                                           1688
Val Pro Arg
560
```

<210> SEQ ID NO 34
<211> LENGTH: 562
<212> TYPE: PRT
<213> ORGANISM: Thermus aquaticus

<400> SEQUENCE: 34

Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
            35                  40                      45

Ala Ala Arg Gly Gly Arg Val His Arg Ala Pro Glu Pro Tyr Lys Ala
        50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
        130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
                180                 185                 190

Leu Glu Ala Glu Val Phe Arg Leu Ala Gly His Pro Phe Asn Leu Asn
            195                 200                 205

Ser Arg Asp Gln Leu Glu Arg Val Leu Phe Asp Glu Leu Gly Leu Pro
        210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
                260                 265                 270

Pro Asp Leu Ile His Pro Arg Thr Gly Arg Leu His Thr Arg Phe Asn
            275                 280                 285

Gln Thr Ala Thr Ala Thr Gly Arg Leu Ser Ser Ser Asp Pro Asn Leu
        290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Arg Ala
        370                 375                 380

```
Ala Lys Thr Ile Asn Phe Gly Val Leu Tyr Gly Met Ser Ala His Arg
385                 390                 395                 400

Leu Ser Gln Glu Leu Ala Ile Pro Tyr Glu Ala Gln Ala Phe Ile
            405                 410                 415

Glu Arg Tyr Phe Leu Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
            435                 440                 445

Arg Arg Arg Tyr Val Pro Asp Leu Glu Ala Arg Val Lys Ser Val Arg
450                 455                 460

Glu Ala Ala Glu Arg Lys Ala Phe Asn Met Pro Val Gln Gly Thr Ala
465                 470                 475                 480

Ala Asp Leu Met Lys Leu Ala Met Val Lys Leu Phe Pro Arg Leu Glu
            485                 490                 495

Glu Met Gly Ala Arg Met Leu Leu Gln Val His Asp Glu Leu Val Leu
            500                 505                 510

Glu Ala Pro Lys Glu Gly Ala Glu Ala Val Ala Arg Leu Ala Lys Glu
            515                 520                 525

Val Met Glu Gly Val Tyr Pro Leu Ala Val Leu Leu Glu Val Glu Val
            530                 535                 540

Gly Ile Gly Glu Asp Trp Leu Ser Ala Lys Glu Ala Ala Ala Leu Val
545                 550                 555                 560

Pro Arg

<210> SEQ ID NO 35
<211> LENGTH: 1688
<212> TYPE: DNA
<213> ORGANISM: Thermus aquaticus
<220> FEATURE:
<221> NAME/KEY: CDS
<222> LOCATION: (3)..(1688)

<400> SEQUENCE: 35 cc atg gcc tct ggt ggc ggt ggc tgt ggt ggc ggt ggc agc ccc aag        47
   Met Ala Ser Gly Gly Gly Gly Cys Gly Gly Gly Gly Ser Pro Lys
   1               5                   10                  15 gcc ctg gag gag gcc ccc tgg ccc ccg ccg gaa ggg gcc ttc gtg ggc       95
Ala Leu Glu Glu Ala Pro Trp Pro Pro Pro Glu Gly Ala Phe Val Gly
                20                  25                  30 ttt gtg ctt tcc cgc aag gag ccc atg tgg gcc gat ctt ctg gcc ctg      143
Phe Val Leu Ser Arg Lys Glu Pro Met Trp Ala Asp Leu Leu Ala Leu
            35                  40                  45 gcc gcc gcc agg ggg ggc cgg gtc cac cgg gcc ccc gag cct tat aaa      191
Ala Ala Ala Arg Gly Gly Arg Val His Arg Ala Pro Glu Pro Tyr Lys
        50                  55                  60 gcc ctc agg gac ctg aag gag gcg cgg ggg ctt ctc gcc aaa gac ctg      239
Ala Leu Arg Asp Leu Lys Glu Ala Arg Gly Leu Leu Ala Lys Asp Leu
65                  70                  75 agc gtt ctg gcc ctg agg gaa ggc ctt ggc ctc ccg ccc ggc gac gac      287
Ser Val Leu Ala Leu Arg Glu Gly Leu Gly Leu Pro Pro Gly Asp Asp
80                  85                  90                  95 ccc atg ctc ctc gcc tac ctc ctg gac cct tcc aac acc acc ccc gag      335
Pro Met Leu Leu Ala Tyr Leu Leu Asp Pro Ser Asn Thr Thr Pro Glu
                100                 105                 110 ggg gtg gcc cgg cgc tac ggc ggg gag tgg acg gag gag gcg ggg gag      383
Gly Val Ala Arg Arg Tyr Gly Gly Glu Trp Thr Glu Glu Ala Gly Glu
            115                 120                 125
```

```
cgg gcc gcc ctt tcc gag agg ctc ttc gcc aac ctg tgg ggg agg ctt    431
Arg Ala Ala Leu Ser Glu Arg Leu Phe Ala Asn Leu Trp Gly Arg Leu
        130                 135                 140 gag ggg gag gag agg ctc ctt tgg ctt tac cgg gag gtg gag agg ccc    479
Glu Gly Glu Glu Arg Leu Leu Trp Leu Tyr Arg Glu Val Glu Arg Pro
145                 150                 155 ctt tcc gct gtc ctg gcc cac atg gag gcc acg ggg gtg cgc ctg gac    527
Leu Ser Ala Val Leu Ala His Met Glu Ala Thr Gly Val Arg Leu Asp
160                 165                 170                 175 gtg gcc tat ctc agg gcc ttg tcc ctg gag gtg gcc gag gag atc gcc    575
Val Ala Tyr Leu Arg Ala Leu Ser Leu Glu Val Ala Glu Glu Ile Ala
            180                 185                 190 cgc ctc gag gcc gag gtc ttc cgc ctg gcc ggc cac ccc ttc aac ctc    623
Arg Leu Glu Ala Glu Val Phe Arg Leu Ala Gly His Pro Phe Asn Leu
                195                 200                 205 aac tcc cgg gac cag ctg gaa agg gtc ctc ttt gac gag cta ggg ctt    671
Asn Ser Arg Asp Gln Leu Glu Arg Val Leu Phe Asp Glu Leu Gly Leu
                    210                 215                 220 ccc gcc atc ggc aag acg gag aag acc ggc aag cgc tcc acc agc gcc    719
Pro Ala Ile Gly Lys Thr Glu Lys Thr Gly Lys Arg Ser Thr Ser Ala
225                 230                 235 gcc gtc ctg gag gcc ctc cgc gag gcc cac ccc atc gtg gag aag atc    767
Ala Val Leu Glu Ala Leu Arg Glu Ala His Pro Ile Val Glu Lys Ile
240                 245                 250                 255 ctg cag tac cgg gag ctc acc aag ctg aag agc acc tac att gac ccc    815
Leu Gln Tyr Arg Glu Leu Thr Lys Leu Lys Ser Thr Tyr Ile Asp Pro
                260                 265                 270 ttg cag gac ctc atc cac ccc agt acg ggc cgc ctc cac acc cgc ttc    863
Leu Gln Asp Leu Ile His Pro Ser Thr Gly Arg Leu His Thr Arg Phe
                275                 280                 285 aac cag acg gcc acg gcc acg ggc agg cta agt agc tcc gat ccc aac    911
Asn Gln Thr Ala Thr Ala Thr Gly Arg Leu Ser Ser Ser Asp Pro Asn
                290                 295                 300 ctc cag aac atc ccc gtc cgc acc ccg ctt ggg cag agg atc cgc cgg    959
Leu Gln Asn Ile Pro Val Arg Thr Pro Leu Gly Gln Arg Ile Arg Arg
305                 310                 315 gcc ttc atc gcc gag gag ggg tgg cta ttg gtg gcc ctg gac tat agc   1007
Ala Phe Ile Ala Glu Glu Gly Trp Leu Leu Val Ala Leu Asp Tyr Ser
320                 325                 330                 335 cag ata gag ctc agg gtg ctg gcc cac ctc tcc ggc gac gag aac ctg   1055
Gln Ile Glu Leu Arg Val Leu Ala His Leu Ser Gly Asp Glu Asn Leu
                340                 345                 350 atc cgg gtc ttc cag gag ggg cgg gac atc cac acg gag acc gcc agc   1103
Ile Arg Val Phe Gln Glu Gly Arg Asp Ile His Thr Glu Thr Ala Ser
                355                 360                 365 tgg atg ttc ggc gtc ccc cgg gag gcc gtg gac ccc ctg atg cgc cgg   1151
Trp Met Phe Gly Val Pro Arg Glu Ala Val Asp Pro Leu Met Arg Arg
                370                 375                 380 gcg gcc aag acc atc aac ttc ggg gtc ctc tac ggc atg tcg gcc cac   1199
Ala Ala Lys Thr Ile Asn Phe Gly Val Leu Tyr Gly Met Ser Ala His
385                 390                 395 cgc ctc tcc cag gag cta gcc atc cct tac gag gag gcc cag gcc ttc   1247
Arg Leu Ser Gln Glu Leu Ala Ile Pro Tyr Glu Glu Ala Gln Ala Phe
400                 405                 410                 415 att gag cgc tac ttt cag agc ttc ccc aag gtg cgg gcc tgg att gag   1295
Ile Glu Arg Tyr Phe Gln Ser Phe Pro Lys Val Arg Ala Trp Ile Glu
                420                 425                 430 aag acc cta gag gag ggc agg agg cgg ggg tac gtg gag acc ctc ttc   1343
Lys Thr Leu Glu Glu Gly Arg Arg Arg Gly Tyr Val Glu Thr Leu Phe
                435                 440                 445
```

```
ggc cgc cgc cgc tac gtg cca gac cta gag gcc cgg gtg aag agc gag      1391
Gly Arg Arg Arg Tyr Val Pro Asp Leu Glu Ala Arg Val Lys Ser Glu
        450                 455                 460 cgg gag gcg gcc gag cgc atg gcc tac aac atg ccc gtc cag ggc acc      1439
Arg Glu Ala Ala Glu Arg Met Ala Tyr Asn Met Pro Val Gln Gly Thr
465                 470                 475 gcc gcc gac ctc atg aag ctg gct atg gtg aag ctc ttc ccc agg ctg      1487
Ala Ala Asp Leu Met Lys Leu Ala Met Val Lys Leu Phe Pro Arg Leu
480                 485                 490                 495 gag gaa atg ggg gcc cgg atg ctc ctt cag gtc cac gac gag ctg gtc      1535
Glu Glu Met Gly Ala Arg Met Leu Leu Gln Val His Asp Glu Leu Val
                500                 505                 510 ctc gag gcc cca aaa gag ggg gcg gag gcc gtg gcc cgg ctg gcc aag      1583
Leu Glu Ala Pro Lys Glu Gly Ala Glu Ala Val Ala Arg Leu Ala Lys
            515                 520                 525 gag gtc atg gag ggg gtg tat ccc ctg gcc gtg ccc ctg gag gcg gag      1631
Glu Val Met Glu Gly Val Tyr Pro Leu Ala Val Pro Leu Glu Ala Glu
        530                 535                 540 gtg ggg ata ggg gag gat tgg ctc tcc gcc aag gag gcg gcc gca ctg      1679
Val Gly Ile Gly Glu Asp Trp Leu Ser Ala Lys Glu Ala Ala Ala Leu
545                 550                 555 gtg ccg cgc                                                           1688
Val Pro Arg
560

<210> SEQ ID NO 36
<211> LENGTH: 562
<212> TYPE: PRT
<213> ORGANISM: Thermus aquaticus

<400> SEQUENCE: 36

Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
        115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205
```

Ser Arg Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Gln Asp Leu Ile His Pro Ser Thr Gly Arg Leu His Thr Arg Phe Asn
        275                 280                 285

Gln Thr Ala Thr Ala Thr Gly Arg Leu Ser Ser Ser Asp Pro Asn Leu
    290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
        355                 360                 365

Met Phe Gly Val Pro Arg Glu Ala Val Asp Pro Leu Met Arg Arg Ala
    370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Gly Tyr Val Glu Thr Leu Phe Gly
        435                 440                 445

Arg Arg Arg Tyr Val Pro Asp Leu Glu Ala Arg Val Lys Ser Glu Arg
    450                 455                 460

Glu Ala Ala Glu Arg Met Ala Tyr Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Gly Ala Glu Ala Val Ala Arg Leu Ala Lys Glu
        515                 520                 525

Val Met Glu Gly Val Tyr Pro Leu Ala Val Pro Leu Glu Ala Glu Val
    530                 535                 540

Gly Ile Gly Glu Asp Trp Leu Ser Ala Lys Glu Ala Ala Ala Leu Val
545                 550                 555                 560

Pro Arg

<210> SEQ ID NO 37
<211> LENGTH: 1688
<212> TYPE: DNA
<213> ORGANISM: Thermus aquaticus
<220> FEATURE:
<221> NAME/KEY: CDS
<222> LOCATION: (3)..(1688)

<400> SEQUENCE: 37

-continued

```
cc atg gcc tct ggt ggc ggt ggc tgt ggt ggc ggt ggc agc ccc aag        47
   Met Ala Ser Gly Gly Gly Gly Cys Gly Gly Gly Gly Ser Pro Lys
   1               5                   10                  15 gcc ctg gag gag gcc ccc tgg ccc ccg ccg gaa ggg gcc ttc gtg ggc        95
Ala Leu Glu Glu Ala Pro Trp Pro Pro Pro Glu Gly Ala Phe Val Gly
                    20                  25                  30 ttt gtg ctt tcc cgc aag gag ccc atg tgg gcc gat ctt ctg gcc ctg      143
Phe Val Leu Ser Arg Lys Glu Pro Met Trp Ala Asp Leu Leu Ala Leu
                35                  40                  45 gcc gcc gcc agg ggg ggc cgg gtc cac cgg gcc ccc gag cct tat aaa      191
Ala Ala Ala Arg Gly Gly Arg Val His Arg Ala Pro Glu Pro Tyr Lys
            50                  55                  60 gcc ctc agg gac ctg aag gag gcg cgg ggg ctt ctc gcc aaa gac ctg      239
Ala Leu Arg Asp Leu Lys Glu Ala Arg Gly Leu Leu Ala Lys Asp Leu
65                  70                  75 agc gtt ctg gcc ctg agg gaa ggc ctt ggc ctc ccg ccc ggc gac gac      287
Ser Val Leu Ala Leu Arg Glu Gly Leu Gly Leu Pro Pro Gly Asp Asp
80                  85                  90                  95 ccc atg ctc ctc gcc tac ctc ctg gac cct tcc aac acc acc ccc gag      335
Pro Met Leu Leu Ala Tyr Leu Leu Asp Pro Ser Asn Thr Thr Pro Glu
                100                 105                 110 ggg gtg gcc cgg cgc tac ggc ggg gag tgg acg gag gag gcg ggg gag      383
Gly Val Ala Arg Arg Tyr Gly Gly Glu Trp Thr Glu Glu Ala Gly Glu
                115                 120                 125 cgg gcc gcc ctt tcc gag agg ctc ttc gcc aac ctg tgg ggg agg ctt      431
Arg Ala Ala Leu Ser Glu Arg Leu Phe Ala Asn Leu Trp Gly Arg Leu
            130                 135                 140 gag ggg gag gag agg ctc ctt tgg ctt tac cgg gag gtg gag agg ccc      479
Glu Gly Glu Glu Arg Leu Leu Trp Leu Tyr Arg Glu Val Glu Arg Pro
145                 150                 155 ctt tcc gct gtc ctg gcc cac atg gag gcc acg ggg gtg cgc ctg gac      527
Leu Ser Ala Val Leu Ala His Met Glu Ala Thr Gly Val Arg Leu Asp
160                 165                 170                 175 gtg gcc tat ctc agg gcc ttg tcc ctg gag gtg gcc gag gag atc gcc      575
Val Ala Tyr Leu Arg Ala Leu Ser Leu Glu Val Ala Glu Glu Ile Ala
                180                 185                 190 cgc ctc gag gcc gag gtc ttc cgc ctg gcc ggc cac ccc ttc aac ctc      623
Arg Leu Glu Ala Glu Val Phe Arg Leu Ala Gly His Pro Phe Asn Leu
            195                 200                 205 aac tcc cgg gac cag ctg gaa agg gtc ctc ttt gac gag cta ggg ctt      671
Asn Ser Arg Asp Gln Leu Glu Arg Val Leu Phe Asp Glu Leu Gly Leu
            210                 215                 220 ccc gcc atc ggc aag acg gag aag acc ggc aag cgc tcc acc agc gcc      719
Pro Ala Ile Gly Lys Thr Glu Lys Thr Gly Lys Arg Ser Thr Ser Ala
225                 230                 235 gcc gtc ctg gag gcc ctc cgc gag gcc cac ccc atc gtg gag aag atc      767
Ala Val Leu Glu Ala Leu Arg Glu Ala His Pro Ile Val Glu Lys Ile
240                 245                 250                 255 ctg cag tac cgg gag ctc acc aag ctg aag agc acc tac att gac ccc      815
Leu Gln Tyr Arg Glu Leu Thr Lys Leu Lys Ser Thr Tyr Ile Asp Pro
                260                 265                 270 ttg ccg gac ctc atc cac ccc agg acg ggc cgc ctc cac acc cgc ttc      863
Leu Pro Asp Leu Ile His Pro Arg Thr Gly Arg Leu His Thr Arg Phe
            275                 280                 285 aac cag acg gcc acg gcc acg ggc agg cta agt agc tcc gat ccc aac      911
Asn Gln Thr Ala Thr Ala Thr Gly Arg Leu Ser Ser Ser Asp Pro Asn
            290                 295                 300 ctc cag aac atc ccc gtc cgc acc ccg ctt ggg cag agg atc cgc cgg      959
Leu Gln Asn Ile Pro Val Arg Thr Pro Leu Gly Gln Arg Ile Arg Arg
```

```
                    305                 310                 315
gcc ttc atc gcc gag gag ggg tgg cta ttg gtg gcc ctg gac tat agc      1007
Ala Phe Ile Ala Glu Glu Gly Trp Leu Leu Val Ala Leu Asp Tyr Ser
320                 325                 330                 335 cag ata gag ctc agg gtg ctg gcc cac ctc tcc ggc gac gag aac ctg      1055
Gln Ile Glu Leu Arg Val Leu Ala His Leu Ser Gly Asp Glu Asn Leu
            340                 345                 350 atc cgg gtc ttc cag gag ggg cgg gac atc cac acg gag acc gcc agc      1103
Ile Arg Val Phe Gln Glu Gly Arg Asp Ile His Thr Glu Thr Ala Ser
        355                 360                 365 tgg atg ttc ggc gtc ccc cgg gag gcc gtg gac ccc ctg atg cgc cgg      1151
Trp Met Phe Gly Val Pro Arg Glu Ala Val Asp Pro Leu Met Arg Arg
    370                 375                 380 gcg gcc aag acc atc aac ttc ggg gtc ctc tac ggc atg tcg gcc cac      1199
Ala Ala Lys Thr Ile Asn Phe Gly Val Leu Tyr Gly Met Ser Ala His
385                 390                 395 cgc ctc tcc cag gag cta gcc atc cct tac gag gag gcc cag gcc ttc      1247
Arg Leu Ser Gln Glu Leu Ala Ile Pro Tyr Glu Glu Ala Gln Ala Phe
400                 405                 410                 415 att gag cgc tac ttt cag agc ttc ccc aag gtg cgg gcc tgg att gag      1295
Ile Glu Arg Tyr Phe Gln Ser Phe Pro Lys Val Arg Ala Trp Ile Glu
            420                 425                 430 aag acc ctg gag gag ggc agg agg cgg ggg tac gtg gag acc ctc ttc      1343
Lys Thr Leu Glu Glu Gly Arg Arg Arg Gly Tyr Val Glu Thr Leu Phe
        435                 440                 445 ggc cgc cgc cgc tac gtg cca gac cta gag gcc cgg gtg aag agc gtg      1391
Gly Arg Arg Arg Tyr Val Pro Asp Leu Glu Ala Arg Val Lys Ser Val
    450                 455                 460 cgg gag gcg gcc gag cgc atg gcc ttc aac atg ccc gtc cag ggc acc      1439
Arg Glu Ala Ala Glu Arg Met Ala Phe Asn Met Pro Val Gln Gly Thr
465                 470                 475 gcc gcc gac ctc gtg aag ctg gct atg gtg aag ctc ttc ccc agg ctg      1487
Ala Ala Asp Leu Val Lys Leu Ala Met Val Lys Leu Phe Pro Arg Leu
480                 485                 490                 495 gag gaa atg ggg gcc agg atg ctc ctt cag gtc cac gac gag ctg gtc      1535
Glu Glu Met Gly Ala Arg Met Leu Leu Gln Val His Asp Glu Leu Val
            500                 505                 510 ctc gag gcc cca aaa gag ggg gcg gag gcc gtg gcc cgg ctg gcc aag      1583
Leu Glu Ala Pro Lys Glu Gly Ala Glu Ala Val Ala Arg Leu Ala Lys
        515                 520                 525 gag gtc atg gag ggg gtg tat ccc ctg gcc gtg ccc ctg gag gtg gag      1631
Glu Val Met Glu Gly Val Tyr Pro Leu Ala Val Pro Leu Glu Val Glu
    530                 535                 540 gtg ggg ata ggg gag gac tgg ctc tcc gcc aag gag gcg gcc gca ctg      1679
Val Gly Ile Gly Glu Asp Trp Leu Ser Ala Lys Glu Ala Ala Ala Leu
545                 550                 555 gtg ccg cgc                                                           1688
Val Pro Arg
560

<210> SEQ ID NO 38
<211> LENGTH: 562
<212> TYPE: PRT
<213> ORGANISM: Thermus aquaticus

<400> SEQUENCE: 38

Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
            20                  25                  30
```

```
Val Leu Ser Arg Lys Glu Pro Met Trp Ala Asp Leu Leu Ala Leu Ala
            35                  40                  45

Ala Ala Arg Gly Gly Arg Val His Arg Ala Pro Glu Pro Tyr Lys Ala
 50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
                115                 120                 125

Ala Ala Leu Ser Glu Arg Leu Phe Ala Asn Leu Trp Gly Arg Leu Glu
            130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
                180                 185                 190

Leu Glu Ala Glu Val Phe Arg Leu Ala Gly His Pro Phe Asn Leu Asn
            195                 200                 205

Ser Arg Asp Gln Leu Glu Arg Val Leu Phe Asp Glu Leu Gly Leu Pro
            210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
                260                 265                 270

Pro Asp Leu Ile His Pro Arg Thr Gly Arg Leu His Thr Arg Phe Asn
            275                 280                 285

Gln Thr Ala Thr Ala Thr Gly Arg Leu Ser Ser Ser Asp Pro Asn Leu
            290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Arg Ala
370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
                420                 425                 430

Thr Leu Glu Glu Gly Arg Arg Arg Gly Tyr Val Glu Thr Leu Phe Gly
            435                 440                 445
```

```
Arg Arg Arg Tyr Val Pro Asp Leu Glu Ala Arg Val Lys Ser Val Arg
        450                 455                 460

Glu Ala Ala Glu Arg Met Ala Phe Asn Met Pro Val Gln Gly Thr Ala
465                 470                 475                 480

Ala Asp Leu Val Lys Leu Ala Met Val Lys Leu Phe Pro Arg Leu Glu
                485                 490                 495

Glu Met Gly Ala Arg Met Leu Leu Gln Val His Asp Glu Leu Val Leu
                500                 505                 510

Glu Ala Pro Lys Glu Gly Ala Glu Ala Val Ala Arg Leu Ala Lys Glu
                515                 520                 525

Val Met Glu Gly Val Tyr Pro Leu Ala Val Pro Leu Glu Val Glu Val
        530                 535                 540

Gly Ile Gly Glu Asp Trp Leu Ser Ala Lys Glu Ala Ala Ala Leu Val
545                 550                 555                 560

Pro Arg
```

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Met Ala Ser Gly Gly Gly Cys Gly Gly Gly
1               5                   10
```

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Ala Ala Ala Leu Val Pro Arg Gly Ser Leu Glu His His His His His
1               5                   10                  15

His
```

<210> SEQ ID NO 41
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Met Lys Tyr Leu Leu Pro Thr Ala Ala Ala Gly Leu Leu Leu Leu Ala
1               5                   10                  15

Ala Gln Pro Ala Met Ala
                20
```

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 42

Met Lys Thr Leu Leu Ala Met Val Leu Val Gly Leu Leu Leu Leu Pro
1               5                   10                  15

Pro Gly Pro Ser Met Ala
            20

<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Met Arg Gly Leu Leu Ala Met Leu Val Ala Gly Leu Leu Leu Leu Pro
1               5                   10                  15

Ile Ala Pro Ala Met Ala
            20

<210> SEQ ID NO 44
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Arg Arg Leu Leu Val Ile Ala Ala Val Gly Leu Leu Leu Leu Leu
1               5                   10                  15

Ala Pro Pro Thr Met Ala
            20

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gcggccgcac tggtgccgcg cggcagcctc gag                               33

<210> SEQ ID NO 46
<211> LENGTH: 148
<212> TYPE: PRT
<213> ORGANISM: Homo sapiens

<400> SEQUENCE: 46

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
                20                  25                  30

Gly Thr Val Met Arg Ser Leu Gly Gln Asn Pro Thr Glu Ala Glu Leu
            35                  40                  45

Gln Asp Met Ile Asn Glu Val Asp Ala Asp Gly Asn Gly Thr Ile Asp
        50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
```

```
                85                  90                  95
Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 47
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Gln Gln Ser Gly Pro Glu Asp Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser Pro Gly Lys Gly Leu Glu Trp Ile
        35                  40                  45

Gly Asp Ile Asn Pro Asn Asn Gly Gly Thr Ser Tyr Asn Gln Lys Phe
    50                  55                  60

Lys Gly Arg Ala Thr Leu Thr Val Asp Lys Ser Ser Thr Ala Tyr
65                  70                  75                  80

Met Glu Leu Arg Ser Leu Thr Ser Glu Asp Ser Ser Val Tyr Tyr Cys
            85                  90                  95

Glu Ser Gln Ser Gly Ala Tyr Trp Gly Gln Gly Thr Thr Val Thr Val
        100                 105                 110

Ser Ala

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Gly Ser Gly Gly Gly Ser Gly Gly Gly Ser Gly
1               5                   10                  15

Gly Gly Gly Ser
            20

<210> SEQ ID NO 49
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Tyr Lys Asp Ile Leu Met Thr Gln Thr Pro Ser Ser Leu Pro Val
1               5                   10                  15
```

```
Ser Leu Gly Asp Gln Ala Ser Ile Ser Cys Arg Ser Ser Gln Ser Ile
            20                  25                  30

Val His Ser Asn Gly Asn Thr Tyr Leu Glu Trp Tyr Leu Gln Lys Pro
        35                  40                  45

Gly Gln Ser Pro Lys Leu Leu Ile Tyr Lys Val Ser Asn Arg Phe Ser
    50                  55                  60

Gly Val Pro Asp Arg Phe Ser Gly Ser Gly Ser Gly Thr Asp Phe Thr
65                  70                  75                  80

Leu Lys Ile Ser Arg Val Glu Ala Glu Asp Leu Gly Val Tyr Tyr Cys
                85                  90                  95

Phe Gln Gly Ser His Val Pro Phe Thr Phe Gly Ser Gly Thr Lys Leu
            100                 105                 110

Glu Ile Lys Arg
            115

<210> SEQ ID NO 50
<211> LENGTH: 291
<212> TYPE: PRT
<213> ORGANISM: Thermus thermophilus

<400> SEQUENCE: 50

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
            115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270
```

```
Ala Phe Leu Glu Arg Leu Glu Phe Gly Ser Leu Leu His Glu Phe Gly
        275                 280                 285

Leu Leu Glu
    290

<210> SEQ ID NO 51
<211> LENGTH: 196
<212> TYPE: PRT
<213> ORGANISM: Escherichia coli

<400> SEQUENCE: 51

Val Ile Ser Tyr Asp Asn Tyr Val Thr Ile Leu Asp Glu Glu Thr Leu
1               5                   10                  15

Lys Ala Trp Ile Ala Lys Leu Glu Lys Ala Pro Val Phe Ala Phe Asp
            20                  25                  30

Thr Glu Thr Asp Ser Leu Asp Asn Ile Ser Ala Asn Leu Val Gly Leu
        35                  40                  45

Ser Phe Ala Ile Glu Pro Gly Val Ala Ala Tyr Ile Pro Val Ala His
    50                  55                  60

Asp Tyr Leu Asp Ala Pro Asp Gln Ile Ser Arg Glu Arg Ala Leu Glu
65                  70                  75                  80

Leu Leu Lys Pro Leu Leu Glu Asp Glu Lys Ala Leu Lys Val Gly Gln
                85                  90                  95

Asn Leu Lys Tyr Asp Arg Gly Ile Leu Ala Asn Tyr Gly Ile Glu Leu
            100                 105                 110

Arg Gly Ile Ala Phe Asp Thr Met Leu Glu Ser Tyr Ile Leu Asn Ser
        115                 120                 125

Val Ala Gly Arg His Asp Met Asp Ser Leu Ala Glu Arg Trp Leu Lys
    130                 135                 140

His Lys Thr Ile Thr Phe Glu Glu Ile Ala Gly Lys Gly Lys Asn Gln
145                 150                 155                 160

Leu Thr Phe Asn Gln Ile Ala Leu Glu Glu Ala Gly Arg Tyr Ala Ala
                165                 170                 175

Glu Asp Ala Asp Val Thr Leu Gln Leu His Leu Lys Met Trp Pro Asp
            180                 185                 190

Leu Gln Lys His
    195

<210> SEQ ID NO 52
<211> LENGTH: 686
<212> TYPE: PRT
<213> ORGANISM: Bacillus circulans

<400> SEQUENCE: 52

Ala Pro Asp Thr Ser Val Ser Asn Lys Gln Asn Phe Ser Thr Asp Val
1               5                   10                  15

Ile Tyr Gln Ile Phe Thr Asp Arg Phe Ser Asp Gly Asn Pro Ala Asn
            20                  25                  30

Asn Pro Thr Gly Ala Ala Phe Asp Gly Thr Cys Thr Asn Leu Arg Leu
        35                  40                  45

Tyr Cys Gly Gly Asp Trp Gln Gly Ile Ile Asn Lys Ile Asn Asp Gly
    50                  55                  60

Tyr Leu Thr Gly Met Gly Val Thr Ala Ile Trp Ile Ser Gln Pro Val
65                  70                  75                  80

Glu Asn Ile Tyr Ser Ile Ile Asn Tyr Ser Gly Val Asn Asn Thr Ala
                85                  90                  95
```

```
Tyr His Gly Tyr Trp Ala Arg Asp Phe Lys Lys Thr Asn Pro Ala Tyr
            100                 105                 110

Gly Thr Ile Ala Asp Phe Gln Asn Leu Ile Ala Ala His Ala Lys
            115                 120                 125

Asn Ile Lys Val Ile Asp Phe Ala Pro Asn His Thr Ser Pro Ala
130                 135                 140

Ser Ser Asp Gln Pro Ser Phe Ala Glu Asn Gly Arg Leu Tyr Asp Asn
145                 150                 155                 160

Gly Thr Leu Leu Gly Gly Tyr Thr Asn Asp Thr Gln Asn Leu Phe His
            165                 170                 175

His Asn Gly Gly Thr Asp Phe Ser Thr Thr Glu Asn Gly Ile Tyr Lys
            180                 185                 190

Asn Leu Tyr Asp Leu Ala Asp Leu Asn His Asn Asn Ser Thr Val Asp
            195                 200                 205

Val Tyr Leu Lys Asp Ala Ile Lys Met Trp Leu Asp Leu Gly Ile Asp
            210                 215                 220

Gly Ile Arg Met Asp Ala Val Lys His Met Pro Phe Gly Trp Gln Lys
225                 230                 235                 240

Ser Phe Met Ala Ala Val Asn Asn Tyr Lys Pro Val Phe Thr Phe Gly
            245                 250                 255

Glu Trp Phe Leu Gly Val Asn Glu Val Ser Pro Glu Asn His Lys Phe
            260                 265                 270

Ala Asn Glu Ser Gly Met Ser Leu Leu Asp Phe Arg Phe Ala Gln Lys
            275                 280                 285

Val Arg Gln Val Phe Arg Asp Asn Thr Asp Asn Met Tyr Gly Leu Lys
            290                 295                 300

Ala Met Leu Glu Gly Ser Ala Ala Asp Tyr Ala Gln Val Asp Asp Gln
305                 310                 315                 320

Val Thr Phe Ile Asp Asn His Asp Met Glu Arg Phe His Ala Ser Asn
            325                 330                 335

Ala Asn Arg Arg Lys Leu Glu Gln Ala Leu Ala Phe Thr Leu Thr Ser
            340                 345                 350

Arg Gly Val Pro Ala Ile Tyr Tyr Gly Thr Glu Gln Tyr Met Ser Gly
            355                 360                 365

Gly Thr Asp Pro Asp Asn Arg Ala Arg Ile Pro Ser Phe Ser Thr Ser
370                 375                 380

Thr Thr Ala Tyr Gln Val Ile Gln Lys Leu Ala Pro Leu Arg Lys Cys
385                 390                 395                 400

Asn Pro Ala Ile Ala Tyr Gly Ser Thr Gln Glu Arg Trp Ile Asn Asn
            405                 410                 415

Asp Val Leu Ile Tyr Glu Arg Lys Phe Gly Ser Asn Val Ala Val Val
            420                 425                 430

Ala Val Asn Arg Asn Leu Asn Ala Pro Ala Ser Ile Ser Gly Leu Val
            435                 440                 445

Thr Ser Leu Pro Gln Gly Ser Tyr Asn Asp Val Leu Gly Gly Leu Leu
            450                 455                 460

Asn Gly Asn Thr Leu Ser Val Gly Ser Gly Ala Ala Ser Asn Phe
465                 470                 475                 480

Thr Leu Ala Ala Gly Gly Thr Ala Val Trp Gln Tyr Thr Ala Ala Thr
            485                 490                 495

Ala Thr Pro Thr Ile Gly His Val Gly Pro Met Met Ala Lys Pro Gly
            500                 505                 510
```

```
Val Thr Ile Thr Ile Asp Gly Arg Gly Phe Gly Ser Lys Gly Thr
        515                 520                 525

Val Tyr Phe Gly Thr Thr Ala Val Ser Gly Ala Asp Ile Thr Ser Trp
    530                 535                 540

Glu Asp Thr Gln Ile Lys Val Lys Ile Pro Ala Val Ala Gly Gly Asn
545                 550                 555                 560

Tyr Asn Ile Lys Val Ala Asn Ala Ala Gly Thr Ala Ser Asn Val Tyr
                565                 570                 575

Asp Asn Phe Glu Val Leu Ser Gly Asp Gln Val Ser Val Arg Phe Val
                580                 585                 590

Val Asn Asn Ala Thr Thr Ala Leu Gly Gln Asn Val Tyr Leu Thr Gly
            595                 600                 605

Ser Val Ser Glu Leu Gly Asn Trp Asp Pro Ala Lys Ala Ile Gly Pro
        610                 615                 620

Met Tyr Asn Gln Val Val Tyr Gln Tyr Pro Asn Trp Tyr Tyr Asp Val
625                 630                 635                 640

Ser Val Pro Ala Gly Lys Thr Ile Glu Phe Lys Phe Leu Lys Lys Gln
                645                 650                 655

Gly Ser Thr Val Thr Trp Glu Gly Gly Ser Asn His Thr Phe Thr Ala
                660                 665                 670

Pro Ser Ser Gly Thr Ala Thr Ile Asn Val Asn Trp Gln Pro
            675                 680                 685

<210> SEQ ID NO 53
<211> LENGTH: 399
<212> TYPE: PRT
<213> ORGANISM: Bordetella pertussis

<400> SEQUENCE: 53

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
                20                  25                  30

Glu Lys Asn Ala Thr Leu Met Phe Arg Leu Val Asn Pro His Ser Thr
            35                  40                  45

Ser Leu Ile Ala Glu Gly Val Ala Thr Lys Gly Leu Gly Val His Ala
        50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
                100                 105                 110

Leu Thr Leu Ser Lys Glu Arg Leu Asp Tyr Leu Arg Gln Ala Gly Leu
            115                 120                 125

Val Thr Gly Met Ala Asp Gly Val Val Ala Ser Asn His Ala Gly Tyr
        130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Phe Glu Ala Val Lys Val
                165                 170                 175

Ile Gly Asn Ala Ala Gly Ile Pro Leu Thr Ala Asp Ile Asp Met Phe
                180                 185                 190

Ala Ile Met Pro His Leu Ser Asn Phe Arg Asp Ser Ala Arg Ser Ser
            195                 200                 205
```

-continued

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Ser Gly Arg Ser Lys Phe Ser Pro Asp Val Leu Glu Thr Val Pro
370                 375                 380

Ala Ser Pro Gly Leu Arg Arg Pro Ser Leu Gly Ala Val Glu Arg
385                 390                 395

<210> SEQ ID NO 54
<211> LENGTH: 275
<212> TYPE: PRT
<213> ORGANISM: Bacillus amyloliquefaciens

<400> SEQUENCE: 54

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val

```
              180                 185                 190
Gly Pro Glu Leu Asp Val Met Ala Pro Gly Val Ser Ile Gln Ser Thr
                195                 200                 205

Leu Pro Gly Asn Lys Tyr Gly Ala Tyr Asn Gly Thr Ser Met Ala Ser
        210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
        260                 265                 270

Ala Ala Gln
        275

<210> SEQ ID NO 55
<211> LENGTH: 182
<212> TYPE: PRT
<213> ORGANISM: Bacillus subtilis

<400> SEQUENCE: 55

Ala Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
            20                  25                  30

Ser Arg Asp Lys Leu Tyr Ala Val Asp Phe Trp Asp Lys Thr Gly Thr
        35                  40                  45

Asn Tyr Asn Asn Gly Pro Val Leu Ser Arg Phe Val Gln Lys Val Leu
    50                  55                  60

Asp Glu Thr Gly Ala Lys Lys Val Asp Ile Val Ala His Ser Met Gly
65                  70                  75                  80

Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
            100                 105                 110

Lys Ala Leu Pro Gly Thr Asp Pro Asn Gln Lys Ile Leu Tyr Thr Ser
        115                 120                 125

Ile Tyr Ser Ser Ala Asp Met Ile Val Met Asn Tyr Leu Ser Arg Leu
    130                 135                 140

Asp Gly Ala Arg Asn Val Gln Ile His Gly Val Gly His Ile Gly Leu
145                 150                 155                 160

Leu Tyr Ser Ser Gln Val Asn Ser Leu Ile Lys Glu Gly Leu Asn Gly
                165                 170                 175

Gly Gly Gln Asn Thr Asn
        180

<210> SEQ ID NO 56
<211> LENGTH: 444
<212> TYPE: DNA
<213> ORGANISM: Homo sapiens

<400> SEQUENCE: 56
gctgaccaac tgactgaaga gcagattgca gaattcaaag aagcttttc  actatttgac       60 aaagatggtg atggaactat aacaacaaag gaattgggaa ctgtaatgag atctcttggg      120
cagaatccca gaagcagag ttacaggac atgattaatg aagtagatgc tgatggtaat       180
ggcacaattg acttccctga atttctgaca atgatggcaa gaaaaatgaa agacacagac      240
```

```
agtgaagaag aaattagaga agcattccgt gtgtttgata aggatggcaa tggctatatt      300
agtgctgcag aacttcgcca tgtgatgaca aaccttggag agaagttaac agatgaagaa      360
gttgatgaaa tgatcaggga agcagatatt gatggtgatg gtcaagtaaa ctatgaagag      420
tttgtacaaa tgatgacagc aaag                                             444

<210> SEQ ID NO 57
<211> LENGTH: 2058
<212> TYPE: DNA
<213> ORGANISM: Bacillus circulans

<400> SEQUENCE: 57
gcgccggata cctcggtatc aacaagcaa aatttcagca ccgacgtcat ctatcaaatt        60
ttcaccgaca ggttttcgga cggcaatccc gccaacaatc cgaccggcgc ggcgtttgac      120
ggaacctgca cgaacctccg gctgtattgc ggcggcgact ggcagggcat catcaacaaa      180
atcaacgacg gttacctgac cgggatgggc gttaccgcca tctggatctc ccagccggtc      240
gaaaacatct acagcatcat caattattcc ggcgtaaaca cacggcctat tcacggctac      300
tgggcccggg acttcaagaa gacgaatccg gcctacggca cgattgcgga cttccagaac      360
ctgatcgccg ccgcgcatgc aaaaaacatc aaagtcatta tcgactttgc cccgaaccat      420
acgtcgcccg cctcgtccga ccagccttcc tttgcggaaa acggccggct gtacgataac      480
ggcacgctgc tcgggggata cacgaacgat acgcagaacc tgttccacca taacggcggc      540
acggactttt ccacgaccga aaacggcatc tacaaaaacc tgtacgatct cgccgacctg      600
aaccataaca acagcaccgt ggacgtctac ttgaaggacg cgatcaaaat gtggctggac      660
ctcggcatcg acggcatccg catggatgcg gtgaagcata tgccgttcgg ctggcagaag      720
agctttatgg ctgccgtcaa caactataag ccggtcttta ccttcggcga atggttcctg      780
ggcgtaaatg aagtgagccc ggaaaaccat aagtttgcca acgaatccgg catgagcctg      840
cttgatttcc gttttgccca aaaggtgcgg caggtgttcc gggacaacac cgacaatatg      900
tacggcctga aggcgatgct ggagggctcc gcagccgatt acgcccaggt ggatgaccag      960
gtgacgttca tcgacaacca tgacatggag cgtttccacg caagcaatgc aaaccgccgg     1020
aagctggagc aagcgcttgc gttcacgctg acctcgcgcg cgtccccgc catttattac      1080 ggcaccgagc agtacatgtc gggcgggacc gatccggaca accgggcgcg gatcccttcc     1140
ttctccacgt cgacgaccgc ctatcaggtc attcaaaagc tggcgccgct cgcaagtgc      1200 aacccggcca tcgcctacgg atcgacgcag gagcgctgga tcaacaacga cgtgctcatt     1260
tatgagcgca aattcggcag caacgttgcc gtcgttgccg tcaaccgcaa tttaaacgcg     1320
ccggcttcca tttcgggact tgtcacttcc ctgccgcaag gcagctacaa cgacgtcctt     1380
ggcggccttc tgaacggcaa cacgttatcg gtaggctccg gcggggccgc ctccaatttc     1440
acgcttgcgg ccggcggcac ggcggtgtgg cagtacaccg cggctacggc gacgccgacc     1500
atcgggcatg tcgggccgat gatggccaag ccgggcgtga cgatcacgat cgacggccgc     1560
ggcttcggct ctagcaaagg caccgtctac ttcggtacga cggcggtgag cggggcggac     1620
atcacgtctt gggaagacac gcagatcaaa gtgaaaattc cggccgtcgc aggcggcaac     1680
tacaacatta agtcgcaaa cgctgccgga acggcaagca atgtgtatga caacttcgag     1740
gtattgtccg gagaccaggt cagcgtccgc ttcgtggtca acaacgcgac gacggccctt     1800
gggcaaaatg tgtacctgac gggcagtgtc agcgagctgg ggactgggga cccggcaaaa     1860
```

| | |
|---|---:|
| gcaatcgggc cgatgtacaa tcaggtcgtt taccaatatc cgaactggta ttatgacgtc | 1920 |
| agcgttccgg ccggcaaaac gatcgagttc aagtttttga aaaaacaagg ctccaccgtc | 1980 |
| acgtgggaag gcggcagcaa ccacaccttc accgcgccgt ccagcggcac cgcgaccatt | 2040 |
| aacgtgaatt ggcagcca | 2058 |

<210> SEQ ID NO 58
<211> LENGTH: 1197
<212> TYPE: DNA
<213> ORGANISM: Bordetella pertussis

<400> SEQUENCE: 58

| | |
|---|---:|
| atgcagcaat cgcatcaggc tggttacgca acgccgccg accgggagtc tggcatcccc | 60 |
| gcagccgtac tcgatggcat caaggccgtg gcgaaggaaa aaaacgccac attgatgttc | 120 |
| cgcctggtca accccattc caccagcctg attgccgaag gggtggccac caaaggattg | 180 |
| ggcgtgcacg ccaagtcgtc cgattggggg ttgcaggcgg gctacattcc cgtcaacccg | 240 |
| aatctttcca aactgttcgg ccgtgcgccc gaggtgatcg cgcgggccga caacgacgtc | 300 |
| aacagcagcc tggcgcatgg ccataccgcg gtcgacctga cgctgtcgaa agagcggctt | 360 |
| gactatctgc ggcaagcggg cctggtcacc ggcatggccg atggcgtggt cgcgagcaac | 420 |
| cacgcaggct acgagcagtt cgagtttcgc gtgaaggaaa cctcggacgg cgctatgcc | 480 |
| gtgcagtatc gccgcaaggg cggcgacgat ttcgaggcgg tcaaggtgat cggcaatgcc | 540 |
| gccggtattc cactgacggc ggatatcgac atgttcgcca ttatgccgca tctgtccaac | 600 |
| ttccgcgact cggcgcgcag ttcggtgacc agcggcgatt cggtgaccga ttacctggcg | 660 |
| cgcacgcggc gggccgccag cgaggccacg gcggcctgg atcgcgaacg catcgacttg | 720 |
| ttgtggaaaa tcgctcgcgc cggcgcccgt tccgcagtgg caccgaggc gcgtcgccag | 780 |
| ttccgctacg acggcgacat gaatatcggc gtgatcaccg atttcgagct ggaagtgcgc | 840 |
| aatgcgctga acaggcgggc gcacgccgtc ggcgcgcagg acgtggtcca gcatggcact | 900 |
| gagcagaaca atccttcc ggaggcagat gagaagattt cgtcgtatc ggccaccggt | 960 |
| gaaagccaga tgctcacgcg cgggcaactg aaggaataca ttggccagca gcgcggcgag | 1020 |
| ggctatgtct tctacgagaa ccgtgcatac ggcgtggcgg ggaaaagcct gttcgacgat | 1080 |
| gggctgggag ccgcgcccgg cgtgccgagc ggacgttcga agttctcgcc ggatgtactg | 1140 |
| gaaacggtgc cggcgtcacc cggattgcgg cggccgtcgc tgggcgcagt ggaacgc | 1197 |

<210> SEQ ID NO 59
<211> LENGTH: 825
<212> TYPE: DNA
<213> ORGANISM: Bacillus amyloliquefaciens

<400> SEQUENCE: 59

| | |
|---|---:|
| gcgcagtccg tgccttacgg cgtatcacaa attaaagccc ctgctctgca ctctcaaggc | 60 |
| tacactggat caaatgttaa agtagcggtt atcgacagcg gtatcgattc ttctcatcct | 120 |
| gatttaaagg tagcaggcgg agccagcatg gttccttctg aaacaaatcc tttccaagac | 180 |
| aacaactctc acggaactca cgttgccggc acagttgcgg ctcttaataa ctcaatcggt | 240 |
| gtattaggcg ttgcgccaag cgcatcactt tacgctgtaa agttctcgg tgctgacggt | 300 |
| tccggccaat acagctggat cattaacgga atcgagtggg cgatcgcaaa caatatggac | 360 |
| gttattaaca tgagcctcgg cggaccttct ggttctgctg ctttaaaagc ggcagttgat | 420 |
| aaagccgttg catccggcgt cgtagtcgtt gcggcagccg gtaacgaagg cacttccggc | 480 |

```
agctcaagca cagtgggcta ccctggtaaa tacccttctg tcattgcagt aggcgctgtt    540
gacagcagca accaaagagc atctttctca agcgtaggac ctgagcttga tgtcatggca    600
cctggcgtat ctatccaaag cacgcttcct ggaaacaaat acggggcgta acggtacg     660 tcaatggcat ctccgcacgt tgccggagcg gctgctttga ttctttctaa gcacccgaac    720
tggacaaaca ctcaagtccg cagcagttta gaaaacacca ctacaaaact tggtgattct    780
ttctactatg gaaaagggct gatcaacgta caggcggcag ctcag                    825

<210> SEQ ID NO 60
<211> LENGTH: 873
<212> TYPE: DNA
<213> ORGANISM: Thermus thermophilus

<400> SEQUENCE: 60
atggaggcga tgcttccgct cttgaaccc aaaggccggg tcctcctggt ggacggccac      60
cacctggcct accgcacctt cttcgccctg aagggcctca ccacgagccg ggcgaaccg     120 gtgcaggcgg tctacggctt cgccaagagc ctcctcaagg ccctgaagga ggacgggtac    180
aaggccgtct tcgtggtctt tgacgccaag gcccccctcct tccgccacga ggcctacgag    240
gcctacaagg cggggagggc cccgaccccc gaggacttcc ccggcagct cgccctcatc      300 aaggagctgg tggacctcct ggggtttacc cgcctcgagg tccccggcta cgaggcggac    360
gacgttctcg ccaccctggc caagaaggcg aaaaggagg ggtacgaggt gcgcatcctc     420
accgccgacc gcgaccctcta ccaactcgtc tccgaccgcg tcgccgtcct ccaccccgag    480
ggccacctca tcaccccgga gtggctttgg gagaagtacg gcctcaggcc ggagcagtgg    540
gtggacttcc gcgccctcgt gggggacccc tccgacaacc tccccggggt caagggcatc    600
ggggagaaga ccgccctcaa gctcctcaag gagtggggaa gcctggaaaa cctcctcaag    660
aacctggacc gggtaaagcc agaaaacgtc cgggagaaga tcaaggccca cctggaagac    720
ctcaggctct ccttggagct ctcccggtg cgcaccgacc tcccctgga ggtggacctc      780 gcccagggc gggagcccga ccggagggg cttagggcct tcctggagag ctggagttc       840 ggcagcctcc tccacgagtt cggcctcctg gag                                 873

<210> SEQ ID NO 61
<211> LENGTH: 588
<212> TYPE: DNA
<213> ORGANISM: Escherichia coli

<400> SEQUENCE: 61
gtgatttctt atgacaacta cgtcaccatc cttgatgaag aaacactgaa agcgtggatt     60
gcgaagctgg aaaagcgcc ggtatttgca tttgataccg aaaccgacag ccttgataac    120
atctctgcta acctggtcgg gctttctttt gctatcgagc caggcgtagc ggcatatatt    180
ccggttgctc atgattatct tgatgcgccc gatcaaatct ctcgcgagcg tgcactcgag    240
ttgctaaaac cgctgctgga agatgaaaag gcgctgaagg tcgggcaaaa cctgaaatac    300
gatcgcggta ttctggcgaa ctacggcatt gaactgcgtg ggattgcgtt tgataccatg    360
ctggagtcct acattctcaa tagcgttgcc ggcgtcacg atatgacag cctcgcggaa    420 cgttggttga agcacaaaac catcactttt gaagagattg ctggtaaagg caaaaatcaa   480
ctgaccttta accagattgc cctcgaagaa gccggacgtt acgccgccga agatgcagat   540
gtcaccttgc agttgcatct gaaaatgtgg ccggatctgc aaaaacac                588
```

<210> SEQ ID NO 62
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 62

```
agc ccc aag gcc ctg gag gag gcc ccc tgg ccc ccg ccg gaa ggg gcc        48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt        96
Phe Val Gly Phe Val Leu Ser Arg Lys Glu Pro Met Trp Ala Asp Leu
            20                  25                  30 ctg gcc ctg gcc gcc gcc agg ggg ggc cgg gtc cac cgg gcc ccc gag       144
Leu Ala Leu Ala Ala Ala Arg Gly Gly Arg Val His Arg Ala Pro Glu
        35                  40                  45 cct tat aaa gcc ctc agg gac ctg aag gag gcg cgg ggg ctt ctc gcc       192
Pro Tyr Lys Ala Leu Arg Asp Leu Lys Glu Ala Arg Gly Leu Leu Ala
    50                  55                  60 aaa gac ctg agc gtt ctg gcc ctg agg gaa ggc ctt ggc ctc ccg ccc       240
Lys Asp Leu Ser Val Leu Ala Leu Arg Glu Gly Leu Gly Leu Pro Pro
65                  70                  75                  80 ggc gac gac ccc atg ctc ctc gcc tac ctc ctg gac cct tcc aac acc       288
Gly Asp Asp Pro Met Leu Leu Ala Tyr Leu Leu Asp Pro Ser Asn Thr
                85                  90                  95 acc ccc gag ggg gtg gcc cgg cgc tac ggc ggg gag tgg acg gag gag       336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg       384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg       432
Gly Arg Leu Glu Gly Glu Glu Arg Leu Leu Trp Leu Tyr Arg Glu Val
    130                 135                 140 gag agg ccc ctt tcc gct gtc ctg gcc cac atg gag gcc acg ggg gtg       480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag       528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc       576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag       624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc       672
Leu Gly Leu Pro Ala Ile Gly Lys Thr Glu Lys Thr Gly Lys Arg Ser
    210                 215                 220 acc agc gcc gcc gtc ctg gag gcc ctc cgc gag gcc cac ccc atc gtg       720
Thr Ser Ala Ala Val Leu Glu Ala Leu Arg Glu Ala His Pro Ile Val
225                 230                 235                 240 ggg aag atc ctg cag tac cgg gag ctc acc aag ctg aag agc acc tac       768
Gly Lys Ile Leu Gln Tyr Arg Glu Leu Thr Lys Leu Lys Ser Thr Tyr
                245                 250                 255 att gac ccc ttg ccg gac ctc atc cac ccc agg acg ggc cgc ctc cac       816
Ile Asp Pro Leu Pro Asp Leu Ile His Pro Arg Thr Gly Arg Leu His
            260                 265                 270
```

| | | |
|---|---|---|
| acc cgc ttc aac cag acg gcc acg gcc acg ggc agg cta agt agc tcc<br>Thr Arg Phe Asn Gln Thr Ala Thr Ala Thr Gly Arg Leu Ser Ser Ser<br>275 280 285 | | 864 |
| gat ccc aac ctc cag aac atc ccc gtc cgc acc ccg ctt ggg cag agg<br>Asp Pro Asn Leu Gln Asn Ile Pro Val Arg Thr Pro Leu Gly Gln Arg<br>290 295 300 | | 912 |
| atc cgc cgg gcc ttc atc gcc gag gag ggg tgg cta ttg gtg gcc ctg<br>Ile Arg Arg Ala Phe Ile Ala Glu Glu Gly Trp Leu Leu Val Ala Leu<br>305 310 315 320 | | 960 |
| gat tat agc cag ata gag ctc agg gtg ctg gcc cac ctc tcc ggc gac<br>Asp Tyr Ser Gln Ile Glu Leu Arg Val Leu Ala His Leu Ser Gly Asp<br>325 330 335 | | 1008 |
| gag aac ctg ata cgg gtc ttc cag gag ggg cgg gac atc cac acg gag<br>Glu Asn Leu Ile Arg Val Phe Gln Glu Gly Arg Asp Ile His Thr Glu<br>340 345 350 | | 1056 |
| acc gcc agc tgg atg ttc ggc gtc ccc cgg gag gcc gtg gac ccc ctg<br>Thr Ala Ser Trp Met Phe Gly Val Pro Arg Glu Ala Val Asp Pro Leu<br>355 360 365 | | 1104 |
| atg cgc cgg gcg gcc aag acc atc aac ttc ggg gtc ctc tac ggc atg<br>Met Arg Arg Ala Ala Lys Thr Ile Asn Phe Gly Val Leu Tyr Gly Met<br>370 375 380 | | 1152 |
| tcg gcc cac cgc ctc tcc cag gag cta gcc atc cct tac gag gag gcc<br>Ser Ala His Arg Leu Ser Gln Glu Leu Ala Ile Pro Tyr Glu Glu Ala<br>385 390 395 400 | | 1200 |
| cag gcc ttc ata gag cgc tgc ttt cag agc ttc ccc aag gtg cgg gcc<br>Gln Ala Phe Ile Glu Arg Cys Phe Gln Ser Phe Pro Lys Val Arg Ala<br>405 410 415 | | 1248 |
| tgg att gag aag acc ctg gag gag ggc agg agg cgg ggg tac gtg gag<br>Trp Ile Glu Lys Thr Leu Glu Glu Gly Arg Arg Arg Gly Tyr Val Glu<br>420 425 430 | | 1296 |
| acc ctc ttc ggc cgc cgc cgc tac gtg cca gac cta gag gcc cgg gtg<br>Thr Leu Phe Gly Arg Arg Arg Tyr Val Pro Asp Leu Glu Ala Arg Val<br>435 440 445 | | 1344 |
| aag agc gtg cgg gag gcg gca gag cgc atg gcc ttc aac atg ccc gtc<br>Lys Ser Val Arg Glu Ala Ala Glu Arg Met Ala Phe Asn Met Pro Val<br>450 455 460 | | 1392 |
| cag ggc acc gcc gcc gac ctc atg aag ctg gct atg gtg aag ctc ttc<br>Gln Gly Thr Ala Ala Asp Leu Met Lys Leu Ala Met Val Lys Leu Phe<br>465 470 475 480 | | 1440 |
| ccc agg ctg gag gaa atg ggg gcc agg atg ctc ctt cag gtc cac gac<br>Pro Arg Leu Glu Glu Met Gly Ala Arg Met Leu Leu Gln Val His Asp<br>485 490 495 | | 1488 |
| gag ctg gtc ctc gag gcc cca aaa gag ggg gcg gag gcc gtg gcc cgg<br>Glu Leu Val Leu Glu Ala Pro Lys Glu Gly Ala Glu Ala Val Ala Arg<br>500 505 510 | | 1536 |
| ctg gtc aag gag gtc atg gag ggg gtg tat ccc ctg gcc gtg ccc ctg<br>Leu Val Lys Glu Val Met Glu Gly Val Tyr Pro Leu Ala Val Pro Leu<br>515 520 525 | | 1584 |
| gag gtg gag gtg ggg ata ggg gag gac tgg ctc tcc gcc aag gag gcg<br>Glu Val Glu Val Gly Ile Gly Glu Asp Trp Leu Ser Ala Lys Glu Ala<br>530 535 540 | | 1632 |
| gcc gc<br>Ala<br>545 | | 1637 |

<210> SEQ ID NO 63
<211> LENGTH: 545
<212> TYPE: PRT
<213> ORGANISM: Thermus aquaticus
<400> SEQUENCE: 63

-continued

```
Ser Pro Lys Ala Leu Glu Ala Pro Trp Pro Pro Glu Gly Ala
 1               5                  10                 15

Phe Val Gly Phe Val Leu Ser Arg Lys Glu Pro Met Trp Ala Asp Leu
                20                  25                  30

Leu Ala Leu Ala Ala Ala Arg Gly Gly Arg Val His Arg Ala Pro Glu
            35                  40                  45

Pro Tyr Lys Ala Leu Arg Asp Leu Lys Glu Ala Arg Gly Leu Leu Ala
 50                  55                  60

Lys Asp Leu Ser Val Leu Ala Leu Arg Glu Gly Gly Leu Pro Pro
 65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
                100                 105                 110

Ala Gly Glu Arg Ala Ala Leu Ser Glu Arg Leu Phe Ala Asn Leu Trp
            115                 120                 125

Gly Arg Leu Glu Gly Glu Glu Arg Leu Leu Trp Leu Tyr Arg Glu Val
 130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
                195                 200                 205

Leu Gly Leu Pro Ala Ile Gly Lys Thr Glu Lys Thr Gly Lys Arg Ser
 210                 215                 220

Thr Ser Ala Ala Val Leu Glu Ala Leu Arg Glu Ala His Pro Ile Val
225                 230                 235                 240

Gly Lys Ile Leu Gln Tyr Arg Glu Leu Thr Lys Leu Lys Ser Thr Tyr
                245                 250                 255

Ile Asp Pro Leu Pro Asp Leu Ile His Pro Arg Thr Gly Arg Leu His
            260                 265                 270

Thr Arg Phe Asn Gln Thr Ala Thr Ala Thr Gly Arg Leu Ser Ser Ser
                275                 280                 285

Asp Pro Asn Leu Gln Asn Ile Pro Val Arg Thr Pro Leu Gly Gln Arg
 290                 295                 300

Ile Arg Arg Ala Phe Ile Ala Glu Glu Gly Trp Leu Leu Val Ala Leu
305                 310                 315                 320

Asp Tyr Ser Gln Ile Glu Leu Arg Val Leu Ala His Leu Ser Gly Asp
                325                 330                 335

Glu Asn Leu Ile Arg Val Phe Gln Glu Gly Arg Asp Ile His Thr Glu
            340                 345                 350

Thr Ala Ser Trp Met Phe Gly Val Pro Arg Glu Ala Val Asp Pro Leu
                355                 360                 365

Met Arg Arg Ala Ala Lys Thr Ile Asn Phe Gly Val Leu Tyr Gly Met
 370                 375                 380

Ser Ala His Arg Leu Ser Gln Glu Leu Ala Ile Pro Tyr Glu Glu Ala
385                 390                 395                 400

Gln Ala Phe Ile Glu Arg Cys Phe Gln Ser Phe Pro Lys Val Arg Ala
                405                 410                 415
```

```
Trp Ile Glu Lys Thr Leu Glu Glu Gly Arg Arg Arg Gly Tyr Val Glu
            420                 425                 430

Thr Leu Phe Gly Arg Arg Arg Tyr Val Pro Asp Leu Glu Ala Arg Val
                435                 440                 445

Lys Ser Val Arg Glu Ala Ala Glu Arg Met Ala Phe Asn Met Pro Val
    450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Met Leu Leu Gln Val His Asp
                    485                 490                 495

Glu Leu Val Leu Glu Ala Pro Lys Glu Gly Ala Glu Ala Val Ala Arg
                500                 505                 510

Leu Val Lys Glu Val Met Glu Gly Val Tyr Pro Leu Ala Val Pro Leu
            515                 520                 525

Glu Val Glu Val Gly Ile Gly Glu Asp Trp Leu Ser Ala Lys Glu Ala
    530                 535                 540

Ala
545

<210> SEQ ID NO 64
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 64 agc ccc aag gcc ctg gag gag gcc ccc tgg ccc ccg ccg gaa ggg gcc      48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt      96
Phe Val Gly Phe Val Leu Ser Arg Lys Glu Pro Met Trp Ala Asp Leu
                20                  25                  30 ctg gcc ctg gcc gcc gcc agg ggg ggc cgg gtc cac cgg gcc ccc gag     144
Leu Ala Leu Ala Ala Ala Arg Gly Gly Arg Val His Arg Ala Pro Glu
            35                  40                  45 cct tat aaa gcc ctc agg gac ctg aag gag gcg cgg ggg ctt ctc gcc     192
Pro Tyr Lys Ala Leu Arg Asp Leu Lys Glu Ala Arg Gly Leu Leu Ala
    50                  55                  60 aaa gac ctg agc gtt ctg gcc ctg agg gaa ggc ctt ggc ctc ccg ccc     240
Lys Asp Leu Ser Val Leu Ala Leu Arg Glu Gly Leu Gly Leu Pro Pro
65                  70                  75                  80 ggc gac gac ccc atg ctc ctc gcc tac ctc ctg gac cct tcc aac acc     288
Gly Asp Asp Pro Met Leu Leu Ala Tyr Leu Leu Asp Pro Ser Asn Thr
                85                  90                  95 acc ccc gag ggg gtg gcc cgg cgc tac ggc ggg gag tgg acg gag gag     336
Thr Pro Glu Gly Val Ala Arg Arg Tyr Gly Gly Glu Trp Thr Glu Glu
                100                 105                 110 gcg ggg gag cgg gcc gcc ctt tcc gag agg ctc ttc gcc aac ctg tgg     384
Ala Gly Glu Arg Ala Ala Leu Ser Glu Arg Leu Phe Ala Asn Leu Trp
            115                 120                 125 ggg agg ctt gag ggg gag gag agg ctc ctt tgg ctt tac cgg gag gtg     432
Gly Arg Leu Glu Gly Glu Glu Arg Leu Leu Trp Leu Tyr Arg Glu Val
        130                 135                 140 gag agg ccc ctt tcc gct gtc ctg gcc cac atg gag gcc acg ggg gtg     480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag     528
```

```
                Arg Leu Asp Val Ala Tyr Leu Arg Ala Leu Ser Leu Glu Val Ala Glu
                            165                 170                 175 gag atc gcc cgc ctc gag gcc gag gtc ttc cgc ctg gcc ggc cgc ccc      576
Glu Ile Ala Arg Leu Glu Ala Glu Val Phe Arg Leu Ala Gly Arg Pro
            180                 185                 190 ttc aac ctc aac tcc cgg gac cag ctg gaa agg gtc ctc ttt gac gag      624
Phe Asn Leu Asn Ser Arg Asp Gln Leu Glu Arg Val Leu Phe Asp Glu
            195                 200                 205 cta ggg ctt ccc gcc atc ggc aag acg gag aag acc ggc aag cgc tcc      672
Leu Gly Leu Pro Ala Ile Gly Lys Thr Glu Lys Thr Gly Lys Arg Ser
        210                 215                 220 acc agc gcc gcc gtc ctg gag gcc ctc cgc gag gcc cac ccc atc gtg      720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac      768
Glu Lys Ile Leu Gln Tyr Arg Glu Leu Thr Lys Leu Lys Ser Thr Tyr
                245                 250                 255 att gac ccc ttg ccg gac ctc atc cac ccc agg acg ggc cgc ctc cac      816
Ile Asp Pro Leu Pro Asp Leu Ile His Pro Arg Thr Gly Arg Leu His
            260                 265                 270 acc cgc ttc aac cag acg gcc acg gcc acg ggc agg cta agt agc tcc      864
Thr Arg Phe Asn Gln Thr Ala Thr Ala Thr Gly Arg Leu Ser Ser Ser
        275                 280                 285 gat ccc aac ctc cag aac atc ccc gtc cgc acc ccg ctt ggg cag agg      912
Asp Pro Asn Leu Gln Asn Ile Pro Val Arg Thr Pro Leu Gly Gln Arg
    290                 295                 300 atc cgc cgg gcc ttc atc gcc gag gag ggg tgg cta ttg gtg gcc ctg      960
Ile Arg Arg Ala Phe Ile Ala Glu Glu Gly Trp Leu Leu Val Ala Leu
305                 310                 315                 320 gac tat agc cag ata gag ctc agg gtg ctg gcc cac ctc tcc ggc gac     1008
Asp Tyr Ser Gln Ile Glu Leu Arg Val Leu Ala His Leu Ser Gly Asp
                325                 330                 335 gag aac ctg atc cgg gtc ttc cag gag ggg cgg gac atc cac acg gag     1056
Glu Asn Leu Ile Arg Val Phe Gln Glu Gly Arg Asp Ile His Thr Glu
            340                 345                 350 acc gcc agc tgg atg ttc ggc gtc ccc cgg gag gcc gtg gac ccc ctg     1104
Thr Ala Ser Trp Met Phe Gly Val Pro Arg Glu Ala Val Asp Pro Leu
        355                 360                 365 atg cgc cgg gcg gcc aag acc atc aac ttc ggg gtc ctc tac ggc atg     1152
Met Arg Arg Ala Ala Lys Thr Ile Asn Phe Gly Val Leu Tyr Gly Met
    370                 375                 380 tcg gcc cac cgc ctc tcc cag gag cta gcc atc cct tac gag gag gcc     1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc     1248
Gln Ala Phe Ile Glu Arg Tyr Phe Gln Ser Phe Pro Lys Val Arg Ala
                405                 410                 415 tgg att gag aag acc ctg gag gag ggc agg agg cgg ggg tac gtg gag     1296
Trp Ile Glu Lys Thr Leu Glu Glu Gly Arg Arg Arg Gly Tyr Val Glu
            420                 425                 430 acc ctc ttc ggc cgc cgc cgc tac gtg cca gac cta gag gcc cgg gtg     1344
Thr Leu Phe Gly Arg Arg Arg Tyr Val Pro Asp Leu Glu Ala Arg Val
        435                 440                 445 aag agc gtg cgg gag gcg gcc gag cgc atg gcc ttc aac atg ccc gtc     1392
Lys Ser Val Arg Glu Ala Ala Glu Arg Met Ala Phe Asn Met Pro Val
    450                 455                 460 cag ggc acc gcc gcc gac ctc atg aag ctg gct atg gtg aag ctc ttc     1440
Gln Gly Thr Ala Ala Asp Leu Met Lys Leu Ala Met Val Lys Leu Phe
465                 470                 475                 480
```

| | | | | | | | | | | | | | | | |
|---|---|---|---|---|---|---|---|---|---|---|---|---|---|---|---|
| ccc | agg | ctg | gag | gaa | atg | ggg | gcc | agg | atg | ctc | ctt | cag | gtc | cac | gac | 1488 |
| Pro | Arg | Leu | Glu | Glu | Met | Gly | Ala | Arg | Met | Leu | Leu | Gln | Val | His | Asp |
| | | | 485 | | | | | 490 | | | | | 495 | | |
| gag | ctg | gtc | ctc | gag | gcc | cca | aaa | gag | ggg | gcg | gag | gcc | gtg | gcc | cgg | 1536 |
| Glu | Leu | Val | Leu | Glu | Ala | Pro | Lys | Glu | Gly | Ala | Glu | Ala | Val | Ala | Arg |
| | 500 | | | | | | 505 | | | | | 510 | | | |
| ctg | gcc | aag | gag | gtc | atg | gag | ggg | gtg | tat | ccc | ctg | gcc | gtg | ccc | ctg | 1584 |
| Leu | Ala | Lys | Glu | Val | Met | Glu | Gly | Val | Tyr | Pro | Leu | Ala | Val | Pro | Leu |
| | | 515 | | | | 520 | | | | | 525 | | | | |
| gag | gtg | gag | gtg | ggg | ata | ggg | gag | gac | cgg | ctc | tcc | gcc | aag | gag | gcg | 1632 |
| Glu | Val | Glu | Val | Gly | Ile | Gly | Glu | Asp | Arg | Leu | Ser | Ala | Lys | Glu | Ala |
| | 530 | | | | | 535 | | | | | 540 | | | | |
| gcc | gc | | | | | | | | | | | | | | | 1637 |
| Ala | | | | | | | | | | | | | | | |
| 545 | | | | | | | | | | | | | | | |

<210> SEQ ID NO 65
<211> LENGTH: 545
<212> TYPE: PRT
<213> ORGANISM: Thermus aquaticus

<400> SEQUENCE: 65

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
                20                  25                  30

Leu Ala Leu Ala Ala Ala Arg Gly Gly Arg Val His Arg Ala Pro Glu
            35                  40                  45

Pro Tyr Lys Ala Leu Arg Asp Leu Lys Glu Ala Arg Gly Leu Leu Ala
    50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
            100                 105                 110

Ala Gly Glu Arg Ala Ala Leu Ser Glu Arg Leu Phe Ala Asn Leu Trp
        115                 120                 125

Gly Arg Leu Glu Gly Glu Glu Arg Leu Leu Trp Leu Tyr Arg Glu Val
    130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
        195                 200                 205

Leu Gly Leu Pro Ala Ile Gly Lys Thr Glu Lys Thr Gly Lys Arg Ser
    210                 215                 220

Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Lys Ser Thr Tyr
                245                 250                 255

Ile Asp Pro Leu Pro Asp Leu Ile His Pro Arg Thr Gly Arg Leu His
            260                 265                 270

```
Thr Arg Phe Asn Gln Thr Ala Thr Ala Thr Gly Arg Leu Ser Ser Ser
            275                 280                 285
Asp Pro Asn Leu Gln Asn Ile Pro Val Arg Thr Pro Leu Gly Gln Arg
        290                 295                 300
Ile Arg Arg Ala Phe Ile Ala Glu Glu Gly Trp Leu Val Ala Leu
305                 310                 315                 320
Asp Tyr Ser Gln Ile Glu Leu Arg Val Leu Ala His Leu Ser Gly Asp
                325                 330                 335
Glu Asn Leu Ile Arg Val Phe Gln Glu Gly Arg Asp Ile His Thr Glu
            340                 345                 350
Thr Ala Ser Trp Met Phe Gly Val Pro Arg Glu Ala Val Asp Pro Leu
        355                 360                 365
Met Arg Arg Ala Ala Lys Thr Ile Asn Phe Gly Val Leu Tyr Gly Met
370                 375                 380
Ser Ala His Arg Leu Ser Gln Glu Leu Ala Ile Pro Tyr Glu Glu Ala
385                 390                 395                 400
Gln Ala Phe Ile Glu Arg Tyr Phe Gln Ser Phe Pro Lys Val Arg Ala
                405                 410                 415
Trp Ile Glu Lys Thr Leu Glu Glu Gly Arg Arg Arg Gly Tyr Val Glu
            420                 425                 430
Thr Leu Phe Gly Arg Arg Arg Tyr Val Pro Asp Leu Glu Ala Arg Val
        435                 440                 445
Lys Ser Val Arg Glu Ala Ala Glu Arg Met Ala Phe Asn Met Pro Val
450                 455                 460
Gln Gly Thr Ala Ala Asp Leu Met Lys Leu Ala Met Val Lys Leu Phe
465                 470                 475                 480
Pro Arg Leu Glu Glu Met Gly Ala Arg Met Leu Leu Gln Val His Asp
                485                 490                 495
Glu Leu Val Leu Glu Ala Pro Lys Glu Gly Ala Glu Ala Val Ala Arg
            500                 505                 510
Leu Ala Lys Glu Val Met Glu Gly Val Tyr Pro Leu Ala Val Pro Leu
        515                 520                 525
Glu Val Glu Val Gly Ile Gly Glu Asp Arg Leu Ser Ala Lys Glu Ala
530                 535                 540
Ala
545

<210> SEQ ID NO 66
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 66 agc ccc aag gcc ctg gag gag gcc ccc tgg ccc ccg ccg gaa ggg gcc      48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt      96
Phe Val Gly Phe Val Leu Ser Arg Lys Glu Pro Met Trp Ala Asp Leu
            20                  25                  30 ctg gcc ctg gcc gcc gcc agg ggg ggc cgg gtc cac cgg gcc ccc gag     144
Leu Ala Leu Ala Ala Ala Arg Gly Gly Arg Val His Arg Ala Pro Glu
        35                  40                  45 cct tat aaa gcc ctc agg gac ctg aag gag gcg cgg ggg ctt ctc gcc     192
Pro Tyr Lys Ala Leu Arg Asp Leu Lys Glu Ala Arg Gly Leu Leu Ala
```

```
                50                    55                    60
aaa gac ctg agc gtt ctg gcc ctg agg gaa ggc ctt ggc ctc ccg ccc       240
Lys Asp Leu Ser Val Leu Ala Leu Arg Glu Gly Leu Gly Leu Pro Pro
 65              70                  75                  80 ggc gac gac ccc atg ctc ctc gcc tac ctc ctg gac cct tcc aac acc       288
Gly Asp Asp Pro Met Leu Leu Ala Tyr Leu Leu Asp Pro Ser Asn Thr
                 85                  90                  95 acc ccc gag ggg gtg gcc cgg cgc tac ggc ggg gag tgg acg gag gag       336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg       384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg       432
Gly Arg Leu Glu Gly Glu Glu Arg Leu Leu Trp Leu Tyr Arg Glu Val
    130                 135                 140 gag agg ccc ctt tcc gct gtc ctg gcc cac atg gag gcc acg ggg gtg       480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag       528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc       576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag       624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc       672
Leu Gly Leu Pro Ala Ile Gly Lys Thr Glu Lys Thr Gly Lys Arg Ser
    210                 215                 220 acc agc gcc gcc gtc ctg gag gcc ctc cgc gag gcc cac ccc atc gtg       720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac       768
Glu Lys Ile Leu Gln Tyr Arg Glu Leu Thr Lys Leu Lys Ser Thr Tyr
                245                 250                 255 att gac ccc ttg ccg gac ctc atc cac ccc agg acg ggc cgc ctc cac       816
Ile Asp Pro Leu Pro Asp Leu Ile His Pro Arg Thr Gly Arg Leu His
            260                 265                 270 acc cgc ttc aac cag acg gcc acg gcc acg ggc agg cta agt agc tcc       864
Thr Arg Phe Asn Gln Thr Ala Thr Ala Thr Gly Arg Leu Ser Ser Ser
        275                 280                 285 gat ccc aac ctc cag aac atc ccc atc cgc acc ccg ctt ggg cag agg       912
Asp Pro Asn Leu Gln Asn Ile Pro Ile Arg Thr Pro Leu Gly Gln Arg
    290                 295                 300 atc cgc cgg gcc ttc atc gcc gag gag ggg tgg cta ttg gtg gcc ctg       960
Ile Arg Arg Ala Phe Ile Ala Glu Glu Gly Trp Leu Leu Val Ala Leu
305                 310                 315                 320 gac tat agc cag ata gag ctc agg gtg ctg gcc cac ctc tcc ggc gac      1008
Asp Tyr Ser Gln Ile Glu Leu Arg Val Leu Ala His Leu Ser Gly Asp
                325                 330                 335 gag aac ctg atc cgg gtc ttc cag gag ggg cgg gac ttc cac acg gag      1056
Glu Asn Leu Ile Arg Val Phe Gln Glu Gly Arg Asp Phe His Thr Glu
            340                 345                 350 acc gcc agc tgg atg ttc ggc gtc ccc cgg gag gcc gtg gac ccc ctg      1104
Thr Ala Ser Trp Met Phe Gly Val Pro Arg Glu Ala Val Asp Pro Leu
        355                 360                 365 atg cgc cgg gcg gcc aag acc atc aac ttc ggg gtc ctc tac ggc atg      1152
```

```
Met Arg Arg Ala Ala Lys Thr Ile Asn Phe Gly Val Leu Tyr Gly Met
    370                 375                 380 tcg gcc cac cgc ctc tcc cag gag cta gcc atc cct tac gag gag gcc      1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc      1248
Gln Ala Phe Ile Glu Arg Tyr Phe Gln Ser Phe Pro Lys Val Arg Ala
                405                 410                 415 tgg att gag aag acc ctg gag gag ggc agg agg cgg ggg tac gtg gag      1296
Trp Ile Glu Lys Thr Leu Glu Glu Gly Arg Arg Arg Gly Tyr Val Glu
            420                 425                 430 acc ctc ttc ggc cgc cgc cgc tac gtg cca gac cta gag gcc cgg gtg      1344
Thr Leu Phe Gly Arg Arg Arg Tyr Val Pro Asp Leu Glu Ala Arg Val
        435                 440                 445 aag agc gtg cgg gag gcg gcc gag cgc aag gcc ttc aac atg ccc gtc      1392
Lys Ser Val Arg Glu Ala Ala Glu Arg Lys Ala Phe Asn Met Pro Val
450                 455                 460 cag ggc acc gcc gcc gac ctc atg aag ctg gct atg gtg aag ctc ttc      1440
Gln Gly Thr Ala Ala Asp Leu Met Lys Leu Ala Met Val Lys Leu Phe
465                 470                 475                 480 ccc agg ctg gag gaa atg gag gcc agg atg ctc ctt cag gtc cac gac      1488
Pro Arg Leu Glu Glu Met Glu Ala Arg Met Leu Leu Gln Val His Asp
                485                 490                 495 gag ctg gtc ctc gag gcc cca aaa gag ggg gcg gag gca gtg gcc cgg      1536
Glu Leu Val Leu Glu Ala Pro Lys Glu Gly Ala Glu Ala Val Ala Arg
            500                 505                 510 ctg gcc aag gag gtc atg gag ggg gtg tat ccc ctg gcc gtg ccc ctg      1584
Leu Ala Lys Glu Val Met Glu Gly Val Tyr Pro Leu Ala Val Pro Leu
        515                 520                 525 gag gtg gag gtg ggg ata ggg gag gac tgg ctc tcc gcc aag gag gcg      1632
Glu Val Glu Val Gly Ile Gly Glu Asp Trp Leu Ser Ala Lys Glu Ala
530                 535                 540 gcc gc                                                                1637
Ala
545

<210> SEQ ID NO 67
<211> LENGTH: 545
<212> TYPE: PRT
<213> ORGANISM: Thermus aquaticus

<400> SEQUENCE: 67

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
                20                  25                  30

Leu Ala Leu Ala Ala Ala Arg Gly Gly Arg Val His Arg Ala Pro Glu
            35                  40                  45

Pro Tyr Lys Ala Leu Arg Asp Leu Lys Glu Ala Arg Gly Leu Leu Ala
        50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
            100                 105                 110

Ala Gly Glu Arg Ala Ala Leu Ser Glu Arg Leu Phe Ala Asn Leu Trp
        115                 120                 125
```

```
Gly Arg Leu Glu Gly Glu Glu Arg Leu Leu Trp Leu Tyr Arg Glu Val
    130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                    165                 170                 175

Glu Ile Ala Arg Leu Glu Ala Glu Val Phe Arg Leu Ala Gly His Pro
                180                 185                 190

Phe Asn Leu Asn Ser Arg Asp Gln Leu Glu Arg Val Leu Phe Asp Glu
                195                 200                 205

Leu Gly Leu Pro Ala Ile Gly Lys Thr Glu Lys Thr Gly Lys Arg Ser
210                 215                 220

Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Lys Ser Thr Tyr
                    245                 250                 255

Ile Asp Pro Leu Pro Asp Leu Ile His Pro Arg Thr Gly Arg Leu His
                260                 265                 270

Thr Arg Phe Asn Gln Thr Ala Thr Ala Thr Gly Arg Leu Ser Ser Ser
            275                 280                 285

Asp Pro Asn Leu Gln Asn Ile Pro Ile Arg Thr Pro Leu Gly Gln Arg
290                 295                 300

Ile Arg Arg Ala Phe Ile Ala Glu Glu Gly Trp Leu Leu Val Ala Leu
305                 310                 315                 320

Asp Tyr Ser Gln Ile Glu Leu Arg Val Leu Ala His Leu Ser Gly Asp
                    325                 330                 335

Glu Asn Leu Ile Arg Val Phe Gln Glu Gly Arg Asp Phe His Thr Glu
                340                 345                 350

Thr Ala Ser Trp Met Phe Gly Val Pro Arg Glu Ala Val Asp Pro Leu
            355                 360                 365

Met Arg Arg Ala Ala Lys Thr Ile Asn Phe Gly Val Leu Tyr Gly Met
370                 375                 380

Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
                    405                 410                 415

Trp Ile Glu Lys Thr Leu Glu Glu Gly Arg Arg Arg Gly Tyr Val Glu
                420                 425                 430

Thr Leu Phe Gly Arg Arg Arg Tyr Val Pro Asp Leu Glu Ala Arg Val
            435                 440                 445

Lys Ser Val Arg Glu Ala Ala Glu Arg Lys Ala Phe Asn Met Pro Val
450                 455                 460

Gln Gly Thr Ala Ala Asp Leu Met Lys Leu Ala Met Val Lys Leu Phe
465                 470                 475                 480

Pro Arg Leu Glu Glu Met Glu Ala Arg Met Leu Leu Gln Val His Asp
                    485                 490                 495

Glu Leu Val Leu Glu Ala Pro Lys Glu Gly Ala Glu Ala Val Ala Arg
                500                 505                 510

Leu Ala Lys Glu Val Met Glu Gly Val Tyr Pro Leu Ala Val Pro Leu
            515                 520                 525

Glu Val Glu Val Gly Ile Gly Glu Asp Trp Leu Ser Ala Lys Glu Ala
530                 535                 540

Ala
```

-continued

545

<210> SEQ ID NO 68
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 68

```
agc ccc aag gcc ctg gag gag gcc ccc tgg ccc ccg ccg gaa ggg gcc        48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt        96
Phe Val Gly Phe Val Leu Ser Arg Lys Glu Pro Met Trp Ala Asp Leu
                20                  25                  30 ctg gcc ctg gcc gcc gcc agg ggg ggc cgg gtc cac cgg gcc ccc gag       144
Leu Ala Leu Ala Ala Ala Arg Gly Gly Arg Val His Arg Ala Pro Glu
            35                  40                  45 cct tat aaa gcc ctc agg gac ctg aag gag gcg cgg ggg ctt ctc gcc       192
Pro Tyr Lys Ala Leu Arg Asp Leu Lys Glu Ala Arg Gly Leu Leu Ala
        50                  55                  60 aaa gac ctg agc gtt ctg gcc ctg agg gaa ggc ctt ggc ctc ccg ccc       240
Lys Asp Leu Ser Val Leu Ala Leu Arg Glu Gly Leu Gly Leu Pro Pro
65                  70                  75                  80 ggc gac gac ccc atg ctc ctc gcc tac ctc ctg gac cct tcc aac acc       288
Gly Asp Asp Pro Met Leu Leu Ala Tyr Leu Leu Asp Pro Ser Asn Thr
                85                  90                  95 acc ccc gag ggg gtg gcc cgg cgc tac ggg ggg gag tgg acg gag gag       336
Thr Pro Glu Gly Val Ala Arg Arg Tyr Gly Gly Glu Trp Thr Glu Glu
                100                 105                 110 gcg ggg gag cgg gcc gcc ctt tcc gag agg ctc ttc gcc aac ctg tgg       384
Ala Gly Glu Arg Ala Ala Leu Ser Glu Arg Leu Phe Ala Asn Leu Trp
            115                 120                 125 ggg agg ctt gag ggg gag gag agg ctc ctt tgg ctt tac cgg gag gtg       432
Gly Arg Leu Glu Gly Glu Glu Arg Leu Leu Trp Leu Tyr Arg Glu Val
        130                 135                 140 gag agg ccc ctt tcc gct gtc ctg gcc cac atg gag gcc acg ggg gtg       480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag       528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc       576
Glu Ile Ala Arg Leu Glu Ala Glu Val Phe Arg Leu Ala Gly His Pro
                180                 185                 190 ttc aac ctc aac tcc cgg gac cag ctg gaa agg gtc ctc ttt gac gag       624
Phe Asn Leu Asn Ser Arg Asp Gln Leu Glu Arg Val Leu Phe Asp Glu
            195                 200                 205 cta ggg ctt ccc gcc atc ggc aag acg gag aag tcc ggc aag cgc tcc       672
Leu Gly Leu Pro Ala Ile Gly Lys Thr Glu Lys Ser Gly Lys Arg Ser
        210                 215                 220 acc agc gcc gcc gtc ctg gag gcc ctc cgc gag gcc cac ccc atc gtg       720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac       768
Glu Lys Ile Leu Gln Tyr Arg Glu Leu Thr Lys Leu Lys Ser Thr Tyr
                245                 250                 255 att gac ccc ttg ccg gac cac atc cac ccc agg acg ggc cgc ctc cac       816
Ile Asp Pro Leu Pro Asp His Ile His Pro Arg Thr Gly Arg Leu His
```

```
                      260                 265                 270
acc cgc ttc aac cag acg gcc acg gcc acg ggc agg cta agt agc tcc          864
Thr Arg Phe Asn Gln Thr Ala Thr Ala Thr Gly Arg Leu Ser Ser Ser
        275                 280                 285 gat ccc aac ctc cag aac atc ccc gtc cgc acc ccg ctt ggg cag agg          912
Asp Pro Asn Leu Gln Asn Ile Pro Val Arg Thr Pro Leu Gly Gln Arg
290                 295                 300 atc cgc cgg gcc ttc atc gcc gag gag ggg tgg cta ttg gtg gcc ctg          960
Ile Arg Arg Ala Phe Ile Ala Glu Glu Gly Trp Leu Leu Val Ala Leu
305                 310                 315                 320 gac tat agc cag ata gag ctc agg gtg ctg gcc cac ctc tcc ggc gac         1008
Asp Tyr Ser Gln Ile Glu Leu Arg Val Leu Ala His Leu Ser Gly Asp
                325                 330                 335 gag aac ctg atc cgg gtc ttc cag gag ggg cgg gac atc cac acg gag         1056
Glu Asn Leu Ile Arg Val Phe Gln Glu Gly Arg Asp Ile His Thr Glu
        340                 345                 350 acc gcc agc tgg atg ttc ggc gtc ccc cgg gag gcc gtg gac ccc ctg         1104
Thr Ala Ser Trp Met Phe Gly Val Pro Arg Glu Ala Val Asp Pro Leu
        355                 360                 365 atg cgc cgg gcg gcc aag acc atc aac ttc ggg gtc ctc tac ggc atg         1152
Met Arg Arg Ala Ala Lys Thr Ile Asn Phe Gly Val Leu Tyr Gly Met
370                 375                 380 tcg gcc cac cgc ctc tcc cag gag cta gcc atc cct tac gag gag gcc         1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc         1248
Gln Ala Phe Ile Glu Arg Tyr Phe Gln Ser Phe Pro Lys Val Arg Ala
                405                 410                 415 tgg att gag aag acc ctg gag gag ggc agg agg cgg ggg tat gtg gag         1296
Trp Ile Glu Lys Thr Leu Glu Glu Gly Arg Arg Arg Gly Tyr Val Glu
                420                 425                 430 acc ctc ttc ggc cgc cgc cgc tac gtg cca gac cta gag gcc cgg gtg         1344
Thr Leu Phe Gly Arg Arg Arg Tyr Val Pro Asp Leu Glu Ala Arg Val
        435                 440                 445 aag agc gtg cgg gag gcg gcc gag cgc atg gcc ttc aac atg ccc gtc         1392
Lys Ser Val Arg Glu Ala Ala Glu Arg Met Ala Phe Asn Met Pro Val
450                 455                 460 cag ggc acc gcc gcc gac ctc atg aag ctg gct atg gtg aag ctc ttc         1440
Gln Gly Thr Ala Ala Asp Leu Met Lys Leu Ala Met Val Lys Leu Phe
465                 470                 475                 480 ccc agg ctg gag gaa atg ggg gcc agg aag ctc ctt cag gtc cac gac         1488
Pro Arg Leu Glu Glu Met Gly Ala Arg Lys Leu Leu Gln Val His Asp
                485                 490                 495 gag ctg gtc ctc gag gcc cca aaa gag ggg gcg gag gcc gtg gcc cgg         1536
Glu Leu Val Leu Glu Ala Pro Lys Glu Gly Ala Glu Ala Val Ala Arg
                500                 505                 510 ctg gcc aag gag gtc atg gag ggg gtg tat ccc ctg gcc gtg ccc ctg         1584
Leu Ala Lys Glu Val Met Glu Gly Val Tyr Pro Leu Ala Val Pro Leu
        515                 520                 525 gag gtg gag gtg ggg ata ggg gag gac tgg ctc tcc gcc aag gag gcg         1632
Glu Val Glu Val Gly Ile Gly Glu Asp Trp Leu Ser Ala Lys Glu Ala
530                 535                 540 gcc gc                                                                   1637
Ala
545

<210> SEQ ID NO 69
<211> LENGTH: 545
<212> TYPE: PRT
<213> ORGANISM: Thermus aquaticus
```

<400> SEQUENCE: 69

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
            20                  25                  30

Leu Ala Leu Ala Ala Ala Arg Gly Gly Arg Val His Arg Ala Pro Glu
        35                  40                  45

Pro Tyr Lys Ala Leu Arg Asp Leu Lys Glu Ala Arg Gly Leu Leu Ala
    50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
                100                 105                 110

Ala Gly Glu Arg Ala Ala Leu Ser Glu Arg Leu Phe Ala Asn Leu Trp
            115                 120                 125

Gly Arg Leu Glu Gly Glu Glu Arg Leu Leu Trp Leu Tyr Arg Glu Val
        130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
        195                 200                 205

Leu Gly Leu Pro Ala Ile Gly Lys Thr Glu Lys Ser Gly Lys Arg Ser
    210                 215                 220

Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Lys Ser Thr Tyr
                245                 250                 255

Ile Asp Pro Leu Pro Asp His Ile His Pro Arg Thr Gly Arg Leu His
            260                 265                 270

Thr Arg Phe Asn Gln Thr Ala Thr Ala Thr Gly Arg Leu Ser Ser Ser
        275                 280                 285

Asp Pro Asn Leu Gln Asn Ile Pro Val Arg Thr Pro Leu Gly Gln Arg
    290                 295                 300

Ile Arg Arg Ala Phe Ile Ala Glu Glu Gly Trp Leu Leu Val Ala Leu
305                 310                 315                 320

Asp Tyr Ser Gln Ile Glu Leu Arg Val Leu Ala His Leu Ser Gly Asp
                325                 330                 335

Glu Asn Leu Ile Arg Val Phe Gln Glu Gly Arg Asp Ile His Thr Glu
            340                 345                 350

Thr Ala Ser Trp Met Phe Gly Val Pro Arg Glu Ala Val Asp Pro Leu
        355                 360                 365

Met Arg Arg Ala Ala Lys Thr Ile Asn Phe Gly Val Leu Tyr Gly Met
    370                 375                 380

Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala

-continued

```
                            405                 410                 415
Trp Ile Glu Lys Thr Leu Glu Glu Gly Arg Arg Gly Tyr Val Glu
                420                 425                 430

Thr Leu Phe Gly Arg Arg Arg Tyr Val Pro Asp Leu Glu Ala Arg Val
            435                 440                 445

Lys Ser Val Arg Glu Ala Ala Glu Arg Met Ala Phe Asn Met Pro Val
        450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Lys Leu Leu Gln Val His Asp
                485                 490                 495

Glu Leu Val Leu Glu Ala Pro Lys Glu Gly Ala Glu Ala Val Ala Arg
            500                 505                 510

Leu Ala Lys Glu Val Met Glu Gly Val Tyr Pro Leu Ala Val Pro Leu
        515                 520                 525

Glu Val Glu Val Gly Ile Gly Glu Asp Trp Leu Ser Ala Lys Glu Ala
    530                 535                 540

Ala
545

<210> SEQ ID NO 70
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 70 agc ccc aag gcc ctg gag gag gcc ccc tgg ccc ccg ccg gaa ggg gcc      48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt      96
Phe Val Gly Phe Val Leu Ser Arg Lys Glu Pro Met Trp Ala Asp Leu
                20                  25                  30 ctg gcc ctg gcc gcc gcc agg ggg ggc cgg gtc cac cgg gcc ccc gag     144
Leu Ala Leu Ala Ala Ala Arg Gly Gly Arg Val His Arg Ala Pro Glu
            35                  40                  45 cct tat aaa gcc ctc agg gac ctg aag gag gcg cgg ggg ctt ctc gcc     192
Pro Tyr Lys Ala Leu Arg Asp Leu Lys Glu Ala Arg Gly Leu Leu Ala
        50                  55                  60 aaa gac ctg agc gtt ctg gcc ctg agg gaa ggc ctt ggc ctc ccg ccc     240
Lys Asp Leu Ser Val Leu Ala Leu Arg Glu Gly Leu Gly Leu Pro Pro
65                  70                  75                  80 ggc gac gac ccc atg ctc ctc gcc tac ctc ctg gac cct tcc aac acc     288
Gly Asp Asp Pro Met Leu Leu Ala Tyr Leu Leu Asp Pro Ser Asn Thr
                85                  90                  95 acc ccc gag ggg gtg gcc cgg cgc tac ggc ggg gag tgg acg gag gag     336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg     384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg     432
Gly Arg Leu Glu Gly Glu Glu Arg Leu Leu Trp Leu Tyr Arg Glu Val
    130                 135                 140 gag agg ccc ctt tcc gct gtc ctg gcc cac atg gag gcc acg ggg gtg     480
Glu Arg Pro Leu Ser Ala Val Leu Ala His Met Glu Ala Thr Gly Val
145                 150                 155                 160
```

```
cgc ctg gac gtg gcc tat ctc agg gcc ttg tcc ctg gag gtg gcc gag      528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc      576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag      624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc      672
Leu Gly Leu Pro Ala Ile Gly Lys Thr Glu Lys Thr Gly Lys Arg Ser
    210                 215                 220 acc agc gcc gcc gtc ctg gag gcc ctc cgc gag gcc cac ccc atc gtg      720
Thr Ser Ala Ala Val Leu Glu Ala Leu Arg Glu Ala His Pro Ile Val
225                 230                 235                 240 gag aag atc ctg cgg tac cgg gag ctc acc aag ctg aag agc acc tac      768
Glu Lys Ile Leu Arg Tyr Arg Glu Leu Thr Lys Leu Lys Ser Thr Tyr
                245                 250                 255 att gac ccc ttg ccg gac ctc atc cac ccc agg acg ggc cgc ctc cac      816
Ile Asp Pro Leu Pro Asp Leu Ile His Pro Arg Thr Gly Arg Leu His
            260                 265                 270 acc cgc ttc aac cag acg gcc acg gcc acg ggc agg cta agt agc tcc      864
Thr Arg Phe Asn Gln Thr Ala Thr Ala Thr Gly Arg Leu Ser Ser Ser
        275                 280                 285 gat ccc aac ctc cag aac atc ccc gtc cgc acc ccg ctt ggg cag agg      912
Asp Pro Asn Leu Gln Asn Ile Pro Val Arg Thr Pro Leu Gly Gln Arg
    290                 295                 300 atc cgc cgg gcc ttc atc gcc gag gag ggg tgg cta ttg gtg gcc ctg      960
Ile Arg Arg Ala Phe Ile Ala Glu Glu Gly Trp Leu Leu Val Ala Leu
305                 310                 315                 320 gac tat agc cag ata gag ctc agg gtg ctg gcc cac ctc tcc ggc gac     1008
Asp Tyr Ser Gln Ile Glu Leu Arg Val Leu Ala His Leu Ser Gly Asp
                325                 330                 335 gag aac ctg atc cgg gtc ttc cag gag ggg cgg gac atc cac acg gag     1056
Glu Asn Leu Ile Arg Val Phe Gln Glu Gly Arg Asp Ile His Thr Glu
            340                 345                 350 acc gcc agc tgg atg ttc ggc gtc ccc cgg gag gcc gtg gac ccc ctg     1104
Thr Ala Ser Trp Met Phe Gly Val Pro Arg Glu Ala Val Asp Pro Leu
        355                 360                 365 atg cgc cgg gcg gcc aag acc atc aac ttc ggg gtc ctc tac ggc atg     1152
Met Arg Arg Ala Ala Lys Thr Ile Asn Phe Gly Val Leu Tyr Gly Met
    370                 375                 380 tcg gcc cac cgc ctc tcc cag gag cta gcc atc cct tac gag gag gcc     1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc     1248
Gln Ala Phe Ile Glu Arg Tyr Phe Gln Ser Phe Pro Lys Val Arg Ala
                405                 410                 415 tgg att gag aag acc ctg gag gag ggc agg agg cgg ggg tac gtg gag     1296
Trp Ile Glu Lys Thr Leu Glu Glu Gly Arg Arg Arg Gly Tyr Val Glu
            420                 425                 430 acc ctc ttc ggc cgc cgc cgc tac gtg cca gac cta gag gcc cgg gtg     1344
Thr Leu Phe Gly Arg Arg Arg Tyr Val Pro Asp Leu Glu Ala Arg Val
        435                 440                 445 aag agc gtg cgg gag gcg gcc gag cgc atg gcc ttc aac atg ccc gtc     1392
Lys Ser Val Arg Glu Ala Ala Glu Arg Met Ala Phe Asn Met Pro Val
    450                 455                 460 cag ggc acc gcc gcc gac ctc atg aag ctg act atg gtg aag ctc ttc     1440
Gln Gly Thr Ala Ala Asp Leu Met Lys Leu Thr Met Val Lys Leu Phe
```

| | | | | | | | | | | | | | | | | |
|---|---|---|---|---|---|---|---|---|---|---|---|---|---|---|---|---|
| | | 465 | | | 470 | | | | 475 | | | | 480 | | | |
| ccc | agg | ctg | gag | gaa | atg | ggg | gcc | agg | atg | ctc | ctt | cag | gtc | cac | gac | 1488 |
| Pro | Arg | Leu | Glu | Glu | Met | Gly | Ala | Arg | Met | Leu | Leu | Gln | Val | His | Asp | |
| | | | | 485 | | | | | 490 | | | | | 495 | | |
| gag | ctg | gtc | ctc | gag | gcc | cca | aaa | gag | ggg | gcg | gag | gcc | gtg | gcc | cgg | 1536 |
| Glu | Leu | Val | Leu | Glu | Ala | Pro | Lys | Glu | Gly | Ala | Glu | Ala | Val | Ala | Arg | |
| | | 500 | | | | | 505 | | | | | 510 | | | | |
| ctg | gcc | aag | gag | gtc | atg | gag | ggg | gtg | tat | ccc | ctg | gcc | gtg | ccc | ctg | 1584 |
| Leu | Ala | Lys | Glu | Val | Met | Glu | Gly | Val | Tyr | Pro | Leu | Ala | Val | Pro | Leu | |
| | | | 515 | | | | | 520 | | | | | 525 | | | |
| gag | gtg | gag | gtg | ggg | ata | ggg | gag | gac | tgg | ctc | tcc | gcc | aag | gag | gcg | 1632 |
| Glu | Val | Glu | Val | Gly | Ile | Gly | Glu | Asp | Trp | Leu | Ser | Ala | Lys | Glu | Ala | |
| | 530 | | | | | 535 | | | | | 540 | | | | | |
| gcc | gc | | | | | | | | | | | | | | | 1637 |
| Ala | | | | | | | | | | | | | | | | |
| 545 | | | | | | | | | | | | | | | | |

<210> SEQ ID NO 71
<211> LENGTH: 545
<212> TYPE: PRT
<213> ORGANISM: Thermus aquaticus

<400> SEQUENCE: 71

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
            20                  25                  30

Leu Ala Leu Ala Ala Ala Arg Gly Gly Arg Val His Arg Ala Pro Glu
        35                  40                  45

Pro Tyr Lys Ala Leu Arg Asp Leu Lys Glu Ala Arg Gly Leu Leu Ala
    50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
            100                 105                 110

Ala Gly Glu Arg Ala Ala Leu Ser Glu Arg Leu Phe Ala Asn Leu Trp
        115                 120                 125

Gly Arg Leu Glu Gly Glu Glu Arg Leu Leu Trp Leu Tyr Arg Glu Val
    130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
        195                 200                 205

Leu Gly Leu Pro Ala Ile Gly Lys Thr Glu Lys Thr Gly Lys Arg Ser
    210                 215                 220

Thr Ser Ala Ala Val Leu Glu Ala Leu Arg Glu Ala His Pro Ile Val
225                 230                 235                 240

Glu Lys Ile Leu Arg Tyr Arg Glu Leu Thr Lys Leu Lys Ser Thr Tyr
                245                 250                 255

Ile Asp Pro Leu Pro Asp Leu Ile His Pro Arg Thr Gly Arg Leu His

```
                    260                 265                 270
Thr Arg Phe Asn Gln Thr Ala Thr Ala Thr Gly Arg Leu Ser Ser Ser
                275                 280                 285

Asp Pro Asn Leu Gln Asn Ile Pro Val Arg Thr Pro Leu Gly Gln Arg
            290                 295                 300

Ile Arg Arg Ala Phe Ile Ala Glu Glu Gly Trp Leu Leu Val Ala Leu
305                 310                 315                 320

Asp Tyr Ser Gln Ile Glu Leu Arg Val Leu Ala His Leu Ser Gly Asp
                325                 330                 335

Glu Asn Leu Ile Arg Val Phe Gln Glu Gly Arg Asp Ile His Thr Glu
            340                 345                 350

Thr Ala Ser Trp Met Phe Gly Val Pro Arg Glu Ala Val Asp Pro Leu
            355                 360                 365

Met Arg Arg Ala Ala Lys Thr Ile Asn Phe Gly Val Leu Tyr Gly Met
370                 375                 380

Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
                405                 410                 415

Trp Ile Glu Lys Thr Leu Glu Glu Gly Arg Arg Arg Gly Tyr Val Glu
                420                 425                 430

Thr Leu Phe Gly Arg Arg Arg Tyr Val Pro Asp Leu Glu Ala Arg Val
            435                 440                 445

Lys Ser Val Arg Glu Ala Ala Glu Arg Met Ala Phe Asn Met Pro Val
450                 455                 460

Gln Gly Thr Ala Ala Asp Leu Met Lys Leu Thr Met Val Lys Leu Phe
465                 470                 475                 480

Pro Arg Leu Glu Glu Met Gly Ala Arg Met Leu Leu Gln Val His Asp
                485                 490                 495

Glu Leu Val Leu Glu Ala Pro Lys Glu Gly Ala Glu Ala Val Ala Arg
            500                 505                 510

Leu Ala Lys Glu Val Met Glu Gly Val Tyr Pro Leu Ala Val Pro Leu
            515                 520                 525

Glu Val Glu Val Gly Ile Gly Glu Asp Trp Leu Ser Ala Lys Glu Ala
            530                 535                 540

Ala
545

<210> SEQ ID NO 72
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 72 agc ccc aag gcc ctg gag gag gcc ccc tgg ccc ccg ccg gaa ggg gcc      48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt      96
Phe Val Gly Phe Val Leu Ser Arg Lys Glu Pro Met Trp Ala Asp Leu
                20                  25                  30 ctg gcc ctg gcc gcc gcc agg ggg ggc cgg gtc cac cgg gcc ccc gag     144
Leu Ala Leu Ala Ala Ala Arg Gly Gly Arg Val His Arg Ala Pro Glu
            35                  40                  45
```

```
cct tat aaa gcc ctc agg gac ctg aag gag gcg cgg ggg ctt ctc gcc       192
Pro Tyr Lys Ala Leu Arg Asp Leu Lys Glu Ala Arg Gly Leu Leu Ala
 50              55                  60 aaa gac ctg agc gtt ctg gcc ctg agg gaa ggc ctt ggc ctc ccg ccc       240
Lys Asp Leu Ser Val Leu Ala Leu Arg Glu Gly Leu Gly Leu Pro Pro
 65              70                  75                  80 ggc gac gac ccc atg ctc ctc gcc tac ctc ctg gac cct tcc aac acc       288
Gly Asp Asp Pro Met Leu Leu Ala Tyr Leu Leu Asp Pro Ser Asn Thr
                 85                  90                  95 acc ccc gag ggg gtg gcc cgg cgc tac ggg ggg gag tgg acg gag gag       336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg       384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg       432
Gly Arg Leu Glu Gly Glu Glu Arg Leu Leu Trp Leu Tyr Arg Glu Val
130                 135                 140 gag agg ccc ctt tcc gct gtc ctg gcc cac atg gag gcc acg ggg gtg       480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag       528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc       576
Glu Ile Ala Arg Leu Glu Ala Glu Val Phe Arg Leu Ala Gly His Pro
            180                 185                 190 ctc aac ctc aac tcc cgg gac cag ctg gaa agg gtc ctc ttt gac gag       624
Leu Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc       672
Leu Gly Leu Pro Ala Ile Gly Lys Thr Glu Lys Thr Gly Lys Arg Ser
210                 215                 220 acc agc gcc gcc gtc ctg gag gcc ctc cgc gag gcc cac ccc atc gtg       720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac       768
Glu Lys Ile Leu Gln Tyr Arg Glu Leu Thr Lys Leu Lys Ser Thr Tyr
                245                 250                 255 att gac ccc ttg cca gac ctc atc cac ccc agg acg ggc cgc ctc cac       816
Ile Asp Pro Leu Pro Asp Leu Ile His Pro Arg Thr Gly Arg Leu His
            260                 265                 270 acc cgc ttc aac cag acg gcc acg gcc acg ggc agg cta agt agc tcc       864
Thr Arg Phe Asn Gln Thr Ala Thr Ala Thr Gly Arg Leu Ser Ser Ser
        275                 280                 285 gat ccc aac ctc cag aac atc ccc gtc cgc acc ccg ctt ggg cag agg       912
Asp Pro Asn Leu Gln Asn Ile Pro Val Arg Thr Pro Leu Gly Gln Arg
290                 295                 300 atc cgc cgg gcc ttc atc gcc gag gag ggg tgg cta ttg gtg gcc ctg       960
Ile Arg Arg Ala Phe Ile Ala Glu Glu Gly Trp Leu Leu Val Ala Leu
305                 310                 315                 320 gac tat agc cag ata gag ctc agg gtg ctg gcc cac ctc tcc ggc gac      1008
Asp Tyr Ser Gln Ile Glu Leu Arg Val Leu Ala His Leu Ser Gly Asp
                325                 330                 335 gag aac ctg atc cgg gtc ttc cag gag ggg cgg gac atc cac acg gag      1056
Glu Asn Leu Ile Arg Val Phe Gln Glu Gly Arg Asp Ile His Thr Glu
            340                 345                 350 acc gcc agc tgg atg ttc ggc gtc ccc cgg gag gcc gtg gac ccc ctg      1104
Thr Ala Ser Trp Met Phe Gly Val Pro Arg Glu Ala Val Asp Pro Leu
        355                 360                 365
```

```
atg cgc cgg gcg gcc aag gcc atc aac ttc ggg gtc ctc tac ggc atg      1152
Met Arg Arg Ala Ala Lys Ala Ile Asn Phe Gly Val Leu Tyr Gly Met
    370                 375                 380 tca gcc cac cgc ctc tcc cag gag cta gcc atc cct tac gag gag gcc      1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc      1248
Gln Ala Phe Ile Glu Arg Tyr Phe Gln Ser Phe Pro Lys Val Arg Ala
                405                 410                 415 tgg att gag aag acc ctg gag gag ggc agg aga cgg ggg tac gtg gag      1296
Trp Ile Glu Lys Thr Leu Glu Glu Gly Arg Arg Arg Gly Tyr Val Glu
            420                 425                 430 acc ctc ttc ggc cgc cgc cgc tat gtg cct gac cta gag gcc cgg gtg      1344
Thr Leu Phe Gly Arg Arg Arg Tyr Val Pro Asp Leu Glu Ala Arg Val
        435                 440                 445 aag agc gtg cgg gag gcg gcc gag cgc atg gcc tac aac atg ccc gtc      1392
Lys Ser Val Arg Glu Ala Ala Glu Arg Met Ala Tyr Asn Met Pro Val
    450                 455                 460 cag ggc acc gcc gcc gac ctc atg aag ctg gct atg gtg aag ctc ttc      1440
Gln Gly Thr Ala Ala Asp Leu Met Lys Leu Ala Met Val Lys Leu Phe
465                 470                 475                 480 acc agg ctg gag gaa acg ggg gcc agg atg ctc ctt cag gtc cac gac      1488
Thr Arg Leu Glu Glu Thr Gly Ala Arg Met Leu Leu Gln Val His Asp
                485                 490                 495 gag ctg gtc ctc gag gcc cct aaa gag ggg gcg gag gcc gtg gcc cgg      1536
Glu Leu Val Leu Glu Ala Pro Lys Glu Gly Ala Glu Ala Val Ala Arg
            500                 505                 510 ctg gcc aag gag gtc atg gag ggg gtg tat ccc ctg gcc gtg ccc ctg      1584
Leu Ala Lys Glu Val Met Glu Gly Val Tyr Pro Leu Ala Val Pro Leu
        515                 520                 525 gag gtg gag gtg ggg ata ggg gag gac tgg ctc tcc gcc aag gag gcg      1632
Glu Val Glu Val Gly Ile Gly Glu Asp Trp Leu Ser Ala Lys Glu Ala
    530                 535                 540 gcc gc                                                                1637
Ala
545

<210> SEQ ID NO 73
<211> LENGTH: 545
<212> TYPE: PRT
<213> ORGANISM: Thermus aquaticus

<400> SEQUENCE: 73

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
                20                  25                  30

Leu Ala Leu Ala Ala Ala Arg Gly Gly Arg Val His Arg Ala Pro Glu
            35                  40                  45

Pro Tyr Lys Ala Leu Arg Asp Leu Lys Glu Ala Arg Gly Leu Leu Ala
        50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
            100                 105                 110

Ala Gly Glu Arg Ala Ala Leu Ser Glu Arg Leu Phe Ala Asn Leu Trp
```

-continued

```
            115                 120                 125
Gly Arg Leu Glu Gly Glu Arg Leu Leu Trp Leu Tyr Arg Glu Val
130                 135                 140
Glu Arg Pro Leu Ser Ala Val Leu Ala His Met Glu Ala Thr Gly Val
145                 150                 155                 160
Arg Leu Asp Val Ala Tyr Leu Arg Ala Leu Ser Leu Glu Val Ala Glu
                165                 170                 175
Glu Ile Ala Arg Leu Glu Ala Glu Val Phe Arg Leu Ala Gly His Pro
                180                 185                 190
Leu Asn Leu Asn Ser Arg Asp Gln Leu Glu Arg Val Leu Phe Asp Glu
                195                 200                 205
Leu Gly Leu Pro Ala Ile Gly Lys Thr Glu Lys Thr Gly Lys Arg Ser
210                 215                 220
Thr Ser Ala Ala Val Leu Glu Ala Leu Arg Glu Ala His Pro Ile Val
225                 230                 235                 240
Glu Lys Ile Leu Gln Tyr Arg Glu Leu Thr Lys Leu Lys Ser Thr Tyr
                245                 250                 255
Ile Asp Pro Leu Pro Asp Leu Ile His Pro Arg Thr Gly Arg Leu His
                260                 265                 270
Thr Arg Phe Asn Gln Thr Ala Thr Ala Thr Gly Arg Leu Ser Ser Ser
                275                 280                 285
Asp Pro Asn Leu Gln Asn Ile Pro Val Arg Thr Pro Leu Gly Gln Arg
290                 295                 300
Ile Arg Arg Ala Phe Ile Ala Glu Glu Gly Trp Leu Leu Val Ala Leu
305                 310                 315                 320
Asp Tyr Ser Gln Ile Glu Leu Arg Val Leu Ala His Leu Ser Gly Asp
                325                 330                 335
Glu Asn Leu Ile Arg Val Phe Gln Glu Gly Arg Asp Ile His Thr Glu
                340                 345                 350
Thr Ala Ser Trp Met Phe Gly Val Pro Arg Glu Ala Val Asp Pro Leu
                355                 360                 365
Met Arg Arg Ala Ala Lys Ala Ile Asn Phe Gly Val Leu Tyr Gly Met
370                 375                 380
Ser Ala His Arg Leu Ser Gln Glu Leu Ala Ile Pro Tyr Glu Glu Ala
385                 390                 395                 400
Gln Ala Phe Ile Glu Arg Tyr Phe Gln Ser Phe Pro Lys Val Arg Ala
                405                 410                 415
Trp Ile Glu Lys Thr Leu Glu Glu Gly Arg Arg Arg Gly Tyr Val Glu
                420                 425                 430
Thr Leu Phe Gly Arg Arg Arg Tyr Val Pro Asp Leu Glu Ala Arg Val
                435                 440                 445
Lys Ser Val Arg Glu Ala Ala Glu Arg Met Ala Tyr Asn Met Pro Val
450                 455                 460
Gln Gly Thr Ala Ala Asp Leu Met Lys Leu Ala Met Val Lys Leu Phe
465                 470                 475                 480
Thr Arg Leu Glu Glu Thr Gly Ala Arg Met Leu Leu Gln Val His Asp
                485                 490                 495
Glu Leu Val Leu Glu Ala Pro Lys Glu Gly Ala Glu Ala Val Ala Arg
                500                 505                 510
Leu Ala Lys Glu Val Met Glu Gly Val Tyr Pro Leu Ala Val Pro Leu
                515                 520                 525
Glu Val Glu Val Gly Ile Gly Glu Asp Trp Leu Ser Ala Lys Glu Ala
530                 535                 540
```

Ala
545

```
<210> SEQ ID NO 74
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 74
```

| | | | | | | | | | | | | | | | | |
|---|---|---|---|---|---|---|---|---|---|---|---|---|---|---|---|---|
| agc | ccc | aag | gcc | ctg | gag | gag | gcc | ccc | tgg | ccc | ccg | ccg | gaa | ggg | gcc | 48 |
| Ser | Pro | Lys | Ala | Leu | Glu | Glu | Ala | Pro | Trp | Pro | Pro | Pro | Glu | Gly | Ala | |
| 1 | | | | 5 | | | | | 10 | | | | | 15 | | |
| ttc | gtg | ggc | ttt | gtg | ctt | tcc | cgc | aag | gag | ccc | atg | tgg | gcc | gat | ctt | 96 |
| Phe | Val | Gly | Phe | Val | Leu | Ser | Arg | Lys | Glu | Pro | Met | Trp | Ala | Asp | Leu | |
| | | 20 | | | | | 25 | | | | | 30 | | | | |
| ctg | gcc | ctg | gcc | gcc | gcc | agg | ggg | ggc | cgg | gtc | cac | cgg | gcc | ccc | gag | 144 |
| Leu | Ala | Leu | Ala | Ala | Ala | Arg | Gly | Gly | Arg | Val | His | Arg | Ala | Pro | Glu | |
| | 35 | | | | | 40 | | | | | 45 | | | | | |
| cct | tat | aaa | gcc | ctc | agg | gac | ctg | aag | gag | gcg | cgg | ggg | ctt | ctc | gcc | 192 |
| Pro | Tyr | Lys | Ala | Leu | Arg | Asp | Leu | Lys | Glu | Ala | Arg | Gly | Leu | Leu | Ala | |
| 50 | | | | | 55 | | | | | 60 | | | | | | |
| aaa | gac | ctg | agc | gtt | ctg | gcc | ctg | agg | gaa | ggc | ctt | ggc | ctc | ccg | ccc | 240 |
| Lys | Asp | Leu | Ser | Val | Leu | Ala | Leu | Arg | Glu | Gly | Leu | Gly | Leu | Pro | Pro | |
| 65 | | | | 70 | | | | | 75 | | | | | 80 | | |
| ggc | gac | gac | ccc | atg | ctc | ctc | gcc | tac | ctc | ctg | gac | cct | tcc | aac | acc | 288 |
| Gly | Asp | Asp | Pro | Met | Leu | Leu | Ala | Tyr | Leu | Leu | Asp | Pro | Ser | Asn | Thr | |
| | | | | 85 | | | | | 90 | | | | | 95 | | |
| acc | ccc | gag | ggg | gtg | gcc | cgg | cgc | tac | ggc | ggg | gag | tgg | acg | gag | gag | 336 |
| Thr | Pro | Glu | Gly | Val | Ala | Arg | Arg | Tyr | Gly | Gly | Glu | Trp | Thr | Glu | Glu | |
| | | | 100 | | | | | 105 | | | | | 110 | | | |
| gcg | ggg | gag | cgg | gcc | gcc | ctt | tcc | gag | agg | ctc | ttc | gcc | aac | ctg | tgg | 384 |
| Ala | Gly | Glu | Arg | Ala | Ala | Leu | Ser | Glu | Arg | Leu | Phe | Ala | Asn | Leu | Trp | |
| | | 115 | | | | | 120 | | | | | 125 | | | | |
| ggg | agg | ctt | gag | ggg | gag | gag | agg | ctc | ctt | tgg | ctt | tac | cgg | gag | gtg | 432 |
| Gly | Arg | Leu | Glu | Gly | Glu | Glu | Arg | Leu | Leu | Trp | Leu | Tyr | Arg | Glu | Val | |
| 130 | | | | | 135 | | | | | 140 | | | | | | |
| gag | agg | ccc | ctt | tcc | gct | gtc | ctg | gcc | cac | atg | gag | gcc | acg | ggg | gtg | 480 |
| Glu | Arg | Pro | Leu | Ser | Ala | Val | Leu | Ala | His | Met | Glu | Ala | Thr | Gly | Val | |
| 145 | | | | | 150 | | | | | 155 | | | | | 160 | |
| cgc | ctg | gac | gtg | gcc | tat | ctc | agg | gcc | ttg | tcc | ctg | gag | gtg | gcc | gag | 528 |
| Arg | Leu | Asp | Val | Ala | Tyr | Leu | Arg | Ala | Leu | Ser | Leu | Glu | Val | Ala | Glu | |
| | | | 165 | | | | | 170 | | | | | 175 | | | |
| gag | atc | gcc | cgc | ctc | gag | gcc | gag | gtc | ttc | cgc | ctg | gcc | ggc | cac | ccc | 576 |
| Glu | Ile | Ala | Arg | Leu | Glu | Ala | Glu | Val | Phe | Arg | Leu | Ala | Gly | His | Pro | |
| | | 180 | | | | | 185 | | | | | 190 | | | | |
| ttc | aac | ctc | aac | tcc | cgg | gac | cag | ctg | gaa | agg | gtc | ctc | ttt | gac | gag | 624 |
| Phe | Asn | Leu | Asn | Ser | Arg | Asp | Gln | Leu | Glu | Arg | Val | Leu | Phe | Asp | Glu | |
| | 195 | | | | | 200 | | | | | 205 | | | | | |
| cta | ggg | ctt | ccc | gcc | atc | ggc | aag | acg | gag | aag | acc | ggc | aag | cgc | tcc | 672 |
| Leu | Gly | Leu | Pro | Ala | Ile | Gly | Lys | Thr | Glu | Lys | Thr | Gly | Lys | Arg | Ser | |
| 210 | | | | | 215 | | | | | 220 | | | | | | |
| acc | agc | gcc | gcc | gtc | ctg | gag | gcc | ctc | cgc | gag | gcc | cac | ccc | atc | gtg | 720 |
| Thr | Ser | Ala | Ala | Val | Leu | Glu | Ala | Leu | Arg | Glu | Ala | His | Pro | Ile | Val | |
| 225 | | | | | 230 | | | | | 235 | | | | | 240 | |
| gag | aag | atc | ctg | cag | tac | cgg | gag | ctc | acc | aag | ctg | aag | agc | acc | tac | 768 |
| Glu | Lys | Ile | Leu | Gln | Tyr | Arg | Glu | Leu | Thr | Lys | Leu | Lys | Ser | Thr | Tyr | |
| | | | 245 | | | | | 250 | | | | | 255 | | | |

| | | |
|---|---|---|
| att gac ccc ttg ccg gac ccc atc cac ccc agg acg ggc cgc ctc cac<br>Ile Asp Pro Leu Pro Asp Pro Ile His Pro Arg Thr Gly Arg Leu His<br>260 265 270 | 816 | |
| acc cgc ttc aac cag acg gcc acg gcc acg ggc agg cta agt agc tcc<br>Thr Arg Phe Asn Gln Thr Ala Thr Ala Thr Gly Arg Leu Ser Ser Ser<br>275 280 285 | 864 | |
| gat ccc aac ctc cag aac atc ccc gtc cgc acc ccg ctt ggg cag agg<br>Asp Pro Asn Leu Gln Asn Ile Pro Val Arg Thr Pro Leu Gly Gln Arg<br>290 295 300 | 912 | |
| atc cgc cgg gcc ttc atc gcc gag gag ggg tgg cta ttg gtg gcc ctg<br>Ile Arg Arg Ala Phe Ile Ala Glu Glu Gly Trp Leu Leu Val Ala Leu<br>305 310 315 320 | 960 | |
| gac tat agc cag ata gag ctc agg gtg ctg gcc cac ctc tcc ggc gac<br>Asp Tyr Ser Gln Ile Glu Leu Arg Val Leu Ala His Leu Ser Gly Asp<br>325 330 335 | 1008 | |
| gag aac ctg atc cgg gtc ttc cag gag ggg cgg gac atc cac acg gag<br>Glu Asn Leu Ile Arg Val Phe Gln Glu Gly Arg Asp Ile His Thr Glu<br>340 345 350 | 1056 | |
| acc gcc agc tgg atg ttc ggc gtc ccc cgg gag gcc gtg gac ccc ctg<br>Thr Ala Ser Trp Met Phe Gly Val Pro Arg Glu Ala Val Asp Pro Leu<br>355 360 365 | 1104 | |
| atg cgc cgg acg gcc aag acc atc aac ttc ggg gtc ctc tac ggc atg<br>Met Arg Arg Thr Ala Lys Thr Ile Asn Phe Gly Val Leu Tyr Gly Met<br>370 375 380 | 1152 | |
| tcg gcc cac cgc ctc tcc cag gag cta gcc atc cct tac gag gag gcc<br>Ser Ala His Arg Leu Ser Gln Glu Leu Ala Ile Pro Tyr Glu Glu Ala<br>385 390 395 400 | 1200 | |
| cag gcc ttc att gag cgc tac ttt cag agc ttc ccc aag gtg cgg gcc<br>Gln Ala Phe Ile Glu Arg Tyr Phe Gln Ser Phe Pro Lys Val Arg Ala<br>405 410 415 | 1248 | |
| tgg att gag aag acc ctg gag gag ggc agg agg cgg ggg tac gtg gag<br>Trp Ile Glu Lys Thr Leu Glu Glu Gly Arg Arg Arg Gly Tyr Val Glu<br>420 425 430 | 1296 | |
| acc ctc ttc ggc cgc cgc cgc tac gtg cca gac cta gag gcc cgg gtg<br>Thr Leu Phe Gly Arg Arg Arg Tyr Val Pro Asp Leu Glu Ala Arg Val<br>435 440 445 | 1344 | |
| aag agc gtg cgg gag gcg gcc gag cgc atg gcc ttc aac atg ccc gtc<br>Lys Ser Val Arg Glu Ala Ala Glu Arg Met Ala Phe Asn Met Pro Val<br>450 455 460 | 1392 | |
| cag ggc acc gcc gcc gac ctc atg aag ctg gct atg gtg aag ctc ttc<br>Gln Gly Thr Ala Ala Asp Leu Met Lys Leu Ala Met Val Lys Leu Phe<br>465 470 475 480 | 1440 | |
| ccc agg ctg gag gaa atg ggg gcc agg atg ctc ctt cag gtc cac gac<br>Pro Arg Leu Glu Glu Met Gly Ala Arg Met Leu Leu Gln Val His Asp<br>485 490 495 | 1488 | |
| gag ctg gtc ctc gag gcc cca aaa gag ggg gcg gag gcc gtg gtc cgg<br>Glu Leu Val Leu Glu Ala Pro Lys Glu Gly Ala Glu Ala Val Val Arg<br>500 505 510 | 1536 | |
| ctg gcc aag gag gtc atg gag ggg gtg tat ccc ctg gcc gtg ccc ctg<br>Leu Ala Lys Glu Val Met Glu Gly Val Tyr Pro Leu Ala Val Pro Leu<br>515 520 525 | 1584 | |
| gag gtg aag gtg ggg ata ggg gag gac tgg ctc tcc gcc aag gag gcg<br>Glu Val Lys Val Gly Ile Gly Glu Asp Trp Leu Ser Ala Lys Glu Ala<br>530 535 540 | 1632 | |
| gcc gc<br>Ala<br>545 | 1637 | |

<210> SEQ ID NO 75
<211> LENGTH: 545

```
<212> TYPE: PRT
<213> ORGANISM: Thermus aquaticus

<400> SEQUENCE: 75

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
                20                  25                  30

Leu Ala Leu Ala Ala Ala Arg Gly Gly Arg Val His Arg Ala Pro Glu
                35                  40                  45

Pro Tyr Lys Ala Leu Arg Asp Leu Lys Glu Ala Arg Gly Leu Leu Ala
        50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
                100                 105                 110

Ala Gly Glu Arg Ala Ala Leu Ser Glu Arg Leu Phe Ala Asn Leu Trp
            115                 120                 125

Gly Arg Leu Glu Gly Glu Glu Arg Leu Leu Trp Leu Tyr Arg Glu Val
        130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
        195                 200                 205

Leu Gly Leu Pro Ala Ile Gly Lys Thr Glu Lys Thr Gly Lys Arg Ser
    210                 215                 220

Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Lys Ser Thr Tyr
                245                 250                 255

Ile Asp Pro Leu Pro Asp Pro Ile His Pro Arg Thr Gly Arg Leu His
            260                 265                 270

Thr Arg Phe Asn Gln Thr Ala Thr Ala Thr Gly Arg Leu Ser Ser Ser
        275                 280                 285

Asp Pro Asn Leu Gln Asn Ile Pro Val Arg Thr Pro Leu Gly Gln Arg
290                 295                 300

Ile Arg Arg Ala Phe Ile Ala Glu Glu Gly Trp Leu Leu Val Ala Leu
305                 310                 315                 320

Asp Tyr Ser Gln Ile Glu Leu Arg Val Leu Ala His Leu Ser Gly Asp
                325                 330                 335

Glu Asn Leu Ile Arg Val Phe Gln Glu Gly Arg Asp Ile His Thr Glu
            340                 345                 350

Thr Ala Ser Trp Met Phe Gly Val Pro Arg Glu Ala Val Asp Pro Leu
        355                 360                 365

Met Arg Arg Thr Ala Lys Thr Ile Asn Phe Gly Val Leu Tyr Gly Met
370                 375                 380

Ser Ala His Arg Leu Ser Gln Glu Leu Ala Ile Pro Tyr Glu Glu Ala
385                 390                 395                 400
```

-continued

```
Gln Ala Phe Ile Glu Arg Tyr Phe Gln Ser Phe Pro Lys Val Arg Ala
                405                 410                 415
Trp Ile Glu Lys Thr Leu Glu Glu Gly Arg Arg Arg Gly Tyr Val Glu
            420                 425                 430
Thr Leu Phe Gly Arg Arg Arg Tyr Val Pro Asp Leu Glu Ala Arg Val
        435                 440                 445
Lys Ser Val Arg Glu Ala Ala Glu Arg Met Ala Phe Asn Met Pro Val
    450                 455                 460
Gln Gly Thr Ala Ala Asp Leu Met Lys Leu Ala Met Val Lys Leu Phe
465                 470                 475                 480
Pro Arg Leu Glu Glu Met Gly Ala Arg Met Leu Leu Gln Val His Asp
                485                 490                 495
Glu Leu Val Leu Glu Ala Pro Lys Glu Gly Ala Glu Ala Val Val Arg
            500                 505                 510
Leu Ala Lys Glu Val Met Glu Gly Val Tyr Pro Leu Ala Val Pro Leu
        515                 520                 525
Glu Val Lys Val Gly Ile Gly Glu Asp Trp Leu Ser Ala Lys Glu Ala
    530                 535                 540
Ala
545
```

<210> SEQ ID NO 76
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 76

```
agc ccc aag gcc ctg gag gag gcc ccc tgg ccc ccg ccg gaa ggg gcc      48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt      96
Phe Val Gly Phe Val Leu Ser Arg Lys Glu Pro Met Trp Ala Asp Leu
            20                  25                  30 ctg gcc ctg gcc gcc gcc agg ggg ggc cgg gtc cac cgg gcc ccc gag     144
Leu Ala Leu Ala Ala Ala Arg Gly Gly Arg Val His Arg Ala Pro Glu
        35                  40                  45 cct tat aaa gcc ctc agg gac ctg aag gag gcg cgg ggg ctt ctc gcc     192
Pro Tyr Lys Ala Leu Arg Asp Leu Lys Glu Ala Arg Gly Leu Leu Ala
    50                  55                  60 aaa gac ctg agc gtt ctg gcc ctg agg gaa ggc ctt ggc ctc ccg ccc     240
Lys Asp Leu Ser Val Leu Ala Leu Arg Glu Gly Leu Gly Leu Pro Pro
65                  70                  75                  80 ggc gac gac ccc atg ctc ctc gcc tac ctc ctg gac cct tcc aac acc     288
Gly Asp Asp Pro Met Leu Leu Ala Tyr Leu Leu Asp Pro Ser Asn Thr
                85                  90                  95 acc ccc gag ggg gtg gcc cgg cgc tac ggc ggg gag tgg acg gag gag     336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg     384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg     432
Gly Arg Leu Glu Gly Glu Glu Arg Leu Leu Trp Leu Tyr Arg Glu Val
    130                 135                 140 gag agg ccc ctt tcc gct gtc ctg gcc cac atg gag gcc acg ggg gtg     480
```

```
                Glu Arg Pro Leu Ser Ala Val Leu Ala His Met Glu Ala Thr Gly Val
                145                 150                 155                 160 cgc ctg gac gtg gcc tat ctc agg gcc ttg tcc ctg gag gtg gcc gag       528
Arg Leu Asp Val Ala Tyr Leu Arg Ala Leu Ser Leu Glu Val Ala Glu
                    165                 170                 175 gag atc gcc cgc ctc gag gcc gag gtc ttc cgc ctg gcc ggc cac ccc       576
Glu Ile Ala Arg Leu Glu Ala Glu Val Phe Arg Leu Ala Gly His Pro
                180                 185                 190 ttc aac ctc aac tcc cgg gac cag ctg gaa agg gtc ctc ttt gac gag       624
Phe Asn Leu Asn Ser Arg Asp Gln Leu Glu Arg Val Leu Phe Asp Glu
                    195                 200                 205 cta ggg ctt ccc gcc atc ggc aag acg gag aag acc ggc aag cgc tcc       672
Leu Gly Leu Pro Ala Ile Gly Lys Thr Glu Lys Thr Gly Lys Arg Ser
                210                 215                 220 acc agc gcc gcc gtc ctg gag gcc ctc cgc gag gcc cac ccc atc gtg       720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac       768
Glu Lys Ile Leu Gln Tyr Arg Glu Leu Thr Lys Leu Lys Ser Thr Tyr
                    245                 250                 255 att gac ccc ttg ccg gac ctc ttc cac ccc agg acg ggc cgc ctc cac       816
Ile Asp Pro Leu Pro Asp Leu Phe His Pro Arg Thr Gly Arg Leu His
                260                 265                 270 acc cgc ttc aac cag acg gcc acg gcc acg ggc agg cta agt agc tcc       864
Thr Arg Phe Asn Gln Thr Ala Thr Ala Thr Gly Arg Leu Ser Ser Ser
                    275                 280                 285 gat ccc aac ctc cag aac atc ccc gtc cgc acc ccg ctt ggg cag agg       912
Asp Pro Asn Leu Gln Asn Ile Pro Val Arg Thr Pro Leu Gly Gln Arg
                290                 295                 300 atc cgc cgg gcc ttc atc gcc gag gag ggg tgg cta ttg gtg gtc ctg       960
Ile Arg Arg Ala Phe Ile Ala Glu Glu Gly Trp Leu Leu Val Val Leu
305                 310                 315                 320 gac tat agt cag ata gag ctc agg gtg ctg gcc cac ctc tcc ggc gac      1008
Asp Tyr Ser Gln Ile Glu Leu Arg Val Leu Ala His Leu Ser Gly Asp
                    325                 330                 335 gag aac ctg atc cgg gtc ttc cag gag ggg cgg gac atc cac acg gag      1056
Glu Asn Leu Ile Arg Val Phe Gln Glu Gly Arg Asp Ile His Thr Glu
                340                 345                 350 acc gcc agc tgg atg ttc ggc gtc ccc cgg gag gcc gtg gac ccc ctg      1104
Thr Ala Ser Trp Met Phe Gly Val Pro Arg Glu Ala Val Asp Pro Leu
                    355                 360                 365 atg cgc cgg gcg gcc aag acc atc aac ttc ggg gtc ctc tac ggc atg      1152
Met Arg Arg Ala Ala Lys Thr Ile Asn Phe Gly Val Leu Tyr Gly Met
                370                 375                 380 tcg gcc cac cgc ctc tcc cag gag cta gcc atc cct tac gag gag gcc      1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc      1248
Gln Ala Phe Ile Glu Arg Tyr Phe Gln Ser Phe Pro Lys Val Arg Ala
                    405                 410                 415 tgg att gag aag acc ctg gag gag ggc agg agg cgg ggg tac gtg gag      1296
Trp Ile Glu Lys Thr Leu Glu Glu Gly Arg Arg Arg Gly Tyr Val Glu
                420                 425                 430 acc ctc ttc ggc cgc cgc cgc tac gtg cca gac cta gag gcc cgg gtg      1344
Thr Leu Phe Gly Arg Arg Arg Tyr Val Pro Asp Leu Glu Ala Arg Val
                    435                 440                 445 aag agc gtg cgg gag gcg gcc gag cgc atg gcc tcc aac atg ccc gtc      1392
Lys Ser Val Arg Glu Ala Ala Glu Arg Met Ala Ser Asn Met Pro Val
                450                 455                 460
```

```
cag ggc acc gcc gcc gac ctc atg aag ctg gct atg gtg aag ctc ttc      1440
Gln Gly Thr Ala Ala Asp Leu Met Lys Leu Ala Met Val Lys Leu Phe
465                 470                 475                 480 ccc agg ctg gag gaa atg ggg gcc agg atg ctc ctt cag gtc cac gac      1488
Pro Arg Leu Glu Glu Met Gly Ala Arg Met Leu Leu Gln Val His Asp
                485                 490                 495 gag ctg gtc ctc gag gcc cca aaa gag ggg gcg gag gcc gtg gcc cgg      1536
Glu Leu Val Leu Glu Ala Pro Lys Glu Gly Ala Glu Ala Val Ala Arg
            500                 505                 510 ctg gcc aag gag gtc atg gag ggg gtg tat ccc ctg gcc gtg ccc ctg      1584
Leu Ala Lys Glu Val Met Glu Gly Val Tyr Pro Leu Ala Val Pro Leu
        515                 520                 525 gag gtg gag gtg ggg ata ggg gag gac tgg ctc tcc gcc aag gag gcg      1632
Glu Val Glu Val Gly Ile Gly Glu Asp Trp Leu Ser Ala Lys Glu Ala
    530                 535                 540 gcc gc                                                                1637
Ala
545

<210> SEQ ID NO 77
<211> LENGTH: 545
<212> TYPE: PRT
<213> ORGANISM: Thermus aquaticus

<400> SEQUENCE: 77

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
                20                  25                  30

Leu Ala Leu Ala Ala Ala Arg Gly Gly Arg Val His Arg Ala Pro Glu
            35                  40                  45

Pro Tyr Lys Ala Leu Arg Asp Leu Lys Glu Ala Arg Gly Leu Leu Ala
        50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
                100                 105                 110

Ala Gly Glu Arg Ala Ala Leu Ser Glu Arg Leu Phe Ala Asn Leu Trp
            115                 120                 125

Gly Arg Leu Glu Gly Glu Glu Arg Leu Leu Trp Leu Tyr Arg Glu Val
        130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
        195                 200                 205

Leu Gly Leu Pro Ala Ile Gly Lys Thr Glu Lys Thr Gly Lys Arg Ser
    210                 215                 220

Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Lys Ser Thr Tyr
                245                 250                 255
```

```
Ile Asp Pro Leu Pro Asp Leu Phe His Pro Arg Thr Gly Arg Leu His
            260                 265                 270

Thr Arg Phe Asn Gln Thr Ala Thr Ala Thr Gly Arg Leu Ser Ser Ser
            275                 280                 285

Asp Pro Asn Leu Gln Asn Ile Pro Val Arg Thr Pro Leu Gly Gln Arg
            290                 295                 300

Ile Arg Arg Ala Phe Ile Ala Glu Gly Trp Leu Leu Val Val Leu
305                 310                 315                 320

Asp Tyr Ser Gln Ile Glu Leu Arg Val Leu Ala His Leu Ser Gly Asp
                325                 330                 335

Glu Asn Leu Ile Arg Val Phe Gln Glu Gly Arg Asp Ile His Thr Glu
            340                 345                 350

Thr Ala Ser Trp Met Phe Gly Val Pro Arg Glu Ala Val Asp Pro Leu
            355                 360                 365

Met Arg Arg Ala Ala Lys Thr Ile Asn Phe Gly Val Leu Tyr Gly Met
370                 375                 380

Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
                405                 410                 415

Trp Ile Glu Lys Thr Leu Glu Glu Gly Arg Arg Arg Gly Tyr Val Glu
            420                 425                 430

Thr Leu Phe Gly Arg Arg Arg Tyr Val Pro Asp Leu Glu Ala Arg Val
            435                 440                 445

Lys Ser Val Arg Glu Ala Ala Glu Arg Met Ala Phe Asn Met Pro Val
450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Met Leu Leu Gln Val His Asp
                485                 490                 495

Glu Leu Val Leu Glu Ala Pro Lys Glu Gly Ala Glu Ala Val Ala Arg
            500                 505                 510

Leu Ala Lys Glu Val Met Glu Gly Val Tyr Pro Leu Ala Val Pro Leu
            515                 520                 525

Glu Val Glu Val Gly Ile Gly Glu Asp Trp Leu Ser Ala Lys Glu Ala
530                 535                 540

Ala
545

<210> SEQ ID NO 78
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 78 agc ccc aag gcc ctg gag gag gcc ccc tgg ccc ccg ccg gaa ggg gcc     48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt     96
Phe Val Gly Phe Val Leu Ser Arg Lys Glu Pro Met Trp Ala Asp Leu
            20                  25                  30 ctg gcc ctg gcc gcc gcc agg ggg ggc cgg gtc cac cgg gcc ccc gag    144
Leu Ala Leu Ala Ala Ala Arg Gly Gly Arg Val His Arg Ala Pro Glu
```

```
                35                  40                  45
cct tat aaa gcc ctc agg gac ctg aag gag gcg cgg ggg ctt ctc gcc    192
Pro Tyr Lys Ala Leu Arg Asp Leu Lys Glu Ala Arg Gly Leu Leu Ala
     50                  55                  60 aaa gac ctg agc gtt ctg gcc ctg agg gaa ggc ctt ggc ctc ccg ccc    240
Lys Asp Leu Ser Val Leu Ala Leu Arg Glu Gly Leu Gly Leu Pro Pro
 65                  70                  75                  80 ggc gac gac ccc atg ctc ctc gcc tac ctc ctg gac cct tcc aac acc    288
Gly Asp Asp Pro Met Leu Leu Ala Tyr Leu Leu Asp Pro Ser Asn Thr
                 85                  90                  95 acc ccc gag ggg gtg gcc cgg cgc tac ggc ggg gag tgg acg gag gag    336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg    384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg    432
Gly Arg Leu Glu Gly Glu Glu Arg Leu Leu Trp Leu Tyr Arg Glu Val
    130                 135                 140 gag agg ccc ctt tcc gct gtc ctg gcc cac atg gag gcc acg ggg gtg    480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag    528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc    576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag    624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc    672
Leu Gly Leu Pro Ala Ile Gly Lys Thr Glu Lys Thr Gly Lys Arg Ser
    210                 215                 220 acc agc gcc gcc gtc ctg gag gcc ctc cgc gag gcc cac ccc atc gtg    720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac    768
Glu Lys Ile Leu Gln Tyr Arg Glu Leu Thr Lys Leu Lys Ser Thr Tyr
                245                 250                 255 att gac ccc ttg ccg gac ctc atc cac ccc agg acg ggc cgc ctc cac    816
Ile Asp Pro Leu Pro Asp Leu Ile His Pro Arg Thr Gly Arg Leu His
            260                 265                 270 acc cgc ttc aac cag acg gcc acg gcc acg ggc agg cta agt agc tcc    864
Thr Arg Phe Asn Gln Thr Ala Thr Ala Thr Gly Arg Leu Ser Ser Ser
        275                 280                 285 gat ccc aac ctc cag aac atc ccc gtc cgc acc ccg ctt ggg cag agg    912
Asp Pro Asn Leu Gln Asn Ile Pro Val Arg Thr Pro Leu Gly Gln Arg
    290                 295                 300 atc cgc cgg gcc ttc atc gcc gag gag ggg tgg cta ttg gtg gcc ctg    960
Ile Arg Arg Ala Phe Ile Ala Glu Glu Gly Trp Leu Leu Val Ala Leu
305                 310                 315                 320 gac tat agc cag ata gag ctc agg gtg ctg gcc cac ctc tcc ggc gac   1008
Asp Tyr Ser Gln Ile Glu Leu Arg Val Leu Ala His Leu Ser Gly Asp
                325                 330                 335 gag aac ctg atc cgg gtc ttc cag gag ggg cgg gac atc cac acg gag   1056
Glu Asn Leu Ile Arg Val Phe Gln Glu Gly Arg Asp Ile His Thr Glu
            340                 345                 350 acc gcc agc tgg atg ttc ggc gtc ccc cga gag gcc gtg gac ccc ctg   1104
```

```
                                                        atg cgc cgg gcg gcc aag acc atc aac ttc ggg gtc ctc tac ggc atg      1152
Thr Ala Ser Trp Met Phe Gly Val Pro Arg Glu Ala Val Asp Pro Leu
        355                 360                 365
atg cgc cgg gcg gcc aag acc atc aac ttc ggg gtc ctc tac ggc atg      1152
Met Arg Arg Ala Ala Lys Thr Ile Asn Phe Gly Val Leu Tyr Gly Met
    370                 375                 380 tcg gcc cac cgc ctc tcc cag gag cta gcc atc cct tac gag gag gcc      1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc      1248
Gln Ala Phe Ile Glu Arg Tyr Phe Gln Ser Phe Pro Lys Val Arg Ala
                405                 410                 415 tgg att gag aag acc ctg gag gag ggc agg agg cgg ggg tac gtg gag      1296
Trp Ile Glu Lys Thr Leu Glu Glu Gly Arg Arg Arg Gly Tyr Val Glu
            420                 425                 430 acc ctc ttc ggt cgc cgc cgc tac gtg cca gac cta gag gcc cgg gtg      1344
Thr Leu Phe Gly Arg Arg Arg Tyr Val Pro Asp Leu Glu Ala Arg Val
        435                 440                 445 aag agc gtg cgg aag gcg gcc gag cgc aag gcc ttc aac atg ccc gtc      1392
Lys Ser Val Arg Lys Ala Ala Glu Arg Lys Ala Phe Asn Met Pro Val
450                 455                 460 cag ggc acc gcc gcc gac ctc atg aag ctg gct atg gtg aag ctc ttc      1440
Gln Gly Thr Ala Ala Asp Leu Met Lys Leu Ala Met Val Lys Leu Phe
465                 470                 475                 480 ccc agg ctg gag gaa atg ggg gcc agg atg ctc ctt cag gtc cac gac      1488
Pro Arg Leu Glu Glu Met Gly Ala Arg Met Leu Leu Gln Val His Asp
                485                 490                 495 gag ctg gtc ctc gag gcc cca aaa gag ggg gcg gag gcc gtg gcc cgg      1536
Glu Leu Val Leu Glu Ala Pro Lys Glu Gly Ala Glu Ala Val Ala Arg
            500                 505                 510 ctg gcc aag gag gtc atg gag ggg gtg tat ccc ctg gcc gtg ccc ctg      1584
Leu Ala Lys Glu Val Met Glu Gly Val Tyr Pro Leu Ala Val Pro Leu
        515                 520                 525 gag gtg gag gtg ggg ata ggg gag gac tgg ctc tcc gcc aag gag gcg      1632
Glu Val Glu Val Gly Ile Gly Glu Asp Trp Leu Ser Ala Lys Glu Ala
    530                 535                 540 gcc gc                                                                1637
Ala
545

<210> SEQ ID NO 79
<211> LENGTH: 545
<212> TYPE: PRT
<213> ORGANISM: Thermus aquaticus

<400> SEQUENCE: 79

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
                20                  25                  30

Leu Ala Leu Ala Ala Ala Arg Gly Gly Arg Val His Arg Ala Pro Glu
            35                  40                  45

Pro Tyr Lys Ala Leu Arg Asp Leu Lys Glu Ala Arg Gly Leu Leu Ala
        50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
            100                 105                 110
```

```
Ala Gly Glu Arg Ala Ala Leu Ser Glu Arg Leu Phe Ala Asn Leu Trp
        115                 120                 125

Gly Arg Leu Glu Gly Glu Arg Leu Leu Trp Leu Tyr Arg Glu Val
    130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
                180                 185                 190

Phe Asn Leu Asn Ser Arg Asp Gln Leu Glu Arg Val Leu Phe Asp Glu
                195                 200                 205

Leu Gly Leu Pro Ala Ile Gly Lys Thr Glu Lys Thr Gly Lys Arg Ser
    210                 215                 220

Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Lys Ser Thr Tyr
                245                 250                 255

Ile Asp Pro Leu Pro Asp Leu Ile His Pro Arg Thr Gly Arg Leu His
                260                 265                 270

Thr Arg Phe Asn Gln Thr Ala Thr Ala Thr Gly Arg Leu Ser Ser Ser
        275                 280                 285

Asp Pro Asn Leu Gln Asn Ile Pro Val Arg Thr Pro Leu Gly Gln Arg
        290                 295                 300

Ile Arg Arg Ala Phe Ile Ala Glu Gly Trp Leu Leu Val Ala Leu
305                 310                 315                 320

Asp Tyr Ser Gln Ile Glu Leu Arg Val Leu Ala His Leu Ser Gly Asp
                325                 330                 335

Glu Asn Leu Ile Arg Val Phe Gln Gly Arg Asp Ile His Thr Glu
                340                 345                 350

Thr Ala Ser Trp Met Phe Gly Val Pro Arg Glu Ala Val Asp Pro Leu
        355                 360                 365

Met Arg Arg Ala Ala Lys Thr Ile Asn Phe Gly Val Leu Tyr Gly Met
370                 375                 380

Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
                405                 410                 415

Trp Ile Glu Lys Thr Leu Glu Glu Gly Arg Arg Gly Tyr Val Glu
                420                 425                 430

Thr Leu Phe Gly Arg Arg Arg Tyr Val Pro Asp Leu Glu Ala Arg Val
        435                 440                 445

Lys Ser Val Arg Lys Ala Ala Glu Arg Lys Ala Phe Asn Met Pro Val
    450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Met Leu Leu Gln Val His Asp
                485                 490                 495

Glu Leu Val Leu Glu Ala Pro Lys Glu Gly Ala Glu Ala Val Ala Arg
                500                 505                 510

Leu Ala Lys Glu Val Met Glu Gly Val Tyr Pro Leu Ala Val Pro Leu
    515                 520                 525
```

```
Glu Val Glu Val Gly Ile Gly Glu Asp Trp Leu Ser Ala Lys Glu Ala
    530                 535                 540

Ala
545

<210> SEQ ID NO 80
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 80 agc ccc aag gcc ctg gag gag gcc ccc tgg ccc ccg ccg gaa ggg gcc        48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt        96
Phe Val Gly Phe Val Leu Ser Arg Lys Glu Pro Met Trp Ala Asp Leu
                20                  25                  30 ctg gcc ctg gcc gcc gcc agg ggg ggc cgg gtc cac cgg gcc ccc gag       144
Leu Ala Leu Ala Ala Ala Arg Gly Gly Arg Val His Arg Ala Pro Glu
            35                  40                  45 cct tat aaa gcc ctc agg gac ctg aag gag gcg cgg ggg ctt ctc gcc       192
Pro Tyr Lys Ala Leu Arg Asp Leu Lys Glu Ala Arg Gly Leu Leu Ala
        50                  55                  60 aaa gac ctg agc gtt ctg gcc ctg agg gaa ggc ctt ggc ctc ccg ccc       240
Lys Asp Leu Ser Val Leu Ala Leu Arg Glu Gly Leu Gly Leu Pro Pro
65                  70                  75                  80 ggc gac gac ccc atg ctc ctc gcc tac ctc ctg gac cct tcc aac acc       288
Gly Asp Asp Pro Met Leu Leu Ala Tyr Leu Leu Asp Pro Ser Asn Thr
                85                  90                  95 acc ccc gag ggg gtg gcc cgg cgc tac ggc ggg gag tgg acg gag gag       336
Thr Pro Glu Gly Val Ala Arg Arg Tyr Gly Gly Glu Trp Thr Glu Glu
                100                 105                 110 gcg ggg gag cgg gcc gcc ctt tcc gag agg ctc ttc gcc aac ctg tgg       384
Ala Gly Glu Arg Ala Ala Leu Ser Glu Arg Leu Phe Ala Asn Leu Trp
            115                 120                 125 ggg agg ctt gag ggg gag gag agg ctc ctt tgg ctt tac cgg gag gtg       432
Gly Arg Leu Glu Gly Glu Glu Arg Leu Leu Trp Leu Tyr Arg Glu Val
        130                 135                 140 gag agg ccc ctt tcc gct gtc ctg gcc cac atg gag gcc acg ggg gtg       480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag       528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc       576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag       624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc       672
Leu Gly Leu Pro Ala Ile Gly Lys Thr Glu Lys Thr Gly Lys Arg Ser
    210                 215                 220 acc agc gcc gcc gtc ctg gag gcc ctc cgc gag gcc cac ccc atc gtg       720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac       768
Glu Lys Ile Leu Gln Tyr Arg Glu Leu Thr Lys Leu Lys Ser Thr Tyr
```

-continued

|   |   |   |
|---|---|---|
| 245 | 250 | 255 |

| att gac ccc ttg ccg gac ctc atc cac ccc agg acg ggc cgc ctc cac | 816 |
| Ile Asp Pro Leu Pro Asp Leu Ile His Pro Arg Thr Gly Arg Leu His | |
| 260 265 270 | |

| acc cgc ttc aac cag acg gcc acg gcc acg ggc agg cta agt agc tcc | 864 |
| Thr Arg Phe Asn Gln Thr Ala Thr Ala Thr Gly Arg Leu Ser Ser Ser | |
| 275 280 285 | |

| gat ccc aac ctc cag aac atc ccc gtc cgc acc ccg ctt ggg cag agg | 912 |
| Asp Pro Asn Leu Gln Asn Ile Pro Val Arg Thr Pro Leu Gly Gln Arg | |
| 290 295 300 | |

| atc cgc cgg gcc ttc atc gcc gag gag ggg tgg cta ttg gtg gcc ctg | 960 |
| Ile Arg Arg Ala Phe Ile Ala Glu Glu Gly Trp Leu Leu Val Ala Leu | |
| 305 310 315 320 | |

| gac tat agc cag ata gag ctc agg gtg ctg gcc cac ctc tcc ggc gac | 1008 |
| Asp Tyr Ser Gln Ile Glu Leu Arg Val Leu Ala His Leu Ser Gly Asp | |
| 325 330 335 | |

| gag aac ctg atc cgg gtc ttc cag gag ggg cgg gac atc cac acg gag | 1056 |
| Glu Asn Leu Ile Arg Val Phe Gln Glu Gly Arg Asp Ile His Thr Glu | |
| 340 345 350 | |

| acc gcc agc tgg atg ttc ggc gtc ccc cgg gag gcc gtg gac ccc ctg | 1104 |
| Thr Ala Ser Trp Met Phe Gly Val Pro Arg Glu Ala Val Asp Pro Leu | |
| 355 360 365 | |

| atg cgc cgg gcg gcc aag acc atc aac ttc ggg gtc ctc tac ggc atg | 1152 |
| Met Arg Arg Ala Ala Lys Thr Ile Asn Phe Gly Val Leu Tyr Gly Met | |
| 370 375 380 | |

| tcg gcc cac cgc ctc tcc cag gag cta gcc atc cct tac gag gag gcc | 1200 |
| Ser Ala His Arg Leu Ser Gln Glu Leu Ala Ile Pro Tyr Glu Glu Ala | |
| 385 390 395 400 | |

| cag gcc ttc att gag cgc tac ttt cag agc ttc ccc aag gtg cgg gcc | 1248 |
| Gln Ala Phe Ile Glu Arg Tyr Phe Gln Ser Phe Pro Lys Val Arg Ala | |
| 405 410 415 | |

| tgg att gag aag acc ctg gag gag ggc agg agg cgg ggg tac gtg gag | 1296 |
| Trp Ile Glu Lys Thr Leu Glu Glu Gly Arg Arg Arg Gly Tyr Val Glu | |
| 420 425 430 | |

| acc ctc ttc ggc cgc cgc cgc tac gtg cca gac cta gag gcc cgg gtg | 1344 |
| Thr Leu Phe Gly Arg Arg Arg Tyr Val Pro Asp Leu Glu Ala Arg Val | |
| 435 440 445 | |

| aag agc gtg cgg gag gcg gcc gag cgc agg gcc ttc aac atg ccc gtc | 1392 |
| Lys Ser Val Arg Glu Ala Ala Glu Arg Arg Ala Phe Asn Met Pro Val | |
| 450 455 460 | |

| cag ggc acc gcc gcc gac ctc atg aag ctg gct atg gtg aag ctc ttc | 1440 |
| Gln Gly Thr Ala Ala Asp Leu Met Lys Leu Ala Met Val Lys Leu Phe | |
| 465 470 475 480 | |

| ccc agg ctg gag gaa atg ggg gcc agg atg ctc ctt cag gtc cac gac | 1488 |
| Pro Arg Leu Glu Glu Met Gly Ala Arg Met Leu Leu Gln Val His Asp | |
| 485 490 495 | |

| gag ctg gtc ctc gag gcc cca aaa gag ggg gcg gag gcc gtg gcc cgg | 1536 |
| Glu Leu Val Leu Glu Ala Pro Lys Glu Gly Ala Glu Ala Val Ala Arg | |
| 500 505 510 | |

| ctg gcc aag gag gtc atg gag ggg gtg tat ccc ctg gcc gtg ccc ctg | 1584 |
| Leu Ala Lys Glu Val Met Glu Gly Val Tyr Pro Leu Ala Val Pro Leu | |
| 515 520 525 | |

| gag gtg gag gtg ggg ata ggg gag gac tgg ctc tcc gcc aag gag gcg | 1632 |
| Glu Val Glu Val Gly Ile Gly Glu Asp Trp Leu Ser Ala Lys Glu Ala | |
| 530 535 540 | |

| gcc gc | 1637 |
| Ala | |
| 545 | |

```
<210> SEQ ID NO 81
<211> LENGTH: 545
<212> TYPE: PRT
<213> ORGANISM: Thermus aquaticus

<400> SEQUENCE: 81

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
                20                  25                  30

Leu Ala Leu Ala Ala Ala Arg Gly Gly Arg Val His Arg Ala Pro Glu
                35                  40                  45

Pro Tyr Lys Ala Leu Arg Asp Leu Lys Glu Ala Arg Gly Leu Leu Ala
            50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                    85                  90                  95

Thr Pro Glu Gly Val Ala Arg Arg Tyr Gly Gly Glu Trp Thr Glu Glu
                100                 105                 110

Ala Gly Glu Arg Ala Ala Leu Ser Glu Arg Leu Phe Ala Asn Leu Trp
            115                 120                 125

Gly Arg Leu Glu Gly Glu Glu Arg Leu Leu Trp Leu Tyr Arg Glu Val
        130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                    165                 170                 175

Glu Ile Ala Arg Leu Glu Ala Glu Val Phe Arg Leu Ala Gly His Pro
                180                 185                 190

Phe Asn Leu Asn Ser Arg Asp Gln Leu Glu Arg Val Leu Phe Asp Glu
            195                 200                 205

Leu Gly Leu Pro Ala Ile Gly Lys Thr Glu Lys Thr Gly Lys Arg Ser
        210                 215                 220

Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Lys Ser Thr Tyr
                    245                 250                 255

Ile Asp Pro Leu Pro Asp Leu Ile His Pro Arg Thr Gly Arg Leu His
                260                 265                 270

Thr Arg Phe Asn Gln Thr Ala Thr Ala Thr Gly Arg Leu Ser Ser Ser
            275                 280                 285

Asp Pro Asn Leu Gln Asn Ile Pro Val Arg Thr Pro Leu Gly Gln Arg
        290                 295                 300

Ile Arg Arg Ala Phe Ile Ala Glu Glu Gly Trp Leu Leu Val Ala Leu
305                 310                 315                 320

Asp Tyr Ser Gln Ile Glu Leu Arg Val Leu Ala His Leu Ser Gly Asp
                    325                 330                 335

Glu Asn Leu Ile Arg Val Phe Gln Glu Gly Arg Asp Ile His Thr Glu
                340                 345                 350

Thr Ala Ser Trp Met Phe Gly Val Pro Arg Glu Ala Val Asp Pro Leu
            355                 360                 365

Met Arg Arg Ala Ala Lys Thr Ile Asn Phe Gly Val Leu Tyr Gly Met
        370                 375                 380
```

```
Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
            405                 410                 415

Trp Ile Glu Lys Thr Leu Glu Glu Gly Arg Arg Arg Gly Tyr Val Glu
            420                 425                 430

Thr Leu Phe Gly Arg Arg Arg Tyr Val Pro Asp Leu Glu Ala Arg Val
            435                 440                 445

Lys Ser Val Arg Glu Ala Ala Glu Arg Arg Ala Phe Asn Met Pro Val
450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Met Leu Leu Gln Val His Asp
                485                 490                 495

Glu Leu Val Leu Glu Ala Pro Lys Glu Gly Ala Glu Ala Val Ala Arg
                500                 505                 510

Leu Ala Lys Glu Val Met Glu Gly Val Tyr Pro Leu Ala Val Pro Leu
            515                 520                 525

Glu Val Glu Val Gly Ile Gly Glu Asp Trp Leu Ser Ala Lys Glu Ala
530                 535                 540

Ala
545

<210> SEQ ID NO 82
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 82 agc ccc aag gcc ctg gag gag gcc ccc tgg ccc ccg ccg gaa ggg gcc      48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt      96
Phe Val Gly Phe Val Leu Ser Arg Lys Glu Pro Met Trp Ala Asp Leu
                20                  25                  30 ctg gcc ctg gcc gcc gcc agg ggg ggc cgg gtc cac cgg gcc ccc gag     144
Leu Ala Leu Ala Ala Ala Arg Gly Gly Arg Val His Arg Ala Pro Glu
            35                  40                  45 cct tat aaa gcc ctc agg gac ctg aag gag gcg cgg ggg ctt ctc gcc     192
Pro Tyr Lys Ala Leu Arg Asp Leu Lys Glu Ala Arg Gly Leu Leu Ala
        50                  55                  60 aaa gac ctg agc gtt ctg gcc ctg agg gaa ggc ctt ggc ctc ccg ccc     240
Lys Asp Leu Ser Val Leu Ala Leu Arg Glu Gly Leu Gly Leu Pro Pro
65                  70                  75                  80 ggc gac gac ccc atg ctc ctc gcc tac ctc ctg gac cct tcc aac acc     288
Gly Asp Asp Pro Met Leu Leu Ala Tyr Leu Leu Asp Pro Ser Asn Thr
                85                  90                  95 acc ccc gag ggg gtg gcc cgg cgc tac ggc ggg gag tgg acg gag gag     336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg     384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg     432
Gly Arg Leu Glu Gly Glu Glu Arg Leu Leu Trp Leu Tyr Arg Glu Val
    130                 135                 140
```

```
gag agg ccc ctt tcc gct gtc ctg gcc cac atg gag gcc acg ggg gtg      480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag      528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc      576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag      624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc      672
Leu Gly Leu Pro Ala Ile Gly Lys Thr Glu Lys Thr Gly Lys Arg Ser
210                 215                 220 acc agc gcc gcc gtc ctg gag gcc ctc cgc gag gcc cac ccc atc gtg      720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac      768
Glu Lys Ile Leu Gln Tyr Arg Glu Leu Thr Lys Leu Lys Ser Thr Tyr
                245                 250                 255 att gac ccc ttg ccg gac ctc atc cac ccc agg acg ggc cgc ctc cac      816
Ile Asp Pro Leu Pro Asp Leu Ile His Pro Arg Thr Gly Arg Leu His
            260                 265                 270 acc cgc ttc aac cag acg gcc acg gcc acg ggc agg cta agt agc tcc      864
Thr Arg Phe Asn Gln Thr Ala Thr Ala Thr Gly Arg Leu Ser Ser Ser
        275                 280                 285 gat ccc aac ctc cag aac atc ccc gtc cgc acc ccg ctt ggg cag agg      912
Asp Pro Asn Leu Gln Asn Ile Pro Val Arg Thr Pro Leu Gly Gln Arg
290                 295                 300 atc cgc cgg gcc ttc atc gcc gag gag ggg tgg cta ttg gtg gtc ctg      960
Ile Arg Arg Ala Phe Ile Ala Glu Glu Gly Trp Leu Leu Val Val Leu
305                 310                 315                 320 gac tat agc cag ata gag ctc agg gtg ctg gcc cac ctc tcc ggc gac     1008
Asp Tyr Ser Gln Ile Glu Leu Arg Val Leu Ala His Leu Ser Gly Asp
                325                 330                 335 gag aac ctg atc cgg gtc ttc cag gag ggg cgg gac atc cac acg gag     1056
Glu Asn Leu Ile Arg Val Phe Gln Glu Gly Arg Asp Ile His Thr Glu
            340                 345                 350 acc gcc agc tgg atg ttc ggc gtc ccc cgg gag gcc gtg gac ccc ctg     1104
Thr Ala Ser Trp Met Phe Gly Val Pro Arg Glu Ala Val Asp Pro Leu
        355                 360                 365 atg cgc cgg gcg gcc aag acc atc aac ttc ggg gtc ctc tac ggc atg     1152
Met Arg Arg Ala Ala Lys Thr Ile Asn Phe Gly Val Leu Tyr Gly Met
370                 375                 380 tcg gcc cac cgc ctc tcc cag gag cta gcc atc cct tac gag gag gcc     1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc     1248
Gln Ala Phe Ile Glu Arg Tyr Phe Gln Ser Phe Pro Lys Val Arg Ala
                405                 410                 415 tgg att gag aag acc ctg gag gag ggc agg agg cgg ggg tac gtg gag     1296
Trp Ile Glu Lys Thr Leu Glu Glu Gly Arg Arg Arg Gly Tyr Val Glu
            420                 425                 430 acc ctc ttc ggc cgc cgc cgc tac gtg cca gac cta gag gcc cgg gtg     1344
Thr Leu Phe Gly Arg Arg Arg Tyr Val Pro Asp Leu Glu Ala Arg Val
        435                 440                 445 aag agc gtg cgg gag gcg gcc gag cgc atg gcc ttc aac atg ccc gtc     1392
Lys Ser Val Arg Glu Ala Ala Glu Arg Met Ala Phe Asn Met Pro Val
```

```
                    450                 455                 460
cag ggc acc gcc gcc gac ctc atg aag ctg gct atg gtg aag ctc ttc       1440
Gln Gly Thr Ala Ala Asp Leu Met Lys Leu Ala Met Val Lys Leu Phe
465                 470                 475                 480 ccc agg ctg gag gaa atg ggg gcc agg atg ctc ctt cag gtc cac gac       1488
Pro Arg Leu Glu Glu Met Gly Ala Arg Met Leu Leu Gln Val His Asp
                    485                 490                 495 gag ctg gtc ctc gag gcc cca aaa gag ggg gcg gag gcc gtg gcc cgg       1536
Glu Leu Val Leu Glu Ala Pro Lys Glu Gly Ala Glu Ala Val Ala Arg
                500                 505                 510 ctg gcc aag gag gtc atg gag ggg gtg tat ccc ctg gcc gtg ccc ctg       1584
Leu Ala Lys Glu Val Met Glu Gly Val Tyr Pro Leu Ala Val Pro Leu
            515                 520                 525 gag gtg gag gtg ggg ata ggg gag gac tgg ctc tcc gcc aag gag gcg       1632
Glu Val Glu Val Gly Ile Gly Glu Asp Trp Leu Ser Ala Lys Glu Ala
        530                 535                 540 gcc gc                                                                 1637
Ala
545

<210> SEQ ID NO 83
<211> LENGTH: 545
<212> TYPE: PRT
<213> ORGANISM: Thermus aquaticus

<400> SEQUENCE: 83

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
            20                  25                  30

Leu Ala Leu Ala Ala Ala Arg Gly Gly Arg Val His Arg Ala Pro Glu
        35                  40                  45

Pro Tyr Lys Ala Leu Arg Asp Leu Lys Glu Ala Arg Gly Leu Leu Ala
    50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
            100                 105                 110

Ala Gly Glu Arg Ala Ala Leu Ser Glu Arg Leu Phe Ala Asn Leu Trp
        115                 120                 125

Gly Arg Leu Glu Gly Glu Glu Arg Leu Leu Trp Leu Tyr Arg Glu Val
    130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
        195                 200                 205

Leu Gly Leu Pro Ala Ile Gly Lys Thr Glu Lys Thr Gly Lys Arg Ser
    210                 215                 220

Thr Ser Ala Ala Val Leu Glu Ala Leu Arg Glu Ala His Pro Ile Val
225                 230                 235                 240
```

```
Glu Lys Ile Leu Gln Tyr Arg Glu Leu Thr Lys Leu Lys Ser Thr Tyr
            245                 250                 255

Ile Asp Pro Leu Pro Asp Leu Ile His Pro Arg Thr Gly Arg Leu His
        260                 265                 270

Thr Arg Phe Asn Gln Thr Ala Thr Ala Thr Gly Arg Leu Ser Ser Ser
    275                 280                 285

Asp Pro Asn Leu Gln Asn Ile Pro Val Arg Thr Pro Leu Gly Gln Arg
290                 295                 300

Ile Arg Arg Ala Phe Ile Ala Glu Glu Gly Trp Leu Leu Val Val Leu
305                 310                 315                 320

Asp Tyr Ser Gln Ile Glu Leu Arg Val Leu Ala His Leu Ser Gly Asp
            325                 330                 335

Glu Asn Leu Ile Arg Val Phe Gln Glu Gly Arg Asp Ile His Thr Glu
        340                 345                 350

Thr Ala Ser Trp Met Phe Gly Val Pro Arg Glu Ala Val Asp Pro Leu
    355                 360                 365

Met Arg Arg Ala Ala Lys Thr Ile Asn Phe Gly Val Leu Tyr Gly Met
370                 375                 380

Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
            405                 410                 415

Trp Ile Glu Lys Thr Leu Glu Glu Gly Arg Arg Arg Gly Tyr Val Glu
        420                 425                 430

Thr Leu Phe Gly Arg Arg Arg Tyr Val Pro Asp Leu Glu Ala Arg Val
    435                 440                 445

Lys Ser Val Arg Glu Ala Ala Glu Arg Met Ala Phe Asn Met Pro Val
450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Met Leu Leu Gln Val His Asp
            485                 490                 495

Glu Leu Val Leu Glu Ala Pro Lys Glu Gly Ala Glu Ala Val Ala Arg
        500                 505                 510

Leu Ala Lys Glu Val Met Glu Gly Val Tyr Pro Leu Ala Val Pro Leu
    515                 520                 525

Glu Val Glu Val Gly Ile Gly Glu Asp Trp Leu Ser Ala Lys Glu Ala
530                 535                 540

Ala
545

<210> SEQ ID NO 84
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 84 agc ccc aag gcc ctg gag gag gcc ccc tgg ccc ccg ccg gaa ggg gcc      48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt      96
Phe Val Gly Phe Val Leu Ser Arg Lys Glu Pro Met Trp Ala Asp Leu
            20                  25                  30
```

```
ctg gcc ctg gcc gcc agg ggg ggc cgg gtc cac cgg gcc ccc gag      144
Leu Ala Leu Ala Ala Arg Gly Gly Arg Val His Arg Ala Pro Glu
         35                  40                  45 cct tat aaa gcc ctc agg gac ctg aag gag gcg cgg ggg ctt ctc gcc  192
Pro Tyr Lys Ala Leu Arg Asp Leu Lys Glu Ala Arg Gly Leu Leu Ala
 50                  55                  60 aaa gac ctg agc gtt ctg gcc ctg agg gaa ggc ctt ggc ctc ccg ccc  240
Lys Asp Leu Ser Val Leu Ala Leu Arg Glu Gly Leu Gly Leu Pro Pro
 65                  70                  75                  80 ggc gac gac ccc atg ctc ctc gcc tac ctc ctg gac cct tcc aac acc  288
Gly Asp Asp Pro Met Leu Leu Ala Tyr Leu Leu Asp Pro Ser Asn Thr
                 85                  90                  95 acc ccc gag ggg gtg gcc cgg cgc tac ggc ggg gag tgg acg gag gag  336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg  384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg  432
Gly Arg Leu Glu Gly Glu Glu Arg Leu Leu Trp Leu Tyr Arg Glu Val
130                 135                 140 gag agg ccc ctt tcc gct gtc ctg gcc cac atg gag gcc acg ggg gtg  480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag  528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc  576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag  624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc  672
Leu Gly Leu Pro Ala Ile Gly Lys Thr Glu Lys Thr Gly Lys Arg Ser
210                 215                 220 acc agc gcc gcc gtc ctg gag gcc ctc cgc gag gcc cac ccc atc gtg  720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac  768
Glu Lys Ile Leu Gln Tyr Arg Glu Leu Thr Lys Leu Lys Ser Thr Tyr
                245                 250                 255 att gac ccc ttg ccg gac ctc atc cac ccc agg acg ggc cgc ctc cac  816
Ile Asp Pro Leu Pro Asp Leu Ile His Pro Arg Thr Gly Arg Leu His
            260                 265                 270 acc cgc ttc aac cag acg gcc acg gcc acg ggc agg cta agt agc tcc  864
Thr Arg Phe Asn Gln Thr Ala Thr Ala Thr Gly Arg Leu Ser Ser Ser
        275                 280                 285 gat ccc aac ctc cag aac atc ccc gtc cgc acc ccg ctt ggg cag agg  912
Asp Pro Asn Leu Gln Asn Ile Pro Val Arg Thr Pro Leu Gly Gln Arg
290                 295                 300 atc cgc cgg gcc ttc atc gcc gag gag ggg tgg cta ttg gtg gcc ctg  960
Ile Arg Arg Ala Phe Ile Ala Glu Glu Gly Trp Leu Leu Val Ala Leu
305                 310                 315                 320 gac tat agc cag ata gag ctc agg gtg ctg gcc cac ctc tcc ggc gac  1008
Asp Tyr Ser Gln Ile Glu Leu Arg Val Leu Ala His Leu Ser Gly Asp
                325                 330                 335 gag aac ctg atc cgg gtc ttc cag gag ggg cgg gac atc cac acg gag  1056
Glu Asn Leu Ile Arg Val Phe Gln Glu Gly Arg Asp Ile His Thr Glu
            340                 345                 350
```

```
acc gcc agc tgg atg ttc ggc gtc ccc cag gag gcc gtg gac ccc ctg      1104
Thr Ala Ser Trp Met Phe Gly Val Pro Gln Glu Ala Val Asp Pro Leu
        355                 360                 365 atg cgc cgg gcg gcc aag acc atc aac ttc ggg gtc ctc tac ggc atg      1152
Met Arg Arg Ala Ala Lys Thr Ile Asn Phe Gly Val Leu Tyr Gly Met
370                 375                 380 tcg gcc cac cgc ctc tcc cag gag cta gcc atc cct tac gag gag gcc      1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc      1248
Gln Ala Phe Ile Glu Arg Tyr Phe Gln Ser Phe Pro Lys Val Arg Ala
                405                 410                 415 tgg att gag aag acc ctg gag gag ggc agg agg cgg ggg tac gtg gag      1296
Trp Ile Glu Lys Thr Leu Glu Glu Gly Arg Arg Arg Gly Tyr Val Glu
            420                 425                 430 acc ctc ttc ggc cgc cgc cgc tac gtg cca gac cta gag gcc cgg gtg      1344
Thr Leu Phe Gly Arg Arg Arg Tyr Val Pro Asp Leu Glu Ala Arg Val
        435                 440                 445 aag agc gtg cgg gag gcg gcc gag cgc atg gcc ttc aac atg ccc gtc      1392
Lys Ser Val Arg Glu Ala Ala Glu Arg Met Ala Phe Asn Met Pro Val
450                 455                 460 cag ggc acc gcc gcc gac ctc atg aag ctg gct atg gtg aag ctc ttc      1440
Gln Gly Thr Ala Ala Asp Leu Met Lys Leu Ala Met Val Lys Leu Phe
465                 470                 475                 480 ccc agg ctg gag gaa atg ggg gcc agg atg ctc ctt cag gtc cac gac      1488
Pro Arg Leu Glu Glu Met Gly Ala Arg Met Leu Leu Gln Val His Asp
                485                 490                 495 gag ctg gtc ctc gag gcc cca aaa gag ggg gcg gag gcc gtg gcc cgg      1536
Glu Leu Val Leu Glu Ala Pro Lys Glu Gly Ala Glu Ala Val Ala Arg
            500                 505                 510 ctg gcc aag gag gtc atg gag ggg gtg tat ccc ctg gcc gtg ccc ctg      1584
Leu Ala Lys Glu Val Met Glu Gly Val Tyr Pro Leu Ala Val Pro Leu
        515                 520                 525 gag gtg gag gtg ggg ata ggg gag gac tgg ctc tcc gcc aag gag gcg      1632
Glu Val Glu Val Gly Ile Gly Glu Asp Trp Leu Ser Ala Lys Glu Ala
530                 535                 540 gcc gc                                                               1637
Ala
545

<210> SEQ ID NO 85
<211> LENGTH: 545
<212> TYPE: PRT
<213> ORGANISM: Thermus aquaticus

<400> SEQUENCE: 85

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
            20                  25                  30

Leu Ala Leu Ala Ala Ala Arg Gly Gly Arg Val His Arg Ala Pro Glu
        35                  40                  45

Pro Tyr Lys Ala Leu Arg Asp Leu Lys Glu Ala Arg Gly Leu Leu Ala
    50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95
```

-continued

Thr Pro Glu Gly Val Ala Arg Arg Tyr Gly Glu Trp Thr Glu Glu
            100                 105                 110

Ala Gly Glu Arg Ala Ala Leu Ser Glu Arg Leu Phe Ala Asn Leu Trp
        115                 120                 125

Gly Arg Leu Glu Gly Glu Arg Leu Leu Trp Leu Tyr Arg Glu Val
    130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
        195                 200                 205

Leu Gly Leu Pro Ala Ile Gly Lys Thr Glu Lys Thr Gly Lys Arg Ser
    210                 215                 220

Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Lys Ser Thr Tyr
                245                 250                 255

Ile Asp Pro Leu Pro Asp Leu Ile His Pro Arg Thr Gly Arg Leu His
            260                 265                 270

Thr Arg Phe Asn Gln Thr Ala Thr Ala Thr Gly Arg Leu Ser Ser Ser
        275                 280                 285

Asp Pro Asn Leu Gln Asn Ile Pro Val Arg Thr Pro Leu Gly Gln Arg
    290                 295                 300

Ile Arg Arg Ala Phe Ile Ala Glu Glu Gly Trp Leu Leu Val Ala Leu
305                 310                 315                 320

Asp Tyr Ser Gln Ile Glu Leu Arg Val Leu Ala His Leu Ser Gly Asp
                325                 330                 335

Glu Asn Leu Ile Arg Val Phe Gln Glu Gly Arg Asp Ile His Thr Glu
            340                 345                 350

Thr Ala Ser Trp Met Phe Gly Val Pro Gln Glu Ala Val Asp Pro Leu
        355                 360                 365

Met Arg Arg Ala Ala Lys Thr Ile Asn Phe Gly Val Leu Tyr Gly Met
    370                 375                 380

Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
                405                 410                 415

Trp Ile Glu Lys Thr Leu Glu Glu Gly Arg Arg Arg Gly Tyr Val Glu
            420                 425                 430

Thr Leu Phe Gly Arg Arg Arg Tyr Val Pro Asp Leu Glu Ala Arg Val
        435                 440                 445

Lys Ser Val Arg Glu Ala Ala Glu Arg Met Ala Phe Asn Met Pro Val
    450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Met Leu Leu Gln Val His Asp
                485                 490                 495

Glu Leu Val Leu Glu Ala Pro Lys Glu Gly Ala Glu Ala Val Ala Arg
            500                 505                 510

Leu Ala Lys Glu Val Met Glu Gly Val Tyr Pro Leu Ala Val Pro Leu

-continued

```
                515                 520                 525
Glu Val Glu Val Gly Ile Gly Glu Asp Trp Leu Ser Ala Lys Glu Ala
        530                 535                 540
Ala
545

<210> SEQ ID NO 86
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 86 agc ccc aag gcc ctg gag gag gcc ccc tgg ccc ccg ccg gaa ggg gcc      48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt      96
Phe Val Gly Phe Val Leu Ser Arg Lys Glu Pro Met Trp Ala Asp Leu
                20                  25                  30 ctg gcc ctg gcc gcc gcc agg ggg ggc cgg gtc cac cgg gcc ccc gag     144
Leu Ala Leu Ala Ala Ala Arg Gly Gly Arg Val His Arg Ala Pro Glu
            35                  40                  45 cct tat aaa gcc ctc agg gac ctg aag gag gcg cgg ggg ctt ctc gcc     192
Pro Tyr Lys Ala Leu Arg Asp Leu Lys Glu Ala Arg Gly Leu Leu Ala
        50                  55                  60 aaa gac ctg agc gtt ctg gcc ctg agg gaa ggc ctt ggc ctc ccg ccc     240
Lys Asp Leu Ser Val Leu Ala Leu Arg Glu Gly Leu Gly Leu Pro Pro
65                  70                  75                  80 ggc gac gac ccc atg ctc ctc gcc tac ctc ctg gac cct tcc aac acc     288
Gly Asp Asp Pro Met Leu Leu Ala Tyr Leu Leu Asp Pro Ser Asn Thr
                85                  90                  95 acc ccc gag ggg gtg gcc cgg cgc tac ggc ggg gag tgg acg gag gag     336
Thr Pro Glu Gly Val Ala Arg Arg Tyr Gly Gly Glu Trp Thr Glu Glu
                100                 105                 110 gcg ggg gag cgg gcc gcc ctt tcc gag agg ctc ttc gcc aac ctg tgg     384
Ala Gly Glu Arg Ala Ala Leu Ser Glu Arg Leu Phe Ala Asn Leu Trp
            115                 120                 125 ggg agg ctt gag ggg gag gag agg ctc ctt tgg ctt tac cgg gag gtg     432
Gly Arg Leu Glu Gly Glu Glu Arg Leu Leu Trp Leu Tyr Arg Glu Val
        130                 135                 140 gag agg ccc ctt tcc gct gtc ctg gcc cac atg gag gcc acg ggg gtg     480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag     528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc     576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag     624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc     672
Leu Gly Leu Pro Ala Ile Gly Lys Thr Glu Lys Thr Gly Lys Arg Ser
    210                 215                 220 acc agc gcc gcc gtc ctg gag gcc ctc cgc gag gcc cac ccc atc gtg     720
Thr Ser Ala Ala Val Leu Glu Ala Leu Arg Glu Ala His Pro Ile Val
225                 230                 235                 240
```

-continued

| | |
|---|---|
| gag aag atc ctg cag tac cgg gag ctc acc aag ctg aag agc acc tac<br>Glu Lys Ile Leu Gln Tyr Arg Glu Leu Thr Lys Leu Lys Ser Thr Tyr<br>245 250 255 | 768 |
| att gac ccc ttg ccg gac ctc atc cac ccc agg acg ggc cgc ctc cac<br>Ile Asp Pro Leu Pro Asp Leu Ile His Pro Arg Thr Gly Arg Leu His<br>260 265 270 | 816 |
| acc cgc ttc aac cag acg gcc acg gcc acg ggc agg cta agt agc tcc<br>Thr Arg Phe Asn Gln Thr Ala Thr Ala Thr Gly Arg Leu Ser Ser Ser<br>275 280 285 | 864 |
| gat ccc aac ctc cag aac atc ccc gtc cgc acc ccg ctt ggg cag agg<br>Asp Pro Asn Leu Gln Asn Ile Pro Val Arg Thr Pro Leu Gly Gln Arg<br>290 295 300 | 912 |
| atc cgc cgg gcc ttc atc gcc gag gag ggg tgg cta ttg gtg gcc ctg<br>Ile Arg Arg Ala Phe Ile Ala Glu Glu Gly Trp Leu Leu Val Ala Leu<br>305 310 315 320 | 960 |
| gac tat agc cag ata gag ctc agg gtg ctg gcc cac ctc tcc ggc gac<br>Asp Tyr Ser Gln Ile Glu Leu Arg Val Leu Ala His Leu Ser Gly Asp<br>325 330 335 | 1008 |
| gag aac ctg atc cgg gtc ttc cag gag ggg cgg gac atc cac acg gag<br>Glu Asn Leu Ile Arg Val Phe Gln Glu Gly Arg Asp Ile His Thr Glu<br>340 345 350 | 1056 |
| acc gcc agc tgg atg ttc ggc gtc ccc cgg gag gcc gtg gac ccc ctg<br>Thr Ala Ser Trp Met Phe Gly Val Pro Arg Glu Ala Val Asp Pro Leu<br>355 360 365 | 1104 |
| atg cgc cgg gcg gcc aag acc atc aac ttc ggg gtc ctc tac ggc atg<br>Met Arg Arg Ala Ala Lys Thr Ile Asn Phe Gly Val Leu Tyr Gly Met<br>370 375 380 | 1152 |
| tcg gcc cac cgc ctc tcc cag gag cta gcc atc cct tac gag gag gcc<br>Ser Ala His Arg Leu Ser Gln Glu Leu Ala Ile Pro Tyr Glu Glu Ala<br>385 390 395 400 | 1200 |
| cag gcc ttc att gag cgc tac ttt cag agc ttc ccc aag gtg cgg gcc<br>Gln Ala Phe Ile Glu Arg Tyr Phe Gln Ser Phe Pro Lys Val Arg Ala<br>405 410 415 | 1248 |
| tgg att gag aag acc ctg gag gag ggc agg agg cgg ggg tac gtg gag<br>Trp Ile Glu Lys Thr Leu Glu Glu Gly Arg Arg Arg Gly Tyr Val Glu<br>420 425 430 | 1296 |
| acc ctc ttc ggc cgc cgc cgc tac gtg cca gac cta gag gcc cgg gtg<br>Thr Leu Phe Gly Arg Arg Arg Tyr Val Pro Asp Leu Glu Ala Arg Val<br>435 440 445 | 1344 |
| aag agc gtg cgg gag gcg gcc gag cgc aag gcc ttc aac atg ccc gtc<br>Lys Ser Val Arg Glu Ala Ala Glu Arg Lys Ala Phe Asn Met Pro Val<br>450 455 460 | 1392 |
| cag ggc acc gcc gcc gac ctc atg aag ctg gct atg gtg aag ctc ttc<br>Gln Gly Thr Ala Ala Asp Leu Met Lys Leu Ala Met Val Lys Leu Phe<br>465 470 475 480 | 1440 |
| ccc agg ctg gag gaa atg ggg gcc agg atg ctc ctt cag gtc cac gac<br>Pro Arg Leu Glu Glu Met Gly Ala Arg Met Leu Leu Gln Val His Asp<br>485 490 495 | 1488 |
| gag ctg gtc ctc gag gcc cca aaa gag ggg gcg gag gcc gtg gcc cgg<br>Glu Leu Val Leu Glu Ala Pro Lys Glu Gly Ala Glu Ala Val Ala Arg<br>500 505 510 | 1536 |
| ctg gcc aag gag gtc atg gag ggg gtg tat ccc ctg gcc gtg ccc ctg<br>Leu Ala Lys Glu Val Met Glu Gly Val Tyr Pro Leu Ala Val Pro Leu<br>515 520 525 | 1584 |
| gag gtg gag gtg ggg ata ggg gag gac tgg ctc tcc gcc aag gag gcg<br>Glu Val Glu Val Gly Ile Gly Glu Asp Trp Leu Ser Ala Lys Glu Ala<br>530 535 540 | 1632 |
| gcc gc<br>Ala<br>545 | 1637 |

<210> SEQ ID NO 87
<211> LENGTH: 545
<212> TYPE: PRT
<213> ORGANISM: Thermus aquaticus

<400> SEQUENCE: 87

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
            20                  25                  30

Leu Ala Leu Ala Ala Ala Arg Gly Gly Arg Val His Arg Ala Pro Glu
        35                  40                  45

Pro Tyr Lys Ala Leu Arg Asp Leu Lys Glu Ala Arg Gly Leu Leu Ala
    50                  55                  60

Lys Asp Leu Ser Val Leu Ala Leu Arg Glu Gly Leu Gly Leu Pro Pro
65              70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
            100                 105                 110

Ala Gly Glu Arg Ala Ala Leu Ser Glu Arg Leu Phe Ala Asn Leu Trp
        115                 120                 125

Gly Arg Leu Glu Gly Glu Glu Arg Leu Leu Trp Leu Tyr Arg Glu Val
    130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
        195                 200                 205

Leu Gly Leu Pro Ala Ile Gly Lys Thr Glu Lys Thr Gly Lys Arg Ser
    210                 215                 220

Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Lys Ser Thr Tyr
                245                 250                 255

Ile Asp Pro Leu Pro Asp Leu Ile His Pro Arg Thr Gly Arg Leu His
            260                 265                 270

Thr Arg Phe Asn Gln Thr Ala Thr Ala Thr Gly Arg Leu Ser Ser Ser
        275                 280                 285

Asp Pro Asn Leu Gln Asn Ile Pro Val Arg Thr Pro Leu Gly Gln Arg
    290                 295                 300

Ile Arg Arg Ala Phe Ile Ala Glu Glu Gly Trp Leu Leu Val Ala Leu
305                 310                 315                 320

Asp Tyr Ser Gln Ile Glu Leu Arg Val Leu Ala His Leu Ser Gly Asp
                325                 330                 335

Glu Asn Leu Ile Arg Val Phe Gln Glu Gly Arg Asp Ile His Thr Glu
            340                 345                 350

Thr Ala Ser Trp Met Phe Gly Val Pro Arg Glu Ala Val Asp Pro Leu
        355                 360                 365

Met Arg Arg Ala Ala Lys Thr Ile Asn Phe Gly Val Leu Tyr Gly Met

```
                370                 375                 380
Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
                405                 410                 415

Trp Ile Glu Lys Thr Leu Glu Glu Gly Arg Arg Arg Gly Tyr Val Glu
            420                 425                 430

Thr Leu Phe Gly Arg Arg Tyr Val Pro Asp Leu Glu Ala Arg Val
            435                 440                 445

Lys Ser Val Arg Glu Ala Ala Glu Arg Lys Ala Phe Asn Met Pro Val
            450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Met Leu Leu Gln Val His Asp
                485                 490                 495

Glu Leu Val Leu Glu Ala Pro Lys Glu Gly Ala Glu Ala Val Ala Arg
            500                 505                 510

Leu Ala Lys Glu Val Met Glu Gly Val Tyr Pro Leu Ala Val Pro Leu
            515                 520                 525

Glu Val Glu Val Gly Ile Gly Glu Asp Trp Leu Ser Ala Lys Glu Ala
            530                 535                 540

Ala
545

<210> SEQ ID NO 88
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 88 agc ccc aag gcc ctg gag gag gcc ccc tgg ccc ccg ccg gaa ggg gcc    48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt    96
Phe Val Gly Phe Val Leu Ser Arg Lys Glu Pro Met Trp Ala Asp Leu
                20                  25                  30 ctg gcc ctg gcc gcc gcc agg ggg ggc cgg gtc cac cgg gcc ccc gag   144
Leu Ala Leu Ala Ala Ala Arg Gly Gly Arg Val His Arg Ala Pro Glu
            35                  40                  45 cct tat aaa gcc ctc agg gac ctg aag gag gcg cgg ggg ctt ctc gcc   192
Pro Tyr Lys Ala Leu Arg Asp Leu Lys Glu Ala Arg Gly Leu Leu Ala
        50                  55                  60 aaa gac ctg agc gtt ctg gcc ctg agg gaa ggc ctt ggc ctc ccg ccc   240
Lys Asp Leu Ser Val Leu Ala Leu Arg Glu Gly Leu Gly Leu Pro Pro
65              70                  75                  80 ggc gac gac ccc atg ctc ctc gcc tac ctc ctg gac cct tcc aac acc   288
Gly Asp Asp Pro Met Leu Leu Ala Tyr Leu Leu Asp Pro Ser Asn Thr
                85                  90                  95 acc ccc gag ggg gtg gcc cgg cgc tac ggc ggg gag tgg acg gag gag   336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg   384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg   432
```

```
        Gly Arg Leu Glu Gly Glu Glu Arg Leu Leu Trp Leu Tyr Arg Glu Val
                130                 135                 140 gag agg ccc ctt tcc gct gtc ctg gcc cac atg gag gcc acg ggg gtg        480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag        528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc        576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag        624
Phe Asn Leu Asn Ser Arg Asp Gln Leu Glu Arg Val Leu Phe Asp Glu
                195                 200                 205 cta ggg ctt ccc gcc atc ggc aag acg gag aag acc ggc aag cgc tcc        672
Leu Gly Leu Pro Ala Ile Gly Lys Thr Glu Lys Thr Gly Lys Arg Ser
210                 215                 220 acc agc gcc gcc gtc ctg gag gcc ctc cgc gag gcc cac ccc atc gtg        720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac        768
Glu Lys Ile Leu Gln Tyr Arg Glu Leu Thr Lys Leu Lys Ser Thr Tyr
                245                 250                 255 att gac ccc ttg ccg gac ctc atc cac ccc agg acg ggc cgc ctc cac        816
Ile Asp Pro Leu Pro Asp Leu Ile His Pro Arg Thr Gly Arg Leu His
            260                 265                 270 acc cgc ttc aac cag acg gcc acg gcc acg ggc agg cta agt agc tcc        864
Thr Arg Phe Asn Gln Thr Ala Thr Ala Thr Gly Arg Leu Ser Ser Ser
                275                 280                 285 gat ccc aac ctc cag aac atc ccc gtc cgc acc ccg ctt ggg cag agg        912
Asp Pro Asn Leu Gln Asn Ile Pro Val Arg Thr Pro Leu Gly Gln Arg
                290                 295                 300 atc cgc cgg gcc ttc atc gcc gag gag ggg tgg cta ttg gtg gcc ctg        960
Ile Arg Arg Ala Phe Ile Ala Glu Glu Gly Trp Leu Leu Val Ala Leu
305                 310                 315                 320 gac tat agc cag ata gag ctc agg gtg ctg gcc cac ctc tcc ggc gac       1008
Asp Tyr Ser Gln Ile Glu Leu Arg Val Leu Ala His Leu Ser Gly Asp
                325                 330                 335 gag aac ctg atc cgg gtc ttc cag gag ggg cgg gac atc cac acg gag       1056
Glu Asn Leu Ile Arg Val Phe Gln Glu Gly Arg Asp Ile His Thr Glu
                340                 345                 350 acc gcc agc tgg atg ttc ggc gtc ccc cgg gag gcc gtg gac ccc ctg       1104
Thr Ala Ser Trp Met Phe Gly Val Pro Arg Glu Ala Val Asp Pro Leu
            355                 360                 365 atg cgc cgg gcg gcc aag acc atc aac ttc ggg gtc ctc tac ggc atg       1152
Met Arg Arg Ala Ala Lys Thr Ile Asn Phe Gly Val Leu Tyr Gly Met
370                 375                 380 tcg gcc cac cgc ctc tcc cag gag cta gcc atc cct tac gag gag gcc       1200
Ser Ala His Arg Leu Ser Gln Glu Leu Ala Ile Pro Tyr Glu Glu Ala
385                 390                 395                 400 cag gcc ttc att gag cgc aac ttt cag agc ttc ccc aag gtg cgg gcc       1248
Gln Ala Phe Ile Glu Arg Asn Phe Gln Ser Phe Pro Lys Val Arg Ala
                405                 410                 415 tgg att gag aag acc ctg gag gag ggc agg agg cgg ggg tac gtg gag       1296
Trp Ile Glu Lys Thr Leu Glu Glu Gly Arg Arg Arg Gly Tyr Val Glu
                420                 425                 430 acc ctc ttc ggc cgc cgc cgc tac gtg cca gac cta gag gcc cgg gtg       1344
Thr Leu Phe Gly Arg Arg Arg Tyr Val Pro Asp Leu Glu Ala Arg Val
            435                 440                 445
```

```
aag agc gtg cgg gag gcg gcc gag cgc atg gcc ttc aac atg ccc gtc    1392
Lys Ser Val Arg Glu Ala Ala Glu Arg Met Ala Phe Asn Met Pro Val
    450                 455                 460 cag ggc acc gcc gcc gac ctc atg aag ctg gct atg gtg aag ctc ttc    1440
Gln Gly Thr Ala Ala Asp Leu Met Lys Leu Ala Met Val Lys Leu Phe
465                 470                 475                 480 ccc agg ctg gag gaa atg ggg gcc agg atg ctc ctt cag gtc cac gac    1488
Pro Arg Leu Glu Glu Met Gly Ala Arg Met Leu Leu Gln Val His Asp
                485                 490                 495 gag ctg gtc ctc gag gcc cca aaa gag ggg gcg gag gcc gtg gcc cgg    1536
Glu Leu Val Leu Glu Ala Pro Lys Glu Gly Ala Glu Ala Val Ala Arg
            500                 505                 510 ctg gcc aag gag gtc atg gag ggg gtg tat ccc ctg gcc gtg ccc ctg    1584
Leu Ala Lys Glu Val Met Glu Gly Val Tyr Pro Leu Ala Val Pro Leu
        515                 520                 525 gag gtg gag gtg ggg ata ggg gag gac tgg ctc tcc gcc aag gag gcg    1632
Glu Val Glu Val Gly Ile Gly Glu Asp Trp Leu Ser Ala Lys Glu Ala
    530                 535                 540 gcc gc                                                             1637
Ala
545

<210> SEQ ID NO 89
<211> LENGTH: 545
<212> TYPE: PRT
<213> ORGANISM: Thermus aquaticus

<400> SEQUENCE: 89

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
                20                  25                  30

Leu Ala Leu Ala Ala Ala Arg Gly Gly Arg Val His Arg Ala Pro Glu
            35                  40                  45

Pro Tyr Lys Ala Leu Arg Asp Leu Lys Glu Ala Arg Gly Leu Leu Ala
        50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
            100                 105                 110

Ala Gly Glu Arg Ala Ala Leu Ser Glu Arg Leu Phe Ala Asn Leu Trp
        115                 120                 125

Gly Arg Leu Glu Gly Glu Glu Arg Leu Leu Trp Leu Tyr Arg Glu Val
    130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
        195                 200                 205

Leu Gly Leu Pro Ala Ile Gly Lys Thr Glu Lys Thr Gly Lys Arg Ser
    210                 215                 220

Thr Ser Ala Ala Val Leu Glu Ala Leu Arg Glu Ala His Pro Ile Val
```

```
                    225                 230                 235                 240
        Glu Lys Ile Leu Gln Tyr Arg Glu Leu Thr Lys Leu Lys Ser Thr Tyr
                        245                 250                 255

Ile Asp Pro Leu Pro Asp Leu Ile His Pro Arg Thr Gly Arg Leu His
                    260                 265                 270

Thr Arg Phe Asn Gln Thr Ala Thr Ala Thr Gly Arg Leu Ser Ser Ser
                275                 280                 285

Asp Pro Asn Leu Gln Asn Ile Pro Val Arg Thr Pro Leu Gly Gln Arg
            290                 295                 300

Ile Arg Arg Ala Phe Ile Ala Glu Gly Trp Leu Leu Val Ala Leu
        305                 310                 315                 320

Asp Tyr Ser Gln Ile Glu Leu Arg Val Leu Ala His Leu Ser Gly Asp
                        325                 330                 335

Glu Asn Leu Ile Arg Val Phe Gln Glu Gly Arg Asp Ile His Thr Glu
                    340                 345                 350

Thr Ala Ser Trp Met Phe Gly Val Pro Arg Glu Ala Val Asp Pro Leu
                355                 360                 365

Met Arg Arg Ala Ala Lys Thr Ile Asn Phe Gly Val Leu Tyr Gly Met
            370                 375                 380

Ser Ala His Arg Leu Ser Gln Glu Leu Ala Ile Pro Tyr Glu Glu Ala
        385                 390                 395                 400

Gln Ala Phe Ile Glu Arg Asn Phe Gln Ser Phe Pro Lys Val Arg Ala
                        405                 410                 415

Trp Ile Glu Lys Thr Leu Glu Glu Gly Arg Arg Arg Gly Tyr Val Glu
                    420                 425                 430

Thr Leu Phe Gly Arg Arg Arg Tyr Val Pro Asp Leu Glu Ala Arg Val
                435                 440                 445

Lys Ser Val Arg Glu Ala Ala Glu Arg Met Ala Phe Asn Met Pro Val
            450                 455                 460

Gln Gly Thr Ala Ala Asp Leu Met Lys Leu Ala Met Val Lys Leu Phe
        465                 470                 475                 480

Pro Arg Leu Glu Glu Met Gly Ala Arg Met Leu Leu Gln Val His Asp
                        485                 490                 495

Glu Leu Val Leu Glu Ala Pro Lys Glu Gly Ala Glu Ala Val Ala Arg
                    500                 505                 510

Leu Ala Lys Glu Val Met Glu Gly Val Tyr Pro Leu Ala Val Pro Leu
                515                 520                 525

Glu Val Glu Val Gly Ile Gly Glu Asp Trp Leu Ser Ala Lys Glu Ala
            530                 535                 540

Ala
        545

<210> SEQ ID NO 90
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 90 agc ccc aag gcc ctg gag gag gcc ccc tgg ccc ccg ccg gaa ggg gcc        48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt        96
Phe Val Gly Phe Val Leu Ser Arg Lys Glu Pro Met Trp Ala Asp Leu
```

```
                    20                  25                  30
ctg gcc ctg gcc gcc gcc agg ggg ggc cgg gtc cac cgg gcc ccc gag       144
Leu Ala Leu Ala Ala Ala Arg Gly Gly Arg Val His Arg Ala Pro Glu
         35                  40                  45 cct tat aaa gcc ctc agg gac ctg aag gag gcg cgg ggg ctt ctc gcc       192
Pro Tyr Lys Ala Leu Arg Asp Leu Lys Glu Ala Arg Gly Leu Leu Ala
     50                  55                  60 aaa gac ctg agc gtt ctg gcc ctg agg gaa ggc ctt ggc ctc ccg ccc       240
Lys Asp Leu Ser Val Leu Ala Leu Arg Glu Gly Leu Gly Leu Pro Pro
 65                  70                  75                  80 ggc gac gac ccc atg ctc ctc gcc tac ctc ctg gac cct tcc aac acc       288
Gly Asp Asp Pro Met Leu Leu Ala Tyr Leu Leu Asp Pro Ser Asn Thr
                 85                  90                  95 acc ccc gag ggg gtg gcc cgg cgc tac ggc ggg gag tgg acg gag gag       336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg       384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg       432
Gly Arg Leu Glu Gly Glu Glu Arg Leu Leu Trp Leu Tyr Arg Glu Val
    130                 135                 140 gag agg ccc ctt tcc gct gtc ctg gcc cac atg gag gcc acg ggg gtg       480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag       528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc       576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag       624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc       672
Leu Gly Leu Pro Ala Ile Gly Lys Thr Glu Lys Thr Gly Lys Arg Ser
    210                 215                 220 acc agc gcc gcc gtc ctg gag gcc ctc cgc gag gcc cac ccc atc gtg       720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac       768
Glu Lys Ile Leu Gln Tyr Arg Glu Leu Thr Lys Leu Lys Ser Thr Tyr
                245                 250                 255 att gac ccc ttg ccg gac ctc atc cac ccc agg acg ggc cgc ctc cac       816
Ile Asp Pro Leu Pro Asp Leu Ile His Pro Arg Thr Gly Arg Leu His
            260                 265                 270 acc cgc ttc aac cag acg gcc acg gcc acg ggc agg cta agt agc tcc       864
Thr Arg Phe Asn Gln Thr Ala Thr Ala Thr Gly Arg Leu Ser Ser Ser
        275                 280                 285 gat ccc aac ctc cag aac atc ccc gtc cgc acc ccg ctt ggg cag agg       912
Asp Pro Asn Leu Gln Asn Ile Pro Val Arg Thr Pro Leu Gly Gln Arg
    290                 295                 300 atc cgc cgg gcc ttc atc gcc gag gag ggg tgg cta ttg gtg gcc ctg       960
Ile Arg Arg Ala Phe Ile Ala Glu Glu Gly Trp Leu Leu Val Ala Leu
305                 310                 315                 320 gac tat agc cag ata gag ctc agg gtg ctg gcc cac ctc tcc ggc gac      1008
Asp Tyr Ser Gln Ile Glu Leu Arg Val Leu Ala His Leu Ser Gly Asp
                325                 330                 335 gag aac ctg atc cgg gtc ttc cag gag ggg cgg gac atc cac acg gag      1056
```

```
Glu Asn Leu Ile Arg Val Phe Gln Glu Gly Arg Asp Ile His Thr Glu
            340                 345                 350 acc gcc agc tgg atg ttc ggc gtc ccc cgg gag gcc gtg gac ccc ctg      1104
Thr Ala Ser Trp Met Phe Gly Val Pro Arg Glu Ala Val Asp Pro Leu
        355                 360                 365 atg cgc cgg gcg gcc aag acc atc aac ttc ggg gtc ctc tac ggc atg      1152
Met Arg Arg Ala Ala Lys Thr Ile Asn Phe Gly Val Leu Tyr Gly Met
370                 375                 380 tcg gcc cac cgc ctc tcc cag gag cta gcc atc cct tac gag gag gcc      1200
Ser Ala His Arg Leu Ser Gln Glu Leu Ala Ile Pro Tyr Glu Glu Ala
385                 390                 395                 400 cag gcc ttc att gag cgc tgc ttt cag agc ttc ccc aag gtg cgg gcc      1248
Gln Ala Phe Ile Glu Arg Cys Phe Gln Ser Phe Pro Lys Val Arg Ala
            405                 410                 415 tgg att gag aag acc ctg gag gag ggc agg agg cgg ggg tac gtg gag      1296
Trp Ile Glu Lys Thr Leu Glu Glu Gly Arg Arg Arg Gly Tyr Val Glu
        420                 425                 430 acc ctc ttc ggc cgc cgc cgc tac gtg cca gac cta gag gcc cgg gtg      1344
Thr Leu Phe Gly Arg Arg Arg Tyr Val Pro Asp Leu Glu Ala Arg Val
    435                 440                 445 aag agc gtg cgg gag gcg gcc gag cgc atg gcc ttc aac atg ccc gtc      1392
Lys Ser Val Arg Glu Ala Ala Glu Arg Met Ala Phe Asn Met Pro Val
450                 455                 460 cag ggc acc gcc gcc gac ctc atg aag ctg gct atg gtg aag ctc ttc      1440
Gln Gly Thr Ala Ala Asp Leu Met Lys Leu Ala Met Val Lys Leu Phe
465                 470                 475                 480 ccc agg ctg gag gaa atg ggg gcc agg atg ctc ctt cag gtc cac gac      1488
Pro Arg Leu Glu Glu Met Gly Ala Arg Met Leu Leu Gln Val His Asp
            485                 490                 495 gag ctg gtc ctc gag gcc cca aaa gag ggg gcg gag gcc gtg gcc cgg      1536
Glu Leu Val Leu Glu Ala Pro Lys Glu Gly Ala Glu Ala Val Ala Arg
        500                 505                 510 ctg gcc aag gag gtc atg gag ggg gtg tat ccc ctg gcc gtg ccc ctg      1584
Leu Ala Lys Glu Val Met Glu Gly Val Tyr Pro Leu Ala Val Pro Leu
    515                 520                 525 gag gtg gag gtg ggg ata ggg gag gac tgg ctc tcc gcc aag gag gcg      1632
Glu Val Glu Val Gly Ile Gly Glu Asp Trp Leu Ser Ala Lys Glu Ala
530                 535                 540 gcc gc                                                                1637
Ala
545

<210> SEQ ID NO 91
<211> LENGTH: 545
<212> TYPE: PRT
<213> ORGANISM: Thermus aquaticus

<400> SEQUENCE: 91

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
            20                  25                  30

Leu Ala Leu Ala Ala Ala Arg Gly Gly Arg Val His Arg Ala Pro Glu
        35                  40                  45

Pro Tyr Lys Ala Leu Arg Asp Leu Lys Glu Ala Arg Gly Leu Leu Ala
    50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
```

```
                   85                  90                  95
Thr Pro Glu Gly Val Arg Arg Tyr Gly Gly Glu Trp Thr Glu Glu
                  100                 105                 110
Ala Gly Glu Arg Ala Ala Leu Ser Glu Arg Leu Phe Ala Asn Leu Trp
                  115                 120                 125
Gly Arg Leu Glu Gly Glu Arg Leu Leu Trp Leu Tyr Arg Glu Val
    130                 135                 140
Glu Arg Pro Leu Ser Ala Val Leu Ala His Met Glu Ala Thr Gly Val
145                 150                 155                 160
Arg Leu Asp Val Ala Tyr Leu Arg Ala Leu Ser Leu Glu Val Ala Glu
                165                 170                 175
Glu Ile Ala Arg Leu Glu Ala Glu Val Phe Arg Leu Ala Gly His Pro
                180                 185                 190
Phe Asn Leu Asn Ser Arg Asp Gln Leu Glu Arg Val Leu Phe Asp Glu
                195                 200                 205
Leu Gly Leu Pro Ala Ile Gly Lys Thr Glu Lys Thr Gly Lys Arg Ser
    210                 215                 220
Thr Ser Ala Ala Val Leu Glu Ala Leu Arg Glu Ala His Pro Ile Val
225                 230                 235                 240
Glu Lys Ile Leu Gln Tyr Arg Glu Leu Thr Lys Leu Lys Ser Thr Tyr
                245                 250                 255
Ile Asp Pro Leu Pro Asp Leu Ile His Pro Arg Thr Gly Arg Leu His
                260                 265                 270
Thr Arg Phe Asn Gln Thr Ala Thr Ala Thr Gly Arg Leu Ser Ser Ser
                275                 280                 285
Asp Pro Asn Leu Gln Asn Ile Pro Val Arg Thr Pro Leu Gly Gln Arg
    290                 295                 300
Ile Arg Arg Ala Phe Ile Ala Glu Glu Gly Trp Leu Leu Val Ala Leu
305                 310                 315                 320
Asp Tyr Ser Gln Ile Glu Leu Arg Val Leu Ala His Leu Ser Gly Asp
                325                 330                 335
Glu Asn Leu Ile Arg Val Phe Gln Glu Gly Arg Asp Ile His Thr Glu
                340                 345                 350
Thr Ala Ser Trp Met Phe Gly Val Pro Arg Glu Ala Val Asp Pro Leu
    355                 360                 365
Met Arg Arg Ala Ala Lys Thr Ile Asn Phe Gly Val Leu Tyr Gly Met
    370                 375                 380
Ser Ala His Arg Leu Ser Gln Glu Leu Ala Ile Pro Tyr Glu Glu Ala
385                 390                 395                 400
Gln Ala Phe Ile Glu Arg Cys Phe Gln Ser Phe Pro Lys Val Arg Ala
                405                 410                 415
Trp Ile Glu Lys Thr Leu Glu Glu Gly Arg Arg Arg Gly Tyr Val Glu
                420                 425                 430
Thr Leu Phe Gly Arg Arg Arg Tyr Val Pro Asp Leu Glu Ala Arg Val
                435                 440                 445
Lys Ser Val Arg Glu Ala Ala Glu Arg Met Ala Phe Asn Met Pro Val
    450                 455                 460
Gln Gly Thr Ala Ala Asp Leu Met Lys Leu Ala Met Val Lys Leu Phe
465                 470                 475                 480
Pro Arg Leu Glu Glu Met Gly Ala Arg Met Leu Leu Gln Val His Asp
                485                 490                 495
Glu Leu Val Leu Glu Ala Pro Lys Glu Gly Ala Glu Ala Val Ala Arg
                500                 505                 510
```

```
Leu Ala Lys Glu Val Met Glu Gly Val Tyr Pro Leu Ala Val Pro Leu
        515                 520                 525
Glu Val Glu Val Gly Ile Gly Glu Asp Trp Leu Ser Ala Lys Glu Ala
    530                 535                 540
Ala
545

<210> SEQ ID NO 92
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 92 agc ccc aag gcc ctg gag gag gcc ccc tgg ccc ccg ccg gaa ggg gcc    48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt    96
Phe Val Gly Phe Val Leu Ser Arg Lys Glu Pro Met Trp Ala Asp Leu
            20                  25                  30 ctg gcc ctg gcc gcc gcc agg ggg ggc cgg gtc cac cgg gcc ccc gag   144
Leu Ala Leu Ala Ala Ala Arg Gly Gly Arg Val His Arg Ala Pro Glu
        35                  40                  45 cct tat aaa gcc ctc agg gac ctg aag gag gcg cgg ggg ctt ctc gcc   192
Pro Tyr Lys Ala Leu Arg Asp Leu Lys Glu Ala Arg Gly Leu Leu Ala
    50                  55                  60 aaa gac ctg agc gtt ctg gcc ctg agg gaa ggc ctt ggc ctc ccg ccc   240
Lys Asp Leu Ser Val Leu Ala Leu Arg Glu Gly Leu Gly Leu Pro Pro
65                  70                  75                  80 ggc gac gac ccc atg ctc ctc gcc tac ctc ctg gac cct tcc aac acc   288
Gly Asp Asp Pro Met Leu Leu Ala Tyr Leu Leu Asp Pro Ser Asn Thr
                85                  90                  95 acc ccc gag ggg gtg gcc cgg cgc tac ggc ggg gag tgg acg gag gag   336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg   384
Ala Gly Glu Arg Ala Ala Leu Ser Glu Arg Leu Phe Ala Asn Leu Trp
        115                 120                 125 ggg agg ctt gag ggg gag gag agg ctc ctt tgg ctt tac cgg gag gtg   432
Gly Arg Leu Glu Gly Glu Glu Arg Leu Leu Trp Leu Tyr Arg Glu Val
    130                 135                 140 gag agg ccc ctt tcc gct gtc ctg gcc cac atg gag gcc acg ggg gtg   480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag   528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc   576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag   624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc   672
Leu Gly Leu Pro Ala Ile Gly Lys Thr Glu Lys Thr Gly Lys Arg Ser
    210                 215                 220 acc agc gcc gcc gtc ctg gag gcc ctc cgc gag gcc cac ccc atc gtg   720
Thr Ser Ala Ala Val Leu Glu Ala Leu Arg Glu Ala His Pro Ile Val
225                 230                 235                 240
```

```
              225                 230                 235                 240
gag aag atc ctg cag tac cgg gag ctc acc aag ctg aag agc acc tac       768
Glu Lys Ile Leu Gln Tyr Arg Glu Leu Thr Lys Leu Lys Ser Thr Tyr
                        245                 250                 255 att gac ccc ttg ccg gac ctc atc cac ccc agg acg ggc cgc ctc cac       816
Ile Asp Pro Leu Pro Asp Leu Ile His Pro Arg Thr Gly Arg Leu His
                260                 265                 270 acc cgc ttc aac cag acg gcc acg gcc acg ggc agg cta agt agc tcc       864
Thr Arg Phe Asn Gln Thr Ala Thr Ala Thr Gly Arg Leu Ser Ser Ser
            275                 280                 285 gat ccc aac ctc cag aac atc ccc gtc cgc acc ccg ctt ggg cag agg       912
Asp Pro Asn Leu Gln Asn Ile Pro Val Arg Thr Pro Leu Gly Gln Arg
        290                 295                 300 atc cgc cgg gcc ttc aac gcc gag gag ggg tgg cta ttg gtg gcc ctg       960
Ile Arg Arg Ala Phe Asn Ala Glu Glu Gly Trp Leu Leu Val Ala Leu
305                 310                 315                 320 gac tat agc cag ata gag ctc agg gtg ctg gcc cac ctc tcc ggc gac      1008
Asp Tyr Ser Gln Ile Glu Leu Arg Val Leu Ala His Leu Ser Gly Asp
                325                 330                 335 gag aac ctg atc cgg gtc ttc cag gag ggg agg gac atc cac acg gag      1056
Glu Asn Leu Ile Arg Val Phe Gln Glu Gly Arg Asp Ile His Thr Glu
            340                 345                 350 acc gcc agc tgg atg ttc ggc gtc ccc cgg gag gcc gtg gac ccc ctg      1104
Thr Ala Ser Trp Met Phe Gly Val Pro Arg Glu Ala Val Asp Pro Leu
        355                 360                 365 atg cgc cgg gcg gcc aag acc atc aac ttc ggg gtc ctc tac ggc atg      1152
Met Arg Arg Ala Ala Lys Thr Ile Asn Phe Gly Val Leu Tyr Gly Met
    370                 375                 380 tcg gcc cac cgc ctc tcc cag gag cta gcc atc cct tac gag gag gcc      1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc      1248
Gln Ala Phe Ile Glu Arg Tyr Phe Gln Ser Phe Pro Lys Val Arg Ala
                405                 410                 415 tgg att gag aag acc ctg gag gag ggc agg agg cgg ggg tac gtg gag      1296
Trp Ile Glu Lys Thr Leu Glu Glu Gly Arg Arg Arg Gly Tyr Val Glu
            420                 425                 430 acc ctc ttc ggc cgc cgc cgc tac gtg cca gac cta gag gcc cgg gtg      1344
Thr Leu Phe Gly Arg Arg Arg Tyr Val Pro Asp Leu Glu Ala Arg Val
        435                 440                 445 aag agc gtg cgg gag gcg gcc gag cgc atg gcc ttc aac atg ccc gtc      1392
Lys Ser Val Arg Glu Ala Ala Glu Arg Met Ala Phe Asn Met Pro Val
    450                 455                 460 cag ggc acc gcc gcc gac ctc atg aag ctg gct atg gtg aag ctc ttc      1440
Gln Gly Thr Ala Ala Asp Leu Met Lys Leu Ala Met Val Lys Leu Phe
465                 470                 475                 480 ccc agg ctg gag gaa atg ggg gcc agg atg ccc ctt cag gtc cac gac      1488
Pro Arg Leu Glu Glu Met Gly Ala Arg Met Pro Leu Gln Val His Asp
                485                 490                 495 gag ctg gtc ctc gag gcc cca aaa gag ggg gcg gag gcc gtg gcc cgg      1536
Glu Leu Val Leu Glu Ala Pro Lys Glu Gly Ala Glu Ala Val Ala Arg
            500                 505                 510 ctg gcc aag gag gtc atg gag ggg gtg tat ccc ctg gcc gtg ccc ctg      1584
Leu Ala Lys Glu Val Met Glu Gly Val Tyr Pro Leu Ala Val Pro Leu
        515                 520                 525 gag gtg aag gtg ggg ata ggg gag gac tgg ctc tcc gcc aag gag gcg      1632
Glu Val Lys Val Gly Ile Gly Glu Asp Trp Leu Ser Ala Lys Glu Ala
    530                 535                 540 gcc gc                                                                1637
```

Ala
545

<210> SEQ ID NO 93
<211> LENGTH: 545
<212> TYPE: PRT
<213> ORGANISM: Thermus aquaticus

<400> SEQUENCE: 93

| | | | | | | | | | | | | | | |
|---|---|---|---|---|---|---|---|---|---|---|---|---|---|---|
| Ser | Pro | Lys | Ala | Leu | Glu | Glu | Ala | Pro | Trp | Pro | Pro | Gly | Ala |
| 1 | | | | 5 | | | | | 10 | | | | 15 |
| Phe | Val | Gly | Phe | Val | Leu | Ser | Arg | Lys | Glu | Pro | Met | Trp | Ala | Asp | Leu |
| | | | 20 | | | | | 25 | | | | | 30 | | |
| Leu | Ala | Leu | Ala | Ala | Ala | Arg | Gly | Gly | Arg | Val | His | Arg | Ala | Pro | Glu |
| | | | 35 | | | | | 40 | | | | | 45 | | |
| Pro | Tyr | Lys | Ala | Leu | Arg | Asp | Leu | Lys | Glu | Ala | Arg | Gly | Leu | Leu | Ala |
| | | 50 | | | | | 55 | | | | | 60 | | | |
| Lys | Asp | Leu | Ser | Val | Leu | Ala | Leu | Arg | Glu | Gly | Leu | Gly | Leu | Pro | Pro |
| 65 | | | | | 70 | | | | | 75 | | | | | 80 |
| Gly | Asp | Asp | Pro | Met | Leu | Leu | Ala | Tyr | Leu | Leu | Asp | Pro | Ser | Asn | Thr |
| | | | | 85 | | | | | 90 | | | | | 95 | |
| Thr | Pro | Glu | Gly | Val | Ala | Arg | Arg | Tyr | Gly | Gly | Glu | Trp | Thr | Glu | Glu |
| | | | 100 | | | | | 105 | | | | | 110 | | |
| Ala | Gly | Glu | Arg | Ala | Ala | Leu | Ser | Glu | Arg | Leu | Phe | Ala | Asn | Leu | Trp |
| | | | 115 | | | | | 120 | | | | | 125 | | |
| Gly | Arg | Leu | Glu | Gly | Glu | Glu | Arg | Leu | Leu | Trp | Leu | Tyr | Arg | Glu | Val |
| | | 130 | | | | | 135 | | | | | 140 | | | |
| Glu | Arg | Pro | Leu | Ser | Ala | Val | Leu | Ala | His | Met | Glu | Ala | Thr | Gly | Val |
| 145 | | | | | 150 | | | | | 155 | | | | | 160 |
| Arg | Leu | Asp | Val | Ala | Tyr | Leu | Arg | Ala | Leu | Ser | Leu | Glu | Val | Ala | Glu |
| | | | | 165 | | | | | 170 | | | | | 175 | |
| Glu | Ile | Ala | Arg | Leu | Glu | Ala | Glu | Val | Phe | Arg | Leu | Ala | Gly | His | Pro |
| | | | 180 | | | | | 185 | | | | | 190 | | |
| Phe | Asn | Leu | Asn | Ser | Arg | Asp | Gln | Leu | Glu | Arg | Val | Leu | Phe | Asp | Glu |
| | | | 195 | | | | | 200 | | | | | 205 | | |
| Leu | Gly | Leu | Pro | Ala | Ile | Gly | Lys | Thr | Glu | Lys | Thr | Gly | Lys | Arg | Ser |
| | | 210 | | | | | 215 | | | | | 220 | | | |
| Thr | Ser | Ala | Ala | Val | Leu | Glu | Ala | Leu | Arg | Glu | Ala | His | Pro | Ile | Val |
| 225 | | | | | 230 | | | | | 235 | | | | | 240 |
| Glu | Lys | Ile | Leu | Gln | Tyr | Arg | Glu | Leu | Thr | Lys | Leu | Lys | Ser | Thr | Tyr |
| | | | | 245 | | | | | 250 | | | | | 255 | |
| Ile | Asp | Pro | Leu | Pro | Asp | Leu | Ile | His | Pro | Arg | Thr | Gly | Arg | Leu | His |
| | | | 260 | | | | | 265 | | | | | 270 | | |
| Thr | Arg | Phe | Asn | Gln | Thr | Ala | Thr | Ala | Thr | Gly | Arg | Leu | Ser | Ser | Ser |
| | | | 275 | | | | | 280 | | | | | 285 | | |
| Asp | Pro | Asn | Leu | Gln | Asn | Ile | Pro | Val | Arg | Thr | Pro | Leu | Gly | Gln | Arg |
| | | | 290 | | | | | 295 | | | | | 300 | | |
| Ile | Arg | Arg | Ala | Phe | Asn | Ala | Glu | Glu | Gly | Trp | Leu | Leu | Val | Ala | Leu |
| 305 | | | | | 310 | | | | | 315 | | | | | 320 |
| Asp | Tyr | Ser | Gln | Ile | Glu | Leu | Arg | Val | Leu | Ala | His | Leu | Ser | Gly | Asp |
| | | | | 325 | | | | | 330 | | | | | 335 | |
| Glu | Asn | Leu | Ile | Arg | Val | Phe | Gln | Glu | Gly | Arg | Asp | Ile | His | Thr | Glu |
| | | | | 340 | | | | | 345 | | | | | 350 | |
| Thr | Ala | Ser | Trp | Met | Phe | Gly | Val | Pro | Arg | Glu | Ala | Val | Asp | Pro | Leu |
| | | | 355 | | | | | 360 | | | | | 365 | | |

```
Met Arg Arg Ala Ala Lys Thr Ile Asn Phe Gly Val Leu Tyr Gly Met
    370                 375                 380

Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
                405                 410                 415

Trp Ile Glu Lys Thr Leu Glu Glu Gly Arg Arg Arg Gly Tyr Val Glu
                420                 425                 430

Thr Leu Phe Gly Arg Arg Tyr Val Pro Asp Leu Glu Ala Arg Val
            435                 440                 445

Lys Ser Val Arg Glu Ala Ala Glu Arg Met Ala Phe Asn Met Pro Val
    450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Met Pro Leu Gln Val His Asp
                485                 490                 495

Glu Leu Val Leu Glu Ala Pro Lys Glu Gly Ala Glu Ala Val Ala Arg
                500                 505                 510

Leu Ala Lys Glu Val Met Glu Gly Val Tyr Pro Leu Ala Val Pro Leu
            515                 520                 525

Glu Val Lys Val Gly Ile Gly Glu Asp Trp Leu Ser Ala Lys Glu Ala
    530                 535                 540

Ala
545

<210> SEQ ID NO 94
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 94 agc ccc aag gcc ctg gag gag gcc ccc tgg ccc ccg ccg gaa ggg gcc      48
Ser Pro Lys Ala Leu Glu Glu Ala Pro Trp Pro Pro Pro Glu Gly Ala
1               5                   10                  15 ttc gtg ggc ttt gtg ctt tcc cgc aag gag ccc atg tgg gcc gat ctt      96
Phe Val Gly Phe Val Leu Ser Arg Lys Glu Pro Met Trp Ala Asp Leu
            20                  25                  30 ctg gcc ctg gcc gcc gcc agg ggg ggc cgg gtc cac cgg gcc ccc gag     144
Leu Ala Leu Ala Ala Ala Arg Gly Gly Arg Val His Arg Ala Pro Glu
        35                  40                  45 cct tat aaa gcc ctc agg gac ctg aag gag gcg cgg ggg ctt ctc gcc     192
Pro Tyr Lys Ala Leu Arg Asp Leu Lys Glu Ala Arg Gly Leu Leu Ala
    50                  55                  60 aaa gac ctg agc gtt ctg gcc ctg agg gaa ggc ctt ggc ctc ccg ccc     240
Lys Asp Leu Ser Val Leu Ala Leu Arg Glu Gly Leu Gly Leu Pro Pro
65                  70                  75                  80 ggc gac gac ccc atg ctc ctc gcc tac ctc ctg gac cct tcc aac acc     288
Gly Asp Asp Pro Met Leu Leu Ala Tyr Leu Leu Asp Pro Ser Asn Thr
                85                  90                  95 acc ccc gag ggg gtg gcc cgg cgc tac ggc ggg gag tgg acg gag gag     336
Thr Pro Glu Gly Val Ala Arg Arg Tyr Gly Gly Glu Trp Thr Glu Glu
            100                 105                 110 gcg ggg gag cgg gcc gcc ctt tcc gag agg ctc ttc gcc aac ctg tgg     384
Ala Gly Glu Arg Ala Ala Leu Ser Glu Arg Leu Phe Ala Asn Leu Trp
        115                 120                 125
```

```
ggg agg ctt gag ggg gag gag agg ctc ctt tgg ctt tac cgg gag gtg    432
Gly Arg Leu Glu Gly Glu Glu Arg Leu Leu Trp Leu Tyr Arg Glu Val
130                 135                 140 gag agg ccc ctt tcc gct gtc ctg gcc cac atg gag gcc acg ggg gtg    480
Glu Arg Pro Leu Ser Ala Val Leu Ala His Met Glu Ala Thr Gly Val
145                 150                 155                 160 cgc ctg gac gtg gcc tat ctc agg gcc ttg tcc ctg gag gtg gcc gag    528
Arg Leu Asp Val Ala Tyr Leu Arg Ala Leu Ser Leu Glu Val Ala Glu
                165                 170                 175 gag atc gcc cgc ctc gag gcc gag gtc ttc cgc ctg gcc ggc cac ccc    576
Glu Ile Ala Arg Leu Glu Ala Glu Val Phe Arg Leu Ala Gly His Pro
            180                 185                 190 ttc aac ctc aac tcc cgg gac cag ctg gaa agg gtc ctc ttt gac gag    624
Phe Asn Leu Asn Ser Arg Asp Gln Leu Glu Arg Val Leu Phe Asp Glu
        195                 200                 205 cta ggg ctt ccc gcc atc ggc aag acg gag aag acc ggc aag cgc tcc    672
Leu Gly Leu Pro Ala Ile Gly Lys Thr Glu Lys Thr Gly Lys Arg Ser
    210                 215                 220 acc agc gcc gcc gtc ctg gag gcc ctc cgc gag gcc cac ccc atc gtg    720
Thr Ser Ala Ala Val Leu Glu Ala Leu Arg Glu Ala His Pro Ile Val
225                 230                 235                 240 gag aag atc ctg cag tac cgg gag ctc acc aag ctg aag agc acc tac    768
Glu Lys Ile Leu Gln Tyr Arg Glu Leu Thr Lys Leu Lys Ser Thr Tyr
                245                 250                 255 att gac ccc ttg ccg gac ctc atc cac ccc agg acg ggc cgc ctc cac    816
Ile Asp Pro Leu Pro Asp Leu Ile His Pro Arg Thr Gly Arg Leu His
            260                 265                 270 acc cgc ttc aac cag acg gcc acg gcc acg ggc agg cta agt agc tcc    864
Thr Arg Phe Asn Gln Thr Ala Thr Ala Thr Gly Arg Leu Ser Ser Ser
        275                 280                 285 gat ccc aac ctc cag aac atc ccc gtc cgc acc ccg ctt ggg cag agg    912
Asp Pro Asn Leu Gln Asn Ile Pro Val Arg Thr Pro Leu Gly Gln Arg
    290                 295                 300 atc cgc cgg gcc ttc atc gcc gag gag ggg tgg cta ttg gtg gcc ctg    960
Ile Arg Arg Ala Phe Ile Ala Glu Glu Gly Trp Leu Leu Val Ala Leu
305                 310                 315                 320 gac tat agc cag ata gag ctc agg gtg ctg gcc cac ctc tcc ggc gac   1008
Asp Tyr Ser Gln Ile Glu Leu Arg Val Leu Ala His Leu Ser Gly Asp
                325                 330                 335 gag aac ctg atc cgg gtc ttc cag gag ggg cgg gac atc cac acg gag   1056
Glu Asn Leu Ile Arg Val Phe Gln Glu Gly Arg Asp Ile His Thr Glu
            340                 345                 350 acc gcc agc tgg atg ttc ggc gtc ccc cgg gag gcc gtg gac ccc ctg   1104
Thr Ala Ser Trp Met Phe Gly Val Pro Arg Glu Ala Val Asp Pro Leu
        355                 360                 365 atg cgc cgg gcg gcc aag acc atc aac ttc ggg gtc ctc tac ggc atg   1152
Met Arg Arg Ala Ala Lys Thr Ile Asn Phe Gly Val Leu Tyr Gly Met
    370                 375                 380 tcg gcc cac cgc ctc tcc cag gag cta gcc atc cct tac gag gag gcc   1200
Ser Ala His Arg Leu Ser Gln Glu Leu Ala Ile Pro Tyr Glu Glu Ala
385                 390                 395                 400 cag gcc ttc att gag cgc tgc ttt cag agc ttc ccc aag gtg cgg gcc   1248
Gln Ala Phe Ile Glu Arg Cys Phe Gln Ser Phe Pro Lys Val Arg Ala
                405                 410                 415 tgg att gag aag acc ctg gag gag ggc agg agg cgg ggg tac gtg gag   1296
Trp Ile Glu Lys Thr Leu Glu Glu Gly Arg Arg Arg Gly Tyr Val Glu
            420                 425                 430 acc ctc ttc ggc cgc cgc cgc tac gtg cca gac cta gag gcc cgg gtg   1344
Thr Leu Phe Gly Arg Arg Arg Tyr Val Pro Asp Leu Glu Ala Arg Val
```

-continued

```
              435                 440                 445
aag agc gtg cgg gag gcg gcc gag cgc atg gcc ttc aac atg ccc gtc    1392
Lys Ser Val Arg Glu Ala Ala Glu Arg Met Ala Phe Asn Met Pro Val
450                 455                 460 cag ggc acc gcc gcc gac ctc atg aag ctg gct atg gtg gag ctc ttc    1440
Gln Gly Thr Ala Ala Asp Leu Met Lys Leu Ala Met Val Glu Leu Phe
465                 470                 475                 480 ccc agg ctg gag gaa atg ggg gcc agg atg ctc ctt cag gtc cac gac    1488
Pro Arg Leu Glu Glu Met Gly Ala Arg Met Leu Leu Gln Val His Asp
                485                 490                 495 gag ctg gtc ctc gag gcc cca aaa gag ggg gcg gag gcc gtg gcc cgg    1536
Glu Leu Val Leu Glu Ala Pro Lys Glu Gly Ala Glu Ala Val Ala Arg
500                 505                 510 ctg gcc aag gag gtc atg gag ggg gtg tat ccc ctg gcc gtg ccc ctg    1584
Leu Ala Lys Glu Val Met Glu Gly Val Tyr Pro Leu Ala Val Pro Leu
515                 520                 525 gag gtg gag gtg ggg ata ggg gag gac tgg ctc tcc gcc aag gag gcg    1632
Glu Val Glu Val Gly Ile Gly Glu Asp Trp Leu Ser Ala Lys Glu Ala
530                 535                 540 gcc gc                                                             1637
Ala
545

<210> SEQ ID NO 95
<211> LENGTH: 545
<212> TYPE: PRT
<213> ORGANISM: Thermus aquaticus

<400> SEQUENCE: 95

Ser Pro Lys Ala Leu Glu Glu Ala Pro Trp Pro Pro Pro Glu Gly Ala
1               5                   10                  15

Phe Val Gly Phe Val Leu Ser Arg Lys Glu Pro Met Trp Ala Asp Leu
                20                  25                  30

Leu Ala Leu Ala Ala Ala Arg Gly Gly Arg Val His Arg Ala Pro Glu
            35                  40                  45

Pro Tyr Lys Ala Leu Arg Asp Leu Lys Glu Ala Arg Gly Leu Leu Ala
        50                  55                  60

Lys Asp Leu Ser Val Leu Ala Leu Arg Glu Gly Leu Gly Leu Pro Pro
65                  70                  75                  80

Gly Asp Asp Pro Met Leu Leu Ala Tyr Leu Leu Asp Pro Ser Asn Thr
                85                  90                  95

Thr Pro Glu Gly Val Ala Arg Arg Tyr Gly Gly Glu Trp Thr Glu Glu
            100                 105                 110

Ala Gly Glu Arg Ala Ala Leu Ser Glu Arg Leu Phe Ala Asn Leu Trp
        115                 120                 125

Gly Arg Leu Glu Gly Glu Glu Arg Leu Leu Trp Leu Tyr Arg Glu Val
    130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
            180                 185                 190

Phe Asn Leu Asn Ser Arg Asp Gln Leu Glu Arg Val Leu Phe Asp Glu
        195                 200                 205

Leu Gly Leu Pro Ala Ile Gly Lys Thr Glu Lys Thr Gly Lys Arg Ser
    210                 215                 220
```

```
Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Ser Thr Tyr
            245                 250                 255

Ile Asp Pro Leu Pro Asp Leu Ile His Pro Arg Thr Gly Arg Leu His
                260                 265                 270

Thr Arg Phe Asn Gln Thr Ala Thr Ala Thr Gly Arg Leu Ser Ser Ser
            275                 280                 285

Asp Pro Asn Leu Gln Asn Ile Pro Val Arg Thr Pro Leu Gly Gln Arg
        290                 295                 300

Ile Arg Arg Ala Phe Ile Ala Glu Glu Gly Trp Leu Leu Val Ala Leu
305                 310                 315                 320

Asp Tyr Ser Gln Ile Glu Leu Arg Val Leu Ala His Leu Ser Gly Asp
                325                 330                 335

Glu Asn Leu Ile Arg Val Phe Gln Gly Arg Asp Ile His Thr Glu
            340                 345                 350

Thr Ala Ser Trp Met Phe Gly Val Pro Arg Glu Ala Val Asp Pro Leu
            355                 360                 365

Met Arg Arg Ala Ala Lys Thr Ile Asn Phe Gly Val Leu Tyr Gly Met
370                 375                 380

Ser Ala His Arg Leu Ser Gln Glu Leu Ala Ile Pro Tyr Glu Glu Ala
385                 390                 395                 400

Gln Ala Phe Ile Glu Arg Cys Phe Gln Ser Phe Pro Lys Val Arg Ala
                405                 410                 415

Trp Ile Glu Lys Thr Leu Glu Glu Gly Arg Arg Arg Gly Tyr Val Glu
            420                 425                 430

Thr Leu Phe Gly Arg Arg Arg Tyr Val Pro Asp Leu Glu Ala Arg Val
            435                 440                 445

Lys Ser Val Arg Glu Ala Ala Glu Arg Met Ala Phe Asn Met Pro Val
        450                 455                 460

Gln Gly Thr Ala Ala Asp Leu Met Lys Leu Ala Met Val Glu Leu Phe
465                 470                 475                 480

Pro Arg Leu Glu Glu Met Gly Ala Arg Met Leu Leu Gln Val His Asp
                485                 490                 495

Glu Leu Val Leu Glu Ala Pro Lys Glu Gly Ala Glu Ala Val Ala Arg
            500                 505                 510

Leu Ala Lys Glu Val Met Glu Gly Val Tyr Pro Leu Ala Val Pro Leu
            515                 520                 525

Glu Val Glu Val Gly Ile Gly Glu Asp Trp Leu Ser Ala Lys Glu Ala
        530                 535                 540

Ala
545

<210> SEQ ID NO 96
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 96 agc ccc aag gcc ctg gag gag gcc ccc tgg ccc ccg ccg gaa ggg gcc      48
Ser Pro Lys Ala Leu Glu Glu Ala Pro Trp Pro Pro Pro Glu Gly Ala
1               5                   10                  15
```

-continued

| | |
|---|---|
| ttc gtg ggc ttt gtg ctt tcc cgc aag gag ccc atg tgg gcc gat ctt<br>Phe Val Gly Phe Val Leu Ser Arg Lys Glu Pro Met Trp Ala Asp Leu<br>20                      25                    30 | 96 |
| ctg gcc ctg gcc gcc gcc agg ggg ggc cgg gtc cac cgg gcc ccc gag<br>Leu Ala Leu Ala Ala Ala Arg Gly Gly Arg Val His Arg Ala Pro Glu<br>35                      40                    45 | 144 |
| cct tat aaa gcc ctc agg gac ctg aag gag gcg cgg ggg ctt ctc gcc<br>Pro Tyr Lys Ala Leu Arg Asp Leu Lys Glu Ala Arg Gly Leu Leu Ala<br>50                      55                    60 | 192 |
| aaa gac ctg agc gtt ctg gcc ctg agg gaa ggc ctt ggc ctc ccg ccc<br>Lys Asp Leu Ser Val Leu Ala Leu Arg Glu Gly Leu Gly Leu Pro Pro<br>65                      70                    75                    80 | 240 |
| ggc gac gac ccc atg ctc ctc gcc tac ctc ctg gac cct tcc aac acc<br>Gly Asp Asp Pro Met Leu Leu Ala Tyr Leu Leu Asp Pro Ser Asn Thr<br>                    85                    90                    95 | 288 |
| acc ccc gag ggg gtg gcc cgg cgc tac ggc ggg gag tgg acg gag gag<br>Thr Pro Glu Gly Val Ala Arg Arg Tyr Gly Gly Glu Trp Thr Glu Glu<br>                  100                    105                  110 | 336 |
| gcg ggg gag cgg gcc gcc ctt tcc gag agg ctc ttc gcc aac ctg tgg<br>Ala Gly Glu Arg Ala Ala Leu Ser Glu Arg Leu Phe Ala Asn Leu Trp<br>             115                    120                  125 | 384 |
| ggg agg ctt gag ggg gag gag agg ctc ctt tgg ctt tac cgg gag gtg<br>Gly Arg Leu Glu Gly Glu Glu Arg Leu Leu Trp Leu Tyr Arg Glu Val<br>130                      135                    140 | 432 |
| gag agg ccc ctt tcc gct gtc ctg gcc cac atg gag gcc acg ggg gtg<br>Glu Arg Pro Leu Ser Ala Val Leu Ala His Met Glu Ala Thr Gly Val<br>145                      150                    155                  160 | 480 |
| cgc ctg gac gtg gcc tat ctc agg gcc ttg tcc ctg gag gtg gcc gag<br>Arg Leu Asp Val Ala Tyr Leu Arg Ala Leu Ser Leu Glu Val Ala Glu<br>                  165                    170                  175 | 528 |
| gag atc gcc cgc ctc gag gcc gag gtc ttc cgc ctg gcc ggc cac ccc<br>Glu Ile Ala Arg Leu Glu Ala Glu Val Phe Arg Leu Ala Gly His Pro<br>                180                    185                  190 | 576 |
| ttc aac ctc aac tcc cgg gac cag ctg gaa agg gtc ctc ttt gac gaa<br>Phe Asn Leu Asn Ser Arg Asp Gln Leu Glu Arg Val Leu Phe Asp Glu<br>             195                    200                  205 | 624 |
| cta ggg ctt ccc gcc atc ggc aag acg gag aag acc ggc aag cgc tcc<br>Leu Gly Leu Pro Ala Ile Gly Lys Thr Glu Lys Thr Gly Lys Arg Ser<br>210                      215                    220 | 672 |
| acc agc gcc gcc gtc ctg gag gcc ctc cgc gag gcc cac ccc atc gtg<br>Thr Ser Ala Ala Val Leu Glu Ala Leu Arg Glu Ala His Pro Ile Val<br>225                      230                    235                  240 | 720 |
| gag aag atc ctg cag tac cgg gag ctc acc aag ctg aag agc acc tac<br>Glu Lys Ile Leu Gln Tyr Arg Glu Leu Thr Lys Leu Lys Ser Thr Tyr<br>                  245                    250                  255 | 768 |
| att gac ccc ttg ccg ggc ctc atc cac ccc agg acg ggc cgc ctc cac<br>Ile Asp Pro Leu Pro Gly Leu Ile His Pro Arg Thr Gly Arg Leu His<br>                260                    265                  270 | 816 |
| acc cgc ttc aac cag acg gcc acg gcc acg ggc agg cta agt agc tcc<br>Thr Arg Phe Asn Gln Thr Ala Thr Ala Thr Gly Arg Leu Ser Ser Ser<br>             275                    280                  285 | 864 |
| gat ccc aac ctc cag aac atc ccc gtc cgc acc ccg ctt ggg cag agg<br>Asp Pro Asn Leu Gln Asn Ile Pro Val Arg Thr Pro Leu Gly Gln Arg<br>290                      295                    300 | 912 |
| atc cgc cgg gcc ttc atc gcc gag gag ggg tgg cta ttg gtg gcc ctg<br>Ile Arg Arg Ala Phe Ile Ala Glu Glu Gly Trp Leu Leu Val Ala Leu<br>305                      310                    315                  320 | 960 |
| gac tat agc cag ata gag ctc agg gtg ctg gcc cac ctc tcc ggc gac<br>Asp Tyr Ser Gln Ile Glu Leu Arg Val Leu Ala His Leu Ser Gly Asp<br>                  325                    330                  335 | 1008 |

```
gag aac ctg atc cgg gtc ttc cag gag ggg cgg gac atc cac acg gag      1056
Glu Asn Leu Ile Arg Val Phe Gln Glu Gly Arg Asp Ile His Thr Glu
        340                 345                 350 acc gcc agc tgg atg ttc ggc gtc ccc cgg gag gcc gtg gac ccc ctg      1104
Thr Ala Ser Trp Met Phe Gly Val Pro Arg Glu Ala Val Asp Pro Leu
355                 360                 365 atg cgc cgg gcg gcc aag acc atc aac ttc ggg gtc ctc tac ggc atg      1152
Met Arg Arg Ala Ala Lys Thr Ile Asn Phe Gly Val Leu Tyr Gly Met
    370                 375                 380 tcg gcc cac cgc ctc tcc cag gag cta gcc atc cct tac gag gag gcc      1200
Ser Ala His Arg Leu Ser Gln Glu Leu Ala Ile Pro Tyr Glu Glu Ala
385                 390                 395                 400 cag gcc ttc att gag cgc tac ttt cag agc ttc ccc aag gtg cgg gcc      1248
Gln Ala Phe Ile Glu Arg Tyr Phe Gln Ser Phe Pro Lys Val Arg Ala
                405                 410                 415 tgg att gag aag acc ctg gag gag ggc agg agg cgg ggg tac gtg gag      1296
Trp Ile Glu Lys Thr Leu Glu Glu Gly Arg Arg Arg Gly Tyr Val Glu
            420                 425                 430 acc ctc ttc ggc cgc cgc cgc tac gtg cca gac cta gag gcc cgg gtg      1344
Thr Leu Phe Gly Arg Arg Arg Tyr Val Pro Asp Leu Glu Ala Arg Val
        435                 440                 445 aag agc gtg cgg gag gcg gcc gag cgc atg gcc ttc aac atg ccc gtc      1392
Lys Ser Val Arg Glu Ala Ala Glu Arg Met Ala Phe Asn Met Pro Val
450                 455                 460 cag ggc acc gcc gcc gac ctc atg aag ctg gct atg gtg aag ctc ttc      1440
Gln Gly Thr Ala Ala Asp Leu Met Lys Leu Ala Met Val Lys Leu Phe
465                 470                 475                 480 ccc agg ctg gag gaa atg ggg gcc agg atg ctc ctt cag atc cac gac      1488
Pro Arg Leu Glu Glu Met Gly Ala Arg Met Leu Leu Gln Ile His Asp
                485                 490                 495 gag ctg gtc ctc gag gcc cca aaa gag ggg gcg gag gcc gtg gcc cgg      1536
Glu Leu Val Leu Glu Ala Pro Lys Glu Gly Ala Glu Ala Val Ala Arg
            500                 505                 510 ctg gcc aag gag gtc atg gag ggg gtg tat ccc ctg gcc gtg ccc ctg      1584
Leu Ala Lys Glu Val Met Glu Gly Val Tyr Pro Leu Ala Val Pro Leu
        515                 520                 525 gag gtg gag gtg ggg ata ggg gag gac tgg ctc tcc gcc aag gag gcg      1632
Glu Val Glu Val Gly Ile Gly Glu Asp Trp Leu Ser Ala Lys Glu Ala
530                 535                 540 gcc gc                                                                1637
Ala
545

<210> SEQ ID NO 97
<211> LENGTH: 545
<212> TYPE: PRT
<213> ORGANISM: Thermus aquaticus

<400> SEQUENCE: 97

Ser Pro Lys Ala Leu Glu Glu Ala Pro Trp Pro Pro Glu Gly Ala
1               5                   10                  15

Phe Val Gly Phe Val Leu Ser Arg Lys Glu Pro Met Trp Ala Asp Leu
            20                  25                  30

Leu Ala Leu Ala Ala Ala Arg Gly Gly Arg Val His Arg Ala Pro Glu
        35                  40                  45

Pro Tyr Lys Ala Leu Arg Asp Leu Lys Glu Ala Arg Gly Leu Leu Ala
    50                  55                  60

Lys Asp Leu Ser Val Leu Ala Leu Arg Glu Gly Leu Gly Leu Pro Pro
65                  70                  75                  80
```

```
Gly Asp Asp Pro Met Leu Leu Ala Tyr Leu Leu Asp Pro Ser Asn Thr
            85                  90                  95

Thr Pro Glu Gly Val Ala Arg Arg Tyr Gly Gly Glu Trp Thr Glu Glu
        100                 105                 110

Ala Gly Glu Arg Ala Ala Leu Ser Glu Arg Leu Phe Ala Asn Leu Trp
        115                 120                 125

Gly Arg Leu Glu Gly Glu Arg Leu Leu Trp Leu Tyr Arg Glu Val
    130                 135                 140

Glu Arg Pro Leu Ser Ala Val Leu Ala His Met Glu Ala Thr Gly Val
145                 150                 155                 160

Arg Leu Asp Val Ala Tyr Leu Arg Ala Leu Ser Leu Glu Val Ala Glu
                165                 170                 175

Glu Ile Ala Arg Leu Glu Ala Glu Val Phe Arg Leu Ala Gly His Pro
                180                 185                 190

Phe Asn Leu Asn Ser Arg Asp Gln Leu Glu Arg Val Leu Phe Asp Glu
                195                 200                 205

Leu Gly Leu Pro Ala Ile Gly Lys Thr Glu Lys Thr Gly Lys Arg Ser
    210                 215                 220

Thr Ser Ala Ala Val Leu Glu Ala Leu Arg Glu Ala His Pro Ile Val
225                 230                 235                 240

Glu Lys Ile Leu Gln Tyr Arg Glu Leu Thr Lys Leu Lys Ser Thr Tyr
                245                 250                 255

Ile Asp Pro Leu Pro Gly Leu Ile His Pro Arg Thr Gly Arg Leu His
                260                 265                 270

Thr Arg Phe Asn Gln Thr Ala Thr Ala Thr Gly Arg Leu Ser Ser Ser
                275                 280                 285

Asp Pro Asn Leu Gln Asn Ile Pro Val Arg Thr Pro Leu Gly Gln Arg
290                 295                 300

Ile Arg Arg Ala Phe Ile Ala Glu Gly Trp Leu Leu Val Ala Leu
305                 310                 315                 320

Asp Tyr Ser Gln Ile Glu Leu Arg Val Leu Ala His Leu Ser Gly Asp
                325                 330                 335

Glu Asn Leu Ile Arg Val Phe Gln Glu Gly Arg Asp Ile His Thr Glu
                340                 345                 350

Thr Ala Ser Trp Met Phe Gly Val Pro Arg Glu Ala Val Asp Pro Leu
            355                 360                 365

Met Arg Arg Ala Ala Lys Thr Ile Asn Phe Gly Val Leu Tyr Gly Met
    370                 375                 380

Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
                405                 410                 415

Trp Ile Glu Lys Thr Leu Glu Glu Gly Arg Arg Arg Gly Tyr Val Glu
                420                 425                 430

Thr Leu Phe Gly Arg Arg Arg Tyr Val Pro Asp Leu Glu Ala Arg Val
            435                 440                 445

Lys Ser Val Arg Glu Ala Ala Glu Arg Met Ala Phe Asn Met Pro Val
    450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Met Leu Leu Gln Ile His Asp
                485                 490                 495
```

```
Glu Leu Val Leu Glu Ala Pro Lys Glu Gly Ala Glu Ala Val Ala Arg
            500                 505                 510

Leu Ala Lys Glu Val Met Glu Gly Val Tyr Pro Leu Ala Val Pro Leu
            515                 520                 525

Glu Val Glu Val Gly Ile Gly Glu Asp Trp Leu Ser Ala Lys Glu Ala
            530                 535                 540

Ala
545

<210> SEQ ID NO 98
<211> LENGTH: 1637
<212> TYPE: DNA
<213> ORGANISM: Thermus aquaticus
<220> FEATURE:
<221> NAME/KEY: CDS
<222> LOCATION: (1)..(1635)

<400> SEQUENCE: 98
```

| | | | | | | | | | | | | | | | | |
|---|---|---|---|---|---|---|---|---|---|---|---|---|---|---|---|---|
| agc | ccc | aag | gcc | ctg | gag | gag | gcc | ccc | tgg | ccc | ccg | ccg | gaa | ggg | gcc | 48 |
| Ser | Pro | Lys | Ala | Leu | Glu | Glu | Ala | Pro | Trp | Pro | Pro | Pro | Glu | Gly | Ala | |
| 1 | | | | 5 | | | | | 10 | | | | | 15 | | |
| ttc | gtg | ggc | ttt | gtg | ctt | tcc | cgc | aag | gag | ccc | atg | tgg | gcc | gat | ctt | 96 |
| Phe | Val | Gly | Phe | Val | Leu | Ser | Arg | Lys | Glu | Pro | Met | Trp | Ala | Asp | Leu | |
| | | | | 20 | | | | | 25 | | | | | 30 | | |
| ctg | gcc | ctg | gcc | gcc | gcc | agg | ggg | ggc | cgg | gtc | cac | cgg | gcc | ccc | gag | 144 |
| Leu | Ala | Leu | Ala | Ala | Ala | Arg | Gly | Gly | Arg | Val | His | Arg | Ala | Pro | Glu | |
| | | 35 | | | | | 40 | | | | | 45 | | | | |
| cct | tat | aaa | gcc | ctc | agg | gac | ctg | aag | gag | gcg | cgg | ggg | ctt | ctc | gcc | 192 |
| Pro | Tyr | Lys | Ala | Leu | Arg | Asp | Leu | Lys | Glu | Ala | Arg | Gly | Leu | Leu | Ala | |
| 50 | | | | | 55 | | | | | 60 | | | | | | |
| aaa | gac | ctg | agc | gtt | ctg | gcc | ctg | agg | gaa | ggc | ctt | ggc | ctc | ccg | ccc | 240 |
| Lys | Asp | Leu | Ser | Val | Leu | Ala | Leu | Arg | Glu | Gly | Leu | Gly | Leu | Pro | Pro | |
| 65 | | | | 70 | | | | | 75 | | | | | 80 | | |
| ggc | gac | gac | ccc | atg | ctc | ctc | gcc | tac | ctc | ctg | gac | cct | tcc | aac | acc | 288 |
| Gly | Asp | Asp | Pro | Met | Leu | Leu | Ala | Tyr | Leu | Leu | Asp | Pro | Ser | Asn | Thr | |
| | | | | 85 | | | | | 90 | | | | | 95 | | |
| acc | ccc | gag | ggg | gtg | gcc | cgg | cgc | tac | ggc | ggg | gag | tgg | acg | gag | gag | 336 |
| Thr | Pro | Glu | Gly | Val | Ala | Arg | Arg | Tyr | Gly | Gly | Glu | Trp | Thr | Glu | Glu | |
| | | | 100 | | | | | 105 | | | | | 110 | | | |
| gcg | ggg | gag | cgg | gcc | gcc | ctt | tcc | gag | agg | ctc | ttc | gcc | aac | ctg | tgg | 384 |
| Ala | Gly | Glu | Arg | Ala | Ala | Leu | Ser | Glu | Arg | Leu | Phe | Ala | Asn | Leu | Trp | |
| | | 115 | | | | | 120 | | | | | 125 | | | | |
| ggg | agg | ctt | gag | ggg | gag | gag | agg | ctc | ctt | tgg | ctt | tac | cgg | gag | gtg | 432 |
| Gly | Arg | Leu | Glu | Gly | Glu | Glu | Arg | Leu | Leu | Trp | Leu | Tyr | Arg | Glu | Val | |
| | 130 | | | | | 135 | | | | | 140 | | | | | |
| gag | agg | ccc | ctt | tcc | gct | gtc | ctg | gcc | cac | atg | gag | gcc | acg | ggg | gtg | 480 |
| Glu | Arg | Pro | Leu | Ser | Ala | Val | Leu | Ala | His | Met | Glu | Ala | Thr | Gly | Val | |
| 145 | | | | | 150 | | | | | 155 | | | | | 160 | |
| cgc | ctg | gac | gtg | gcc | tat | ctc | agg | gcc | ttg | tcc | ctg | gag | gtg | gcc | gag | 528 |
| Arg | Leu | Asp | Val | Ala | Tyr | Leu | Arg | Ala | Leu | Ser | Leu | Glu | Val | Ala | Glu | |
| | | | | 165 | | | | | 170 | | | | | 175 | | |
| gag | atc | gcc | cgc | ctc | gag | gcc | gag | gtc | ttc | cgc | ctg | gcc | ggc | cac | ccc | 576 |
| Glu | Ile | Ala | Arg | Leu | Glu | Ala | Glu | Val | Phe | Arg | Leu | Ala | Gly | His | Pro | |
| | | | 180 | | | | | 185 | | | | | 190 | | | |
| ttc | aac | ctc | aac | tcc | cgg | gac | cag | ctg | gaa | agg | gtc | ctc | ttt | gac | gag | 624 |
| Phe | Asn | Leu | Asn | Ser | Arg | Asp | Gln | Leu | Glu | Arg | Val | Leu | Phe | Asp | Glu | |
| | | 195 | | | | | 200 | | | | | 205 | | | | |
| cta | ggg | ctt | ccc | gcc | atc | ggc | aag | acg | gag | aag | acc | ggc | aag | cgc | tcc | 672 |
| Leu | Gly | Leu | Pro | Ala | Ile | Gly | Lys | Thr | Glu | Lys | Thr | Gly | Lys | Arg | Ser | |
| | 210 | | | | | 215 | | | | | 220 | | | | | |

-continued

| | | |
|---|---|---|
| acc agc gcc gcc gtc ctg gag gcc ctc cgc gag gcc cac ccc atc gtg<br>Thr Ser Ala Ala Val Leu Glu Ala Leu Arg Glu Ala His Pro Ile Val<br>225                         230                       235                    240 | 720 |
| gag aag atc ctg cag tac cgg gag ctc acc aag ctg aag agc acc tac<br>Glu Lys Ile Leu Gln Tyr Arg Glu Leu Thr Lys Leu Lys Ser Thr Tyr<br>                  245                     250                     255 | 768 |
| att gac ccc ttg ccg gac ctc atc cac ccc agg acg ggc cgc ctc cac<br>Ile Asp Pro Leu Pro Asp Leu Ile His Pro Arg Thr Gly Arg Leu His<br>                  260                     265                    270 | 816 |
| acc cgc ttc aac cag acg gcc acg gcc acg ggc agg cta agt agc tcc<br>Thr Arg Phe Asn Gln Thr Ala Thr Ala Thr Gly Arg Leu Ser Ser Ser<br>         275                     280                     285 | 864 |
| gat ccc aac ctc cag aac atc ccc gtc cgc acc ccg ctt ggg cag agg<br>Asp Pro Asn Leu Gln Asn Ile Pro Val Arg Thr Pro Leu Gly Gln Arg<br>290                       295                     300 | 912 |
| atc cgc cgg gcc ttc atc gcc gag gag ggg tgg cta ttg gtg gcc ctg<br>Ile Arg Arg Ala Phe Ile Ala Glu Glu Gly Trp Leu Leu Val Ala Leu<br>305                       310                     315                  320 | 960 |
| gac tat aac cag ata gag ctc agg gtg ctg gcc cac ctc tcc ggc gac<br>Asp Tyr Asn Gln Ile Glu Leu Arg Val Leu Ala His Leu Ser Gly Asp<br>                  325                     330                    335 | 1008 |
| gag aac ctg atc cgg gtc ttc cag gag ggg cgg gac atc cac acg gag<br>Glu Asn Leu Ile Arg Val Phe Gln Glu Gly Arg Asp Ile His Thr Glu<br>         340                     345                     350 | 1056 |
| acc gcc agc tgg atg ttc ggc gtc ccc cgg gag gcc gtg gac ccc ctg<br>Thr Ala Ser Trp Met Phe Gly Val Pro Arg Glu Ala Val Asp Pro Leu<br>355                       360                     365 | 1104 |
| atg cgc cgg gcg gcc aag acc atc aac ttc ggg gtc ctc tac ggc atg<br>Met Arg Arg Ala Ala Lys Thr Ile Asn Phe Gly Val Leu Tyr Gly Met<br>370                       375                     380 | 1152 |
| tcg gcc cac cgc ctc tcc cag gag cta gcc atc cct tac gag gag gcc<br>Ser Ala His Arg Leu Ser Gln Glu Leu Ala Ile Pro Tyr Glu Glu Ala<br>385                       390                     395                  400 | 1200 |
| cag gcc ttc att gag cgc tac ttt cag agc ttc ccc aag gtg cgg gcc<br>Gln Ala Phe Ile Glu Arg Tyr Phe Gln Ser Phe Pro Lys Val Arg Ala<br>                  405                     410                    415 | 1248 |
| tgg att gag aag acc ctg gag gag ggc agg agg cgg ggg tac gtg gag<br>Trp Ile Glu Lys Thr Leu Glu Glu Gly Arg Arg Arg Gly Tyr Val Glu<br>         420                     425                     430 | 1296 |
| acc ctc ttc ggc cgc cgc cgc tac gtg cca gac cta gag gcc cgg gtg<br>Thr Leu Phe Gly Arg Arg Arg Tyr Val Pro Asp Leu Glu Ala Arg Val<br>435                       440                     445 | 1344 |
| aag agc gtg cgg gag gcg gcc gag cgc atg gcc ttc aac atg ccc gtc<br>Lys Ser Val Arg Glu Ala Ala Glu Arg Met Ala Phe Asn Met Pro Val<br>450                       455                     460 | 1392 |
| cag ggc acc gcc gcc gac ctc atg aag ctg gct atg gtg aag ctc ttc<br>Gln Gly Thr Ala Ala Asp Leu Met Lys Leu Ala Met Val Lys Leu Phe<br>465                         470                     475                  480 | 1440 |
| ccc agg ctg gag gaa atg ggg gcc agg atg ctc ctt cag gtc cac gac<br>Pro Arg Leu Glu Glu Met Gly Ala Arg Met Leu Leu Gln Val His Asp<br>                  485                     490                    495 | 1488 |
| gag ctg gtc ctc gag gcc cca aaa gag ggg gcg gag gcc gtg gcc cgg<br>Glu Leu Val Leu Glu Ala Pro Lys Glu Gly Ala Glu Ala Val Ala Arg<br>         500                     505                     510 | 1536 |
| ctg gcc aag gag gtc atg gag ggg gtg tat ccc ctg gcc gtg tcc ctg<br>Leu Ala Lys Glu Val Met Glu Gly Val Tyr Pro Leu Ala Val Ser Leu<br>515                       520                     525 | 1584 |
| gag gtg gag gtg ggg ata ggg gag gac tgg ctc tcc gcc aag gag gcg<br>Glu Val Glu Val Gly Ile Gly Glu Asp Trp Leu Ser Ala Lys Glu Ala<br>530                       535                     540 | 1632 |

```
gcc gc                                                                  1637
Ala
545
```

<210> SEQ ID NO 99
<211> LENGTH: 545
<212> TYPE: PRT
<213> ORGANISM: Thermus aquaticus

<400> SEQUENCE: 99

| | | | | | | | | | | | | | | |
|---|---|---|---|---|---|---|---|---|---|---|---|---|---|---|
| Ser | Pro | Lys | Ala | Leu | Glu | Glu | Ala | Pro | Trp | Pro | Pro | Glu | Gly | Ala |
| 1 | | | | 5 | | | | | 10 | | | | | 15 |
| Phe | Val | Gly | Phe | Val | Leu | Ser | Arg | Lys | Glu | Pro | Met | Trp | Ala | Asp | Leu |
| | | | 20 | | | | | 25 | | | | | 30 | | |
| Leu | Ala | Leu | Ala | Ala | Ala | Arg | Gly | Gly | Arg | Val | His | Arg | Ala | Pro | Glu |
| | | 35 | | | | | 40 | | | | | 45 | | | |
| Pro | Tyr | Lys | Ala | Leu | Arg | Asp | Leu | Lys | Glu | Ala | Arg | Gly | Leu | Leu | Ala |
| | 50 | | | | | 55 | | | | | 60 | | | | |
| Lys | Asp | Leu | Ser | Val | Leu | Ala | Leu | Arg | Glu | Gly | Leu | Gly | Leu | Pro | Pro |
| 65 | | | | 70 | | | | | 75 | | | | | 80 | |
| Gly | Asp | Asp | Pro | Met | Leu | Leu | Ala | Tyr | Leu | Leu | Asp | Pro | Ser | Asn | Thr |
| | | | | 85 | | | | | 90 | | | | | 95 | |
| Thr | Pro | Glu | Gly | Val | Ala | Arg | Arg | Tyr | Gly | Gly | Glu | Trp | Thr | Glu | Glu |
| | | | 100 | | | | | 105 | | | | | 110 | | |
| Ala | Gly | Glu | Arg | Ala | Ala | Leu | Ser | Glu | Arg | Leu | Phe | Ala | Asn | Leu | Trp |
| | | 115 | | | | | 120 | | | | | 125 | | | |
| Gly | Arg | Leu | Glu | Gly | Glu | Glu | Arg | Leu | Leu | Trp | Leu | Tyr | Arg | Glu | Val |
| | 130 | | | | | 135 | | | | | 140 | | | | |
| Glu | Arg | Pro | Leu | Ser | Ala | Val | Leu | Ala | His | Met | Glu | Ala | Thr | Gly | Val |
| 145 | | | | 150 | | | | | 155 | | | | | 160 | |
| Arg | Leu | Asp | Val | Ala | Tyr | Leu | Arg | Ala | Leu | Ser | Leu | Glu | Val | Ala | Glu |
| | | | | 165 | | | | | 170 | | | | | 175 | |
| Glu | Ile | Ala | Arg | Leu | Glu | Ala | Glu | Val | Phe | Arg | Leu | Ala | Gly | His | Pro |
| | | | 180 | | | | | 185 | | | | | 190 | | |
| Phe | Asn | Leu | Asn | Ser | Arg | Asp | Gln | Leu | Glu | Arg | Val | Leu | Phe | Asp | Glu |
| | | 195 | | | | | 200 | | | | | 205 | | | |
| Leu | Gly | Leu | Pro | Ala | Ile | Gly | Lys | Thr | Glu | Lys | Thr | Gly | Lys | Arg | Ser |
| | 210 | | | | | 215 | | | | | 220 | | | | |
| Thr | Ser | Ala | Ala | Val | Leu | Glu | Ala | Leu | Arg | Glu | Ala | His | Pro | Ile | Val |
| 225 | | | | 230 | | | | | 235 | | | | | 240 | |
| Glu | Lys | Ile | Leu | Gln | Tyr | Arg | Glu | Leu | Thr | Lys | Leu | Lys | Ser | Thr | Tyr |
| | | | | 245 | | | | | 250 | | | | | 255 | |
| Ile | Asp | Pro | Leu | Pro | Asp | Leu | Ile | His | Pro | Arg | Thr | Gly | Arg | Leu | His |
| | | | 260 | | | | | 265 | | | | | 270 | | |
| Thr | Arg | Phe | Asn | Gln | Thr | Ala | Thr | Ala | Thr | Gly | Arg | Leu | Ser | Ser | Ser |
| | | 275 | | | | | 280 | | | | | 285 | | | |
| Asp | Pro | Asn | Leu | Gln | Asn | Ile | Pro | Val | Arg | Thr | Pro | Leu | Gly | Gln | Arg |
| | 290 | | | | | 295 | | | | | 300 | | | | |
| Ile | Arg | Arg | Ala | Phe | Ile | Ala | Glu | Gly | Trp | Leu | Leu | Val | Ala | Leu |
| 305 | | | | 310 | | | | | 315 | | | | | 320 |
| Asp | Tyr | Asn | Gln | Ile | Glu | Leu | Arg | Val | Leu | Ala | His | Leu | Ser | Gly | Asp |
| | | | | 325 | | | | | 330 | | | | | 335 | |
| Glu | Asn | Leu | Ile | Arg | Val | Phe | Gln | Glu | Gly | Arg | Asp | Ile | His | Thr | Glu |
| | | | 340 | | | | | 345 | | | | | 350 | | |

```
Thr Ala Ser Trp Met Phe Gly Val Pro Arg Glu Ala Val Asp Pro Leu
            355                 360                 365

Met Arg Arg Ala Ala Lys Thr Ile Asn Phe Gly Val Leu Tyr Gly Met
370                 375                 380

Ser Ala His Arg Leu Ser Gln Glu Leu Ala Ile Pro Tyr Glu Glu Ala
385                 390                 395                 400

Gln Ala Phe Ile Glu Arg Tyr Phe Gln Ser Phe Pro Lys Val Arg Ala
                405                 410                 415

Trp Ile Glu Lys Thr Leu Glu Glu Gly Arg Arg Arg Gly Tyr Val Glu
                420                 425                 430

Thr Leu Phe Gly Arg Arg Arg Tyr Val Pro Asp Leu Glu Ala Arg Val
            435                 440                 445

Lys Ser Val Arg Glu Ala Ala Glu Arg Met Ala Phe Asn Met Pro Val
450                 455                 460

Gln Gly Thr Ala Ala Asp Leu Met Lys Leu Ala Met Val Lys Leu Phe
465                 470                 475                 480

Pro Arg Leu Glu Glu Met Gly Ala Arg Met Leu Leu Gln Val His Asp
                485                 490                 495

Glu Leu Val Leu Glu Ala Pro Lys Glu Gly Ala Glu Ala Val Ala Arg
                500                 505                 510

Leu Ala Lys Glu Val Met Glu Gly Val Tyr Pro Leu Ala Val Ser Leu
            515                 520                 525

Glu Val Glu Val Gly Ile Gly Glu Asp Trp Leu Ser Ala Lys Glu Ala
530                 535                 540

Ala
545

<210> SEQ ID NO 100
<211> LENGTH: 832
<212> TYPE: PRT
<213> ORGANISM: Thermus aquaticus

<400> SEQUENCE: 100

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175
```

```
Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590
```

```
Arg Ile Arg Arg Ala Phe Ile Ala Glu Glu Gly Trp Leu Val Ala
            595                 600                 605

Leu Asp Tyr Ser Gln Ile Glu Leu Arg Val Leu Ala His Leu Ser Gly
610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
            725                 730                 735

Val Lys Ser Val Arg Glu Ala Ala Glu Arg Met Ala Phe Asn Met Pro
740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggatggaacc gctggagagc aactg                                      25

<210> SEQ ID NO 102
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gatctctctg attttcttg cgtcg                                       25

<210> SEQ ID NO 103
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 103
aagccuacga cuccgaacug accgugcuac caau                              34

<210> SEQ ID NO 104
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
aagccuacua cuccgaacug accgugcuac caau                              34

<210> SEQ ID NO 105
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
aagccuacaa cuccgaacug accgugcuac caau                              34

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
attggtagca cggtcagttc ggagt                                        25

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Gly Gly Gly Gly
1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

His His His His His His
1               5
```

METHODS FOR OBTAINING THERMOSTABLE ENZYMES, DNA POLYMERASE I VARIANTS FROM *THERMUS AQUATICUS* HAVING NEW CATALYTIC ACTIVITIES, METHODS FOR OBTAINING THE SAME, AND APPLICATIONS TO THE SAME

FIELD OF THE INVENTION

The present invention provides a method for obtaining thermostable enzymes. The present invention also provides variants of DNA polymerase I from *Thermus aquaticus*. The present invention further provides methods of identifying mutant DNA polymerases having enhanced catalytic activity. The present invention also provides polynucleotides, expression systems, and host cells encoding the mutant DNA polymerases. Still further, the present invention provides a method to carry out reverse transcriptase-polymerase chain reaction (RT-PCR) and kits to facilitate the same.

DISCUSSION OF THE BACKGROUND

Filamentous phage display is commonly used as a method to establish a link between a protein expressed as a fusion with a phage coat protein and its corresponding gene located within the phage particle (Marks et al., 1992). The use of filamentous phage particles as a chemical reagent provides further a strategy to create a complex between an enzyme, its gene and a substrate (Jestin et al., 1999). This substrate can be cross-linked on the surface of filamentous phage using the nucleophilic properties of coat proteins. If the enzyme is active, conversion of the substrate to the product yields a phage particle cross-linked with the product, which can be captured by affinity chromatography (Jestin et al., 1999).

Several similar approaches based on product formation for the isolation of genes encoding enzymes using phage display have been described in the literature for various enzymes (Fastrez et al., 2002). These in vitro selections of proteins for catalytic activity are well suited for use with large repertoires of about $10^8$ proteins or more. Several libraries of enzyme variants on phage have been constructed and catalytically active proteins with wild type like activities have been isolated (Atwell & Wells, 1999; Heinis et al., 2001; Ponsard et al., 2001; Ting et al., 2001). Mutants with different substrate specificities have been also obtained (Xia et al., 2002). In these studies, the fraction of active variants in the libraries can be large and it remains unclear how rare an enzyme can be in the initial protein library so as to be selected after iterative selection cycles. Accordingly, there remains a critical need for an efficient process for making and identifying thermostable enzymes possessing a desired catalytic activity (see discussion in Vichier-Guerre & Jestin, 2003).

Reverse transcriptases are enzymes that are present generally in certain animal viruses (i.e., retroviruses), which are used in vitro to make complementary DNA (cDNA) from an MRNA template. Practically, reverse transcriptases have engendered significant interest for their use in reverse transcriptase-polymerase chain reaction (RT-PCR). As such, these proteins lend themselves to be a model system for development of an efficient method of making thennostable enzymes having a desired activity.

RNA generally contains secondary structures and complex tertiary sections, accordingly it is highly desired that the RNA be copied in its entirety by reverse transcription to ensure that integrity of cDNA is maintained with high accuracy. However, due to the often complicated secondary and tertiary structures of RNA, the denaturation temperatures are generally about 90° C. and, as such, the reverse transcriptase must be capable of withstanding these extreme conditions while maintaining catalytic efficiency.

The classically utilized enzymes for RT-PCR have been isolated from the AMV (Avian myeloblastosis virus) or MMLV (Moloney murine leukemia virus); however, these enzymes suffer from a critical limitation in that they are not thennostable. In fact, the maximum temperature tolerated by most commercially available reverse transcriptases is about 70° C.

One common approach to overcome this limitation in the existing technology with the previously described polymerases has been the use of a protein chaperones in addition to the polymerase. However, this method leads to problems associated with environmental compatibility metal ion requirements, multi-stage procedures, and overall inconvenience. Accordingly, an alternative strategy has been to use thermostable reverse transcriptases. This approach makes it possible to perform multiple denaturation and reverse transcription cycles using only a single enzyme.

To this end, the DNA-dependent DNA polymerase I of *Thermus aquaticus* (i.e., Taq polymerase), is thermostable and has reverse transcriptase activity only in the presence of manganese. However, when the manganese ion concentration is maintained in the millimolar range the fidelity of the enzyme is affected. It has been suggested that the thermostable DNA-dependent DNA polymerase of *Bacillus stearothermophilus* has reverse transcriptase activity, even in absence of magnesium, but in this case it is necessary to add a thermostable DNA polymerase for the PCR.

Therefore, there remains a critical need for high efficiency, thermostable enzymes that are capable of catalyzing reverse transcription and subsequent DNA polymerization in "one-pot" RT-PCR. Accordingly, the present invention provides an isolated population of thermostable reverse transcriptases, which are active in absence of manganese, by directed evolution of the Stoffel fragment of the Taq polymerase.

SUMMARY OF THE INVENTION

It is an object of the present invention to provide a method of identifying thermostable mutant polypeptides having a catalytic activity by:

a) packaging a vector in which a gene or fragment thereof encoding variants of a catalytic domain responsible for the catalytic activity fused to a gene encoding a phage coat protein;

b) isolation and purification of phage particles;

c) heating the phage-mutant polypeptide at a temperature ranging from 50° C. to 90° C. for a time ranging from less than 1 minute to several hours;

d) cross-linking a specific substrate with a phage particle;

e) forming a reaction product from the substrate catalyzed by the thermostable mutant protein on phage, wherein the temperature is optionally regulated to be the same or greater or lower than the temperature of (c);

f) selecting the phage particles comprising a variant nucleotidic sequence encoding for the catalytic domain responsible for the catalytic activity at the regulated temperature, by capturing the reaction product or screening for said reaction product;

g) infecting *E. coli* with the phage particles selected at step (f);

h) incubating the infected *E. coli*; and i) assessing catalytic activity of the proteins corresponding to isolated genes.

It is an object of the present invention to provide a thermostable mutant DNA polymerase having at least 80% homology, preferably at least 90%, more preferably at least 95%, most preferably at least 97.5%, to the Stoffel fragment of DNA polymerase I obtained from *Thermus aquaticus* (residues 13-555 of SEQ ID NO: 26, which correspond to residues 290-832 of the wild-type DNA polymerase I from *Thermus aquaticus* (SEQ ID NO: 100)).

To this end, the present invention provides thermostable polypeptides having at least 80% homology, preferably at least 90%, more preferably at least 95%, most preferably at least 97.5%, to residues 13-555 of SEQ ID NO: 26, wherein said polypeptide has at least one mutation selected from the group consisting of a mutation in amino acids 461-490 of SEQ ID NO: 26 (738 to 767 of the Taq polymerase wild-type sequence SEQ ID NO: 100), A331T (position 608 of the Taq polymerase wild-type sequence SEQ ID NO: 100), S335N (position 612 of the Taq polymerase wild-type sequence SEQ ID NO: 100), M470K (position 747 of the Taq polymerase wild-type sequence SEQ ID NO: 100), M470R (position 747 of the Taq polymerase wild-type sequence SEQ ID NO: 100), F472Y (position 749 of the Taq polymerase wild-type sequence SEQ ID NO: 100), M484V (position 761 of the Taq polymerase wild-type sequence SEQ ID NO: 100), M484T position 761 of the Taq polymerase wild-type sequence SEQ ID NO: 100), and W550R (position 827 of the Taq polymerase wild-type sequence SEQ ID NO: 100), and wherein said polypeptide has improved DNA polymerase activity and retains 5'-3' exonuclease activity. In an object of the present invention, the 3'-5' exonuclease activity of the mutant polypeptide is inactive.

In an object of the present invention, the thermostable mutant DNA polymerase also has a mutation at one or more position selected from A331, L332, D333, Y334, and S335 of SEQ ID NO: 26 (positions 608-612 of the Taq polymerase wild-type sequence SEQ ID NO: 100).

Therefore, in an object of the present invention, the thermostable mutant DNA polymerase has at least 80% identity to residues 13-335 of SEQ ID NO: 26 and has a mutation at one or more position selected from H203, F205, T232, E253, Q257, D274, L275, I276, V309, I322, A331, L332, D333, Y334, S335, I361, R374, A384, T387, Y419, P493, M498, G499, M502, L503, V506, R518, A523, A526, P539, E543, and W550 of SEQ ID NO: 26. The present invention also embraces polynucleotides encoding the same.

The present invention also provides thermostable polypeptides having at least 80% homology, preferably at least 90%, more preferably at least 95%, most preferably at least 97.5%, to residues 13-335 of SEQ ID NO: 26, wherein said polypeptide has at least one mutation selected from the group consisting of H203R (position 480 of the Taq polymerase wild-type sequence SEQ ID NO: 100), F205L (position 482 of the Taq polymerase wild-type sequence SEQ ID NO: 100), T232S (position 509 of the Taq polymerase wild-type sequence SEQ ID NO: 100), E253G (position 530 of the Taq polymerase wild-type sequence SEQ ID NO: 100), Q257R (position 534 of the Taq polymerase wild-type sequence SEQ ID NO: 100), D274G (position 551 of the Taq polymerase wild-type sequence SEQ ID NO: 100), L275H (position 552 of the Taq polymerase wild-type sequence SEQ ID NO: 100), L275P (position 552 of the Taq polymerase wild-type sequence SEQ ID NO: 100), I276F (position 553 of the Taq polymerase wild-type sequence SEQ ID NO: 100), V309I (position 586 of the Taq polymerase wild-type sequence SEQ ID NO: 100), I322N (position 599 of the Taq polymerase wild-type sequence SEQ ID NO: 100), A331V (position 608 of the Taq polymerase wild-type sequence SEQ ID NO: 100), S335N (position 612 of the Taq polymerase wild-type sequence SEQ ID NO: 100), I361F (position 638 of the Taq polymerase wild-type sequence SEQ ID NO: 100), R374Q (position 651 of the Taq polymerase wild-type sequence SEQ ID NO: 100), A384T (position 661 of the Taq polymerase wild-type sequence SEQ ID NO: 100), T387A (position 664 of the Taq polymerase wild-type sequence SEQ ID NO: 100), Y419C (position 696 of the Taq polymerase wild-type sequence SEQ ID NO: 100), Y419N (position 696 of the Taq polymerase wild-type sequence SEQ ID NO: 100), E465K (position 742 of the Taq polymerase wild-type sequence SEQ ID NO: 100), M470K (position 747 of the Taq polymerase wild-type sequence SEQ ID NO: 100), M470R (position 747 of the Taq polymerase wild-type sequence SEQ ID NO: 100), F472Y (position 749 of the Taq polymerase wild-type sequence SEQ ID NO: 100), F472S (position 749 of the Taq polymerase wild-type sequence SEQ ID NO: 100), A487T (position 764 of the Taq polymerase wild-type sequence SEQ ID NO: 100), K490E (position 767 of the Taq polymerase wild-type sequence SEQ ID NO: 100), P493T (position 770 of the Taq polymerase wild-type sequence SEQ ID NO: 100), M498T (position 775 of the Taq polymerase wild-type sequence SEQ ID NO: 100), G499E (position 776 of the Taq polymerase wild-type sequence SEQ ID NO: 100), M502K (position 779 of the Taq polymerase wild-type sequence SEQ ID NO: 100), L503P (position 780 of the Taq polymerase wild-type sequence SEQ ID NO: 100), V506I (position 783 of the Taq polymerase wild-type sequence SEQ ID NO: 100), A523V (position 800 of the Taq polymerase wild-type sequence SEQ ID NO: 100), A526V (position 803 of the Taq polymerase wild-type sequence SEQ ID NO: 100), P539S (position 816 of the Taq polymerase wild-type sequence SEQ ID NO: 100), E543K (position 820 of the Taq polymerase wild-type sequence SEQ ID NO: 100), and W550R (position 827 of the Taq polymerase wild-type sequence SEQ ID NO: 100), and wherein said polypeptide has improved DNA polymerase activity and retains 5'-3' exonuclease activity. In an object of the present invention, the 3'-5' exonuclease activity of the mutant polypeptide is inactive.

In a particular object of the present invention, the mutant DNA polynerase has a sequence corresponding to residues 13-335 of one of the following sequences: SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, and SEQ ID NO: 38.

In another object of the present invention, the mutant DNA polymerase has a sequence corresponding to residues 1-543 of one of the following sequences: SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, and SEQ ID NO: 99. Further, in another object of the present invention are polynucleotides that encode for the aforementioned thermnostable mutant DNA polymerases.

In yet another object of the present invention is a kit for DNA amplification, which contains: (a) one or more of the aforementioned thermostable mutant DNA polymerases; (b) a concentrated buffer solution, wherein when said concentrated buffer is admixed with the isolated polypeptide the overall buffer concentration is 1×; (c) one or more divalent metal ion (e.g., $Mg^{2+}$ or $Mn^{2+}$); and (d) deoxyribonucleotides.

In yet another object of the present invention is a method of reverse transcribing RNA by utilizing the inventive thermostable mutant DNA polymerases.

In still a further object of the present invention is a phage-display method for identifying thermostable mutant DNA polymerases in which the Stoffel fragment has been mutated, while the DNA polymerase activity and 5'-3' exonuclease activity has been maintained and/or enhanced.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below. In the following legends, polymerase e corresponds to SEQ ID NO: 26 containing a R518G mutation (see Examples).

Figure 1:
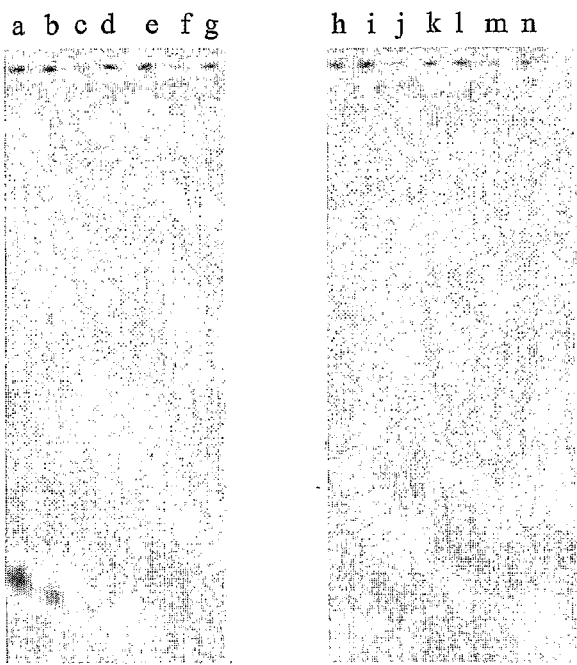
FIG. 1 shows the reverse transcriptase activity of phage-polymerases assessed as obtained after different rounds of selection in the presence of $Mg^{2+}$ or $Mn^{2+}$ ions. The lane labels correspond to the following.

| MnCl2 | MgCl$_2$ |
|---|---|
| a: phage-polymerases of round 6 | h: phage-polymerases of round 6 |
| b: phage-polymerases of round 5 | i: phage-polymerases of round 5 |
| c: phage-polymerases of round 4 | j: phage-polymerases of round 4 |
| d: phage-polymerases of round 3 | k: phage-polymerases of round 3 |
| e: phage-polymerases of round 2 | l: phage-polymerases of round 2 |
| f: phage-polymerases of round 1 | m: phage-polymerases of round 1 |
| g: phage-polymerases of initial population | n: phage-polymerases of initial population |

Figure 2:
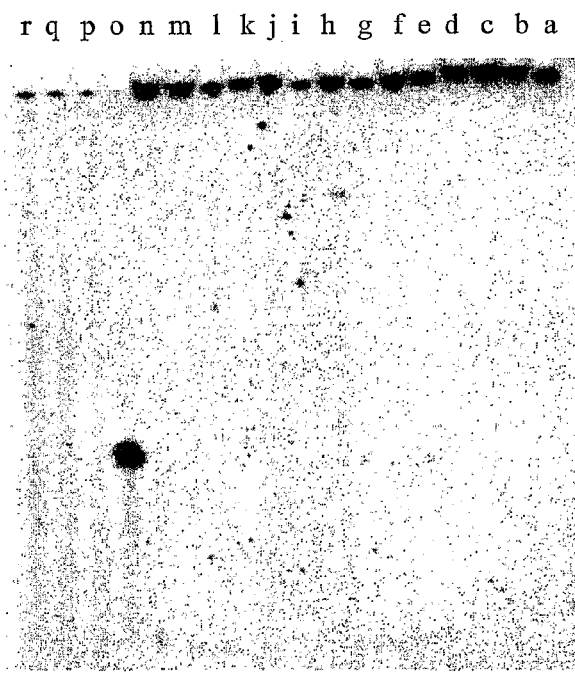

FIG. 2 shows the reverse transcriptase activity of phage-polymerases assessed as obtained after different rounds of selection in the presence of $Mg^{2+}$ ions. The lane designations in FIG. 2 are as follows:

| Phage-polymerase preheated at 65° C. for 5 min. | Phage-polymerase not preheated |
|---|---|
| a: phage-polymerases of initial population | h: phage-polymerases of initial population |
| b: phage-polymerases of round 1 | i: phage-polymerases of round 1 |
| c: phage-polymerases of round 2 | j: phage-polymerases of round 2 |
| d: phage-polymerases of round 3 | k: phage-polymerases of round 3 |
| e: phage-polymerases of round 4 | l: phage-polymerases of round 4 |
| f: phage-polymerases of round 5 | m: phage-polymerases of round 5 |
| g: phage-polymerases of round 6 | n: phage-polymerases of round 6 |
| | o: control AMV-RT, 1 U |
| | p: control AMV-RT, 0.1 U |
| | q: control AMV-RT, 0.01 U |
| | r: control AMV-RT, 0.001 U |

Figure 3:
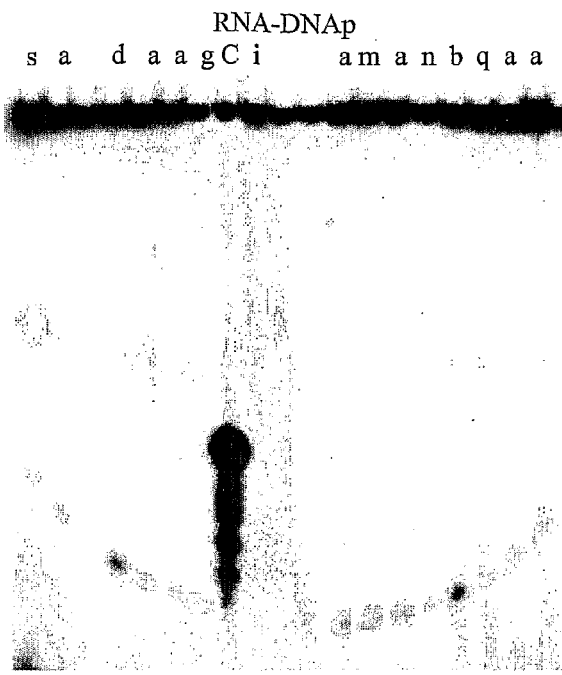

FIG. 3 shows the reverse transcriptase activity of various monoclonal phage-polymerases obtained after round 6 in the presence of $Mg^{2+}$ ions. The lane designations in FIG. 3 are as follows: s=SEQ ID NO: 38; a=SEQ ID NO: 20; d=SEQ ID NO: 24; g=SEQ ID NO: 28; C=AMV-RT; i=SEQ ID NO: 30; m=SEQ ID NO: 32; n=SEQ ID NO: 34; b=SEQ ID NO: 22; and q=SEQ ID NO: NO: 36.

Figure 4:
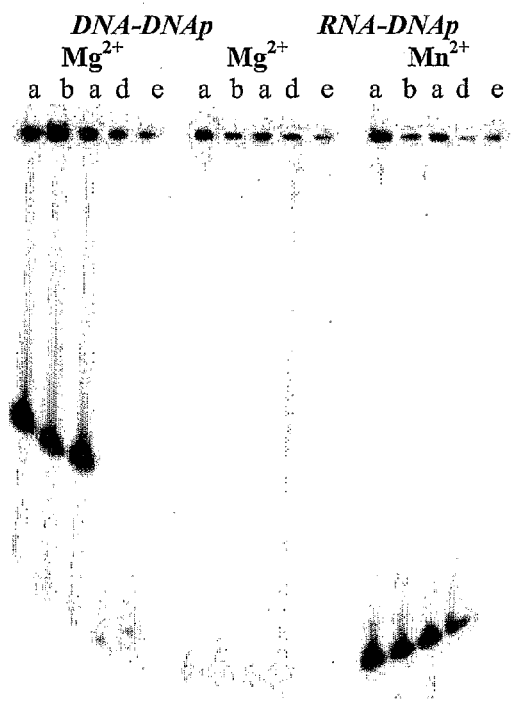

FIG. 4 shows the reverse transcriptase activities and the polymerase activities of monoclonal phage-polymerases obtained after the round 6 in the presence of $Mg^{2+}$ or $Mn^{2+}$ ions. The lane designations in FIG. 4 are as follows: a=SEQ ID NO: 20; b=SEQ ID NO: 22; d=SEQ ID NO: 24; and e=SEQ ID NO: 26 (containing an R518G mutation).

Figure 5:

FIG. 5 shows purified mutant polymerases a, b, and d used in polymerase chain reaction. The lanes in the gel appearing in FIG. 5 include the tlhree clones corresponding to clones a, b and d on FIG. 4. In addition, the positive control was performed using the Stoffel fragment polymerase e and the polymerase AMV-RT (Promega). The lanes in FIG. 5 are as follows:

lane 1: : molecular weight marker: PhiX phage DNA digested by HaeIII
lane 2: control AMV-RT
lane 3: b=SEQ ID NO: 22
lane 4: a=SEQ ID NO: 20
lane 5: e=SEQ ID NO: 26 (containing an R518G mutation)
lane 6: d=SEQ ID NO: 24

Figure 6:
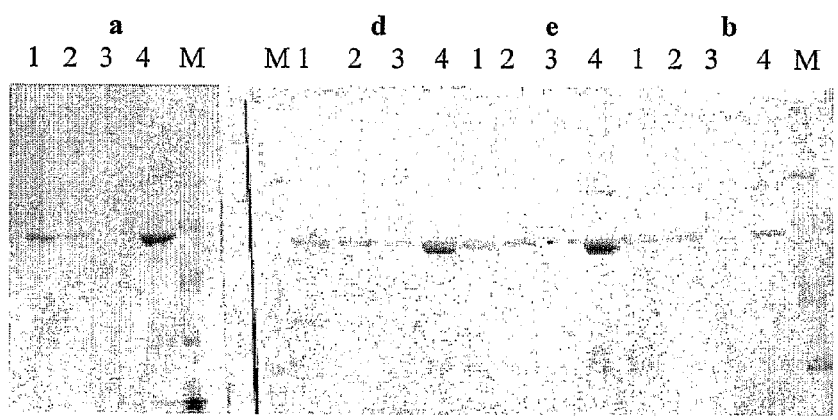

FIG. 6 shows the purification control of proteins after $Co^{+2}$ affinity chromatography.

Variant a
Well 1=8 μl Fraction 1
Well 2=8 μl Fraction 2
Well 3=8 μl Fraction 3
Well 4=8 μl Fractions 1+2+3 pooled and concentrated on Ultra Amicon 4 column (Millipore).
OD (a)=0.869 mg/ml.
Variant d
Well 1=8 μl Fraction 1
Well 2=8 μl Fraction 2
Well 3=8 μl Fraction 3
Well 4=8 μl Fractions 1+2+3 pooled and concentrated on Ultra Amicon 4 column (Millipore).
OD (d)=0.908 mg/ml.
Variant e
Well 1=8 μl Fraction 1
Well 2=8 μl Fraction 2
Well 3=8 μl Fraction 3
Well 4=8 μl Fractions 1+2+3 pooled and concentrated on Ultra Amicon 4 column (Millipore).
OD (e)=0.958 mg/ml.
Variant b
Well 1=8 μl Fraction 1
Well 2=8 μl Fraction 2
Well 3=8 μl Fraction 3
Well 4=8 μl Fractions 1+2+3 pooled and concentrated on Ultra Amicon 4 column (Millipore).
OD (b)=0.514 mg/ml.
M is the low range SDS PAGE molecular weight standards. Low Range (BIO-RAD, Ref. 161-0304). Bands located at 97.4 kDa; 66.2 kDa; 45 kDa; 31 kDa; 21 kDa and 14.4 kDa.

Figure 7:
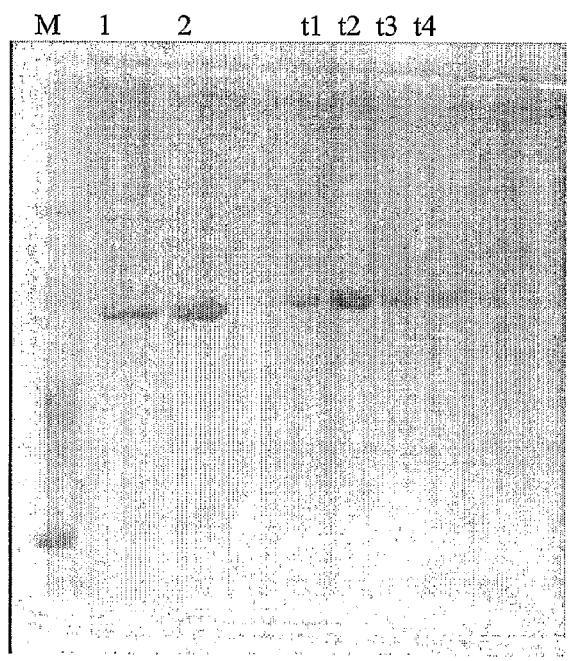

FIG. 7 shows protein e purification by $Co^{2+}$ affinity chromatography followed by heparin affinity chromatography.

Lanes 1 and 2 correspond to the protein e after purification by affinity chromatography on a $Co^{2+}$ colunmn. Lanes t1, t2, t3, t4 corresponds to the most concentrated fractions after the two-step purification by affinity chromatography, first on a $Co^{2+}$ column and second on a heparin column. M is the low range SDS PAGE molecular weight standards (Biorad).

Figure 8:
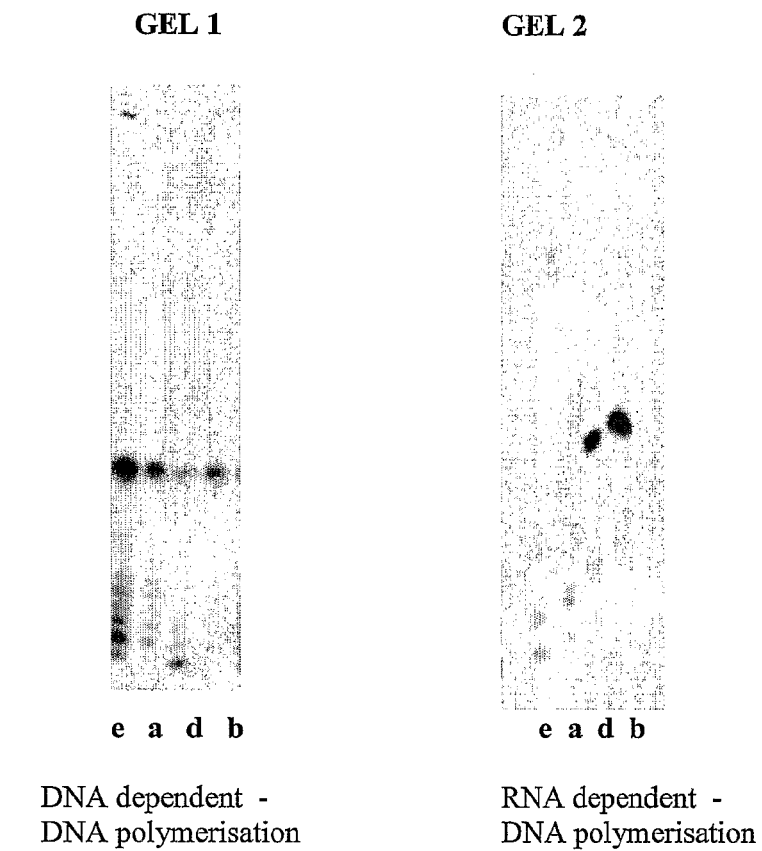

FIG. 8 shows 20% Polyacrylamide gels electrophoresis obtained with variants e, a, d and b for the test of primer extension.

Figure 9:
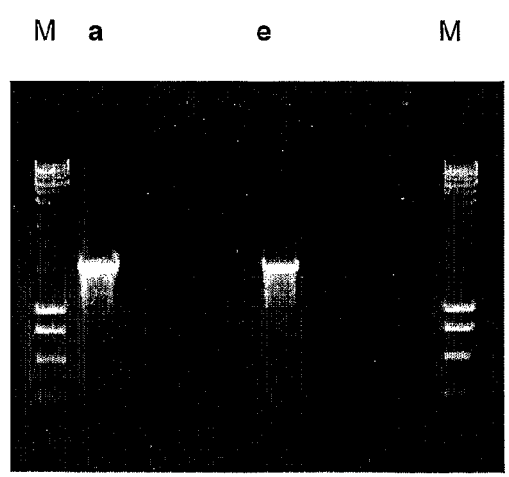

FIG. 9 shows products of PCR with polymerase e and variant a as shown by agarose gel after electrophoresis. M is the marker Smartladder (Eurogentec).

Figure 10:
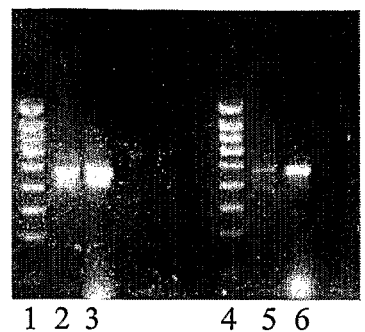

FIG. 10 shows the results of a PCR reaction using variant a. Results shown on a 2% agarose gel: deposit of 15 μl of amplification product.
Product of amplification=475 bp.
1. SmartLadder 100 bp (EUROGENTEC, Ref MW-1800-02, 200 lanes, Smallfragment)

Figure 11:
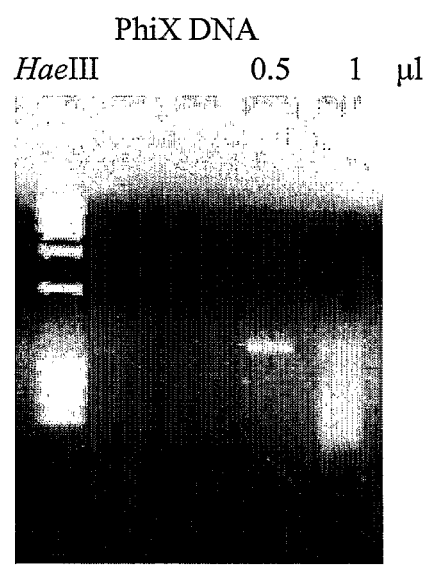

2. Variant a MJ Research
3. Variant a/MJ Research
4. SmartLadder 100 bp
5. Variant a/Applied BioSystems
6. Variant a/Applied BioSystems FIG. 11 shows Product of RT PCR "one pot" with variant a. As shown in the agarose gel after electrophoresis, M is the marker of phage PhiX DNA digested by the restriction enzyme HaeIII.

Figure 12:
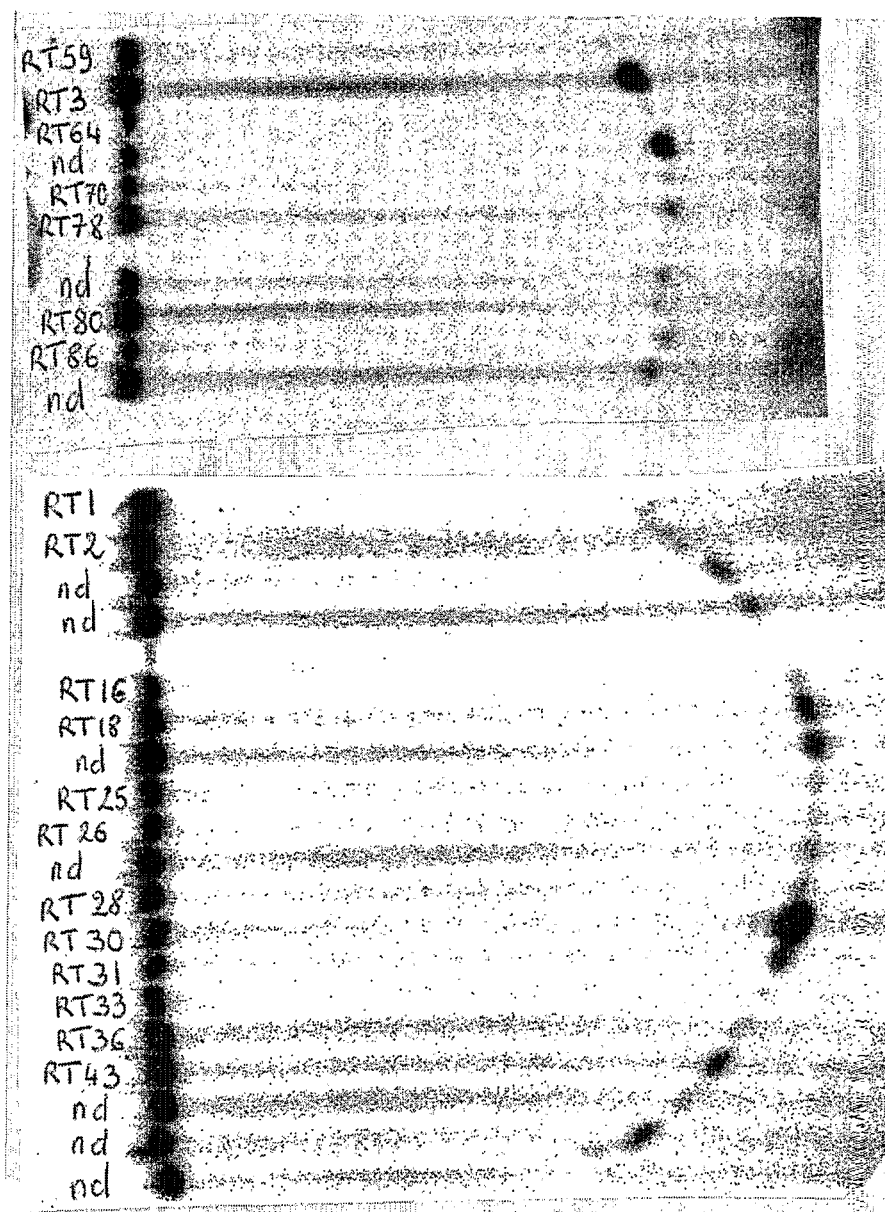

FIG. 12 shows the reverse transcriptase activity of various monoclonal phage-polymerases obtained after round 6 in the presence of $Mg^{2+}$ ions. The lane designations in FIG. 12 are as follows: rt1=SEQ ID NO: 63; rt2=SEQ ID NO: 65; rt3=SEQ ID NO: 67; rt16=SEQ ID NO: 69; rt18=SEQ ID NO: 71; rt25=SEQ ID NO: 73; Rt26=SEQ ID NO: 75; rt28=SEQ ID NO: 77; rt30=SEQ ID NO: 79; Rt31=SEQ ID NO: 81; rt33=SEQ ID NO: 83; rt36=SEQ ID NO: 85; rt43=SEQ ID NO: 87; Rt59=SEQ ID NO: 89; rt64=SEQ ID NO: 91; rt70=SEQ ID NO: 93; rt78=SEQ ID NO: 95; rt80=SEQ ID NO: 97; rt86=SEQ ID NO: 99; and nd=not described here.

DETAILED DESCRIPTION OF THE INVENTION

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present invention provides a method of identifying thermostable mutant polypeptides having a catalytic activity comprising:

a) packaging a vector in which a gene or fragment thereof encoding variants of a catalytic domain responsible for the catalytic activity fused to a gene encoding a phage coat protein;

b) isolation and purification of phage particles;

c) heating the phage-mutant polypeptide at a temperature ranging from 50° C. to 90° C., preferably from 55° C. to 65° C., more preferably at 65° C. for a time ranging from 30 seconds to several hours, preferably from 1 minute to 3 hours, more preferably from 5 minutes to 2 hours, most preferably 10 minutes to 1 hour;

d) cross-linking a specific substrate with a phage particle;

e) forming a reaction product from the substrate catalyzed by the thermostable mutant polypeptide on phage, wherein the temperature is optionally regulated to be the same or greater or lower than the temperature of (c) (i.e., from 25° C. to 70° C., preferably from 37° C. to 70° C. and more preferably at 65° C.);

f) selecting the phage particles comprising a variant nucleotidic sequence encoding for the catalytic domain responsible for the catalytic activity at the regulated temperature, by capturing the reaction product or screening for said reaction product;

g) infecting *E. coli* with phage particles selected at (f);

h) incubating the infected *E. coli*; and i) assessing catalytic activity of the proteins corresponding to isolated genes.

In the embodiment above, the gene or fragment thereof encoding variants of a catalytic domain may be directly or indirectly fused to the gene encoding a phage coat protein. When the gene or fragment thereof encoding variants of a catalytic domain and the gene encoding a phage coat protein are indirectly fused it is preferred that the fusion be through a peptide or polypeptide linker.

Within this above-recited embodiment, steps (a) to (h) may be repeated 0 to 20 times, preferably 1 to 15 times, more preferably 2 to 10 times, most preferably 3 to 7 times.

The method comprising a single cycle (repeated 0 times) is particularly adapted to high throughput screening, when steps are repeated from 3 to 7 times, the method is better adapted for classical empirical screening.

The peptide utilized within this embodiment is selected from the group consisting of: a flexible linker such as a glycine rich linker such as $(SG_4)_n$ (SEQ ID NO: 107) or the sequence $SG_4CG_4$ (residues 3-12 of SEQ ID NO: 39), human calmodulin (SEQ ID NO: 46, the DNA encoding SEQ ID NO: 46 is SEQ ID NO: 56), and hexahistidine (SEQ ID NO: 108) binding single chain variable fragment (Grütter M.G., 2002) consisting of:

(i) Anti-His Tag Antibody 3D5 Variable Heavy Chain (SEQ ID NO: 47)

(ii) Linker (SEQ ID NO: 48)

(iii) Anti-His Tag Antibody 3D5 Variable Light Chain (SEQ ID NO: 49).

Moreover, the polypeptide linker is selected from the group consisting of: any protein binding the substrate at high temperature, any catalytic domain such as 5' to 3' exonuclease (from *Thermus thermophilus*, SEQ ID NO: 50), or 3' to 5' exonuclease (from *E. coli*, SEQ ID NO: 51), Catalytic domain of *Bacillus circulans* cyclodextringlycosyltransferase (SEQ ID NO: 52 the DNA is in SEQ ID NO: 57), Catalytic domain of *Bordetella pertussis* adenylate cyclase (SEQ ID NO: 53—the DNA is in SEQ ID NO: 58), *Bacillus amyloliquefaciens* serine protease subtilisin (SEQ ID NO: 54—the DNA is in SEQ ID NO: 59), and Catalytic domain of *Bacillus subtilis* lipase A (SEQ ID NO: 55, Quax W. J., 2003).

As used in the present invention, the cross-linking between the specific substrate of the catalytic domain of the polypeptide with the phage particle is made by a cross-linking agent selected from the group consisting of a: maleimidyl group, iodoacetyl group, disulfide derivative and any other thermostable link (conducting to a stable protein-protein interaction or protein-molecule interaction).

In a preferred embodiment, the catalytic domain may be the catalytic domain of an enzyme selected from the group consisting of: a polymerase, an alpha-amylase (substrate such as starch), a lipase (substrate such as ester), a protease (modified or not modified peptide or polypeptide as substrate), a cyclodextringlycosyltransferase, and an adenylate cyclase.

In another embodiment, the assessment of the catalytic activity of step (f) is made by means of a DNA polymerization.

In yet another embodiment of the present invention, step (b) may be performed after (e) of cross-linking or during (h) of assesing catalytic activity.

As a general method for the isolation of thermostable enzymes and their genes the following should be noted:

First, the gene encoding variants of a catalytic domain are fused to the gene gencoding a phage coat protein (such as filamentous phage g3, g6, g7, g9 or g8 protein or of other phage/virus particles) either directly or using a peptide or polypeptide linker such as a short peptide sequence or a protein or a protein domain. These genes encoding phage coat proteins may be fused either at the 3' or at the 5' terminus depending on whether the N- or the C-termini of the proteins are located on the outside of the particle.

This is done either using a phage vector or a phagemid vector used with a helper phage.

Second, the phage-variant enzymes may be heated at a preferred temperature of 65° C. for 1 minute or for several hours as appropriate. This step can be performed before or after the substrate cross-linking (maleimidyl group derivatised substrate (DNA primer) crosslinked to the phage particle) and catalysis (DNA polymerisation) steps. Catalysis is preferably at 65° C. for 2 minutes, but can be done at any temperature between 0° C. and 100° C. Crosslinking is typically performed for 2 hours at 37° C., but can be done at other temperatures (higher temperature may increase maleimidyl hydrolysis versus maleimidyl phage cross-linking).

It is worth noting that the link between the gene and the corresponding enzyme variants is unaltered by high temperatures and the phage particle are still infective and the genes selected can be amplified by E. coli after infection (cf. for example, Kristensen P, Winter G., 1998).

By way of example of the aforementioned embodiments, the present invention relates to a purified, thermostable DNA polymerase purified from Thermus aquaticus and recombinant means for producing the enzyme. Thermostable DNA polymerases are useful in many recombinant DNA techniques, especially nucleic acid amplification by the polymerase chain reaction (PCR).

Directed protein-evolution strategies generally make use of a link between a protein and the encoding DNA. In phage-display technology, this link is provided by fusion of the protein with a coat-protein that is incorporated into the phage particle containing the DNA. Optimization of this link can be achieved by adjusting the signal sequence of the fusion.

Linking of a gene to its corresponding polypeptide is a central step in directed protein evolution toward new functions. Filamentous bacteriophage particles have been extensively used to establish this linkage between a gene of interest and its protein expressed as a fusion product with a phage coat protein for incorporation into the phage particle. Libraries of proteins displayed on phage can be subjected to in vitro selection to isolate proteins with desired properties together with their genes.

Creating a link between a gene and a single corresponding protein was achieved by making use of a phagemid for expression of the fusion protein and of a helper phage for assembly of the phage particles. This approach, yielding a monovalent display of protein, was found to be essential to avoid avidity effects or chelate effects, which introduce strong biases during in vitro selections for affinity. However, it also produces phage particles that do not display any protein of interest and which thereby represent a background in evolution experiments.

To optimize the link between a gene and a single corresponding protein, several methods have been used. For example, the periplasmic factor Skp was found to improve the display of single-chain Fv antibodies on filamentous phage (Bothmann, H. and Pluckthun, A., 1998). In a previous study, the present inventors showed that specific signal sequences for optimal display on phage of the Taq DNA polymerase I Stoffel fragment can be isolated from a library of more than $10^7$ signal sequences derived from pelB (Jestin, J. L., Volioti, G. and Winter, G., 2001). Signal sequences, once translated, are recognized by the bacterial protein export machinery. The polypeptide is then exported in the bacterial periplasm before cleavage of the signal peptide by the signal peptidase, thereby releasing the mature protein.

A short sequence, m ($SG_4CG_4$; residues 3-12 of SEQ ID NO: 39), at the C-terminus of the signal sequence, was initially introduced as a potential cross-linking site of substrates on phage that may be useful for selections by catalytic activity. This glycine-rich sequence may also be important for preventing structure formation at the peptidase cleavage site or for defining two independently folding units in the pre-protein. The glycine-rich sequence may then improve the signal sequence processing and finally lead to a greater ratio of protein fusions on phage. The present inventors, therefore, evaluated the effect of a selected signal sequence on the display of proteins on phage, as well as the effect of the m sequence at the C-terminus of the signal peptide.

In an embodiment of the present invention is a method of identifying thermostable mutant polymerases derived from the Stoffel fragment of Taq comprising:

a) packaging a vector in which a polynucleotide encoding a phage coat protein is fused to a polynucleotide encoding a protein having at least 80% identity to residues 13-555 of SEQ ID NO: 26 into a phage;
    b) expressing the fusion protein;
    c) isolation (selection) of phage particles;
    d) infecting E. coli and incubating the infected E. coli;
    e) detecting the fusion protein;
    f) assessing polymerase activity.

In this method, evolutionarily advantageous mutants may be identified by repeating steps (b)-(f) 0 to 25 times, preferably 0-20 times, more preferably 1-15 times, a most preferably 2 to 10 times. The method comprising one cycle (repeated 0 times) is particularly adapted to high throughput screening, when steps are repeated from 3 to 7 times, the method is better adapted for classical emprirical screening.

In a preferred embodiment, the phage coat protein is fused to said polynucleotide encoding a protein having at least 80% identity to residues 13-555 of SEQ ID NO: 26 by way of a linker having a sequence represented by residues 3-12 of SEQ ID 39.

By way of example, Applicants provide the following exemplary discussion of the phage-display method of the present invention and refer to Strobel et al., 2003, which is incorporated herein by reference in its entirety:

The amino acid signal sequences are that may be attached to the N-terminus of the proteins of the present invention:

```
pelB:    MKYLLPTAAAGLLLLAAQPAMA;   (SEQ ID NO: 41)

17:      MKTLLAMVLVGLLLLPPGPSMA;   (SEQ ID NO: 42)

I10:     MRGLLAMLVAGLLLLPIAPAMA;   (SEQ ID NO: 43)
and

I12:     MRRLLVIAAVGLLLLLAPPTMA.   (SEQ ID NO: 44)
```

The present inventors goal was to increase the display of proteins at the surface of filamentous phages. As model proteins, the present inventors chose the catalytic domains of adenylate cyclases from E. coli (ACE) and from B. pertussis (ACB). The present inventors also examined the display of two different enzymes, an adenylate cyclase and the Stoffel fragment of Taq DNA polymerase I, incorporated into phage particles as single polypeptide fusion products with minor coat protein p3. In this work, the present inventors evaluated the effects of two signal peptides (pelB and 17) and of the short peptide (m; residues 3-12 of SEQ ID NO: 39) at the N-terminus of the fusion of these enzymes with p3. One other construct, deriving from the selected signal peptide I12, is also mentioned here, and the data are summarized together with previously published data for the selected signal sequences 110 and 112 (Jestin et al., 2001).

The phage particles were produced by using a helper phage, KM13 (Kristensen et al., 1998), for assembly of the particles, and by using phagemids pHEN1 (Hoogenboom, H. R., Griffiths, A. D., Johnson, K. S., et al., 1991), pHEN117, and pHEN1112 (Jestin et al., 2001) encoding the p3 fusion proteins. These phagemid vectors differ in their signal sequence: pelB is from Erwinia caratovora pectate lyase B (Lei, S. P., Lin, H. C., Wang, S. S., Callaway, J., et al., 1987), whereas signal sequences 17, 110, and 112, were selected from a library of more than $10^7$ signal sequences for optimal display of the Stoffel fragment on filamentous phage (Jestin et al., 2001). For all 17 phagemids encoding the different fusion proteins described in this work, the present inventors observed standard titers of infective particles, which were all in the range of $1.4 \times 10^{10}$-$7.8 \times 10^{10}$ phages/mL of culture medium. Furthermore, enzymatic activities were detected for all phage-cyclase particles by thin layer chromatography and by HPLC (data not shown).

The efficiency of protein display on phage was evaluated through two approaches. The first makes use of the engineered helper phage KM13 (Kristensen et al., 1998) to measure the fraction of infective phage particles that display a fusion product. The p3 fusion protein provided by the phagemid and the p3 protein provided by the helper phage compete for incorporation into the phage particles. The helper phage p3 is engineered so as to contain a protease cleavage site between domains 2 and 3 of p3. In phage particles that contain only helper p3 copies, no full p3 copy is available for bacterial infection after protease treatment: the phage particles are noninfective. If a phage particle has incorporated a p3 fusion protein, one copy of the three-p3 domains remains after protease cleavage, and is sufficient for infection of E. coli. The trypsin-resistant fraction of phage is therefore a measure of protein display on infective phages. With this method, the display of fusion proteins was found to vary over more than two orders of magnitude for each cyclase, depending on the signal sequence and on neighboring sequences. Among the phagemid vectors containing the selected signal sequence 17, three of the four fusion proteins that the present inventors studied (AC-p3 and AC-Stoffel-p3, where AC is the adenylate cyclase catalytic domain of E. coli or B. pertussis) were remarkably well incorporated into phage particles: more than one phage particle out of ten displayed an enzyme. No more than one particle in 300 displayed the E. coli cyclase fused to the Stoffel fragment and to protein 3, and better display of this protein could not be found among the constructs tested.

The peptide m, $SG_4CG_4$ (residues 3-12 of SEQ ID NO: 39), at the N-terminus of the mature fusion protein, was found to increase the display of B. pertussis cyclase-polymerase fusion on phage, by 100-fold for signal sequence 17 and by 10-fold for pelB. For this fusion, the worst display ratios are significantly improved with peptide m. Display of B. pertussis cyclase on phage was high in all cases, such that a marginal improvement due to the m peptide was found for signal sequence 17, and improvement within the limits of experimental error for pelB. Concerning the E. coli cyclase protein, peptide m decreases the latter's display by a factor of 30 to 40. For the E. coli cyclase-polymerase fusion, peptide m showed no significant effect with the signal sequence pelB and a small improvement with signal sequence 17.

Significant effects of the signal sequence on phage display were detected for three of the four fusions in the present inventors' study: from 5- to about 20-fold improvements in display on phage were noted for substitution of pelB by signal sequence 17. In the case of the B. pertussis cyclase-p3 fusion protein, incorporation of the fusion protein into phage particles was high, whether the signal sequence was pelB, 17, or 112. Indeed, for the selected signal sequence 112, up to 40% of infective phage particles displayed an enzyme at the surface of filamentous phage.

When two enzymes were simultaneously displayed on phage (either E. coli or B. pertussis adenylate cyclase and the Stoffel fragment polymerase), the present inventors noted that the incorporation of p3 fusion products was significantly reduced in most cases. Remarkably, about half of the infective phage particles displayed a B. pertussis adenylate cyclase-Stoffel fragment polymerase-p3 protein fusion when the selected signal sequence 17 and the short N-terminal peptide m were present in the construct.

The second approach to estimating the level of fusion proteins incorporated into phage particles relies on the detection of p3 domain 3 by a monoclonal antibody (Tesar, M., Beckmann, C., Rottgen, P., et al., 1995) after SDS-PAGE and Western blotting of denatured phage particles. These results are in accordance with the data the present inventors obtained by measuring the trypsin-resistant fraction of infective phages. All fusion products expressed on phage and which correspond to a trypsin-resistant fraction of phage higher than 0.1 are indeed observed by Western blot analysis.

The present inventors aim to direct the evolution of adenylate cyclases by in vitro selection using a chemistry involving filamentous phage. This should provide a tool for the engineering of adenylate cyclases as well as a strategy for the functional cloning of this class of enzymes. Recent in vitro selection methods for catalytic activity using phage display have been designed as affinity chromatography methods for the reaction product linked to the phage enzyme that catalyzed the reaction from substrate to product. These selection methods were established with enzymes such as nuclease (Pedersen, H., Hölder, S., Sutherlin, D. P., et al., 1998), DNA polymerase (Jestin et al., 1999), peptidase (Dematris, S., Huber, A., et al., 1999; Heinis, C., Huber, A. et al., 2001), peptide ligase (Atwell et al., 1999), and beta-lactamase (Ponsard et al., 2001). They require an efficient display of enzyme on phage and a method to link the substrate/product to phage-enzymes.

In the work reported here, the present inventors investigated the display of adenylate cyclases from B. pertussis and from E. coli on filamentous phage, and the display of two independent enzymes, an adenylate cyclase and the Taq DNA polymerase I Stoffel fragment. The Stoffel fragment (Lawyer, F. C., Stoffel, S., Saiki, R. K., et al., 1989) could be used as a tool to establish an in vitro selection for cyclase activity as follows: the polymerase domain may serve as an anchor of the substrate ATP on phage through double-stranded DNA used as a linker with a high affinity for the fusion protein. Another approach to cross-linking substrate and phage involves introduction of the thiol group of a cysteine residue within peptide m ($SG_4CG_4$) (residues 3-12 of SEQ ID NO: 39), at the N-terminus of the mature fusion protein and at the C-terminus of the fusion protein's signal sequence (Jestin et al., 1999).

The signal sequences 17, 110, and 112, used in the present inventors' study had been selected from large libraries of pelB mutants for optimal display of the Stoffel fragment-p3 protein fused to the peptide m (Jestin et al., 2001). It was therefore important to further investigate which sequence context was essential for selection of these signal sequences, either the short peptide m or the entire gene. Interestingly, the present inventors found that the presence or the absence of this short peptide, $SG_4CG_4$ (residues 3-12 of SEQ ID NO: 39), can yield up to 100-fold increases in the display of a fusion protein on filamentous phage. This strong effect was observed for the *B. pertussis* cyclase-Stoffel-p3 fusion as well as for the *E. coli* cyclase-p3 fusion in the case of the signal sequence 17 (Table 2). Of further note is that the signal sequences 17 and 112, yield generally better levels of protein display on phage than does pelB (FIG. 3). This improved display of proteins might be ascribed to the different targeting modes of the signal sequences. These selected signal sequences that improve the display of proteins on phage should therefore be useful in other systems.

Our study highlights the important effects of the signal sequence and of a short peptide at the C-terminus of the signal sequence on the display of proteins on phage. Apart from the previously stated conclusions that the selected signal sequence 17 often yields an improved display as compared with pelB, and that sequence m can have drastic effects on the level of protein display, the set of protein fusions described here is not sufficient to define any further rules about sequences and optimal display of proteins on phage. Indeed, incorporation of a fusion protein into a phage particle is the result of a complex sequence of events involving fusion gene transcription and translation, folding, and export of the fusion protein, as well as cleavage of the signal sequence.

Two approaches, however, can be envisaged for efficient display of proteins on bacteriophage. First, directed signal peptide evolution experiments can be undertaken for any defined protein so as to isolate a signal sequence for optimal display on phage. This approach was described previously in the case of the Stoffel fragment of Taq DNA polymerase I (Jestin et al., 2001). A more straightforward and quicker approach consists of the screening of several phagemid vectors that differ in their signal sequences and, more generally, in their regulatory sequences. In this report the present inventors have shown that for three of the four fusion proteins tested, excellent cyclase display levels can be obtained: more than one phage in ten displays an enzyme. Such display levels for large proteins should be useful for further approaches to directed protein evolution.

With use of the phagemid strategy, almost every particle expresses a p3 copy provided by the phagemid if no gene fusion has been engineered or if the insert from the gene fusion has been deleted. On the contrary, about one phage particle in a thousand incorporates large fusion proteins such as cyclase-Stoffel fragment-p3 fusions. This indicates that for an equal mixture of two genes, thousand-fold differences in expression of the corresponding proteins on phage particles can be obtained. This bias may be of no importance if enrichment factors per selection round are much larger than $10^3$, but it may otherwise significantly alter the outcome of evolution experiments. Similar protein expression levels on phage of different genes would be useful to minimize biases introduced by successive amplifications in evolution experiments. The use of sets of phagemid vectors that differ by their signal sequences and by neighboring sequences might be of interest for better representation of protein libraries on filamentous phage. Additionally, the display of two distinct enzymes on single phage particles might be useful to direct their coevolution, especially in the case of two enzymes involved in the same metabolic pathway with an unstable reaction intermediate.

By insertion or by deletion of the short peptide sequence $SG_4CG_4$ (m; residues 3-12 of SEQ ID NO: 39) at the C-terminus of the signal sequence (i.e., immediately upstream (N-terminal) to the variant Stoffel fragments of the present invention), the present inventors have shown that two enzymes can be very efficiently expressed as single polypeptides on the surface of filamentous bacteriophage by using the phagemid strategy. The model proteins described in this study are the catalytic domains of adenylate cyclases of *B. pertussis* or of *E. coli*, fused or not fused to the Stoffel-fragment DNA polymerase.

On average, the present inventors found the best display levels for the selected signal sequence 17, which had been previously selected from a large library for optimal display on phage of the Stoffel fragment, and not for the commonly used signal sequence pelB. Yet the present inventors observed striking differences in display levels of these enzymes on the surfaces of phage particles, depending on the short N-terminal peptide m. The findings reported here should be useful for the display of large and of cytoplasmic proteins on filamentous phage particles, and more generally for protein engineering using phage display.

It is important to note that within the present application the terms "protein," "polymerase," "enzyme," "clone," and "variant" are considered to be equivalent terms when used to qualify, name, or otherwise designate the mutant Stoffel fragments of the present invention. Further, in the context of the present invention the term "Stoffel fragment," "the Stoffel fragment of DNA polymerase I obtained from *Thermus aquaticus*" or similar terms are used herein, and is frequently associated with SEQ ID NO: 26. Also in the present invention variant e is used in conjunction with SEQ ID NO: 26, as this sequence corresponds to the native Stoffel fragment of DNA polymerase I obtained from *Thermus aquaticus*, but contains a R518G (in the context of the full-length Taq sequence, this is a R795G mutation). It is to be understood that reference to variant e is sometimes used as a short hand for residues 13-555 of SEQ ID NO: 26, wherein SEQ ID NO: 26 actually corresponds to the native Stoffel fragment of DNA polymerase I obtained from *Thermus aquaticus*.

Residues 1-12 of SEQ ID NO: 26 correspond to SEQ ID NO: 39, which contain 2 residues from the signal sequence (MetAla) and 10 residues ($SerGly_4CysGly_4$) (residues 3-12 of SEQ ID NO: 39) corresponding to a linker that had been introduced at N-terminus of the mature fusion protein on phage so as to introduce a cysteine residue that might be important for substrate cross-linking on phage. Further residues 556-562 correspond to residues 1-7 of SEQ ID NO: 40, which is the resultant sequence following thrombin cleavage of the sequence of SEQ ID NO: 40. It should also be understood that the present invention embraces sequences corresponding to residues 13-555 of SEQ ID NO: 26 as defined herein, as well as sequences in which the N-terminus and C-terminus contain signal sequences, linker sequences, purification tags, and/or fusion constructs.

The term "thermostable" enzyme refers to an enzyme that is stable over a temperature range of approximately 55° C. to 105° C. In particular, thermostable enzymes in accordance with the present invention are heat resistant and catalyze the template directed DNA synthesis. Preferably, the activity of the thermostable enzymes of the present is at least 50% of activity, preferably at least 75%, more preferably at least 85%, of the wild-type enzyme activity over the same temperature range. In a particularly preferred embodiment, the thermostable enzyme of the present invention exhibits at least 50% of activity, preferably at least 75%, more preferably at least 85%, of the wild-type enzyme activity when said wild-type enzyme activity is measured under optimal conditions. Moreover, it is preferable that the "thermostable" enzyme does not become irreversibly denatured when subjected to the elevated temperatures and incubation time for denaturation of double-stranded nucleic acids, as well as the repetitive cycling between denaturation, annealing, and extension inherent to PCR-based techniques.

As used herein, the term "reduced" or "inhibited" means decreasing the activity of one or more enzymes either directly or indirectly. The definition of these terms also includes the reduction of the in vitro activity, either directly or indirectly, of one or more enzymes.

The term "enhanced" as used herein means increasing the activity or concentration one or more polypeptides, which are encoded by the corresponding DNA. Enhancement can be achieved with the aid of various manipulations of the bacterial cell, including mutation of the protein, replacement of the expression regulatory sequence, etc.

In order to achieve enhancement, particularly over-expression, the number of copies of the corresponding gene can be increased, a strong promoter can be "operably linked," or the promoter- and regulation region or the ribosome binding site which is situated upstream of the structural gene can be mutated. In this regard, the term "operably linked" refers to the positioning of the coding sequence such that a promoter, regulator, and/or control sequence will function to direct the expression of the protein encoded by the coding sequence located downstream therefrom.

Expression cassettes that are incorporated upstream of the structural gene act in the same manner. In addition, it is possible to increase expression by employing inducible promoters. A gene can also be used which encodes a corresponding enzyme with a high activity. Expression can also be improved by measures for extending the life of the mRNA. Furthermore, preventing the degradation of the enzyme increases activity as a whole. Moreover, these measures can optionally be combined in any desired manner. The definition of these terms also includes the enhancement of the in vitro activity, either directly or indirectly, of one or more enzymes.

It is to be understood that the in addition to the following variant Stoffel polypeptides and polynucleotides encoding the same, the present invention also embraces full-length Taq polymerase enzymes in which the specifically identified mutations have been effectuated. The present invention further embraces full-length polymerases beyond those of the genus Thermus in which the domain equivalent in function to the Stoffel fragment is replaced by the variant sequences of the present invention thereby imparted or enhancing thermostability of the resultant polymerase. The skilled artisan would readily appreciate methods of mutagenesis and/or subcloning to alter the sequence of the Taq polymerase to incorporate the same. Further, the references cited herein, such as Maniatis, Molecular Cloning: A Laboratory Manual, Cold Spring Harbor Laboratory, p. 412 (1982), provide such techniques.

A gene (polynucleotide) can be used which encodes a corresponding or variant polymerase having at least 80% homology to amino acid residues 13-555 of SEQ ID NO: 26. These genes (polynucleotides) can encode various mutations. For example, a mutation of one or more amino acids in amino acids 461-490 of SEQ ID NO: 26 (738 to 767 of the Taq polymerase wild-type sequence SEQ ID NO: 100). Further examples of mutations include mutations at positions M470, F472, M484, and W550, A331, and S335. In a preferred embodiment, the mutation may be at least one of H203, F205, T232, E253, Q257, D274, L275, I276, V309, I322, A331, L332, D333, Y334, S335, I361, R374, A384, T387, Y419, P493, M498, G499, M502, L503, V506, R518, A523, A526, P539, E543, and W550.

In a preferred embodiment, these mutations are A331T, S335N, M470K, M470R, F472Y, M484V, M484T, and W550R. In a particularly preferred embodiment, the polynucleotides of the present invention encode polypeptides having one or more of the aforementioned mutations and share at least 85% identity, at least 90% identity, at least 95% identity, or at least 97.5% identity to the polypeptide comprising amino acid residues 13-555 of SEQ ID NO: 26. Moreover, polynucleotides of the present invention encode polypeptides that have DNA polymerase activity and/or 5'-3' exonuclease activity. More particularly, the polynucleotides of the present invention encode polypeptides that are capable of catalyzing the reverse transcription of RNA.

In the present invention, the polynucleotide may encode a polypeptide contain at least one mutation at a position selected from the group consisting of A331, L332, D333, Y334, and S335.

The polynucleotide may encode a polypeptide of the present invention which has amino acid sequence of residues 13-555 of a sequence selected from the group consisting of SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, and SEQ ID NO: 38.

Within the context of the present application, the preferred polynucleotides possess a polynucleotide sequence corresponding to nucleotides 39-1667 of a sequence selected from the group consisting of SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, and SEQ ID NO: 37.

In another embodiment of the present invention, are thermostable polypeptides having at least 80% homology, preferably at least 90%, more preferably at least 95%, most preferably at least 97.5%, to residues 13-555 of SEQ ID NO: 26, wherein said polypeptide has at least one mutation selected from the group consisting of H203R (position 480 of the Taq polymerase wild-type sequence SEQ ID NO: 100), F205L (position 482 of the Taq polymerase wild-type sequence SEQ ID NO: 100), T232S (position 509 of the Taq polymerase wild-type sequence SEQ ID NO: 100), E253G (position 530 of the Taq polymerase wild-type sequence SEQ ID NO: 100), Q257R (position 534 of the Taq polymerase wild-type sequence SEQ ID NO: 100), D274G (position 551 of the Taq polymerase wild-type sequence SEQ ID NO: 100), L275H (position 552 of the Taq polymerase wild-type sequence SEQ ID NO: 100), L275P (position 552 of the Taq polymerase wild-type sequence SEQ ID NO: 100), I276F (position 553 of the Taq polymerase wild-type sequence SEQ ID NO: 100), V309I (position 586 of the Taq polymerase wild-type sequence SEQ ID NO: 100), I322N (position 599 of the Taq polymerase wild-type sequence SEQ ID NO: 100), A331V (position 608 of the Taq polymerase wild-type sequence SEQ ID NO: 100), S335N (position 612 of the Taq polymerase wild-type sequence SEQ ID NO: 100), I361F (position 638 of the Taq polymerase wild-type sequence SEQ ID NO: 100), R374Q (position 651 of the Taq polymerase wild-type sequence SEQ ID NO: 100), A384T (position 661 of the Taq polymerase wild-type sequence SEQ ID NO: 100), T387A (position 664 of the Taq polymerase wild-type sequence SEQ ID NO: 100), Y419C (position 696 of the Taq polymerase wild-type sequence SEQ ID NO: 100), Y419N (position 696 of the Taq polymerase wild-type sequence SEQ ID NO: 100), E465K (position 742 of the Taq polymerase wild-type sequence SEQ ID NO: 100), M470K (position 747 of the Taq polymerase wild-type sequence SEQ ID NO: 100), M470R (position 747 of the Taq polymerase wild-type sequence SEQ ID NO: 100), F472Y (position 749 of the Taq polymerase wild-type sequence SEQ ID NO: 100), F472S (position 749 of the Taq polymerase wild-type sequence SEQ ID NO: 100), A487T (position 764 of the Taq polymerase wild-type sequence SEQ ID NO: 100), K490E (position 767 of the Taq polymerase wild-type sequence SEQ ID NO: 100), P493T (position 770 of the Taq polymerase wild-type sequence SEQ ID NO: 100), M498T (position 775 of the Taq polymerase wild-type sequence SEQ ID NO: 100), G499E (position 776 of the Taq polymerase wild-type sequence SEQ ID NO: 100), M502K (position 779 of the Taq polymerase wild-type sequence SEQ ID NO: 100), L503P (position 780 of the Taq polymerase wild-type sequence SEQ ID NO: 100), V506I (position 783 of the Taq polymerase wild-type sequence SEQ ID NO: 100), A523V (position 800 of the Taq polymerase wild-type sequence SEQ ID NO: 100), A526V (position 803 of the Taq polymerase wild-type sequence SEQ ID NO: 100), P539S (position 816 of the Taq polymerase wild-type sequence SEQ ID NO: 100), E543K (position 820 of the Taq polymerase wild-type sequence SEQ ID NO: 100), and W550R (position 827 of the Taq polymerase wild-type sequence SEQ ID NO: 100), and wherein said polypeptide has improved DNA polymerase activity and retains 5'-3' exonuclease activity. In an object of the present invention, the 3'-5' exonuclease activity of the mutant polypeptide is inactive.

Moreover, the present invention provides for polynucleotides that encode for the aforementioned thermostable polypeptides within this embodiment.

In the present invention, the polynucleotide may encode a polypeptide having a sequence of residues 1-543 from a sequence selected from the group consisting of SEQ ID NO: 63, SEQ ID NO: 65, SEQ ID NO: 67, SEQ ID NO: 69, SEQ ID NO: 71, SEQ ID NO: 73, SEQ ID NO: 75, SEQ II) NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, and SEQ ID NO: 99.

Within the context of the present application, the preferred polynucleotides possess a polynucleotide sequence corresponding to nucleotides 1-1629 of a sequence selected from the group consisting of SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, and SEQ ID NO: 98.

In another embodiment of the present invention, the mutant DNA polymerase has a sequence corresponding to residues 1-543 of one of the following sequences: SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, and SEQ ID NO: 99.

Within the scope of the present invention are also polynucleotides that are homologous to the aforementioned sequences. In the context of the present application, a polynucleotide sequence is "homologous" with the sequence according to the invention if at least 80%, preferably at least 90%, more preferably 95%, and most preferably 97.5% of its base composition and base sequence corresponds to the sequence according to the invention. It is to be understood that, as evinced by the Examples of the present invention and the phage-display method highlighted herein, screening of theoretical mutations within the scope of the present invention would require nothing more than a technician's level of skill in the art. More specifically, as is routine in the art, with the identification of a candidate sequence the artisan would assay and screen one or all possible permutations of the said sequence to identify mutants possessing the same or better DNA polymerase activity, reverse transcriptase activity, and/or 5'-3' exonuclease activity.

The expression "homologous amino acids" denotes those that have corresponding properties, particularly with regard to their charge, hydrophobic character, steric properties, etc.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The terms "isolated" or "purified" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins that contain two or more amino acids that are bound via peptide bonds. A "polypeptide" as used herein is understood to mean a sequence of several amino acid residues linked by peptide bonds. Such amino acids are known in the art and encompass the unmodified and modified amino acids. In addition, one or more modifications known in the art such as glycosylation, phosphorylation, etc may modify the polypeptide.

The term "homologous" as used herein is understood to mean two or more proteins from the same species or from a different species. Within the meaning of this term, said two or more polypeptides share at least 80% identity to residues 13-555 of the polypeptide of SEQ ID NO: 26 and can have the mutations discussed herein. In a particularly preferred embodiment, the polypeptides of the present invention have one or more of the aforementioned mutations and share at least 85% identity, at least 90% identity, at least 95% identity, or at least 97.5% identity to residues 13-555 of the polypeptide of SEQ ID NO: 26. Moreover, the polypeptides of the present invention have DNA polymerase activity and/or 5'-3' exonuclease activity. More particularly, the polypeptides of the present invention are capable of catalyzing the reverse transcription of mRNA.

In the present invention, the polypeptide may contain one or more mutations, such as A331, L332, D333, Y334, and S335.

The isolated polypeptide of the present invention has an amino acid sequence corresponding to residues 13-555 of a sequence selected from the group consisting of SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, and SEQ ID NO: 38.

Further, the mutant DNA polymerase may have a sequence corresponding to residues 1-543 of one of the following sequences: SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, and SEQ ID NO: 99.

In an embodiment of the present invention are mutations concerning alanine in position 331 (A331), and serine in position 335 (S335) that may have particular importance derived from the fact that they are surrounding the aspartic acid D in position 333 which is responsible for the chelation of $Mn^{2+}$ or $Mg^{2+}$. Thus, in one embodiment of the present invention, mutations of one or more amino acids 10 amino acids upstream and/or 10 amino acids downstream of this site are provided.

The expression "homologous amino acids" denotes those that have corresponding properties, particularly with regard to their charge, hydrophobic character, steric properties, etc.

Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilize said function. As such, these conservative amino acid replacements are also envisaged as being within the scope of the present invention.

The present invention also relates to DNA sequences that hybridize with the DNA sequence that encodes a corresponding or variant polymerase having at least 80% homology, preferably at least 90%, more preferably at least 95%, most preferably at least 97.5%, to residues 13-555 of SEQ ID NO: 26, the polypeptides having the mutations described herein. The present invention also relates to DNA sequences that are produced by polymerase chain reaction (PCR) using oligonucleotide primers that result from the DNA sequence that encodes a corresponding or variant polymerase having at least 80% homology, preferably at least 90%, more preferably at least 95%, most preferably at least 97.5%, to residues 13-555 of SEQ ID NO: 26, wherein the polypeptide has at least one mutation as described herein, or fragments thereof. Oligonucleotides of this type typically have a length of at least 15 nucleotides.

The terms "stringent conditions" or "stringent hybridization conditions" includes reference to conditions under which a polynucleotide will hybridize to its target sequence, to a detectably greater degree than other sequences (e.g., at least 2-fold over background). As used herein, stringent hybridization conditions are those conditions which allow hybridization between polynucleotides that are 80%, 85%, 90%, 95%, or 97.5% homologous as determined using conventional homology programs, an example of which is UWGCG sequence analysis program available from the University of Wisconsin. (Devereaux et al., 1984). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138:267-284 (1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Thus, with the foregoing information, the skilled artisan can identify and isolated polynucleotides, which are substantially similar to the present polynucleotides. In isolating such a polynucleotide, the polynucleotide can be used as the present polynucleotide in, for example, to express a polypeptide having DNA polymerase activity and 5'-3' exonuclease activity.

One embodiment of the present invention is methods of screening for polynucleotides, which have substantial homology to the polynucleotides of the present invention, preferably those polynucleotides encoding a polypeptide having DNA polymerase activity and/or 5'-3' exonuclease activity.

The polynucleotide sequences of the present invention can be carried on one or more suitable plasmid vectors, as known in the art for bacteria or the like.

Host cells useful in the present invention include any cell having the capacity to be infected or transfected by phages or vectors comprising the polynucleotide sequences encoding the enzymes described herein and, preferably also express the thermostable enzymes as described herein. Suitable host cells for expression include prokaryotes, yeast, archae, and other eukaryotic cells. Appropriate cloning and expression vectors for use with bacterial, fungal, yeast, and mammalian cellular hosts are well known in the art, e.g., Pouwels et al. (1985). The vector may be a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsulated virus by well-known techniques for infection and transduction. Viral vectors may be replication competent or replication defective. In the latter case viral propagation generally will occur only in complementing host cells. Cell-free translation systems could also be employed to produce the enzymes using RNAs derived from the present DNA constructs.

Prokaryotes useful as host cells in the present invention include gram negative or gram-positive organisms such as *E. coli* or *Bacilli*. In a prokaryotic host cell, a polypeptide may include a N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include β-lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector.

Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., 1978; and Goeddel et al., 1979), tryptophan (trp) promoter system (Goeddel et al., 1980), and tac promoter (Maniatis, Molecular Cloning: A Laboratory Manual, Cold Spring Harbor Laboratory, p. 412 (1982)).

Yeasts useful as host cells in the present invention include those from the genus *Saccharomyces, Pichia, K. Actinomycetes* and *Kluyveromyces*. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., 1980) or other glycolytic enzymes (Holland et al., 1978) such as enolase, glyceraldehyde-3-phosphate dehydrogenase, hexokinase, pyruvatee decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991). Other suitable promoters and vectors for yeast and yeast transformation protocols are well known in the art.

Those of skill in the art are familiar with yeast transformation protocols that may be employed in the present invention. One such protocol is described by Hinnen et al., (1978). The Hinnen protocol selects for Trp$^+$ transformants in a selective medium, wherein the selective medium consists of 0.67% yeast nitrogen base, 0.5% casamino acids, 2% glucose, 10 μg/ml adenine, and 20 μg/ml uracil.

Mammalian or insect host cell culture systems well known in the art could also be employed to express recombinant polypeptides, e.g., Baculovirus systems for production of heterologous proteins in insect cells (Luckow and Summers, (1988)) or Chinese hamster ovary (CHO) cells for mammalian expression may be used. Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

The enzymes of the present invention may, when beneficial, be expressed as a fusion protein that has the enzyme attached to a fusion segment. The fusion segment often aids in protein purification, e.g., by permitting the fusion protein to be isolated and purified by affinity chromatography. Fusion proteins can be produced by culturing a recombinant cell transformed with a fusion nucleic acid sequence that encodes a protein including the fusion segment attached to either the carboxyl and/or amino terminal end of the enzyme.

In one embodiment, it may be advantageous for propagating the polynucleotide to carry it in a bacterial or fungal strain with the appropriate vector suitable for the cell type. Common methods of propagating polynucleotides and producing proteins in these cell types are known in the art and are described, for example, in Maniatis et al. (1982) and Sambrook et al. (1989).

In one embodiment of the present invention are monoclonal phages:

1. SJL q deposited under Budapest treaty as CNCM I-3168 in the Collection Nationale de Cultures de Microorganismes (CNCM, Institut Pasteur 25 rue du docteur Roux 75724 Paris cedex 15 France), on Feb. 27, 2004.

2. SJL d deposited under Budapest treaty as CNCM I-3169 in the Collection Nationale de Cultures de Microorganismes (CNCM, Institut Pasteur 25 rue du docteur Roux 75724 Paris cedex 15 France) on Feb. 27, 2004.

3. SJL l deposited under Budapest treaty as CNCM I-3170 in the Collection Nationale de Cultures de Microorganismes (CNCM, Institut Pasteur 25 rue du docteur Roux 75724 Paris cedex 15 France) on Feb. 27, 2004.

4. SJL s deposited under Budapest treaty as CNCM I-3171 in the Collection Nationale de Cultures de Microorganismes (CNCM, Institut Pasteur 25 rue du docteur Roux 75724 Paris cedex 15 France) on Feb. 27, 2004.

5. SJL b deposited under Budapest treaty as CNCM I-3172 in the Collection Nationale de Cultures de Microorganismes (CNCM, Institut Pasteur 25 rue du docteur Roux 75724 Paris cedex 15 France) on Feb. 27, 2004.

6. SJL n deposited under Budapest treaty as CNCM I-3173 in the Collection Nationale de Cultures de Microorganismes (CNCM, Institut Pasteur 25 rue du docteur Roux 75724 Paris cedex 15 France) on Feb. 27, 2004.

7. SJL g deposited under Budapest treaty as CNCM I-3174 in the Collection Nationale de Cultures de Microorganismes (CNCM, Institut Pasteur 25 rue du docteur Roux 75724 Paris cedex 15 France) on Feb. 27, 2004.

8. SJL m deposited under Budapest treaty as CNCM I-3175 in the Collection Nationale de Cultures de Microorganismes (CNCM, Institut Pasteur 25 rue du docteur Roux 75724 Paris cedex 15 France) on Feb. 27, 2004.

9. SJL a deposited under Budapest treaty as CNCM I-3176 in the Collection Nationale de Cultures de Microorganismes (CNCM, Institut Pasteur 25 rue du docteur Roux 75724 Paris cedex 15 France) on Feb. 27, 2004.

10. SVG VIII-176 deposited as CNCM I-3158 in the Collection Nationale de Cultures de Microorganismes (CNCM) on Feb. 10, 2004.

In an embodiment of the present invention is a kit for amplifying DNA containing:
  an isolated thermostable polypeptide, wherein said polypeptide has at least 80% homology to residues 13-555 of SEQ ID NO: 26, wherein said polypeptide has at least one mutation at a position selected from the group consisting of M470, F472, M484, R518, and W550, more preferably selected from the group consisting of M470K, M470R, F472Y, M484V, M484T, R518G, and W550R, and wherein said polypeptide has DNA polymerase activity and 5'-3' exonuclease activity;
  a concentrated buffer solution, wherein when said concentrated buffer is admixed with the isolated polypeptide the overall buffer concentration is 1×;
  one or more divalent metal ions; and
  deoxyribonucleotides.

In this embodiment, the preferred divalent metal ion is $Mg^{2+}$. In an other embodiment, the metal ion may also be $Mn^{2+}$. In this connection, the concentration of the divalent metal ion ranges from 0.1 to 5 mM, preferably from 1 to 3 mM, more preferably from 2 to 2.5 mM. However, if the reaction is performed in a phosphate buffer, a buffer containing EDTA, or a buffer containing any other magnesium chelator, the concentration of magnesium may be increased to up to 100 mM.

For the kit of the present invention the isolated thermostable polypeptide may be in a form selected from the group consisting of a lyophilized form, a solution form in a suitable buffer or carrier, and a frozen form in a suitable buffer or carrier.

The kit of the present invention may also include a 5' to 3' exonuclease and/or a 3' to 5' exonuclease. A preferred 5' to 3' exonuclease has a sequence as in SEQ ID NO: 50 (the DNA is in SEQ ID NO: 60) and the 3' to 5' exonuclease as in SEQ ID NO: 51 (the DNA is in SEQ ID NO: 61).

With respect to the suitable buffer or carrier, the following components may be used:
Tris-HCl, KCl, Triton-X100, dimethylsulfoxide, tetramethyl ammonium chloride, etc.

In the present invention, the concentrated buffer solution corresponds to a stock solution that has a concentration ranging from 1.5× to 10×, where the concentration is measured in relation to the final reaction concentration (1×). To this end, the buffer solution (1×) contains the following components: 10 mM Tris-HCl, pH at 25° C. of 9, 50 mM KCl, 0.1% Triton-X100.

For the kit according to the present invention, the stock concentration of the deoxyribonucleotides ranges from 50 µM to 200 mM, preferably from 75 µM to 150 mM, more preferably 100 µM to 100 mM, for each dNTP. Moreover, the concentration of each dNTP in the PCR reaction according to the present invention should range from 10 µM to 500 µM, preferably from 25 µM to 400 µM, more preferably 50 µM to 300 µM. As used in the present invention, the term "deoxyribonucleotides" includes: dATP, dCTP, dGTP, and dTTP. It is to be understood that within the scope of the present invention, the kit may include in place of or in addition to the aforementioned components, RNA precursors, minor ("rare") bases, and/or labelled bases.

In another embodiment of the present invention is a method of amplifying DNA from a culture and/or purified stock solution of DNA and/or mRNA by utilizing a thermostable polypeptide according to the present invention. To this end, protocols for conducting PCR and RT-PCR would be readily appreciated by the skilled artisan. However, for sake of completeness, the artisan is directed to the following exemplary references for protocols for conducting PCR and RT-PCR (see, for example, Rougeon, F, et al.; 1975; Rougeon, F, et al., 1976; Grabko, V. I., et al., 1996; and Perler, F., et al., 1996).

With reference to reverse transcribing RNA, a preferred method includes:

a) providing a reverse transcription reaction mixture comprising said RNA, a primer, a divalent cation, and an isolated thermostable polypeptide comprising an amino acid sequence having at least 80% homology to residues 13-555 of SEQ ID NO: 26, wherein said polypeptide has at least one mutation at a position selected from the group consisting of H203, F205, T232, E253, Q257, D274, L275, I276, V309, I322, A331, L332, D333, Y334, S335, I361, R374, A384, T387, Y419, M470, F472, M484, P493, M498, G499, M502, L503, V506, R518, A523, A526, P539, E543, and W550, more preferably selected from the group consisting of: M470K, M470R, F472Y, M484V, M484T, R518G, and W550R; or H203R, F205L, T232S, E253G, Q257R, D274G, L275H, L275P, I276F, V309I, I322N, A331V, S335N, I361F, R374Q, A384T, T387A, Y419C, Y419N, E465K, M470K, M470R, F472Y, F472S, A487T, K490E, P493T, M498T, G499E, M502K, L503P, V506I, R518G, A523V, A526V, P539S, E543K, and W550R, and wherein said polypeptide has DNA polymerase activity and 5'-3' exonuclease activity in a suitable buffer; and b) treating said reaction mixture at a temperature and under conditions suitable for said isolated polypeptide to initiate synthesis of an extension product of said primer to provide a cDNA molecule complementary to said RNA.

It is to be understood that the skilled artisan would appreciate that the thermal cycling should be optimized to account for variations in the enzyme selected, the template to be reverse transcribed, the primers to be used to facilitate amplification (i.e., with respect to the melting and annealing temperatures), and the relative concentrations to be used for each of the reaction components. Such optimization is well within the purview of the skilled artisan; however, exemplary protocols may include the following:

TABLE 2

PCR protocols

|  | a | b | c | d | e | # of repeated Cycles |
|---|---|---|---|---|---|---|
| PCR 1 | 94° C., 3' | 94° C., 1' | 66° C., 1' | 72° C., 2' | 72° C., 15' | b – d = 30 |
| PCR 2 | 94° C., 3' | 94° C., 1' | 62° C., 1' | 72° C., 2' | 72° C., 15' | b – d = 30 |
| PCR 3 | 94° C., 3' | 94° C., 30" | 59° C., 30" | 72° C., 1' | 72° C., 15' | b – d = 30 |
| PCR 4 | 94° C., 3' | 94° C., 30" | 68° C., 1.5' | 68° C., 6' |  | b – c = 35 |
| PCR 5 | 94° C., 1' | 94° C., 30" | 70° C., 30" | 72° C., 1' | 72° C., 15' | b – d = 25 |
| PCR 6 | 94° C., 3' | 94° C., 30" | 59° C., 30" | 72° C., 1' | 72° C., 15' | b – d = 35 |
| PCR 7 | 94° C., 3' | 94° C., 1' | 58° C., 1' | 72° C., 2' | 72° C., 15' | b – d = 35 |

Moreover, it is to be understood that contemplated in the present invention is that with the polypeptide of the present invention the skilled artisan would appreciate that the buffer components and buffer concentrations should also be optimized. To this end, in a preferred embodiment, the kit of the present invention may be utilized.

As used above, the phrases "selected from the group consisting of," "chosen from," and the like include mixtures of the specified materials.

The term 'selection' relates to the parallel processing of a variants' catalytic activity (cf. affinity chromatography for the reaction product crosslinked to active phage-polymerase mutants allows the 'simultaneous' treatment of the population of phage-polymerase mutants). Selection can be achieved for a population of more than $10^7$ mutants as described herein, for more than $10^{10}$ variants and possibly for up to $10^{14}$ variants. A straightforward screening of several tens of variants of the selected population enriched into active enzymes is sufficient to isolate catalysts of interest.

The term 'screening' relates to the serial processing of a variants' catalytic activity (cf. serial assays ran by a robot one well after the next one). High throughput-screening is typically done for $10^4$ mutants, and generally less than $10^7$ mutants.

The advantage of selection over high throughput screening is that a much larger population of mutant proteins can be analyzed for a desired catalytic activity; provided an appropriate selection strategy is available (the one described herein is one such example).

In one embodiment of a method of obtaining a thermostable variant enzyme is provided. This method comprises the following:

a) selection of enzymes expressed at the surface of phage particles and identifying at least a thermostable variant conserving its active; catalytic domain at regulated temperature according to the method of identifying thermostable mutant polypeptides having a catalytic activity as described herein, b) isolating and sequencing a DNA encoding said identified thermostable variant;

c) preparing a vector comprising the DNA of step (b);

d) transfecting or infecting cells with the vector obtained at step c);

e) expressing the thermostable variant enzyme from the cells and optionally, f) recovering, isolating and purifying said thermostable variant enzyme expressed at step (e).

Where a numerical limit or range is stated herein, the endpoints are included. Also, all values and subranges within a numerical limit or range are specifically included as if explicitly written out.

The above written description of the invention provides a manner and process of making and using it such that any person skilled in this art is enabled to make and use the same, this enablement being provided in particular for the subject matter of the appended claims, which make up a part of the original description.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Materials and Methods

Buffers

Buffer A (1×):

50 mM Tris-HCl at pH 8.3 at 25° C., 50 mM KCl, 10 mM MgCl$_2$, 0.5 mM spermidine, 10 mM dithiothreitol Buffer B (1×):

20 mM Tris-HCl at pH 8.8 at 25° C., 10 mM KCl, 10 mM (NH$_4$)$_2$SO$_4$, 2 mM MgSO$_4$, 0.1% Triton X-100, 0.1 g/l BSA Buffer C (1×):

10 mM Tris-HCl at pH 9.0 at 25° C., 50 mM KCl, 0.1% Triton X-100

Synthesis of Substrates for Selection

Deoxyoligonucleotides were prepared by solid phase synthesis on a DNA synthesizer (Expedite™, Millipore). The 5'-maleimidyl derivatized primer TAA CAC GAC AAA GCG CAA GAT GTG GCG T (SEQ ID NO: 13) was synthesized as described previously (Jestin et al., 1999) purified on a C18 reverse phase HPLC column, and characterized by electrospray mass spectroscopy 8998.4/8999.9 (measured/calculated). 5-[-N-[N-(N-biotinyl-ε-aminocaproyl)-γ-aminobutyryl]-3-aminoallyl]-2'deoxy-uridine-5'-triphosphate (biotin-dUTP) was purchased from Sigma and the other deoxynucleotide triphosphates dATP, dCTP and dGTP were obtained from Roche-Boehringer.

Library Construction

Three phagemids libraries were mixed for phage preparation. The first two libraries (I: FseI/NotI and II: PstI/NheI) derive from mutagenic PCR amplification of the wild-type Taq gene in the presence of manganese [I: reference (Fromant, Blanquet, Plateau, 1995) with $MnCl_2$: 0.5 mM; II: reference (Cadwell, Joyce, PCR methods and amplifications, Mutagenic PCR, 3, S136-S140) with four distinct $MnCl_2$ concentrations (0.5, 0.35, 0.25 and 0.125 mM)] using following primers (I) SEQ ID NO: 1 and SEQ ID NO: 2, PCR 1, or (II) SEQ ID NO: 3 and SEQ ID NO: 4, PCR 2 (for primers: see Table 1, and for cycle settings: see Table 2).

The third phagemids library (III) was constructed by oligonucleotide assembly using the wild-type Taq gene. First, four PCR fragments were prepared using Taq polymerase (PCR 3, see Table 2), the wild-type Stoffel fragment gene as template and the following primer pairs (5-6), (7-8), (9-10) and (11-2) in buffer C 1X (for primers: see Table 1).

After purification with the QIAquick PCR Purification kit (QIAGEN), the four PCR fragments were assembled in a second PCR round using the kit GC-Advantage obtained from Clontech under PCR 4 (see Table 2), using buffer D 1X. The crude PCR product was then amplified by PCR using PCR 5 protocol, the GC-Advantage kit, and the primers 1 and 2 in buffer D 1X. Subsequently, the product was purified using the QIAquick Gel extraction gel (QIAGEN).

Buffer D 1×

40 mM Tricine-KOH (pH 9.2)

15 mM KOAc 3.5 mM $Mg(OAc)_2$

5% DMSO 3.75 μg/ml BSA 0.005% Nonidet P-40

0.005% Tween-20

After subdloning into pHENI vectors using restriction sites FseI/NotI or PstI/NheI, $1.1×10^7$ distinct clones were obtained by electroporation in *E. coli* strain TG1.

TABLE 1

Oligonuleotides and primers

| SEQ ID NO: | Oligonucleotide sequences |
|---|---|
| 1 | TAACAATAGGCCGGCCACCCCTTC |
| 2 | GAGTTTTTGTTCTGCGGC |
| 3 | TTTAATCATCTGCAGTACCGGGAGCTC |
| 4 | TTCATTCTTGCTAGCTCCTGGGAGAGGC |
| 5 | CCG GCC ACC CCT TC(C AR/A VY)C TCA AC(C AR/A VY)CGG GAC CAG CTG GAA AG |
| 6 | GGA TGA GGT CCG GCA A(YT G/RB T) (YT G/RB T)AA T(YT G/RB T)GG TGC T CT TCA GCT T(YT G/RB T)GA GCT CCC GGT ACT GCA GG |
| 7 | CAA CCA GAC GGC CAC G(CA R/AV Y)AC GGG CAG GCT A(CA R/AV Y)AG CTC C(CA R/AV Y)CC CAA CCT CCA GAA CAT CC |
| 8 | CCG CCT CCC GCA C(YT G/RB T)CT TCA C(YT G/RB T)GG CCT CTA GGT CTG GCA C |
| 9 | CCT GCA GTA CCG GGA GCT C(CA R/AV Y)AA GCT GAA GAG CAC C (CA R/AV Y)AT T(CA R/AV Y)(CA R/AV Y)TT GCC GGA CCT CAT CC |
| 10 | GGA TGT TCT GGA GGT TGG G(YTG/RBT)GG AGC T(YTG/RBT)TA GCC TGC CCG T(YTG/RBT)CG TGG CCG TCT GGT TG |
| 11 | GTG CCA GAC CTA GAG GCC (CAR/AVY) GTG AAG (CAR/AVY) GTG CGG G AG GCG G |
| 12 | AAA UAC AAC AAU AAA ACG CCA CAU CUU GCG |
| 13 | TAA CAC GAC AAA GCG CAA GAT GTG GCG T |
| 14 | AAA TAC AAC AAT AAA ACG CCA CAT CTT GCG |
| 15 | TTCATTCTTGCTAGCTCCTGGGAGAGGC |
| 16 | GAG AAG ATC CTG CAG TAC CGG GAG C |
| 17 | GACCAAC ATCAAGACTGCC |
| 18 | TTGGCCAGGAACTTGTCC |

TABLE 2

| | PCR cycles | | | | | # of repeated Cycles |
|---|---|---|---|---|---|---|
| | a | b | c | d | e | |
| PCR 1 | 94° C., 3' | 94° C., 1' | 66° C., 1' | 72° C., 2' | 72° C., 15' | b – d = 30 |
| PCR 2 | 94° C., 3' | 94° C., 1' | 62° C., 1' | 72° C., 2' | 72° C., 15' | b – d = 30 |
| PCR 3 | 94° C., 3' | 94° C., 30" | 59° C., 30" | 72° C., 1' | 72° C., 15' | b – d = 30 |
| PCR 4 | 94° C., 3' | 94° C., 30" | 68° C., 1.5' | 68° C., 6' | | b – c = 35 |
| PCR 5 | 94° C., 1' | 94° C., 30" | 70° C., 30" | 72° C., 1' | 72° C., 15' | b – d = 25 |
| PCR 6 | 94° C., 3' | 94° C., 30" | 59° C., 30" | 72° C., 1' | 72° C., 15' | b – d = 35 |
| PCR 7 | 94° C., 3' | 94° C., 1' | 58° C., 1' | 72° C., 2' | 72° C., 15' | b – d = 35 |

Phage Preparation and Selection

For phage preparation, E. coli TG1 transformed by the phagemid library and grown to an optical density of 0.3 at 600 nm were infected by a twenty-fold excess of helper phage. Phage particles were produced at 30° C. for 19 hours in a 2×TY medium containing 100 mg/l ampicillin, 25 mg/l kanamycin. After removal of bacteria by two centrifugation (4000 rpm, 4° C.), phage particles in the supernatant were purified by two precipitations in 4% polyethyleneglycol in 0.5 M NaCl, resuspended in 1 ml of PBS (25 mM $Na_2HPO_4$, 100 mM NaCl, pH 7.4), and dialyzed four times against PBS over a period of 24 hours. The pH of the final solution was raised to pH 8.

The protocol for selection was as described previously (Jestin et al., 1999), except that $10^{10}$ infectious phages particles were used after heating at 65° C. for 5 minutes and that DNA polymerization was done at 65° C. for 2 minutes.

Substrate cross-linking on phage was done by incubating the phage particles with 10 µM maleimidyl-derivatized primer, 50 µM RNA template of SEQ ID NO: 12 in the presence of 10 mM magnesium chloride at 37° C. for 2 hours and polymerization during 2 minutes at 65° C. after addition of 3 µM biotin-dUTP and 1 µM dVTP.

The reactions were blocked by addition of one volume of 0.25 M ethylene diamine tetra-acetate. The phage mixture was added to 300 µl of streptavidin-coated superparamagnetic beads (Dynabeads M-280, Dynal). After 30 minutes at room temperature, the beads were washed seven times and resuspended in 200 µl PBS.

The phage-bead mixture was incubated for 10 min at 37° C. after addition of one-tenth, in volume, of trypsin (0.1 g/l). 1.8 mL of E. coli TG1 was then added for infection during 25 min at 37° C. Bacteria were plated on 530 $cm^2$ Petri dishes (Corning) with a 2×TY medium containing ampicillin (0.1 g/1). After 12 hours at 30° C., bacteria were scraped from the plates and about $2\times10^9$ cells were used for preparation of the phage particles.

Variant Polymerases

All variant Stoffel fragment sequences appearing in the following examples correspond to residues 13-555 of SEQ ID NO: 26, which in turn correspond to residues 290-832 of SEQ ID NO: 100, which contain one or more mutations. A summary of the mutations, the sequence designator (e.g., "s," "a," "m," etc.), and the sequence identifier (i.e., SEQ ID NO) appear in the Table at the end of the Examples. Each of the variants in the following examples contain a R795G mutation (i.e., residue corresponding to 518 in the sequence of SEQ ID NO: 26); however, this mutation need not be present within the context of the present invention. In other words, the present invention embraces variants corresponding to the above in which R795 is conserved. It should be noted that the only mutation appearing in variant e is the R795G mutation, otherwise this sequence corresponds to the wild-type Stoffel fragment (residues 13-555 of SEQ ID NO: 26).

RT-polymerization and Polymerization Activity Assay Using Phage-polymerase

In the following examples, the activity of the different mutant phage-polymerases was assayed by incorporation of radiolabeled alpha $^{32}P$ dTTP.

Example 1

Polyclonal Phage-polymerases (FIG. 1)

In this example, the reverse transcriptase activity of phage-polymerases was assessed in the presence of $Mg^{2+}$ or $Mn^{2+}$ ions as obtained after different rounds of selection in the presence of $Mg^{2+}$ ions. In these experiments, two reverse transcription (RT) mixes were used. The final concentration of each component in a reaction was: 10 µM RNA (SEQ ID NO: 12); 5 µM DNA (SEQ ID NO: 13); 0.25 mM dNTP; 3 mM $MgCl_2$ or 2.5 mM $MnCl_2$.

Each 1.9 µl aliquot of the reaction mix was further added to 15 µl of phage-polymerases (about $10^8$ particles) after a given selection round heated for 5 min at 65° C. The solutions were then incubated at 37° C. for 15 min. The reactions were stopped by adding 15 µl of EDTA/formamide containing denaturation solution, heating for 3 min. at 94° C., and placed on ice. The incorporation of alpha $^{32}P$-dTTP was determined on 20% polyacrylamide gel; 15 µl of the final reaction volume were loaded.

The lane designations in FIG. 1 are as follows:

| $MnCl2$ | $MgCl_2$ |
|---|---|
| a: phage-polymerases of round 6 | h: phage-polymerases of round 6 |
| b: phage-polymerases of round 5 | i: phage-polymerases of round 5 |
| c: phage-polymerases of round 4 | j: phage-polymerases of round 4 |
| d: phage-polymerases of round 3 | k: phage-polymerases of round 3 |
| e: phage-polymerases of round 2 | l: phage-polymerases of round 2 |
| f: phage-polymerases of round 1 | m: phage-polymerases of round 1 |
| g: phage-polymerases of initial population | n: phage-polymerases of initial population |

This experiment demonstrated that:
A RT-activity is present using phage-polymerase obtained after round 5 (i) or 6 (h) of selection in presence of $Mg^{2+}$.
A high RT-activity was detected at the round 3 (d) in the presence of $Mn^{2+}$ and for further rounds.

Example 2

Polyclonal Phage-polymerases (FIG. 2)

In this example, the reverse transcriptase activity of phage-polymerases was assessed as obtained after different rounds of selection in the presence of $Mg^{2+}$ ions. In these experiments, a reverse transcription (RT) mix was used. The final concentration of each component in a reaction was: 10 µM RNA (SEQ ID NO: 12); 5 µM DNA (SEQ ID NO: 13); 0.25 mM dNTP; 3 mM $MgCl_2$.

Each 1.2 µl aliquot of the reaction mix was further mixed with 15 µl of phage-polymerase polymerases (about $10^8$ particles) after one round of selection round, either not preheated or heated 5 min at 65° C. before reaction of polymerization. The solutions were then incubated at 37° C. for 15 min. The reactions were stopped by adding 15 µl of the denaturation solution, heating for 3 min. at 94° C. and placing on ice.

The incorporation of alpha $^{32}P$-dTTP was determined on 20% polyacrylamide gel; 15 µl of the final reaction volume were loaded. The positive control was performed with addition of different concentration of commercial AMV reverse transcriptase (Promega).

The lane designations in FIG. 2 are as follows:

| Phage-porymerase preheated at 65° C. for 5 min. | Phage-polymerase not preheated |
|---|---|
| a: phage-polymerases of initial population | h: phage-polymerases of initial population |
| b: phage-polymerases of round 1 | i: phage-polymerases of round 1 |
| c: phage-polymerases of round 2 | j: phage-polymerases of round 2 |
| d: phage-polymerases of round 3 | k: phage-polymerases of round 3 |
| e: phage-polymerases of round 4 | l: phage-polymerases of round 4 |

| Phage-porymerase preheated at 65° C. for 5 min. | Phage-polymerase not preheated |
|---|---|
| f: phage-polymerases of round 5<br>g: phage-polymerases of round 6 | m: phage-polymerases of round 5<br>n: phage-polymerases of round 6<br>o: control AMV-RT, 1 U<br>p: control AMV-RT, 0.1 U<br>q: control AMV-RT, 0.01 U<br>r: control AMV-RT, 0.001 U |

This experiment demonstrated that:

A RT-activity is present using phage-polymerase obtained after round 5 or 6 of selection preheated for 5 min. at 65° C. (f and g) or not (m and n) as in FIG. 1 in presence of $Mg^{2+}$.

A high RT-activity was detected using 1 unit of AMV-RT (o) but no activity was detected using decreasing concentration of AMV-RT.

Example 3

Monoclonal Phage-polymerases (FIG. 3)

In this example, the reverse transcriptase activity of various monoclonal phage-polymerases obtained after round 6 in the presence of $Mg^{2+}$ ions was assessed. In these experiments, a reverse transcription (RT) mix was prepared in which the final concentration of each component in a reaction was: 10 µM RNA (SEQ ID NO: 12); 5 µM DNA (SEQ ID NO: 13); 0.25 mM dNTP; 3 mM $MgCl_2$.

Each 1.45 µl aliquot of the reaction mix was further mixed with 15 µl of phage-polymerase heated for 5 min at 65° C. The solutions were then incubated at 37° C. for 20 min. The reactions were stopped by adding 15 µl of denaturation solution, heating for 3 min. at 94° C., and placed on ice.

The incorporation of alpha $^{32}$P-dTTP was determined on a 20% polyacrylamide gel; 15 µl of the final reaction volume were loaded. The positive control was performed using the AMV-RT (Promega), lane C.

The different monoclonal phage-polymerases were obtained among the phage-polymerases of round 6. The phage-polymerases present various DNA-polymerase RNA-dependant activities. The lane designations in FIG. 3 are as follows: s=SEQ ID NO: 38; a=SEQ ID NO: 20; d=SEQ ID NO: 24; g=SEQ ID NO: 28; C=AMV-RT; i=SEQ ID NO: 30; m=SEQ ID NO: 32; n=SEQ ID NO: 34; b=SEQ ID NO: 22; and q=SEQ ID NO: NO: 36.

The clones a, b, and d possess a high RT-activity, which were further studied as reported in FIG. 4. Randomly chosen clones from the selected populations were assayed for monoclonal phage-polymerase reverse transcriptase activity and that further sequencing of the corresponding mutant genes revealed identical sequences (for example, 7 clones reported in the figure were found to have the same sequence noted a).

Example 4

Monoclonal Phage-polymerases (FIG. 4)

In this example, the reverse transcriptase and the polymerase activities of monoclonal phage-polymerases obtained after the round 6 in the presence of $Mg^{2+}$ or $Mn^{2+}$ ions was assessed. In these experiments, the final concentration of each component in a reaction was:

10 µM RNA (SEQ ID NO: 12); 5 µM DNA (SEQ ID NO: 13); 0.25 mM dNTP; 3 mM $MgCl_2$ or 2.5 mM $MnCl_2$; and 1 µM DNA (SEQ ID NO: 14); 1 µM DNA (SEQ ID NO: 13); 0.25 mM dNTP; 3 mM $MgCl_2$ or 2.5 mM $MnCl_2$;

2 µl aliquots of the reaction mix were further added to 15 µl of each phage-polymerase pre-heated for 5 min at 65° C. The solutions were then incubated at 37° C. for 15 min. The reactions were stopped by adding 15 µl of denaturation solution, heating 3 min. at 94° C., and placed on ice.

The incorporation of alpha $^{32}$P-dTTP was determined on polyacrylamide gel; 15 µl of the final reaction volume were loaded. The positive control was performed using the phage Stoffel fragment (e).

The lane designations in FIG. 4 are as follows: a=SEQ ID NO: 20; b=SEQ ID NO: 22; d=SEQ ID NO: 24; and e=SEQ ID NO: 26 (containing an R518G mutation).

Three families of phage polymerase were characterized among the phage-polymerases of round 6.

The phage-polymerases a and b present a high DNA-polymerase DNA-dependent activity, which is higher than that of Stoffel phage-polymerase.

The phage-polymerases b and d present a high DNA-polymerase RNA-dependent activity, which is higher than that of the Stoffel phage-polymerase e (not detectable, see FIG. 4) or than the phage-polymerase a, whatever the conditions in the presence of magnesium or of manganese.

The phage-polymerase d shows a poor DNA-polymerase DNA-dependent activity, which is lower than the activity of the Stoffel phage-polymerase.

Construction and Overproducing Clones

Three phagemids corresponding to clones a, b and d on FIG. 4 were isolated from individual colonies of *E. coli* strain TG1. The plasmid DNA was prepared and purified using Wizard Plus miniprep kits. The phagemids were cleaved with NcoI and NotI restriction endonucleases and the fragments ligated into an expression vector deriving from pET-28b(+) (Novagen) that had been cleaved with NcoI and NotI and dephosphorylated with alkaline phosphatase. This pET vector contains a sequence for the thrombin cleavage site between the NotI and XhoI restriction sites of pET 28b(+) (GCGGCCGCACTGGTGCCGCGCGGCAGCCTCGAG; SEQ ID NO: 45).

Recombinant plasmids were transformed in *E. coli* strain BL21(DE3) pLysS and plated on 2YT media with kanamycin and chloramphenicol. Correct plasmid constructions were initially identified by restriction analysis of plasmid miniprep.

*E. coli* strain BL21(DE3) pLysS, used as a host for recombinant plasmids to over produce the mutant polymerase, was grown in 2YT medium supplemented with 10 µg/ml kanamycin and 25 µg/ml chloramphenicol to propagate plasmids. At an optical density of 0.6 at 600 nm, 1 mM of isopropyl-1-thio-β-D-galactopyranoside (IPTG) was added to induce production of enzyme for 5 hours.

Purification of Mutant Polymerases

Mutants were prepared from 500 ml batches of cells. 2YT media plus kanamycin and chloramphenicol was inoculated with bacteria (containing a recombinant plasmid) freshly picked on a plate and grown at 37 ° C. to an absorbance at 600 nm of approximately 0.5. Subsequently, IPTG was added to a final concentration of 1 mM and the cultures were allowed to further grow for 5 h.

Cells were harvested by centrifugation at 15000 g and 4° C. for 10 min., resuspended in 30 ml of lysis buffer (50 mM $Na_2HPO_4$, 300 mM NaCl, 5 mM imidazole, pH=8), lysed 3 times for 45 sec by ultrasound. Cell debris were removed by centrifugation at 10000 g and 4° C. for 15 min.

Mutant polymerases were recovered from this clarified lysate and purified using Ni-NTA agarose (QIAGEN).

Example 5

Purified Mutant Polymerases a, b, and d Used in RT-polymerase Chain Reaction (FIG. 5)

The positive control was performed using the polymerase AMV-RT (Promega). These studies were performed using the three clones corresponding on clones a, b and d in FIG. 4.

The reverse transcription was performed at 65° C. during 1 h using the following conditions.

| Control RT mix | |
| --- | --- |
| Component | Amount |
| RNA from rabbit globin (sigma), 20 µg/ml | 1 µl |
| primer 17 (5 µM) | 0.4 µl |
| primer 18 (5 µM) | 0.4 µl |
| buffer A (**)AMV-RT 5× | 3 µl |
| dNTP 2.5 mM | 0.8 µl |
| AMV-RT 10 U/µl | 3 µl |
| water | 6.4 µl |

(**) See buffer A composition above

| RT mix | |
| --- | --- |
| Component | Amount |
| RNA from rabbit globin (sigma), 20 (µg/ml | 1 µl |
| primer 17 (5 µM) | 0.4 µl |
| primer 18 (5 µM) | 0.4 µl |
| MgCl$_2$ 25 mM | 0.75 |
| buffer C (***) | 1.5 µl |
| dNTP 2.5 mM | 0.8 µl |
| mutant polymerase a, b, d or the Stoffel fragment e | 3 µl |
| water | 7.15 µl |

(***) See buffer C composition above

The PCR was performed using PCR 7 (see table 2) and following conditions.

| PCR mix | |
| --- | --- |
| Component | Amount |
| Buffer B 10× | 20 µl |
| primer 17 (50 µM) | 4 µl |
| primer 18 (50 µM) | 4 µl |
| dNTP | 2 µl |
| water | 164.5 µl |
| Taq DNA polymerase (5 U/µl) | 5 µl |
| Pfu polymerase (3 U/µl) | 0.5 µl |

19 µl aliquot of the PCR mix was added to 1 µl of the RT reaction product.

A RT-PCR product of 372 bp was detectable using mutant polymerases b and d.

The lanes in the gel appearing in FIG. 5 include the three clones corresponding to clones a, b and d on FIG. 4. In addition, the positive control was performed using the Stoffel fragment polymerase e and the commercial AMV-RT (Promega). The lanes in FIG. 5 are as follows:

lane 1: molecular weight marker: PhiX phage DNA digested by HaeIII.
lane 2: control AMV-RT
lane 3: b=SEQ ID NO: 22
lane 4: a=SEQ ID NO: 20
lane 5: e=SEQ ID NO: 26 (containing an R518G mutation)
lane 6: d=SEQ ID NO: 24

Example 6

Optimization of the production and of the purification of the polymerases

Variant polymerases were expressed in *Escherichia coli* strain BL21(DE3) pLysS using a pET vector. The inventors improved the yield and the reproducibility of production of these proteins by (a) a chemical lysis of the cells and (b) a pre-purification by heating at 80° C. for 10 or 15 minutes (denaturation, elimination by precipitation and centrifugation of the proteins thermically unstable).

The optimization of the two steps (a) and (b) allows a more effective purification of variants by chromatography.

After affinity chromatography by using the six histidine tag, inventors obtained, starting from about 1.2 to 1.6 liters of culture, until about 0.1 to 0.3 mg of protein of purity, estimated on polyacrylamide gel, comprised between 80% and 90% Further purification steps were done prior to kinetic studies (see Example 10).

Protocol of Production and Purification of Proteins:
Production of Variants d, b, a and e.
  Electroporation of 50 µl of electro-competent cells BL21 (DE3) pLysS by the expression pET plasmid containing mutated or wild-type genes (e, fragment of Stoffel of the Taq polymerase) coding for the proteins polymerases to be produced.
  Incubation 1 hour at 37° C. in 3 ml of 2YT medium under agitation.
  Spreading out with beads of 100 and 200 µl per Petri dish containing 2YT agarose with kanamycin (10 µg/ml) and chloramphenicol (30 µg/ml).
  Incubation at 37° C. for 16 hours.
  The colonies are recovered and suspended in 400 ml of 2YT medium with kanamycin (10 µg/ml) and chloramphenicol (30 µg/ml).
  Incubation at 37° C. of the culture until the OD at 600 nm is about 0.6.
  Induction of the expression of the proteins by addition of IPTG (1 mM final concentration).
  Incubation about 16 hours at 37° C. under agitation.
  Centrifugation of the cultures at 8000 rpm, 10 min., 4° C.
Purification
  The pellets were treated by 45 ml of BugBuster (BugBuster Protein Extraction Reagent-NOVAGEN, Ref. 70584).
  Incubation at room temperature under agitation 20-40 min.
  Centrifugation at 10000 rpm, 10 min., 21° C.
  Supernatants were recovered and treated 10 min. at 80° C. under agitation prior to coiling at 4° C.
  Centrifugation at 10000 rpm, 10 min., 4° C.
Capture of the Proteins by Affinity Chromatography for the His Tag
  The Talon Metal Affinity Resin (2 ml., Clontech) was washed twice with the buffer BBW (50 mM sodium phosphates, 300 mM NaCl, pH=7) prior to incubation for 30 minutes at 4° C. with the supernatant.
  After three washing steps with the BBW buffer (20 ml.), the proteins were eluted from the resin.
Elution
  Add to each resin pellet to be eluted, 2 ml of 1× Elution Buffer: hnidazole Elution (pH7, 50 mM Sodium Phosphates, 300 mM NaCl, 150 mM imidazole).

FRACTION 1: Homogenize 10 min. with at cold temperature and centrifuge 700 g, 3 min., 4° C. Recover the supernatant (2 ml). Add 2 ml 1× Elution Buffer, Homogenize 5 min.

FRACTION 2: Centrifuge 700 g, 3min., 4° C. Recover supernatant (2ml). Add 2 ml 1× Elution Buffer, Homogenize 5 min.

FRACTION 3: Centrifuge 700 g, 3 min., 4° C. Recover supernatant (2ml).

Preserve an aliquot of some µl of each fraction, at 4° C., for its migration on 10% Acrylamide Gel.

Concentration and Elimination of Proteins of Small Molecular Weight

Pool the three fractions=4-5 ml and chromatography them on Ultra-4 column AMICON, 50000NMWL, (Amicon Ultra centrifugal filter devices with low-binding Ultracel membrane—MILLIPORE, Ref. UFC8 050 24).

Centrifuge 15 min., 3000 g, 25° C.

Washing and/or change buffer by addition to the column of 4 ml of 100 mM Tris pH 8 buffer.

Centrifuge 15 min., 3000 g, 25° C.

Obtaining of 30 µl of each purified and concentrated protein.

Addition of 270 µl of storage buffer [50 mM Tris HCl pH8; 100 mM NaCl; 0,1 mM EDTA; 1 mM DTT] (final volume=300 µl)

The concentrated and purified proteins are stored at 4° C.

The purity and the concentration of the purified polymerases are evaluated by SDS PAGE.

Protein dosage is carried out on 1/10 diluted samples in Tris 100 mM pH 8 buffer, with the BioPhotometer 6131 (Eppendorf)

Purification Control

Polyacrylamide gels were stained with Coomassie Blue (see FIGS. 6 and 7);

M is the SDS PAGE molecular weight standards. Low Range (BIO-RAD, Ref. 161-0304). Bands at 97.4 kDa; 66.2 kDa; 45 kDa; 31 kDa; 21 kDa and 14.4 kDa.

Catalytic Properties of the Polymerases:

Example 7

Primer Extension

The three variants of interest (proteins with the histidine tag) were used in a primer extension assay using radiolabelled primers. These variants have a strong DNA-dependent DNA-polymerase activity at 65° C. For two of them (b and a) this activity was almost the same as that of the fragment of Stoffel (e) produced and purified under the same conditions (see FIG. 8: Gel 1).

On the other hand, reverse transcriptase activity detected at 65° C. for both variants d and b (respectively a) is much higher than the reverse transcriptase activity obtained in the presence of magnesium for the fragment e (see FIG. 8: Gel 2).

The present inventors also checked the thermal stability of these variants. The DNA-dependent DNA-polymerase activity was maintained after an incubation of proteins 45 min. at 65° C. This maintenance of the catalytic activity DNA-dependent DNA-polymerase on variants was necessary for the design of a protocol of "RT-PCR one-pot".

The inventors confirm that the method of the present invention should allow the acquisition of polymerase variants having the catalytic activities required for such of "RT-PCR one-pot" protocol. One embodiment is given in Example 9.

Products of Primer Extension with Polymerases e, a, d and b:

DNA polymerases e, a, b and d were prepared and further purified using the six-histidines tag as described in the paragraph before Example 6.

Materials:

A mixture consisting of 1 µl of variant histidine tagged enzymes e (960 mg/l), a (870 mg/l), b (910 mg/l) and d (510 mg/l), template (the oligoribonucleotide of SEQ ID NO: 12 or the deoxyribonucleotide of SEQ ID NO: 14), DNA primer 13 (SEQ ID NO: 13), 0.25 mM dNTP, 3 mM MgCl$_2$ in buffer B 1× was incubated at 65° C. for 5 minutes. After denaturation at 94° C., the samples were loaded on a 20% polyacrylamide gel for electrophoresis.

Method:

GEL 1: 1 µl of the concentrated fraction of each variant is added to 15 µl of the reaction mixture [0.5 µM DNA template (AAATACAACAATAAAACGCCACATCTTGCG; SEQ ID NO 14); 0.5 µM DNA (TAACACGACAAAGCGCAAGATGTGGCGT; SEQ ID NO: 13); 0.25 mM dNTP; 3 mM MgCl$_2$; 1× buffer C].

Polymerization is carried out at 65° C. during 5 min.

The reaction is stopped by addition of 15 µl of solution of denaturation, heated at 94° C. and then placed at 4° C.

15 µl of each sample are deposited onto the gel.

GEL 2: 1 µl of the concentrated fraction of each variant is added to 15 µl of the reaction mixture [10 µM RNA (AAAUACAACAAUAAAACGCCACAUCUUGCG; SEQ ID NO: 12); 5 µM DNA (TAACACGACAAAGCGCAAGATGTGGCGT; SEQ ID NO: 13); 0.25 mM dNTP; 3 mM MgCl$_2$; 1× buffer C].

Polymerization is carried out at 65° C. during 5 min.

The reaction is stopped by addition of 15 µl of solution of denaturation, heated at 94° C. and then is placed at 4° C.

15 µl of each sample are deposited on each gel.

The results for gels 1 and 2 are shown in FIG. 8.

Example 8

Optimization of PCR:

The present inventors have developed a PCR protocol for the amplification of DNA fragments. The hybridization of the primers to the template and the polymerization are carried out at 65° C. The PCR reaction of a DNA template by variants a and e were tested. Materials and methods are described below and results are shown in FIG. 9.

Furthermore, the PCR reaction of a DNA template by variant a, for which kinetic analysis was made, was tested on two different thermocyclers (MJ Research and Applied Biosystems), the results obtained with these machines are comparable for the amplification of a fragment of about 450 bp (see FIG. 9). This result was extended to the amplification of a fragment of about 1560 bp (see FIG. 10).

Briefly, the catalytic properties of variant a evaluated by PCR are very similar to those of the Stoffel fragment of the Taq polymerase (e).

Products of PCR with polymerase e and variant a (FIG. 9):

PCR Reaction Mixture (for 20 µl)

| | |
|---|---|
| Variants a and e (purified and diluted 1/10 in Tris 100 mM) | 1.5 µl |
| Thermophilic DNA Polymerase 10× buffer, Magnesium Free, Promega | 2 µl |
| Primer 1 fwd (100 µM) | 0.125 µl |
| Primer 2 rev (100 µM) | 0.125 µl |
| dNTP at 25 mM | 0.2 µl |
| DNA template (pGL2-luciferase, 10 ng) | 1 µl |

-continued

| MgCl$_2$ (25 mM) | 1 µl |
| H$_2$O | 9.05 ml |

Temperature Cycle on PTC-100 (MJ RESEARCH)
94° C., 1 min.; [94° C., 20 sec; 65° C., 4 min]$_{40\ cycles}$; 65° C., 15 min.
Sequences of the Primers

```
Primer 1 fwd:
GGA TGG AAC CGC TGG AGA GCA ACT G    (SEQ ID NO: 101)

Primer 2 rev:
GAT CTC TCT GAT TTT TCT TGC GTC G    (SEQ ID NO: 102)
```

In a 20 µl reaction volume, 1.5, µl of polymerases e (960 mg/l) or a (870 mg/l) were mixed with 10 ng of template (plasmid pGL2-luciferase, Promega), 0.6 µM primer 111 (GGA TGG AAC CGC TGG AGA GCA ACT G; SEQ ID NO: 101), 0.6 µM primer 112 (GAT CTC TCT GAT TTT TCT TGC GTC G; SEQ ID NO: 102)), 0.25 mM dNTP, 2.5 mM MgCl$_2$ in buffer B 1× prior to incubation at the following temperature/time steps (94° C./1 min.) (94° C./20 sec; 65° C./4 min)$_{40}$ cycles (65° C./15 min.) on a PTC100 thermocycler (MJ Research) to yield an about 1560 bp long PCR product as shown on the figure representing the agarose gel after electrophoresis. M is the marker Smartladder (Eurogentec).
Variant a: Obtaining a Fragment of 475 bp (FIG. 10)
Reaction mixture for PCR (for 20 µl of reaction)

| Variant a | 1.5 µl |
| Thermophilic DNA Polymerase 10× buffer, Magnesium Free, Promega | 2 µl |
| Primer 1 Fwd (50 µM) | 0.5 µl |
| Primer 2 Rev (50 µM) | 0.5 µl |
| dNTP set (25 mM) | 0.2 µl |
| MgCl$_2$ (25 mM) | 1 µl |
| DNA template (pHEN1-Taq, about 10 ng) | 1 µl |
| H$_2$O | 13.3 µl |

Temperature cycles on PTC-100 (MJ RESEARCH)
94° C., 1 min.; [94° C., 20 s; 65° C., 4 min]35 cycles; 65° C., 15 min.
Temperature cycles on GeneAmp PCR System-9700 (Applied BioSystems)
94° C., 1 min.; [94° C., 20 s; 66, 5° C., 4 min]40 cycles; 65° C., 15 min.
Sequences of the Primers

```
                                     (SEQ ID NO: 16)
Primer 1 fwd: GAG AAG ATC CTG CAG TAC CGG GAG C (SEQ ID NO: 4)
Primer 2 rev: TTC ATT CTT GCT AGC TCC TGG GAG AGG C
```

RT-PCR
Subsequent to optimisation of the temperature cycles, the buffer and the additives used, the present inventors realized a reaction of "RT-PCR one-pot" with variant a without addition of reagents after the beginning of the reaction (Example 9 and FIG. 11). This result was been reproduced for two distinct buffers containing magnesium ions (without manganese ions) on two different thermocyclers with the same batch from RNA (rabbit globin mRNA, Sigma R1253) and the same batch of variant a.

The present inventors tested this RNA in a "RT-PCR one-pot" reaction using the commercial kit of Applied Biosystems (GeneAmp AccuRT RNA PCR). The RNA is amplified in the form of a slightly visible band.

Example 9

RT-PCR "One Pot" (FIG. 11)

Reaction mixture of RT-PCR "one-pot" (or 25 µl of reaction)

| Variant a | 1 µl ( column 5); 0.5 (column 4) |
| Thermophilic DNA Polymerase 10× buffer, Magnesium Free, Promega | 2.5 µl |
| Primer 1 fwd (50 µM) | 0.25 µl |
| Primer 2 rev (50 µM) | 0.25 µl |
| dNTP set (25 mM) | 0.25 µl |
| MgCl$_2$ (25 mM) | 0.75 µl |
| mRNA globin SIGMA (20 ng/µl) | 0.25 µl |
| Adjuvant 1 | 1 µl |
| Adjuvant 2 | 0.4 µl |
| H$_2$O | 18.35 µl |

Cycle Temperature on PTC-100 (MJ RESEARCH)
94° C., 15 s.; 65° C., 45 min.; [94° C., 20 s; 65° C., 4 min]$_{32\ cycles}$; 65° C., 15 min.
Sequences of the Primers:

```
Primer 1 fwd:
TTG GCC AGG AAC TTG TCC       (SEQ ID NO: 18)

Primer 2 rev:
GAC CAA CAT CAA GAC TGC C     (SEQ ID NO: 17)
```

Amplification product=372 bp.
In a 25 µl reaction volume, 0.5 or 1 ml of purified and six histidines-tagged polymerase a (117 mg/l) were mixed with 5 ng of template (rabbit globin messenger RNA, Sigma), 0.5 µM primer 113 (GAC CAA CAT CAA GAC TGC C; SEQ ID NO: 17), 0.5 µM primer 114 (TTG GCC AGG AAC TTG TCC (SEQ ID NO: 18), 0.25 mM dNTP in a manganese-free buffer B 1× containing 1.25 mM MgCl$_2$, 1 mg acetamide and 8 µM tetramethyl ammonium chloride, prior to incubation at the following temperature/time steps (94° C./15 s; 65° C./45 min.)(94° C./30 s; 65° C./4 min)$_{32\ cycles}$ (65° C., 15 min.) on a thermocycler (Biometra) to yield an about 372 bp long PCR product as shown in FIG. 11 representing the agarose gel after electrophoresis. M is the marker of phage PhiX DNA digested by the restriction enzyme HaeIII.

Example 10

Kinetic Parameters for Variant a

For evaluation of the kinetic parameters, polymerase a after purification by affinity chromatography for the histidine tag was cleaved at 23° C. by the protease thrombin for release of the tag and further purified on a heparin column (Pharmacia) prior to characterisation by SELDI TOF mass spectrometry. Remaining His-tagged polymerases were finally removed by incubation with Co$^{2+}$ resin (Talon Metal Affinity resin).

| $k_{cat}$ | $0.1\ s^{-1}$ |
| $K_m$(dNTP) | $3.10^{-5}\ mol\ l^{-1}$ |
| $k_{cat}/K_m$(dNTP) | $3.10^3\ l \cdot mol^{-1} \cdot s^{-1}$ | for the RNA templates (AAG CCU ACG ACU CCG AAC UGA CCG UGC UAC CAA U; SEQ ID NO: 103), (AAG CCU ACU ACU CCG AAC UGA CCG UGC UAC CAA U; SEQ ID NO: 104), (AAG CCU ACA ACU CCG AAC UGA CCG UGC UAC CAA U; SEQ ID NO: 105) and for the primer DNA (A TTG GTA GCA CGG TCA GTT CGG AGT; SEQ ID NO: 106) and for dNTPs (N=A, C or T).

The catalytic efficiency for RNA-dependent DNA-polymerisation measured as $k_{cat}/K_m$(dNTP) is about ten fold higher for variant a than variant e.

Example 11

Identification of New Variants 96 clones were isolated starting from the population selected from phage-polymerases after the sixth cycle from evolution directed towards the reverse transcriptase activity. 91 genes coding for the variant of polymerase were sequenced and characterized. 19 additional and distinct sequences to those described in the examples above, labelled "rtX" appearing in the table below, were identified. The corresponding phages-polymerases were prepared as previously described. The catalytic activities of the phage-polymerases were controlled by primer extension by using radio-labelled primers. In these assays for phage-polynierases, some variants have a whole DNA-dependent—DNA-polymerase activity at 65° C. In these assays, some variants seem to have a very strong RNA-dependent DNA-polymerase activity at 65° C. The results for this study are shown in FIG. 12.

These results will enable the inventors to establish a link between the sequence and the catalytic activity of the phages-polymerases selected. These data support a utility in "RT-PCR one-pot".

Summary of the Taq Sequence Variants Above

In the N-terminus of the purified proteins, the signal sequence appearing in SEQ ID NOs: 19-38 polynucleotide sequence—odd nunmbered sequences, protein sequence—even numbered sequences) is not taken in account, i.e., the peptide having the sequence MASG$_4$CG$_4$ (SEQ ID NO: 39), which has been introduced upstream of the sequence SPKA (amino acids 13-16 of SEQ ID NO: 26). The latter sequence corresponds to the Stoffel fragment beginning (S being the amino acid occupying the position number 290 in the Taq polymerase sequence).

In the C-terminus of the purified proteins, the sequence AAALVPRGSLEH$_6$ (SEQ ID NO: 40) comprising a site of cleavage by thrombin appearing in SEQ ID NOs: 19-38 (polynucleotide sequence—odd numbered sequences, protein sequence—even numbered sequences), as well as a polyhistidine tag that was introduced to facilitate further purification of the protein are also not taken into account or are not essential for the sequences of the present invention.

Further, the C-terminal alanine dipeptide appearing in SEQ ID NOs: 62-99 (polynucleotide sequence—even numbered sequences, protein sequence—odd numbered sequences) can similarly be removed to obtain the sequences of the present invention.

Clearly, the present invention contemplates and embraces sequences that have been modified to contain one or more of the following: a N-terminal leader/signal sequence, an N-terminal fusion, the remainder of the N-terminal region (residues 1-200) of the Taq polymerase wild-type sequence SEQ ID NO: 100, a C-terminal cap resulting from protease cleavage (e.g., thrombin), a C-terminal fusion, a C-terminal purification tag, etc.

In a particularly preferred embodiment of the preseint invention are the following variants of the Taq polymerase. More particularly preferred are the variants represented by residues 13-555 of SEQ ID NOs: 20, 22, 24, 28, 30, 32, 34, 36, and 38, and the variants represented by residues 1-543 of SEQ ID NOs: 62, 64, 66, 68, 70, 72, 74, 76, 78, 80, 82, 84, 86, 88, 90, 92, 94, 96, and 98.

| Mutations assessment[1,2] | sequence | SEQ ID NO: |
|---|---|---|
| M761V | "s" | 38 |
| M761T, D547G, I584V | "a" | 20 |
| W827R | "m" | 32 |
| W827R, E520G, A608T | "b" | 22 |
| W827R, A517V, T664S, F769S | "g" | 28 |
| M747K, Q698L, P816L | "n" | 34 |
| M747R, W604R, S612N, V730L, R736Q, S739N, N483Q, S486Q, T539N, Y545Q, D547T, P548Q, A570Q, D578Q, A597T | "d" | 24 |
| F749Y, A568V | "i" | 30 |
| F749Y, P550Q, R556S, V740E, V819A | "q" | 36 |
| Stoffel Fragment (e)[3] | "e" | 26 |
| E530G, Y696C, A803V | "rt1" | 63 |
| H480R, W827R | "rt2" | 65 |
| V586I, I638F, M747K, G776E | "rt3" | 67 |
| T509S, L552H, M779K | "rt16" | 69 |
| Q534R, A764T | "rt18" | 71 |
| F482L, T664A, F749Y, P770T, M775T | "rt25" | 73 |
| L552P, A661T, A800V, E820K | "rt26" | 75 |
| I553F, A608V, F749S | "rt28" | 77 |
| E742K, M747K | "rt30" | 79 |
| M747R | "rt31" | 81 |
| A608V | "rt33" | 83 |
| R651Q | "rt36" | 85 |
| M747K | "rt43" | 87 |
| Y696N | "rt59" | 89 |
| Y696C | "rt64" | 91 |
| I599N, L780P, E820K | "rt70" | 93 |
| Y696C, K767E | "rt78" | 95 |
| D551G,V783I | "rt80" | 97 |
| S612N, P816S | "rt86" | 99 |

[1]Amino acid numbers correspond to position in the Taq polymerase wild-type sequence SEQ ID NO: 100.
[2]All sequences contain a R795G mutation (i.e., residue corresponding to 518 in the sequence of SEQ ID NO: 26); however, this mutation need not be present within the context of the present invention. In other words, the present invention embraces variants corresponding to the above in which R795 is conserved.
[3]Wild-type Stoffel fragment (residues 13-555 of SEQ ID NO: 26) listed for reference purposes; however, as stated herein above, variant e also contains a R795G mutation, which is not reflected in SEQ ID NO: 26 appearing in the Sequence Listing.

Numerous modifications and variations on the present invention are possible in light of the above teachings. It is, therefore, to be understood that within the scope of the accompanying claims, the invention may be practiced otherwise than as specifically described herein.

REFERENCES

1. Bothmann, H. and Plückthun, A. (1998) Selection for a periplasmic factor improving phage display and functional periplasmic expression. *Nat. Biotech.* 16, 376-380.

2. Jestin, J. L., Volioti, G. and Winter, G. (2001) Improving the display of proteins on filamentous phage. *Res. Microbiol.* 152, 187-191.

3. Holland, M. M., Leib, T. K., and Gerlt, J. A. (1988) Isolation and characterization of a small catalytic domain released from the adenylate cyclase from *Escherichia coli* by digestion with trypsin. *J. Biol. Chem.* 263, 14661-14668.

4. Ladant, D., Glaser, P., and Ullmann, A. (1992) Insertional mutagenesis of Bordetella pertussis adenylate cyclase. *J. Biol. Chem.* 267, 2244-2250.

5. Hoogenboom, H. R., Griffiths, A. D., Johnson, K. S., et al. (1991) Multi-subunit proteins on the surface of filamentous phage: methodologies for displaying antibody Fab heavy and light chains. *Nucl. Acids Res.* 19, 4133-4137.

6. Kristensen, P. and Winter, G. (1998) Proteolytic selection for protein folding using filamentous bacteriophages. *Fold. Design* 3, 321-328.

7. Lei, S. P., Lin, H. C., Wang, S. S., Callaway, J., et al. (1987) Characterization of the *Erwinia carotovora* pelB gene and its product pectate lyase. *J. Bacteriol.* 169, 4379-4383.

8. Tesar, M., Beckmann, C., Rottgen, P., et al. (1995) Monoclonal antibody against pIII of filamentous phage: an immunological tool to study pIII fusion protein expression in phage display systems. *Immunotechnology* 1, 53-64.

9. Pedersen, H., Hölder, S., Sutherlin, D. P., et al. (1998) A method for directed evolution and functional cloning of enzymes. *Proc. Natl. Acad. Sci. USA* 95, 10523-10528.

10. Jestin, J. L., Kristensen, P., and Winter, G. (1999) A method for the selection of catalytic activity using phage display and proximity coupling. *Angew. Chem. Int. Ed.* 38, 1124-1127.

11. Dematris, S., Huber, A., et al. (1999) A strategy for the isolation of catalytic activities from repertoires of enzymes displayed on phage. *J. Mol. Biol.* 286, 617-633.

12. Heinis, C., Huber, A. et al. (2001) Selection of catalytically active biotin ligase and trypsin mutants by phage display. *Protein Eng.* 14, 1043-1052.

13. Atwell, S. and Wells, J. A. (1999) Selection for improved subtiligases by phage display. *Proc. Natl. Acad. Sci. USA* 96, 9497-9502.

14. Ponsard, I., Galleni, M., Soumillion, P., Fastrez, J., Selection of metalloenzymes by catalytic activity using phage display and catalytic elution. *Chembiochem.* 2, 253-259.

15. Lawyer, F. C., Stoffel, S., Saiki, R. K., et al. (1989) Isolation, characterisation and expression in *E. coli* of the DNA polymerase gene from *Thermus aquaticus*. *J. Biol. Chem.* 264, 6427-6437.

16. Marks et al., (1992) Molecular evolution of proteins on filamentous phage, Mimicking the strategy of the immune system. *J. Biol. Chem.* 267, 16007-16010.

17. Vichier-Gurre & Jestin, (2003) Iterative cycles of in vitro protein selection for DNA polymerase activity, *Biocat. & Biotransf.* 21, 75-78.

18. Fastrez et al., (2002) Investigation of phage display for the directed evolution of enzymes," In: Brackmann, S. and Johnsson, K. eds., *Directed Molecular Evolution of Proteins* (Wiley VCH, Weinheim), pp 79-110

19. Grütter M. G., *J. Mol. Biol.*, 2002, 318, 135-147.

20. Ting et al. (2001) Phage-display evolution of tyrosine kinases with altered nucleotide specificity. *Biopol.* 60, 220-228.

21. Xia et al. (2002) Directed evolution of novel polymerase activities: mutation of a DNA polymerase into an efficient RNA polymerase. *Proc. Natl. Acad. Sci. USA* 99, 6597-6602.

22. Rougeon, F., Kourilsky, P., Mach, B. Insertion of a rabbit beta-globin gene sequence into an *E.coli* plasmid *Nucl. Acids Res.*, 1975, 2, 2365-2378.

23. Rougeon, F., Mach, B. Stepwise biosynthesis in vitro of globin genes from globin mRNA by DNA polymerase of avian myeloblastosis virus *Proc. Natl. Acad. Sci. USA,* 1976, 73, 3418-3422.

24. Grabko, V. I., Chistyakova, L. G., Lyapustin, V. N., Korobko, V. G., Miroshnikov, A. I., Reverse transcription, amplification and sequencing of poliovirus RNA by Taq DNA polymerase *FEBS Letters,* 1996, 387, 189-192.

25. Perler, F., Kumar, S., Kong, H. Thermostable DNA polymerases *Adv. Prot. Chem.,* 1996, 48, 377-435.

26. Quax W. J., 2003, J. Biotechnol., 101, 19-28.

27. Strobel et al., Molec. Biotech., 2003, vol. 24, pp. 1-9.

28. Devereaux et al., 1984, Nucl. Acids Res., 12:387-397.

29. Chang et al., 1978, Nature 275:615.

30. Goeddel et al., 1979, Nature 281:544.

31. Hitzeman et al., 1980, J. Biol. Chem. 255:2073.

32. Holland et al., Biochem., 17:4900.

33. Fleer et al., 1991, Gene, 107:285-195.

34. Hinnen et al., 1978, Proceedings of the National Academy of Sciences USA, 75:1929.

35. Fromant, Blanquet, Plateau, 1995, Anal. Biochem., 224, 347-353.

36. Pouwels et al. Cloning Vectors: A Laboratory Manual, Elsevier, New York (1985)

37. Goeddel et al., Nucl. Acids Res. 8:4057, 1980

38. Maniatis, Molecular Cloning: A Laboratory Manual, Cold Spring Harbor Laboratory, (1982)

39. Luckow and Summers, Bio/Technology 6:47 (1988)

40. Sambrook et al., Molecular Cloning: A Laboratory Manual, Cold Spring Harbor Laboratory Press, New York (1989)

41. Cadwell, Joyce, PCR methods and amplifications, Mutagenic PCR, 3, S136-S140

The invention claimed is:

1. An isolated or purified polynucleotide that encodes a polypeptide having at least 95% identity to residues 13-555 of SEQ ID NO: 26 and contains a mutation at position W550 of SEQ ID NO: 26, wherein said polypeptide has DNA polymerase activity, and wherein said polypeptide comprises at least one other mutation within residues 13-555 of SEQ ID NO: 26.

2. The isolated or purified polynucleotide of claim 1 that has at least one mutation at an amino acid residue between residue 461 to 490 of SEQ ID NO: 26.

3. The isolated or purified polynucleotide of claim 1, wherein said polypeptide has at least one mutation in amino acids 461 to 490 of SEQ ID NO: 26, or at a position selected from the group consisting of H203, F205, T232, E253, Q257, D274, L275, I276, V309, I322, A331, L332, D333, Y334, S335, I361, R374, A384, T387, Y419, P493, M498, G499, M502, L503, V506, R518, A523, A526, P539, and E543.

4. The isolated or purified polynucleotide of claim 1 that encodes a polypeptide having at least one mutation selected from the group consisting of A331T, S335N, M470K, M470R, F472Y, M484V, M484T, R518, and W550R.

5. The isolated or purified polynucleotide of claim 1, wherein said polypeptide has at least 97.5% identity to residues 13-555 of SEQ ID NO: 26.

6. The isolated or purified polynucleotide of claim 1 that encodes an amino acid sequence selected from the group consisting of SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, and SEQ ID NO: 38.

7. The purified polynucleotide of claim 1 that encodes a polypeptide that has a mutation at R518.

8. The purified polynucleotide of claim 7 that encodes a polypeptide that has a mutation R518G.

9. The isolated or purified polynucleotide of claim 1 that encodes a polypeptide that has at least one mutation selected from the group consisting of H203R, F205L, T232S, E253G, Q257R, D274G, L275H, L275P, I276F, V309I, I322N, A331V, S335N, I361F, R374Q, A384T, T387A, Y419C, Y419N, E465K, M470K, M470R, F472Y, F472S, A487T, K490E, P493T, M498T, G499E, M502K, L503P, V506I, R518G, A523V, A526V, P539S, E543K, and W550R.

10. The isolated or purified polynucleotide of claim 9 that encodes a polypeptide that comprises an amino acid sequence selected from the group consisting of SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, and SEQ ID NO: 99.

11. The isolated or purified polynucleotide of claim 1 that comprises a sequence selected from the group consisting of SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, and SEQ ID NO: 37.

12. The isolated or purified polynucleotide of claim 1 that comprises a polynucleotide sequence selected from the group consisting of SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, and SEQ ID NO: 98.

13. An isolated or purified polynucleotide that is fully complementary to the polynucleotide of claim 1.

14. A vector comprising the isolated or purified polynucleotide of claim 1.

15. The vector of claim 14, wherein said polynucleotide is operably linked to a heterologous expression sequence.

16. A host cell comprising the isolated or purified polynucleotide of claim 1.

17. The isolated or purified polynucleotide of claim 1 that encodes a polypeptide comprising residues 13-555 of SEQ ID NO: 26 except that it contains a mutation at position W550 of SEQ ID NO: 26 that replaces tryptophan (W) with another amino acid residue.

18. The isolated or purified polynucleotide of claim 1 that encodes a polypeptide comprising residues 13-555 of SEQ ID NO: 26 except that it contains a mutation at position W550 of SEQ ID NO: 26 that replaces tryptophan (W) with an arginine (R) residue.

* * * * *